US009428508B2

(12) United States Patent
Xiao et al.

(10) Patent No.: US 9,428,508 B2
(45) Date of Patent: Aug. 30, 2016

(54) 2,4-DIAMINO-6,7-DIHYDRO-5H-PYRROLO[2,3]PYRIMIDINE DERIVATIVES AS FAK/PYK2 INHIBITORS

(75) Inventors: Dengming Xiao, Beijing (CN); Liang Cheng, Beijing (CN); Xijie Liu, Beijing (CN); Yuandong Hu, Beijing (CN); Xinhe Xu, Beijing (CN); Zhihua Liu, Beijing (CN); Lipeng Zhang, Beijing (CN); Wei Wu, Beijing (CN); Shulong Wang, Beijing (CN); Yu Shen, Beijing (CN); Gen Li, Beijing (CN); Yin Wang, Beijing (CN); Sheng Zhao, Beijing (CN); Chonglong Li, Beijing (CN); Jia Tang, Beijing (CN); Honghao Yu, Beijing (CN)

(73) Assignee: Centaurus BioPharma Co., Ltd., Beijing (CN)

( * ) Notice: Subject to any disclaimer, the term of this patent is extended or adjusted under 35 U.S.C. 154(b) by 0 days.

(21) Appl. No.: 13/978,475

(22) PCT Filed: Jan. 7, 2012

(86) PCT No.: PCT/CN2012/070122
§ 371 (c)(1),
(2), (4) Date: Jul. 5, 2013

(87) PCT Pub. No.: WO2012/092880
PCT Pub. Date: Jul. 12, 2012

(65) Prior Publication Data
US 2013/0281438 A1    Oct. 24, 2013

Related U.S. Application Data

(60) Provisional application No. 61/457,217, filed on Feb. 2, 2011.

(30) Foreign Application Priority Data

Jan. 7, 2011  (CN) .......................... 2011 1 0002776

(51) Int. Cl.
| | | |
|---|---|---|
| C07D 487/04 | (2006.01) | |
| C07D 413/12 | (2006.01) | |
| A61K 31/519 | (2006.01) | |
| A61K 31/5377 | (2006.01) | |
| A61K 31/541 | (2006.01) | |
| A61K 31/4523 | (2006.01) | |
| A61P 35/00 | (2006.01) | |
| C07D 401/12 | (2006.01) | |
| C07D 493/12 | (2006.01) | |
| C07D 417/12 | (2006.01) | |

(52) U.S. Cl.
CPC ......... *C07D 487/04* (2013.01); *A61K 31/4523* (2013.01); *A61K 31/519* (2013.01); *A61K 31/5377* (2013.01); *A61K 31/541* (2013.01); *C07D 401/12* (2013.01); *C07D 413/12* (2013.01); *C07D 417/12* (2013.01); *C07D 493/12* (2013.01)

(58) Field of Classification Search
CPC  C07D 487/04; C07D 403/12; C07D 401/12; C07D 413/12; C07D 417/12; A61K 31/519; A61K 31/5377; A61K 31/541; A61K 31/4523
USPC ......... 544/280, 117; 514/265.1, 255.1, 236.2
See application file for complete search history.

(56) References Cited

U.S. PATENT DOCUMENTS

2010/0160356 A1    6/2010  Heinrich et al.

FOREIGN PATENT DOCUMENTS

| CN | 1518552 A | 8/2004 |
|---|---|---|
| CN | 1918158 A | 2/2007 |
| CN | 101594871 A | 12/2009 |
| JP | H0782174 A | 3/1995 |
| WO | WO 03/000695 A1 | 1/2003 |
| WO | WO 2004/043367 A2 | 5/2004 |
| WO | WO 2005/080393 A1 | 9/2005 |
| WO | WO 2007/115620 A2 | 10/2007 |
| WO | WO 2007/140222 A2 | 12/2007 |
| WO | WO 2009/131687 A2 | 10/2009 |

OTHER PUBLICATIONS

Infusino et al. Microvasc Res. Jan. 2012 ; 83(1): 89-96.*
Roemer et al. Current Opinion in Microbiology 2013, 16:538-548.*
Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p4.*
Dermer et al., Bio/Technology, 1994, 12:320.*
Golub et al., Science, 286, 531-537, 1999.*

(Continued)

*Primary Examiner* — Venkataraman Balasubramanian
(74) *Attorney, Agent, or Firm* — Leason Ellis LLP.

(57) ABSTRACT

The invention relates to a novel class of 2,4-diamino-6,7-dihydro-5H-pyrrolo[2,3]pyrimidine derivatives as a FAK and/or Pyk2 inhibitor, to a process for their preparation, and to a composition thereof, as well as to use of the compounds for the inhibiting FAK and/or Pyk2 and method for the treatment of a FAK and/or Pyk2 mediated disorder or disease.

3 Claims, No Drawings

(56) References Cited

OTHER PUBLICATIONS

Ferrara, N, Oncology, 69 Suppl. 3, 11-16, 2005.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., Oncogene 19, 5651-5661,2000.*
Turner et al., Current Pharmaceutical Design. 2, 209-224, 1996.*
Sugar et al., Diagno Microbiol. Infect. Dis. 21" 129-133, 1995.*
Snyder et al., J. Med. Liban 48(4): 208-214, 2000. PubMed Abstract.*
Vippagunta et al., Advanced Drug Delivery Reviews 48: 3-26, 2001.*
Wolff Manfred E. "Burger's Medicinal Chemistry, 5ed, Part 1" John Wiley & Sons, 1995, pp. 975-977.*
Banker, G.S. et al, "Modern Pharmaceutices, 3ed.", Marcel Dekker, New York. 1996, pp. 451 and 596.*
Ulrich J. Kirk-Ohmer Encyclopedia of Chemical Technology, pp. 1-7, 2002.*
European Search Report Application No. EP 12732345.9 dated Jun. 3, 2014.
Beviglia et al., "Focal adhesion kinase N-terminus in breast carcinoma cells induces rounding, detachment and apoptosis," *BioChem J.*, 2003, vol. 373(Pt 1): pp. 201-210.
Smith et al., "Effect of focal adhesion kinase (FAK) downregulation with FAK antisense oligonucleotides and 5-fluorouracil on the viability of melanoma cell lines," *Melanoma Res.*, 2005, vol. 15(5); pp. 357-362.
Halder et al., "Focal adhesion kinase silencing augments docetaxel-mediated apoptosis in ovarian cancer cells," *Clin. Cancer Res.*, 2005, vol. 11(24 Pt 1): pp. 8829-8836.
van Nimwegen et al., "Requirement for focal adhesion kinase in the early phase of mammary adenocarcinoma lung metastasis formation," *Cancer Res.*, 2005, vol. 65(11): pp. 4698-4706.
Mitre et al., "Intrinsic focal adhesion kinase activity controls orthotopic breast carcinoma metastasis via the regulation of urokinase plasminogen activator expression in a syngeneic tumor model," *Oncogene*, 2006, vol. 25(32): pp. 4429-4440.
Xu et al., "Attenuation of the expression of the focal adhesion kinase induces apoptosis in tumor cells," *Cell Growth and Differ.*, 1996, vol. 7(4): pp. 413-418.
Kazuyoshi Aso, et al., "Synthesis and Antitumor Activity of Pyrrolo [2,3-d]pyrimidine Antifolates with a Bridge Chain Containing a Nitrogen Atom," *Chem. Pharm. Bull.* vol. 43(2) 256-261 (1995), pp. 1-7/E.
George B Okide, "Synthesis of substituted five-and six-membered nitrogen heterocycles from 1-chloro-2-azapropenylium and 1-chloro-2, 4-iazabutenylium salts," *Indian Journal of Chemistry*, vol. 22B, Apr. 1993, pp. 422-426.
Takahata, Hiroki et al., "Activated lactams new synthesis of azacycloalka[2,3-d] pyrimidine and [2,3-c] pyrazole derivatives," *International Journal of Methods in Synthetic Organic Chemistry*, (1983) vol. 3, pp. 169-248.
Japanese Office Action of Application No. 2013-547804 dated Sep. 8, 2015.
Chinese Office Action No. 20128000482.1, mailed Jan. 29, 2016.

* cited by examiner

US 9,428,508 B2

2,4-DIAMINO-6,7-DIHYDRO-5H-PYRROLO[2,3]PYRIMIDINE DERIVATIVES AS FAK/PYK2 INHIBITORS

CROSS-REFERENCE TO RELATED PATENT APPLICATIONS

This application is a U.S. National Phase application under 35 U.S.C. §371 of International Patent Application No. PCT/CN2012/070122, filed Jan. 7, 2012, and claims the benefit of Chinese Patent Application No. 201110002776.3, filed Jan. 7. 2011, and the U.S. Provisional Patent Application No. 61/457,217, filed Feb. 2, 2011, all of which are incorporated by reference herein. The International application was published in English on Jul. 12, 2012 as International Publication No. WO/2012/092880 under PCT Article 21(2).

FIELD OF THE INVENTION

The invention relates to a novel class of 2,4-diamino-6, 7-dihydro-5H-pyrrolo[2,3]pyrimidine derivatives that inhibit Focal Adhesion Kinases (FAK/Pyk2), to a process for their preparation, and to a composition thereof, as well as to use of the compounds for the inhibiting FAK and/or Pyk2 and method for the treatment of a FAK and/or Pyk2 mediated disorder or disease, for example, a proliferative disorder or disease.

BACKGROUND OF THE INVENTION

FAK (Focal Adhesion Kinase) is a nonreceptor tyrosine kinase which transduces signaling from a group of stimuli (e.g., integrins, cytokines, chemokines, and growth factors) to control a variety of cellular pathways and processes, including cell proliferation, migration, morphology, and cell survival. FAK is activated by FAC (focal adhesion complex)-associated growth factors and integrins. The binding to integrins of EMC (extracellular matrix) leads to the activation of FAK. The activation of FAK can be further enhanced by co-stimulation of the growth factors by ECM associated growth factors, such as bFGF, EGF or PDGF. Focal adhesion complex assembly and disassembly are essential for cell attachment and movement. FAK doesn't phosphorylate other proteins. However, activated FAK autophosphorylates and binds Src kinase which in turn phosphorylate other sites of FAK and other FAK binding proteins such as Cas and paxillin. Phosphorylated FAK provides the docking site for mediators of multiple signaling events and consequently involves in the regulation of cell growth and survival through activation of PI3K/Akt/mTOR and Grb2/SOS/RAS/Raf/MEK/ERK pathways. Overexpression of FAK has been associated with malignancy in a variety of cancers. Inhibition of FAK has been shown the inhibition of tumor growth in different cancer cells (Beviglia et al 2003, BioChem J. 373: 201-210, Smith et al 2005, Melanoma Res. 15:357-362, Haider et al 2005, Clin. Cancer Res. 11: 8829-8836, van Nimwegen et al 2005, Cancer Res. 65:4698-4706, Mitra et al 2006, Oncogene 25: 4429-4440). However, inhibition of FAK in normal human fibrolasts or immortalized mammary cells didn't cause loss of attachment or apoptosis (Xu et al 1996 Cell Growth and Diff. 7: 413-418). Furthermore, loss of FAK activity (reconstitution of FAK−/− cells with kinase-dead FAK) reduced growth of v-Src tumors in mice and decreased angiogenesis. Therefore, Inhibition of FAK is a potential therapy for the treatment of hyper-proliferative diseases such as cancers.

Pyk2 is the only member of the FAK family with 48% amino acid identity. Although the role of Pyk2 in tumorigenesis is not well-established yet, there is some evidence that Pyk2 plays a compensatory role FAK knockout mouse model. Therefor, dual inhibition of FAK and Pyk2 may considerably augment the anti-angiogenic effect.

SUMMARY OF THE INVENTION

The present invention discloses a series of novel 2,4-diamino-6,7-dihydro-5H-pyrrolo[2,3]pyrimidine derivatives, or a pharmaceutically acceptable salt, solvate, polymorph, tautomer or prodrug thereof, which possess FAK and/or Pyk2 inhibitory activity and are useful for a FAK and/or Pyk2 mediated disorder or disease such as antiproliferation and/or antiproapoptotic and/or antiinvasive and/or anti-cell motility and/or antiangiogenisis and can be used in methods of treatment of a disorder in mammal, preferably in human, or in animal body, for example in inhibiting tumor growth and metastatasis in cancers. The invention also relates to the process for the manufacture of said 2,4-diamino-6,7-dihydro-5H-pyrrolo[2,3]pyrimidine compounds, or a pharmaceutically acceptable salt, solvate, polymorph, tautomer or prodrug thereof, to a pharmaceutical composition containing the said compound, or a pharmaceutically acceptable salt, solvate, poly-morph, tautomer or prodrug thereof and to their use in the manufacture of medicaments with antiproliferation and/or antiproapoptotic and/or antiinvasive and/or anti-cell motility and/or antiangiogenic activity.

The present invention also discloses the methods of using 2,4-diamino-6,7-dihydro-5H-pyrrolo[2,3]pyrimidine compounds, or a pharmaceutically acceptable salt, solvate, polymorph, tautomer or prodrug thereof, in treatment of FAK and/or Pyk2 mediated disorders or diseases such as cancers.

In an aspect, the present invention provides a compound represented by formula (I):

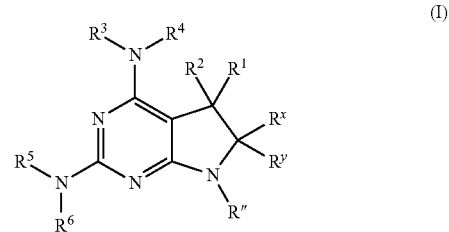

or a pharmaceutically acceptable salt, solvate, poly-morph, tautomer or prodrug thereof, wherein:

$R^1$ and $R^2$ are independently selected from the group consisting of hydrogen, halogen, cyano, nitro, hydroxy, optionally substituted alkyl, optionally substituted cycloalkyl, optionally substituted alkenyl, optionally substituted alkynyl, and optionally substituted alkoxy; or $R^1$ and $R^2$, together with the carbon atom to which they link, form an optionally substituted cycloalkyl or an optionally substituted heterocyclyl;

$R^3$ and $R^4$ are independently selected from the group consisting of hydrogen, optionally substituted alkyl, optionally substituted cycloalkyl, optionally substituted aryl, optionally substituted arylalkyl, optionally substituted heterocyclyl, optionally substituted heteroaryl, —$COR^7$, —$SO_2R^8$, —$SOR^9$;

R$^5$ and R$^6$ are independently selected from the group consisting of hydrogen, optionally substituted alkyl, optionally substituted cycloalkyl, optionally substituted aryl, optionally substituted heterocyclyl, optionally substituted heteroaryl, —COR$^{10}$, —SO$_2$R$^{11}$, and —SOR$^{12}$;

R$^7$, R$^8$, R$^9$, R$^{10}$, R$^{11}$ and R$^{12}$ are independently selected from the group consisting of optionally substituted alkyl, optionally substituted cycloalkyl, optionally substituted aryl, and optionally substituted heteroaryl;

R$^x$ and R$^y$ are independently selected from the group consisting of hydrogen, halogen, cyano, nitro, hydroxy, optionally substituted alkyl, optionally substituted cycloalkyl, optionally substituted alkenyl, optionally substituted alkynyl and optionally substituted alkoxy; and R" is selected from the group consisting of hydrogen, optionally substituted alkyl, optionally substituted cycloalkyl, optionally substituted alkenyl, optionally substituted alkynyl, and optionally substituted alkoxy.

The compound of invention can also be represented by following formula Ia:

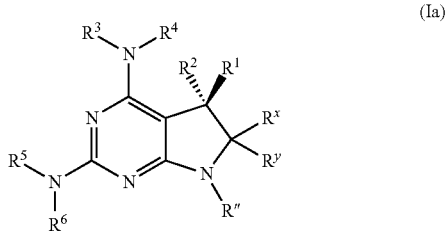

wherein, the definitions of R$^1$, R$^2$, R$^3$, R$^4$, R$^5$, R$^6$, R$^x$, R$^y$ and R" are the same as above in formula I. Whatever the formula is formula I or Ia, the compounds represented by these two formulas include all possible stereoisomers, regioisomers, diastereomers, enantiomers or epimers and mixtures thereof as described hereinafter in the invention.

In another embodiment, in formula (I) or (Ia), R$^1$ and R$^2$ are independently selected from the group consisting of hydrogen, halogen, cyano, nitro, hydroxy, optionally substituted C$_1$-C$_6$ alkyl, optionally substituted C$_3$-C$_8$ cycloalkyl, optionally substituted C$_2$-C$_6$ alkenyl, optionally substituted C$_2$-C$_6$ alkynyl, and optionally substituted C$_1$-C$_6$ alkoxy; or R$^1$ and R$^2$, together with the carbon atom to which they link, form an optionally substituted C$_3$-C$_8$ cycloalkyl or an optionally substituted heterocyclyl;

R$^3$ and R$^4$ are independently selected from the group consisting of hydrogen, optionally substituted C$_1$-C$_6$ alkyl, optionally substituted C$_3$-C$_8$ cycloalkyl, optionally substituted C$_6$-C$_{10}$ aryl, optionally substituted C$_6$-C$_{10}$ aryl-C$_1$-C$_6$ alkyl, optionally substituted heterocyclyl, optionally substituted heteroaryl, —COR$^7$, —SO$_2$R$^8$, —SOR$^9$;

R$^5$ and R$^6$ are independently selected from the group consisting of hydrogen, optionally substituted C$_1$-C$_6$ alkyl, optionally substituted C$_3$-C$_6$ cycloalkyl, optionally substituted C$_6$-C$_{10}$ aryl, optionally substituted heterocyclyl, optionally substituted heteroaryl, —COR$^{10}$, —SO$_2$R$^{11}$, and —SOR$^{12}$;

R$^7$, R$^8$, R$^9$, R$^{10}$, R$^{11}$ and R$^{12}$ are independently selected from the group consisting of optionally substituted C$_1$-C$_6$ alkyl, optionally substituted C$_3$-C$_8$ cycloalkyl, optionally substituted C$_6$-C$_{10}$ aryl, and optionally substituted heteroaryl;

R$^x$ and R$^y$ are independently selected from the group consisting of hydrogen, halogen, cyano, nitro, hydroxy, optionally substituted C$_1$-C$_6$ alkyl, optionally substituted C$_3$-C$_8$ cycloalkyl, optionally substituted C$_2$-C$_6$ alkenyl, optionally substituted C$_2$-C$_6$ alkynyl and optionally substituted C$_1$-C$_6$ alkoxy; and R" is selected from the group consisting of hydrogen, optionally substituted C$_1$-C$_6$ alkyl, optionally substituted C$_3$-C$_8$ cycloalkyl, optionally substituted C$_2$-C$_6$ alkenyl, optionally substituted C$_2$-C$_6$ alkynyl, and optionally substituted C$_1$-C$_6$ alkoxy.

In another embodiment, the invention provides some preferable compounds of Formula I or Ia or a pharmaceutically acceptable salt, solvate, poly-morph, tautomer or prodrug thereof, wherein R$^1$ and R$^2$ are independently selected from the group consisting of hydrogen, optionally substituted C$_1$-C$_6$ alkyl, optionally substituted C$_3$-C$_8$ cycloalkyl or C$_3$-C$_6$ cycloalkyl, optionally substituted C$_2$-C$_6$ alkenyl, optionally substituted C$_2$-C$_6$ alkynyl, and optionally substituted C$_1$-C$_6$ alkoxy; or R$^1$ and R$^2$, together with the carbon atom to which they link, form an optionally substituted C$_3$-C$_8$ cycloalkyl or C$_3$-C$_6$ cycloalkyl.

In another embodiment, the invention provides some preferable compounds of Formula I or Ia or a pharmaceutically acceptable salt, solvate, poly-morph, tautomer or prodrug thereof, wherein R$^5$ and R$^6$ are independently selected from the group consisting of hydrogen, optionally substituted C$_6$-C$_{10}$ aryl, optionally substituted 5-15 membered heterocyclyl with 1-4 heteroatoms selected from N, O and S, optionally substituted 5-10 membered heteroaryl with 1-4 heteroatoms selected from N, O and S.

In another embodiment, the invention provides some preferable compounds of Formula I or Ia or a pharmaceutically acceptable salt, solvate, poly-morph, tautomer or prodrug thereof, wherein R$^5$ and R$^6$ are independently selected from the group consisting of hydrogen, aryl, substituted aryl, heteroaryl, substituted heteroaryl; more preferably, R$^5$ and R$^6$ are independently selected from the group consisting of hydrogen, 5-7 membered aryl, substituted 5-7 membered aryl, 5-7 membered heteroaryl and substituted 5-7 membered heteroaryl with one or more N, O or S as the heteroatoms; and the substituted 5-7 membered aryl or heteroaryl is substituted with at least one of the groups selected from unsubstituted or substituted C$_1$-C$_6$ alkyl, C$_3$-C$_6$ cycloalkyl, C$_2$-C$_6$ alkenyl, C$_2$-C$_6$ alkynyl, and C$_1$-C$_6$ alkoxy.

In another embodiment, the invention provides some preferable compounds of Formula I or Formula Ia or a pharmaceutically acceptable salt, solvate, poly-morph, tautomer or prodrug thereof, wherein R$^3$ and R$^4$ are independently selected from the group consisting of hydrogen, optionally substituted C$_3$-C$_8$ cycloalkyl, optionally substituted C$_6$-C$_{10}$ aryl, optionally substituted C$_{6-10}$ aryl-C$_{1-6}$ alkyl, optionally substituted 5-15 membered heterocyclyl with 1-4 heteroatoms selected from N, O and S, and optionally substituted 5-10 membered heteroaryl with 1-4 heteroatoms selected from N, O and S.

In another embodiment, the invention provides some preferable compounds of Formula (I) or (Ia) or a pharmaceutically acceptable salt, solvate, poly-morph, tautomer or prodrug thereof, wherein R$^3$ and R$^4$ are independently selected from the group consisting of hydrogen, aryl, substituted aryl, C$_1$-C$_6$ alkylaryl, substituted C$_1$-C$_6$ alkylaryl, heteroaryl and substituted heteroaryl; more preferably, R$^3$ and R$^4$ are independently selected from the group consisting of hydrogen, 5-7 membered aryl, substituted 5-7 membered aryl, unsubstituted or substituted C$_1$-C$_6$ alkylphenyl, 5-7 membered heteroaryl and substituted 5-7 membered heteroaryl with one or more N, O or S as the heteroatoms; and the substituted 5-7 membered aryl or heteroaryl is substituted with at least one of the groups selected from halogen, $C_1$-$C_6$ alkoxy, $C_1$-$C_6$ alkyl, $C_3$-$C_6$ cycloalkyl, monoalkylamino, dialkylamino, cycloamino, heterocycloamino, arylamino, heteroarylamino, —$NR^{23}C(O)R^{24}$, —$NR^{23}SO_2R^{25}$, —$CONR^{23}R^{26}$, and —$SO_2NR^{23}R^{26}$; in which $R^{23}$ and $R^{26}$ are independently selected from the group consisting of hydrogen, unsubstituted or substituted $C_1$-$C_6$ alkyl and $C_3$-$C_6$ cycloalkyl; or $R^{23}$ and $R^{26}$ together form an unsubstituted or substituted 5-7 membered heterocycle with the nitrogen atom attached thereto; $R^{24}$ and $R^{25}$ are independently selected from the group consisting of unsubstituted or substituted $C_1$-$C_6$ alkyl, unsubstituted or substituted cycloalkyl, aryl, substituted aryl, heteroaryl and substituted heteroaryl; more preferably, the $R^{24}$ and $R^{25}$ are independently selected from the group consisting of unsubstituted or substituted $C_1$-$C_6$ alkyl, unsubstituted or substituted $C_3$-$C_6$ cycloalkyl, 5-7 membered aryl, substituted 5-7 membered aryl, 5-7 membered heteroaryl and substituted 5-7 membered heteroaryl; or a pharmaceutically acceptable salt, solvate, poly-morph, tautomer or prodrug thereof.

In another embodiment, the invention provides some preferable compounds of Formula I or Formula Ia or a pharmaceutically acceptable salt, solvate, poly-morph, tautomer or prodrug thereof, wherein $R^x$ and $R^y$ are both hydrogen.

In another embodiment, the present invention provides a subclass of the compound of formula (I) represented by the following formula (II) or (IIa):

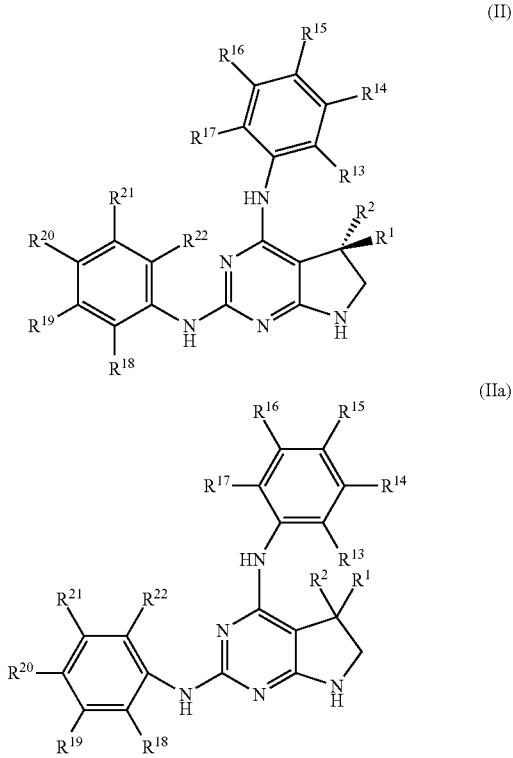

or a pharmaceutically acceptable salt, solvate, poly-morph, tautomer or prodrug thereof, wherein:
$R^1$ and $R^2$ are independently selected from the group consisting of hydrogen, halogen, trifluoromethyl, cyano, nitro, hydroxy, $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy; or $R^1$ and $R^2$ together with carbon atom attached thereto form $C_3$-$C_4$ cycloalkyl or substituted $C_3$-$C_4$ cycloalkyl;

$R^{13}$, $R^{14}$, $R^{15}$, $R^{16}$, $R^{17}$, $R^{18}$, $R^{19}$, $R^{20}$, $R^{21}$ and $R^{22}$ are independently selected from the group consisting of hydrogen, halogen, optionally substituted $C_1$-$C_6$ alkoxy, optionally substituted $C_1$-$C_6$ alkyl, optionally substituted $C_3$-$C_6$ cycloalkyl, optionally substituted monoalkylamino, optionally substituted dialkylamino, optionally substituted cycloamino, optionally substituted heterocycloamino, optionally substituted arylamino, optionally substituted heteroarylamino, —C(O)—$R^{24}$, —$NR^{23}C(O)R^{24}$, —$NR^{23}SO_2R^{25}$, —$NR^{23}SOR^{25}$, —$CONR^{23}R^{26}$, —$SO_2NR^{23}R^{26}$, —$SONR^{23}R^{26}$ and —P(=O)—$R^{25}$; or the group pair of $R^{13}R^{14}$, $R^{14}R^{15}$, $R^{15}R^{16}$, $R^{16}R^{17}$, $R^{18}R^{19}$, $R^{19}R^{20}$, $R^{20}R^{21}$ and $R^{21}R^{22}$ independently form an unsubstituted or substituted 5-8 membered cycle (including aryl or heteroaryl) or heterocycle together with the carbon atoms of phenyl group attached thereto; wherein, $R^{23}$ and $R^{26}$ are independently selected from the group consisting of hydrogen, unsubstituted or substituted $C_1$-$C_6$ alkyl, $C_3$-$C_6$ cycloalkyl and aryl (for example $C_{6-10}$ aryl), or $R^{23}$ and $R^{26}$ together form an unsubstituted or substituted 5-7 membered heterocycle with the nitrogen atom attached thereto, or one of $R^{23}$ and $R^{26}$ together with nitrogen attached thereto form a heterocycle (for example, 5-8 membered heterocyclyl); $R^{24}$ and $R^{25}$ are independently selected from the group consisting of optionally substituted $C_1$-$C_6$ alkyl, optionally substituted $C_3$-$C_6$ cycloalkyl, optionally substituted aryl, optionally substituted heteroaryl. Whatever the formula is formula (II) or (IIa), the compounds represented by these two formulas include all possible stereoisomers, regioisomers, diastereomers, enantiomers or epimers and mixtures thereof as described hereinafter in the invention.

In another embodiment, the present invention provides a subclass of the compound of formula (I) represented by formula (II) or (IIa), or a pharmaceutically acceptable salt, solvate, poly-morph, tautomer or prodrug thereof, wherein:
$R^1$ and $R^2$ are independently selected from the group consisting of hydrogen, halogen, cyano, nitro, hydroxy, optionally substituted $C_1$-$C_6$ alkyl, optionally substituted $C_3$-$C_8$ cycloalkyl, optionally substituted $C_2$-$C_6$ alkenyl, optionally substituted $C_2$-$C_6$ alkynyl, optionally substituted $C_1$-$C_6$ alkoxy; or $R^1$ and $R^2$, together with the carbon atom to which they link, form an optionally substituted $C_3$-$C_8$ cycloalkyl (or $C_3$-$C_6$ cycloalkyl, $C_3$-$C_4$ cycloalkyl);

$R^{13}$, $R^{14}$, $R^{15}$, $R^{16}$, $R^{17}$, $R^{18}$, $R^{19}$, $R^{20}$, $R^{21}$ and $R^{22}$ are independently selected from the group consisting of hydrogen, halogen, optionally substituted $C_1$-$C_6$ alkyl, optionally substituted $C_3$-$C_8$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_6$-$C_{10}$ aryl, optionally substituted 5-15 membered heterocyclyl with 1-4 heteroatoms selected from N, O or S, optionally substituted 5-10 membered heteroaryl with 1-4 heteroatoms selected from N, O or S, optionally substituted mono-$C_1$-$C_6$ alkylamino, optionally substituted di-$C_1$-$C_6$ alkylamino, optionally substituted mono-$C_1$-$C_6$ alkylaminoacyl, optionally substituted di-$C_1$-$C_6$ alkylaminoacyl, optionally substituted 5-12 membered heterocyclyl-acyl with 1-3 heteroatoms selected from N, O or S, optionally substituted $C_1$-$C_6$ alkylamido, aminosulfonyl, optionally substituted mono-$C_1$-$C_6$ alkylaminosulfonyl, optionally substituted di-$C_1$-$C_6$ alkylaminosulfonyl, aminosulfinyl, optionally substituted mono-$C_1$-$C_6$ alkylaminosulfonyl, optionally substituted di-$C_1$-$C_6$ alkylaminosulfinyl, and optionally substituted $C_1$-$C_6$ alkylsulfonamido.

In another embodiment, the present invention provides a subclass of the compound of formula (I) represented by the following formula (III) or Formula (IIIa):

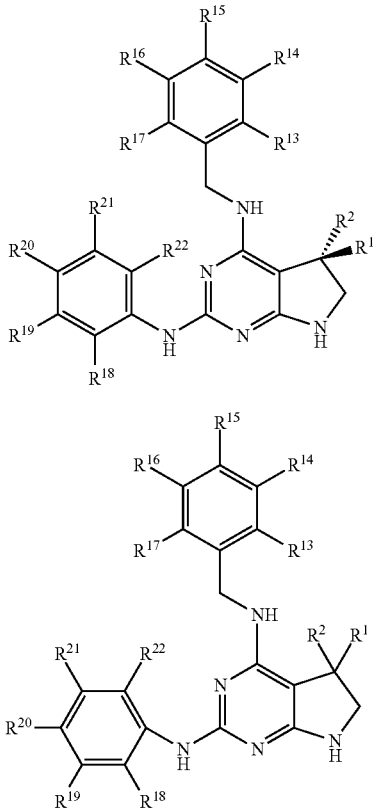

or a pharmaceutically acceptable salt, solvate, poly-morph, tautomer or prodrug thereof, wherein:

$R^1$ and $R^2$ are independently selected from the group consisting of hydrogen, halogen, trifluoromethyl, cyano, nitro, hydroxy, $C_1$-$C_6$ alkoxy, $C_1$-$C_6$ alkyl, $C_3$-$C_6$ cycloalkyl, monoalkylamino, dialkylamino, cycloamino, heterocycloamino, arylamino, heteroarylamino, —$NR^{23}C(O)R^{24}$, —$NR^{23}SO_2R^{25}$, —$CONR^{23}R^{26}$; —$SO_2NR^{23}R^{26}$;

$R^{23}$ and $R^{26}$ are independently selected from hydrogen, $C_1$-$C_6$ alkyl, and $C_3$-$C_6$ cycloalkyl; and $R^{24}$ and $R^{25}$ are independently selected from $C_1$-$C_6$ alkyl, $C_3$-$C_6$ cycloalkyl, aryl, substituted aryl, heteroaryl, and substituted heteroaryl; wherein the group pair of $R^{13}R^{14}$, $R^{14}R^{15}$, $R^{15}R^{16}$, $R^{16}R^{17}$, $R^{18}R^{19}$, $R^{19}R^{20}$, $R^{20}R^{21}$ and $R^{21}R^{22}$ independently form an unsubstituted or substituted 5-8 membered cycle (including aryl or heteroaryl) or heterocycle together with the carbon atoms of phenyl group attached thereto.

Whatever the formula is formula (III) or (IIIa), the compounds represented by these two formulas include all possible stereoisomers, regioisomers, diastereomers, enantiomers or epimers and mixtures thereof as described hereinafter in the invention.

In another embodiment, the present invention provides a subclass of the compound of formula (I) represented by formula (III) or (IIIa), or a pharmaceutically acceptable salt, solvate, poly-morph, tautomer or prodrug thereof, wherein: $R^1$ and $R^2$ are independently selected from the group consisting of hydrogen, halogen, cyano, nitro, hydroxy, optionally substituted $C_1$-$C_6$ alkyl, optionally substituted $C_3$-$C_8$ cycloalkyl, optionally substituted $C_2$-$C_6$ alkenyl, optionally substituted $C_2$-$C_6$ alkynyl, optionally substituted $C_1$-$C_6$ alkoxy; or $R^1$ and $R^2$, together with the carbon atom to which they link, form an optionally substituted $C_3$-$C_8$ cycloalkyl;

$R^{13}$, $R^{14}$, $R^{15}$, $R^{16}$, $R^{17}$, $R^{18}$, $R^{19}$, $R^{20}$, $R^{21}$ and $R^{22}$ are independently selected from the group consisting of hydrogen, halogen, optionally substituted $C_1$-$C_6$ alkyl, optionally substituted $C_3$-$C_8$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_6$-$C_{10}$ aryl, optionally substituted 5-15 membered heterocyclyl with 1-4 heteroatoms selected from N, O or S, optionally substituted 5-10 membered heteroaryl with 1-4 heteroatoms selected from N, O or S, optionally substituted mono-$C_1$-$C_6$ alkylamino, optionally substituted di-$C_1$-$C_6$ alkylamino, optionally substituted mono-$C_1$-$C_6$ alkylaminoacyl, optionally substituted di-$C_1$-$C_6$ alkylaminoacyl, optionally substituted 5-12 membered heterocyclyl-acyl with 1-3 heteroatoms selected from N, O or S, optionally substituted $C_1$-$C_6$ alkylamido, aminosulfonyl, optionally substituted mono-$C_1$-$C_6$ alkylaminosulfonyl, optionally substituted di-$C_1$-$C_6$ alkylaminosulfonyl, aminosulfinyl, optionally substituted mono-$C_1$-$C_6$ alkylaminosulfinyl, optionally substituted di-$C_1$-$C_6$ alkylaminosulfinyl, and optionally substituted $C_1$-$C_6$ alkylsulfonamido.

In another embodiment, the invention provides some preferable compounds of formulas (II), (IIa), (III) and (IIIa) or a pharmaceutically acceptable salt, solvate, poly-morph, tautomer or prodrug thereof, wherein $R^{13}$, $R^{14}$, $R^{15}$, $R^{16}$ and $R^{17}$ are independently selected from the group consisting of hydrogen, —$NR^{23}C(O)R^{24}$, —$NR^{23}SO_2R^{25}$, —$CONR^{23}R^{26}$, and —$SO_2NR^{23}R^{26}$. The definitions of $R^{23}$-$R^{26}$ are the same as above. In another embodiment, the invention provides some preferable compounds of formula (II), (IIa), (III) and (IIIa) or a pharmaceutically acceptable salt, solvate, poly-morph, tautomer or prodrug thereof, wherein $R^{18}$, $R^{19}$, $R^{20}$, $R^{21}$ and $R^{22}$ are independently selected from the group consisting of hydrogen, optionally substituted $C_1$-$C_6$ alkoxy, optionally substituted $C_1$-$C_6$ alkyl, optionally substituted $C_3$-$C_6$ cycloalkyl, optionally substituted 5-7 membered heterocycle with one or more N, O and S as the heteroatoms; or the group pair of $R^{18}R^{19}$, $R^{19}R^{20}$, $R^{20}R^{21}$ and $R^{21}R^{22}$ independently form an optionally substituted 5-15 (or 5-10, 5-8) membered cycle (including aryl or heteroaryl) or heterocycle together with the carbon atoms of phenyl group attached thereto, in which the optionally substituted cycle or heterocycle is substituted with oxo, optionally substituted $C_1$-$C_6$ alkoxy, $C_1$-$C_6$ alkyl, $C_3$-$C_6$ cycloalkyl or 5-7 membered heterocyclo$C_1$-$C_6$ alkyl.

In another aspect, the invention provides compounds of formula (I), selected from the following compounds:

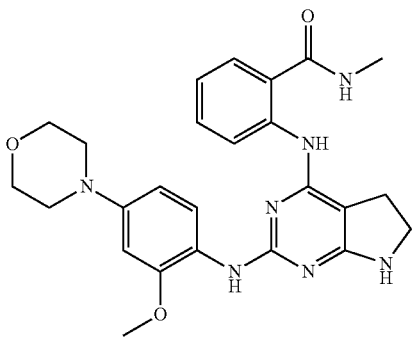

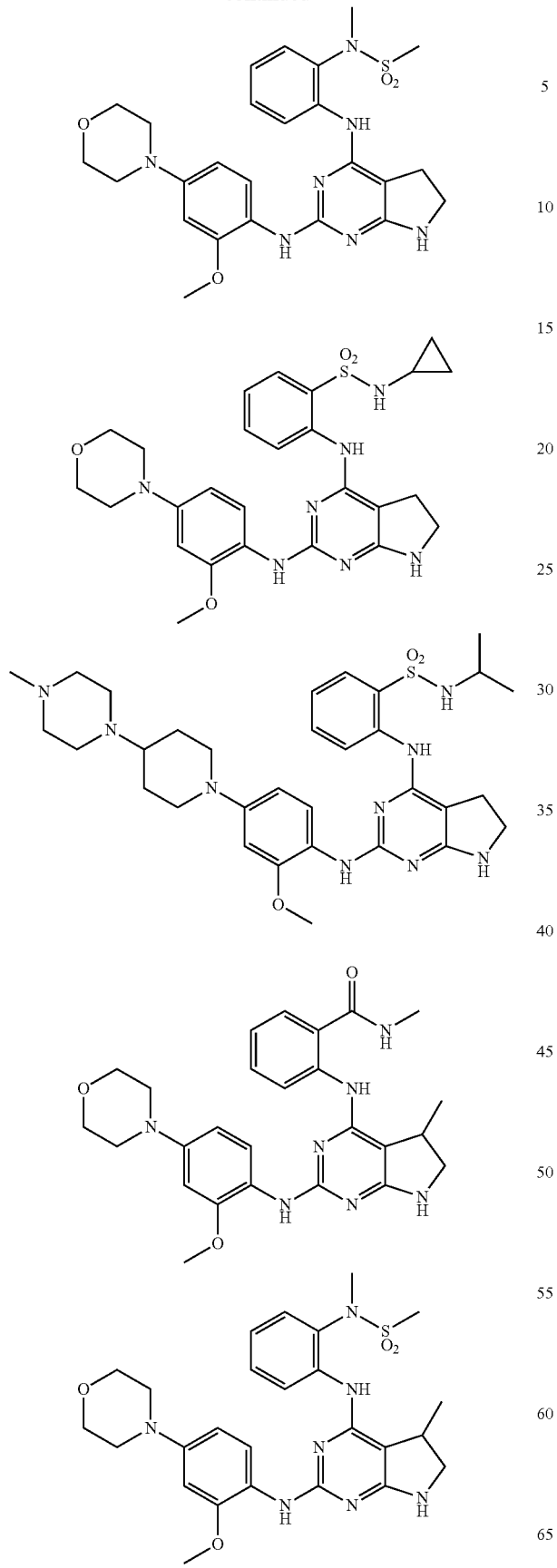
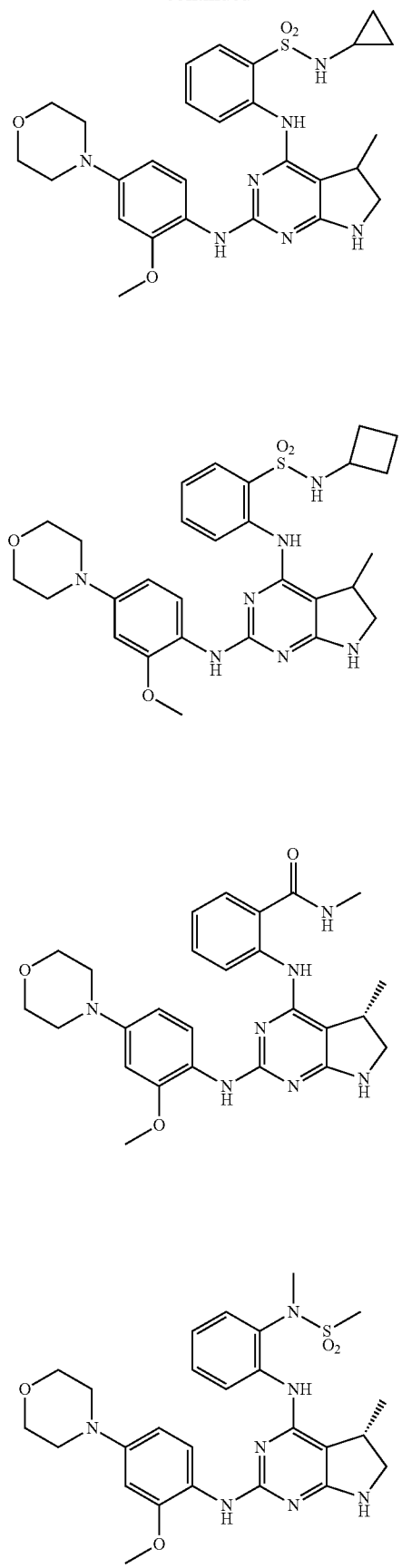

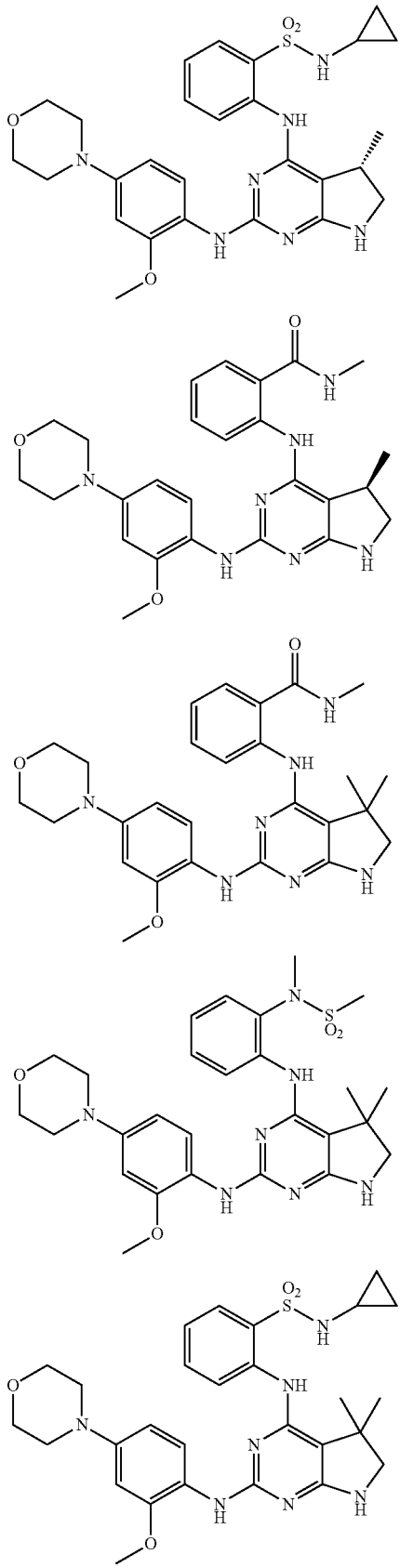

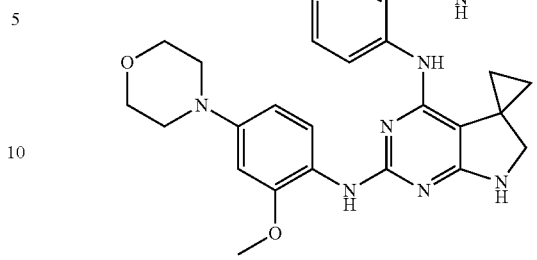

or a pharmaceutically acceptable salt, solvate, poly-morph, tautomer or prodrug thereof.

In another aspect, the invention provides the compound of the invention, or a pharmaceutically acceptable salt, solvate, poly-morph, tautomer or prodrug thereof, for use as a medicament. Preferably, the medicament has an antiproliferative and/or proapoptotic activity.

In another aspect, the invention provides a pharmaceutical composition comprising the compound of the present invention or a pharmaceutically acceptable salt, solvate, polymorph, tautomer or prodrug thereof. In some embodiments, the pharmaceutical composition of the invention further comprises a pharmaceutically acceptable carrier, diluents, excipient and/or adjuvant, such as preservatives, agents for delaying absorption, fillers, binders, adsorbents, buffers, disintegrating agents, solubilizing agents, other carriers, and other inert ingredients. Methods of formulating the composition are well-known in the art.

In another aspect, the invention provides a method for inhibiting FAK and/or Pyk2, comprising contacting the compound of the invention to FAK and/or Pyk2.

In another aspect, the invention provides a method of the treatment or prophylaxis of a FAK and/or Pyk2 mediated disorder or disease, comprising administering to an individual in need thereof a therapeutically effective amount of the compound or composition of the invention. Preferably, the disorder or disease is a cancer, infection, inflammatory or autoimmune disease. More preferably, the disorder or disease is a cancer. In some embodiments, the individual is a mammal, more preferably is a human.

In another aspect, the invention provides use of a compound of the invention or a pharmaceutically acceptable salt, solvate, poly-morph, tautomer or prodrug thereof in the preparation of a pharmaceutical composition for inhibiting FAK and/or Pyk2. Preferably, the pharmaceutical composition is used for the treatment or prophylaxis of a FAK and/or Pyk2 mediated disorder or disease. More preferably, the disorder or disease is a proliferative disorder. In an embodiment, the proliferative disorder is a cancer. In another embodiment, the proliferative disorder is an inflammatory disease.

In another aspect, the invention, relates to pharmaceutical preparations comprising a compound of general formula (I) and at least one further cytostatic or cytotoxic active substance, different from formula (I), optionally in the form of tautomers, the racemates, the enantiomers, the diastereomers and the mixtures thereof, and optionally the pharmaceutically acceptable acid addition salts thereof.

In other aspects, the present invention is directed to a pharmaceutical composition comprising a compound of the invention or a pharmaceutically acceptable salt, solvate, polymorph, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineopiastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of formula I.

In other aspects, the present invention is directed to a method for inhibiting FAK and/or Pyk2. The method comprises contacting said FAK and/or Pyk2 with an amount of a composition comprising a compound of formula I or a pharmaceutically acceptable salt, solvate, polymorph, tautomer or prodrug thereof, sufficient to inhibit said kinase, wherein said kinase is inhibited. In some embodiments, the present invention is directed to a method for selectively inhibiting FAK and/or Pyk2.

In other aspects, the present invention is directed to use of a compound of formula I or a pharmaceutically acceptable salt, solvate, polymorph, tautomer or prodrug thereof in the preparation of a pharmaceutical composition for inhibiting FAK and/or Pyk2.

In further or additional embodiments, the kinase is at least about 1% inhibited. In further or additional embodiments the kinase is at least about 2% inhibited. In further or additional embodiments the kinase is at least about 3% inhibited. In further or additional embodiments the kinase is at least about 4% inhibited. In further or additional embodiments the kinase is at least about 5% inhibited. In further or additional embodiments the kinase is at least about 10% inhibited. In further or additional embodiments the kinase is at least about 20% inhibited. In further or additional embodiments the kinase is at least about 25% inhibited. In further or additional embodiments the kinase is at least about 30% inhibited. In further or additional embodiments the kinase is at least about 40% inhibited. In further or additional embodiments the kinase is at least about 50% inhibited. In further or additional embodiments the kinase is at least about 60% inhibited. In further or additional embodiments the kinase is at least about 70% inhibited. In further or additional embodiments the kinase is at least about 75% inhibited. In further or additional embodiments the kinase is at least about 80% inhibited. In further or additional embodiments the kinase is at least about 90% inhibited. In further or additional embodiments the kinase is essentially completely inhibited. In further or additional embodiments the contacting occurs within a cell. In further or additional embodiments the cell is a mammalian cell. In further or additional embodiments the mammalian cell is a human cell. In further or additional embodiments, FAK and/or Pyk2 is inhibited with a composition comprising a pharmaceutically acceptable salt of a compound of formula I. In other aspects, the present invention is directed to a method of treatment of a FAK and/or Pyk2 mediated disorder in an individual suffering from said disorder comprising administering to said individual an effective amount of a composition comprising a compound of formula I or a pharmaceutically acceptable salt, solvate, polymorph, tautomer or prodrug thereof. In other aspects, the present invention is directed to use of a compound of formula I or a pharmaceutically acceptable salt, solvate, polymorph, tautomer or prodrug thereof in the preparation of a pharmaceutical composition for treating a FAK and/or Pyk2 mediated disorder.

In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution and suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the FAK and/or Pyk2 mediated disorder is a mammal. In further or additional embodiments, the individual is a human. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the FAK and/or Pyk2 mediated disorder is selected from the group consisting of inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the FAK and/or Pyk2 mediated disorder is an inflammatory disease. In further or additional embodiments, the FAK and/or Pyk2 mediated disorder is a proliferative disease. In further or additional embodiments, the FAK and/or Pyk2 mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, tautomer or prodrug thereof.

In other aspects, the present invention is directed to use of a compound of formula I or a pharmaceutically acceptable salt, solvate, polymorph, tautomer or prodrug thereof in the preparation of a pharmaceutical composition for degrading and/or inhibiting the growth of or killing a cancer cell.

In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I is used.

In other aspects, the present invention is directed to a method for the treatment or prophylaxis of a proliferative disease in an individual comprising administering to said individual an effective amount of a composition comprising a compound of formula I or a pharmaceutically acceptable salt, solvate, polymorph, tautomer or pro-drug thereof.

In other aspects, the present invention is directed to use of a compound of formula I or a pharmaceutically acceptable salt, solvate, polymorph, tautomer or prodrug thereof in the preparation of a pharmaceutical composition for the treatment or prophylaxis of a proliferative disease.

In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of an inflammatory disease in an individual comprising administering to said individual an effective amount of a composition comprising a compound of formula I or a pharmaceutically acceptable salt, solvate, polymorph, tautomer or prodrug thereof.

In other aspects, the present invention is directed to use of a compound of formula I or a pharmaceutically acceptable salt, solvate, polymorph, tautomer or prodrug thereof in the preparation of a pharmaceutical composition for the treatment or prophylaxis of an inflammatory disease.

In further or additional embodiments, the inflammatory disease is selected from chronic inflammatory diseases, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of formula I is administered in combination with an additional therapy. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of cancer in an individual comprising administering to said individual an effective amount of a composition comprising a compound of formula I or a pharmaceutically acceptable salt, solvate, polymorph, tautomer or prodrug thereof.

In other aspects, the present invention is directed to use of a compound of formula I or a pharmaceutically acceptable salt, solvate, polymorph, tautomer or prodrug thereof in the preparation of a pharmaceutical composition for the treatment or prophylaxis of a cancer.

In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or a pharmaceutically acceptable salt, solvate, polymorph, tautomer or prodrug thereof.

In other aspects, the present invention is directed to use of a compound of formula I or a pharmaceutically acceptable salt, solvate, polymorph, tautomer or prodrug thereof in the preparation of a pharmaceutical composition for reducing the size of a tumor, inhibiting tumor size increase, reducing tumor proliferation or preventing tumor proliferation.

In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 80%.

In some embodiments, tumor proliferation is reduced by at least 90%. In some embodiments, tumor proliferation is reduced by at least 95%. In some embodiments, tumor proliferation is prevented. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method for achieving an effect in a patient comprising the administration of an effective amount of a composition comprising a compound of formula I or a pharmaceutically acceptable salt, solvate, polymorph, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases.

In other aspects, the present invention is directed to use of a compound of formula I or a pharmaceutically acceptable salt, solvate, polymorph, tautomer or prodrug thereof in the preparation of a pharmaceutical composition for the inhibiting various cancers, immunological diseases, and/or inflammatory diseases.

In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg body weight/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a process for preparing a compound of formula I or a pharmaceutically acceptable salt, solvate, polymorph, tautomer or prodrug thereof.

DETAILED DESCRIPTION OF THE INVENTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure. The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_n$, includes $C_1$-$C_2$, $C_1$-$C_3$ . . . $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—$CH_2$), ethylene (—$CH_2CH_2$), propylene (—$CH_2CH_2CH_2$), isopropylene (—$CH(CH_3)CH_2$) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (CH—$CH_2$), 1-propenyl ($CH_2CH$=$CH_2$), isopropenyl [C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (CH—CH), the propenylene isomers (e.g., $CH_2CH$=CH and C($CH_3$)=CH) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

The term "aromatic" as used herein, refers to a planar, cyclic or polycyclic, ring moiety having a delocalized π-electron system containing 4n+2 π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of heteroaryl group includes pyridyl, 2,3-dihydrobenzo[b][1,4]dioxinyl, 2,3,4,5-tetrahydro-1H-benzo[b]azepinyl, benzimidazolyl, quinolinyl, acridinyl, bipyridinyl, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heterocyclyl", "heterocycle" or "heterocyclo" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

A non-limiting example of "heterocyclyl", "heterocycle" or "heterocyclo" includes morpholine, azinyl, azetidinyl, oxetanyl, thietanyl, homopiperidinyl, piperidyl, oxepanyl, thiepanyl, oxazepinyl, diazepinyl, thiazepinyl, 1,2,3,6-tetrahydropyridinyl, 2-pyrrolinyl, 3-pyrrolinyl, pyrrolidinyl, indolinyl, 2H-pyranyl, piperazinyl, 2-oxopiperidiyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, (S,S-dioxothio)piperidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "carbocyclyl" or "carbocycle" as used herein, alone or in combination, refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "alkoxy" as used herein, alone or in combination, refers to an alkyl ether radical, O-alkyl, including the groups O-aliphatic and O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tertbutoxy and the like.

The term "sulfinyl" as used herein, alone or in combination, refers to the diradical —S(O).

The term "sulfonyl" as used herein, alone or in combination, refers to the diradical —S(O)$_2$.

The terms "sulfonamide", "sulfonamido" and "sulfonamidyl" as used herein, alone or in combination, refer to the diradical groups —S(O)$_2$—NH— and —NH—S(O)$_2$.

In the present application, where any of the above groups is indicated as "optionally substituted", said group is optionally substituted with one or more groups selected from halogen, hydroxy, optionally substituted $C_1$-$C_6$ alkyl, optionally substituted $C_3$-$C_6$ cycloalkyl, optionally substituted $C_2$-$C_6$ alkenyl, optionally substituted $C_2$-$C_6$ alkynyl, optionally substituted $C_1$-$C_6$ alkoxy, optionally substituted $C_6$-$C_{10}$ aryl, optionally substituted 5-15 membered heterocyclyl with 1-4 heteroatoms selected from N, O or S, optionally substituted 5-10 membered heteroaryl with 1-4 heteroatoms selected from N, O or S, optionally substituted mono-$C_1$-$C_6$ alkylamino, optionally substituted di-$C_1$-$C_6$ alkylamino, optionally substituted mono-$C_1$-$C_6$ alkylaminoacyl, optionally substituted di-$C_1$-$C_6$ alkylaminoacyl, optionally substituted 5-12 membered heterocyclyl-acyl with 1-3 heteroatoms selected from N, O or S, optionally substituted $C_1$-$C_6$ alkylamido, aminosulfonyl, optionally substituted mono-$C_1$-$C_6$ alkylaminosulfonyl, optionally substituted di-$C_1$-$C_6$ alkylaminosulfonyl, aminosulfinyl, optionally substituted mono-$C_1$-$C_6$ alkylaminosulfinyl, optionally substituted di-$C_1$-$C_6$ alkylaminosulfinyl, and optionally substituted $C_1$-$C_6$ alkylsulfonamido. For the purpose of the present application, a group may be substituted in sequence for at most three times. The above listed groups are the same as the substituents for substituting the groups indicated as "substituted" (for example "substituted alkyl") in the definitions of the groups in Formulas I, Ia, II, IIa, III, IIIa.

Certain Pharmaceutical Terminology

The term "FAK/Pyk2 inhibitor" as used herein refers to a compound that exhibits an $IC_{50}$, with respect to FAK and/or Pyk2 activity, of no more than about 100 M or not more than about 50 M, as measured in the FAK/Pyk2 activity assay described generally herein. "$IC_{50}$" is that concentration of inhibitor which reduces the activity of an enzyme (e.g., FAK and/or Pyk2) to half-maximal level. Compounds described herein have been discovered to exhibit inhibition against FAK and/or Pyk2. Compounds of the present invention preferably exhibit an $IC_{50}$ with respect to FAK and/or Pyk2 of no more than about 10 M, more preferably, no more than about M, even more preferably not more than about 1 M, and most preferably, not more than about 200 nM, as measured in the FAK/Pyk2 activity assay described herein.

The term "selective," "selectively," or "selectivity" as used herein refers to a compound of this invention having a lower $IC_{50}$ value for a FAK and/or Pyk2 as compared to any other enzymes (e.g., at least 2, 5, 10 or more-fold lower).

The term "subject", "patient" or "individual" as used herein in reference to individuals suffering from a disorder, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering"; "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, and intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as carrier and/or excipients, though not limited to stabilizers, diluents, dispersing agents, suspending agents, thickening agents, etc.

The term "carrier" as used herein, may refer to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, y-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, IV' $(C_{1-4}$ alkyl$)_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

SYNTHETIC PROCEDURES AND EXAMPLES

Methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein.

The compounds of formula I wherein one of $R^3$ and $R^4$ is hydrogen, one of $R^5$ and $R^6$ is hydrogen, and R" is hydrogen shown as the following formula is taken as an example to illustrate the preparation of the compounds of formula I.

General Protocol I: Synthesis of 2,4-dichloro-6,7-dihydro-5H-pyrrolo[2,3-d]pyrimidines

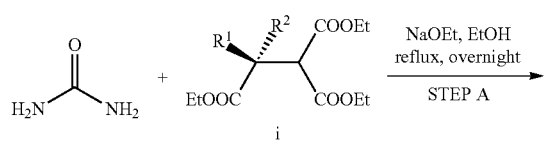

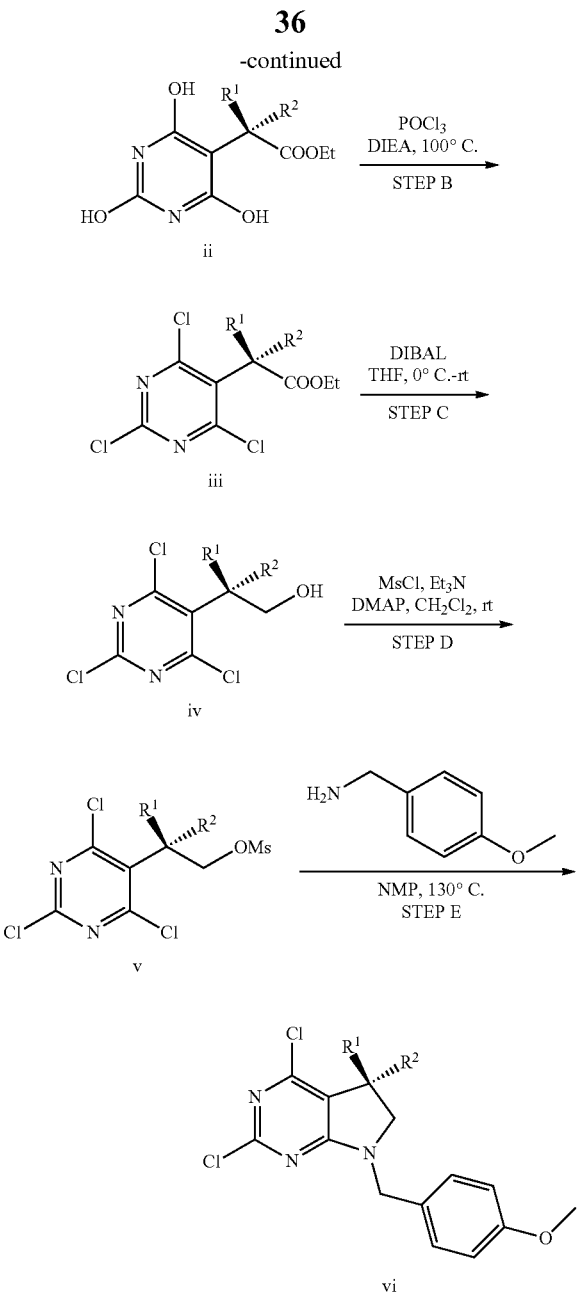

General Protocol II: Synthesis of 6,7-dihydro-5H-pyrrolo[2,3-d]pyrimidine-2,4-diamines

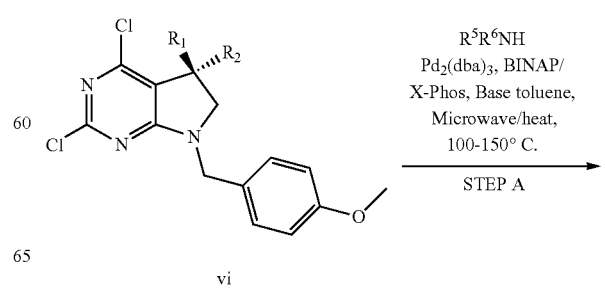

-continued

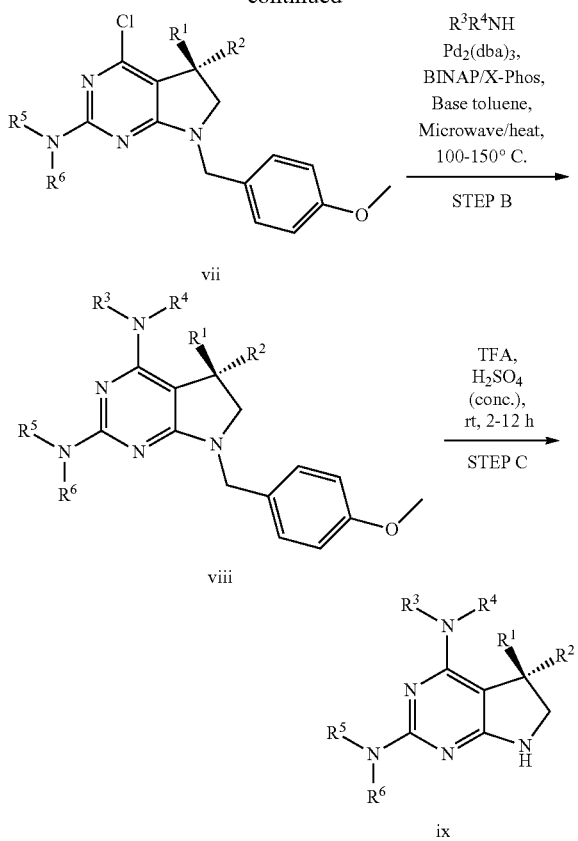

Step A: To a solution of anhydrous ethanol was added sodium (1.5 eq.) in pieces. After all the sodium dissolved, 1,1,2-tricarboxylates (i, 1.0 eq.) and urea (1.0 eq.) was added respectively. The reaction mixture was heated at reflux overnight and cooled to room temperature, evaporated to dryness. The residue was diluted with water and acidified by diluted hydrochloric acid (2 N). The mixture was evaporated and purified by silica gel chromatography to afford the product 2-(2,4,6-trihydroxypyrimidin-5-yl)acetates (ii).

Step B: To a solution of 2-(2,4,6-trihydroxypyrimidin-5-yl)acetates (ii, 1.0 eq.) in phosphoryl trichloride was added N,N'-diisopropylethylamine (2.0 eq.) dropwise. After the addition was over, the reaction mixture was heated at 100° C. for 1-12 hours. Most of phosphoryl trichloride was removed under reduced pressure and the residue was basified by aqueous sodium bicarbonate. The aqueous phase was extracted with ethyl acetate, and the organic extracts were combined, washed by brine, dried over anhydrous sodium sulfate, evaporated and purified by silica gel chromatography to afford the product 2-(2,4,6-trichloropyrimidin-5-yl)acetates (iii).

Step C: To a solution of 2-(2,4,6-trichloropyrimidin-5-yl)acetates (iii, 1.0 eq.) in anhydrous tetrahydrofuran at 0° C. was added diisobutylaluminium hydride (3.0-4.0 eq.) dropwise. The reaction mixture was continued stirring for another 2-12 hours and then quenched by diluted hydrochloric acid (1 N). The aqueous phase was extracted with ethyl acetate, and the organic phases were combined, washed by brine, dried over anhydrous sodium sulfate, and evaporated to afford the product 2-(2,4,6-trichloropyrimidin-5-yl)ethanols (iv), which was used for the next step without purification.

Step D: To a solution of 2-(2,4,6-trichloropyrimidin-5-yl) ethanols (iv, 1.0 eq.) in dichloromethane was added methanesulfonyl chloride (2.0 eq.), triethyl amine (2.0 eq.) and catalytic amount of 4-dimethylaminopyridine respectively. The reaction mixture was stirred at room temperature for 1-12 hours, evaporated and purified by silica gel chromatography to afford the product 2-(2,4,6-trichloropyrimidin-5-yl)ethyl methanesulfonates (v).

Step E: To a solution of 2-(2,4,6-trichloropyrimidin-5-yl) ethyl methanesulfonates (v, 1.0 eq.) in N-methyl-2-pyrrolidone was added (4-methoxyphenyl)methanamine (1.5 eq.) and triethyl amine (10.0 eq.). The reaction mixture was stirred at 130° C. for 1-3 hours. After cooling to room temperature, the mixture was poured into water. The aqueous phase was extracted with ethyl acetate, and the organic phases were combined, washed by brine, dried over anhydrous sodium sulfate, evaporated and purified by silica gel chromatography to afford the product 2,4-dichloro-7-(4-methoxybenzyl)-6,7-dihydro-5H-pyrrolo[2,3-d]pyrimidines (vi, Intermediates A1-A3).

Intermediate A1

2,4-dichloro-7-(4-methoxybenzyl)-6,7-dihydro-5H-pyrrolo[2,3-d]pyrimidine

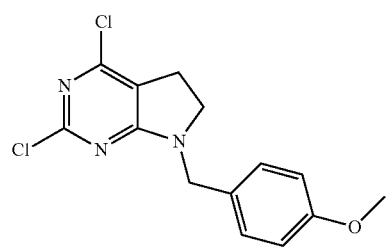 [SMILES: COc1ccc(CN2CCc3c(Cl)nc(Cl)nc32)cc1]

Step A: ethyl 2-(2,4,6-trihydroxypyrimidin-5-yl)acetate

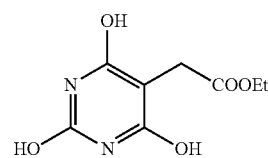 [SMILES: CCOC(=O)Cc1c(O)nc(O)nc1O]

According to General Protocol I, 2,4-dichloro-7-(4-methoxybenzyl)-6,7-dihydro-5H-pyrrolo[2,3-d]pyrimidine was prepared from triethyl ethane-1,1,2-tricarboxylate (10 g, 41 mmol) and urea (2.44 g, 41 mmol), and isolated as a pale-yellow solid (4.6 g, yield 35%).

Step B: ethyl 2-(2,4,6-trichloropyrimidin-5-yl)acetate

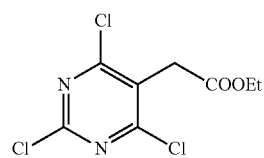 [SMILES: CCOC(=O)Cc1c(Cl)nc(Cl)nc1Cl]

According to General Protocol I, ethyl 2-(2,4,6-trichloropyrimidin-5-yl)acetate was prepared from ethyl 2-(2,4,6-trihydroxypyrimidin-5-yl)acetate (2.5 g, 12 mmol), phosphoryl trichloride (20 mL) and N,N-diisopropylethylamine (4 mL), and isolated as a pale-yellow oil (860 mg, yield 27%). $^1$H NMR (400 MHz, CDCl$_3$) δ ppm 4.20-4.25 (q, 2H, J=7.2 Hz), 3.94 (s, 2H), 1.27-1.30 (t, 3H, J=7.2 Hz).

Step C: 2-(2,4,6-trichloropyrimidin-5-yl)ethanol

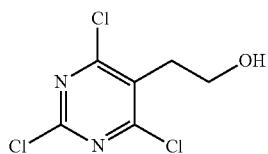

According to General Protocol I, 2-(2,4,6-trichloropyrimidin-5-yl)ethanol was prepared from ethyl 2-(2,4,6-trichloropyrimidin-5-yl)acetate (860 mg, 3.2 mmol) and diisobutylaluminium hydride (1.0 M in hexane, 10 mL, 10 mmol), and isolated as a colorless oil (720 mg, yield 99%).

Step D: 2-(2,4,6-trichloropyrimidin-5-yl)ethyl methanesulfonate

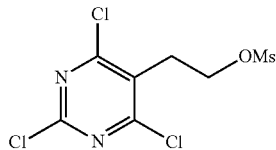 [SMILES: CS(=O)(=O)OCCc1c(Cl)nc(Cl)nc1Cl]

According to General Protocol I, 2-(2,4,6-trichloropyrimidin-5-yl)ethyl methanesulfonate was prepared from 2-(2,4,6-trichloropyrimidin-5-yl)ethanol (720 mg, 3.2 mmol), methanesulfonyl chloride (814 mg, 7.1 mmol) and treiethylamine (1 mL), and isolated as a pale-yellow oil (660 mg, yield 68%). $^1$H NMR (400 MHz, CDCl$_3$) δ ppm 4.39-4.44 (m, 2H), 3.29-3.36 (m, 2H), 3.08 (s, 3H).

Step E/Intermediate A1

2,4-dichloro-7-(4-methoxybenzyl)-6,7-dihydro-5H-pyrrolo[2,3-d]pyrimidine

According to General Protocol I, 2,4-dichloro-7-(4-methoxybenzyl)-6,7-dihydro-5H-pyrrolo[2,3-d]pyrimidine was prepared from 2-(2,4,6-trichloropyrimidin-5-yl)ethyl methanesulfonate (480 mg, 1.57 mmol) and (4-methoxyphenyl)methanamine (325 mg, 2.37 mmol), and isolated as a yellow solid (660 mg, yield 68%). $^1$H NMR (400 MHz, CDCl$_3$) δ ppm 7.18-7.20 (dd, 2H, J=2.0 Hz, 6.8 Hz), 6.86-6.88 (dd, 2H, J=2.0 Hz, 6.4 Hz), 4.53 (s, 2H), 3.80 (s, 3H), 3.54-3.58 (t, 2H, J=8.8 Hz), 2.95-3.00 (t, 2H, J=8.8 Hz).

Intermediate A2

(±)-2,4-dichloro-7-(4-methoxybenzyl)-5-methyl-6,7-dihydro-5H-pyrrolo[2,3-d]pyrimidine

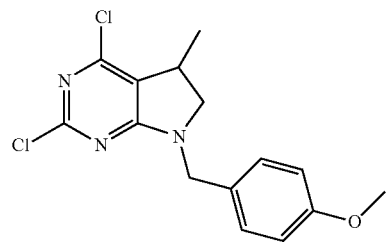 [SMILES: COc1ccc(CN2CC(C)c3c(Cl)nc(Cl)nc32)cc1]

Step A: (±)-triethyl propane-1,1,2-tricarboxylate

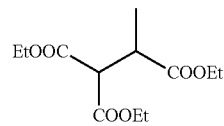

To a solution of anhydrous ethanol (500 mL) was added sodium (9 g, 0.39 mol) in pieces. After all the sodium dissolved, diethyl malonate (50 g, 0.31 mol) was added dropwise at 0° C., and the mixture was stirred at 0° C. for another 30 minutes, followed by the addition of (±)-ethyl 2-bromopropanoate (56.5 g, 0.31 mol) dropwise. The mixture was warmed to room temperature for 1 hour and then heated at reflux for 12 hours. After cooling to room temperature, most of solvents were removed, and the residue was diluted with ethyl acetate. The organic phase was washed by brine, dried over anhydrous sodium sulfate and evaporated to afford the product (±)-triethyl propane-1,1,2-tricarboxylate (67.8 g, yield 83.4%), which was used for the next step without purification.

Step B: (±)-ethyl 2-(2,4,6-trihydroxypyrimidin-5-yl)propanoate

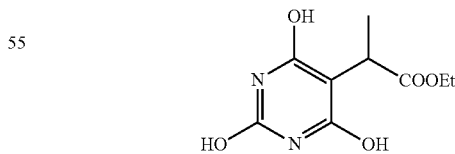

According to General Protocol I, (±)-ethyl 2-(2,4,6-trihydroxypyrimidin-5-yl)propanoate was prepared from sodium (1.9 g, 83 mmol), (±)-triethyl propane-1,1,2-tricarboxylate (14.2 g, 55 mmol) and urea (3.3 g, 55 mmol) and isolated as a red-yellow oil (6 g, yield 48%), which was used for the next step without purification.

Step C: (±)-ethyl 2-(2,4,6-trichloropyrimidin-5-yl)propanoate

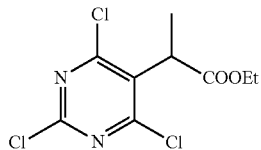 [SMILES: CCOC(=O)C(C)c1c(Cl)nc(Cl)nc1Cl]

According to General Protocol I, (±)-ethyl 2-(2,4,6-trichloropyrimidin-5-yl)propanoate was prepared from (±)-ethyl 2-(2,4,6-trihydroxypyrimidin-5-yl)propanoate (6 g, 12 mmol), phosphoryl trichloride (30 mL) and N,N'-diisopropylethylamine (7.5 mL) and isolated as a yellow oil (2.3 g, yield 31%). $^1$H NMR (400 MHz, CDCl$_3$) δ ppm 4.31-4.37 (m, 1H), 4.17-4.25 (m, 2H), 1.55-1.57 (m, 3H), 1.22-1.26 (m, 3H).

Step D: (±)-2-(2,4,6-trichloropyrimidin-5-yl)propan-1-ol

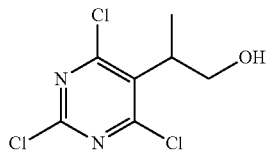

According to General Protocol I, (±)-2-(2,4,6-trichloropyrimidin-5-yl)propan-1-ol was prepared from (±)-ethyl 2-(2,4,6-trichloropyrimidin-5-yl)propanoate (2.3 g, 8 mmol) and diisobutylaluminium hydride (1.0 M in hexane, 10 mL, 10 mmol) and isolated as a pale-yellow oil (260 mg, yield 13%). $^1$H NMR (400 MHz, CDCl$_3$) δ ppm 4.17-4.11 (m, 1H), 3.97-3.93 (m, 1H), 3.89-3.83 (m, 1H), 1.54 (s, 1H), 1.40-1.38 (d, 3H, J=7.2 Hz).

Step E: (±)-2-(2,4,6-trichloropyrimidin-5-yl)propyl methanesulfonate

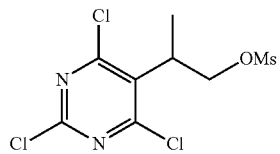

According to General Protocol I, (±)-2-(2,4,6-trichloropyrimidin-5-yl)propyl methanesulfonate was prepared from (±)-2-(2,4,6-trichloropyrimidin-5-yl)propan-1-ol (260 mg, 1.1 mmol), methanesulfonyl chloride (247 mg, 2.1 mmol) and triethyl amine (0.2 mL) and isolated as a pale-yellow oil (300 mg, yield 87%). $^1$H NMR (400 MHz, CDCl$_3$) δ ppm 4.73-4.68 (t, 1H, J=9.2 Hz), 4.53-4.49 (dd, 1H, J=6.8 Hz, 10.4 Hz), 4.13-4.06 (m, 1H), 3.00 (s, 3H), 1.48-1.46 (d, 3H, J=7.2 Hz).

Step F/Intermediate A2

(±)-2,4-dichloro-7-(4-methoxybenzyl)-5-methyl-6,7-dihydro-5H-pyrrolo[2,3-d]pyrimidine According to General Protocol I, (±)-2,4-dichloro-7-(4-methoxybenzyl)-5-methyl-6,7-dihydro-5H-pyrrolo[2,3-d]pyrimidine was prepared from (±)-2-(2,4,6-trichloropyrimidin-5-yl)propyl methanesulfonate (300 mg, 0.94 mmol), (4-methoxyphenyl)methanamine (192 mg, 1.4 mmol) and triethyl amine (2 mL), and isolated as a yellow (190 mg, yield 63%). $^1$H NMR (400 MHz, CDCl$_3$) δ ppm 7.18-7.16 (d, 2H, J=8.4 Hz), 6.88-6.86 (dd, 2H, J=2.0 Hz, 6.4 Hz), 4.53 (s, 2H), 3.80 (s, 3H), 3.70-3.65 (t, 1H, J=10.0 Hz), 3.35-3.34 (m, 1H), 3.11-3.07 (q, 1H, J=4.8 Hz), 1.31-1.29 (m, 3H).

Intermediate A3

(S)-2,4-dichloro-7-(4-methoxybenzyl)-5-methyl-6,7-dihydro-5H-pyrrolo[2,3-d]pyrimidine

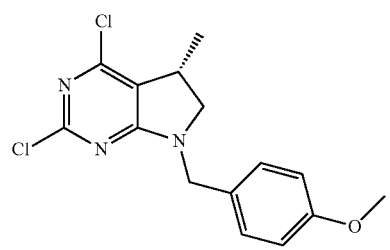 [SMILES: COc1ccc(CN2C[C@@H](C)c3c(Cl)nc(Cl)nc32)cc1]

Step A: (S)-ethyl 2-(methylsulfonyloxy)propanoate

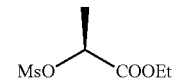

To a solution of (L)-ethyl lactate (124 g, 1.05 mol) and triethyl amine (126 g, 1.25 mol) in toluene at 10-15° C. was added methanesulfonyl chloride (124 g, 1.08 mol) dropwise for about 2 hours. The mixture was allowed to warm to about 20° C. and the solid was filtered off. The solution was washed with water and dried, concentrated to afford the product (S)-ethyl 2-(methylsulfonyloxy)propanoate (199 g, yield 96.7%).

Step B: (S)-1,1-dibenzyl 2-ethyl propane-1,1,2-tricarboxylate

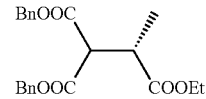

To a solution of (S)-ethyl 2-(methylsulfonyloxy)propanoate (28.4 g, 0.1 mol) in N,N'-dimethylformamide (400 mL) was added dibenzyl malonate (23.5 g, 0.12 mol) and cesium fluoride (15.2 g, 0.1 mol). The mixture was heated at 50° C. for 2 days. After cooled to room temperature, the mixture was poured into water and then extracted with ethyl acetate. The organic phases were combined, washed with brine, water and dried over anhydrous sodium sulfate, and then concentrated to afford the crude product (S)-1,1-dibenzyl 2-ethyl propane-1,1,2-tricarboxylate, which was purified by silica gel chromatography (23 g, yield 60%).

Step C: (S)-2-(1-ethoxy-1-oxopropan-2-yl)malonic acid

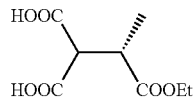

To the solution of (S)-1,1-dibenzyl 2-ethyl propane-1,1,2-tricarboxylate (23 g, 0.06 mol) in methanol (500 mL) was added palladium on carbon (10%, 2 g), and then the mixture was stirred under an atmosphere of hydrogen at room temperature overnight. The catalyst was filtrated and the filtrate was concentrated under reduced pressure to afford the crude product (S)-2-(1-ethoxy-1-oxopropan-2-yl)malonic acid, which was purified by silica gel chromatography (10 g, yield 83%).

Step D: (S)-ethyl 2-(2,4,6-trioxohexahydropyrimidin-5-yl)propanoate

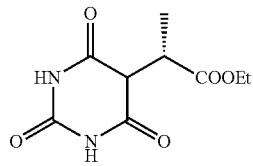 [SMILES: CCOC(=O)[C@@H](C)C1C(=O)NC(=O)NC1=O]

A suspension of (S)-2-(1-ethoxy-1-oxopropan-2-yl)malonic acid (5 g, 25 mmol) and urea (1.8 g, 29.4 mmol) in acetic anhydride (15 mL) was placed in a microwave reactor and allowed to react under microwave irradiation at 60° C. for 30 minutes. After cooled to room temperature, the mixture was quenched by sodium bicarbonate and extracted with ethyl acetate. The organic phases were combined, dried over anhydrous sodium sulfate, concentrated and purified by silica gel chromatography to afford the product (S)-ethyl 2-(2,4,6-trioxohexahydropyrimidin-5-yl)propanoate (2.85 g, yield 50%).

Step E: (S)-ethyl 2-(2,4,6-trichloropyrimidin-5-yl)propanoate

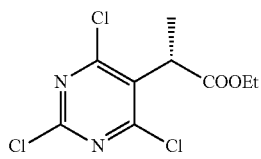 [SMILES: CCOC(=O)[C@@H](C)c1c(Cl)nc(Cl)nc1Cl]

According to General Protocol I, (S)-ethyl 2-(2,4,6-trichloropyrimidin-5-yl)propanoate was prepared from (S)-ethyl 2-(2,4,6-trioxohexahydropyrimidin-5-yl)propanoate (5.6 g, 25 m mol), phosphoryl trichloride (20 mL) and N,N'-diisopropylethylamine (5 mL) and isolated as a yellow oil (2.8 g, yield 40%). $^1$H NMR (400 MHz, CDCl$_3$) δ ppm 4.30-4.36 (q, 1H, J=7.2 Hz), 4.16-4.25 (m, 2H), 1.54-1.56 (d, 3H, J=7.6 Hz), 1.22-1.25 (m, 3H).

Step F: (S)-2-(2,4,6-trichloropyrimidin-5-yl)propan-1-ol

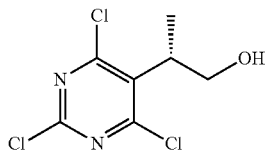

According to General Protocol I, (S)-2-(2,4,6-trichloropyrimidin-5-yl)propan-1-ol was prepared from (S)-ethyl 2-(2,4,6-trichloropyrimidin-5-yl)propanoate (1.0 g, 3.55 mmol) and diisobutylaluminium hydride (1.0 M in hexane, 10.6 mL, 10.6 mmol) and isolated as a pale-yellow oil (200 mg, yield 25%). $^1$H NMR (400 MHz, CDCl$_3$) δ ppm 4.13-4.17 (m, 1H), 3.83-3.96 (m, 2H), 1.79 (s, 1H), 1.38-1.40 (d, 3H, J=7.2 Hz).

Step G: (S)-2-(2,4,6-trichloropyrimidin-5-yl)propyl methanesulfonate

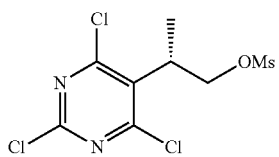 [SMILES: C[C@H](COS(C)(=O)=O)c1c(Cl)nc(Cl)nc1Cl]

According to General Protocol I, (S)-2-(2,4,6-trichloropyrimidin-5-yl)propyl methanesulfonate was prepared from (S)-2-(2,4,6-trichloropyrimidin-5-yl)propan-1-ol (200 mg, 0.83 mmol), methanesulfonyl chloride (191 mg, 1.66 mmol) and triethyl amine (166 mg, 1.66 mmol) and isolated as a pale-yellow oil (185 mg, yield 70%).

Step H/Intermediate A3

(S)-2,4-dichloro-7-(4-methoxybenzyl)-5-methyl-6,7-dihydro-5H-pyrrolo[2,3-d]pyrimidine According to General Protocol I, (S)-2,4-dichloro-7-(4-methoxybenzyl)-5-methyl-6,7-dihydro-5H-pyrrolo[2,3-d]pyrimidine was prepared from (S)-2-(2,4,6-trichloropyrimidin-5-yl)propyl methanesulfonate (185 mg, 0.578 mmol), (4-methoxyphenyl)methanamine (120 mg, 0.867 mmol) and triethyl amine (117 mg, 1.156 mmol), and isolated as a yellow (120 mg, yield 64%). $^1$H NMR (400 MHz, CDCl$_3$) δ ppm 7.16-7.19 (d, 2H, J=8.8 Hz), 6.86-6.88 (d, 2H, J=8.4 Hz), 4.54 (s, 2H), 3.80 (s, 3H), 3.66-3.71 (t, 1H, J=6.0 Hz), 3.33-3.36 (m, 1H), 3.08-3.12 (dd, 1H, J=4.4 Hz, 10.0 Hz), 1.29-1.31 (d, 3H, J=6.8 Hz).

Intermediate A4

2,4-dichloro-7-(4-methoxybenzyl)-5,5-dimethyl-6,7-dihydro-5H-pyrrolo[2,3-d]pyrimidine

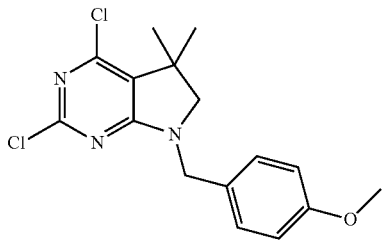 [SMILES: COc1ccc(CN2CC(C)(C)c3c(Cl)nc(Cl)nc32)cc1]

Intermediate A4 was synthesized according to the scheme as following:

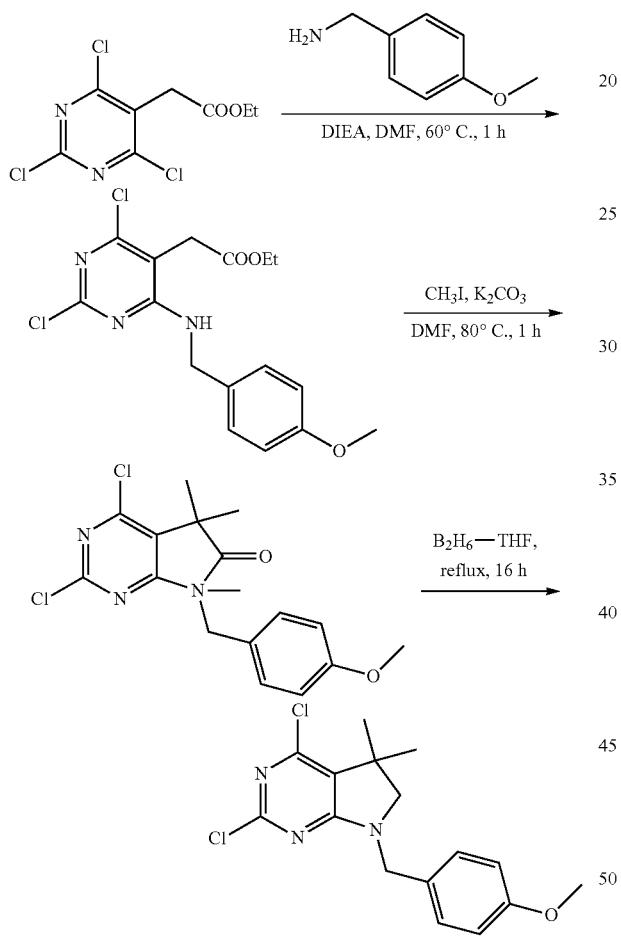

Step A: ethyl 2-(2,4-dichloro-6-(4-methoxybenzylamino)pyrimidin-5-yl)acetate

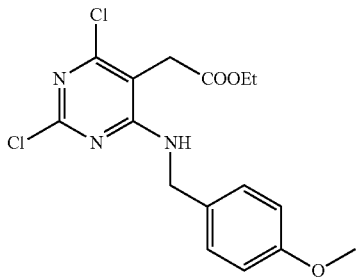 [SMILES: CCOC(=O)Cc1c(Cl)nc(Cl)nc1NCc1ccc(OC)cc1]

To a solution of ethyl 2-(2,4,6-trichloropyrimidin-5-yl)acetate (from Intermediate A1, 200 mg, 0.74 mmol) in N,N'-dimethylformamide (5 mL) was added (4-methoxyphenyl)methanamine (112 mg, 0.82 mmol) and N,N'-diisopropylethylamine (115 mg, 0.89 mmol). The resulting mixture was stirred at 60° C. for 1 hour, quenched by water and then extracted with ethyl acetate. The organic phases were combined, washed by diluted hydrochloric acid (1 N), water and brine, dried over anhydrous sodium sulfate, evaporated and purified by silica gel chromatography to afford the product ethyl 2-(2,4-dichloro-6-(4-methoxybenzylamino)pyrimidin-5-yl)acetate. $^1$H-NMR (400 MHz, CDCl$_3$) δ ppm 7.26-7.28 (m, 2H), 6.88-6.90 (dd, 2H, J=2.0 Hz, 6.4 Hz), 6.15 (s, 1H), 4.60-4.62 (d, 2H, J=5.2 Hz), 4.11-4.16 (q, 2H, J=7.2 Hz), 3.81 (s, 3H), 3.60 (s, 2H), 1.21-1.26 (t, 3H, J=6.4 Hz).

Step B: 2,4-dichloro-7-(4-methoxybenzyl)-5,5-dimethyl-5H-pyrrolo[2,3-d]pyrimidin-6(7H)-one

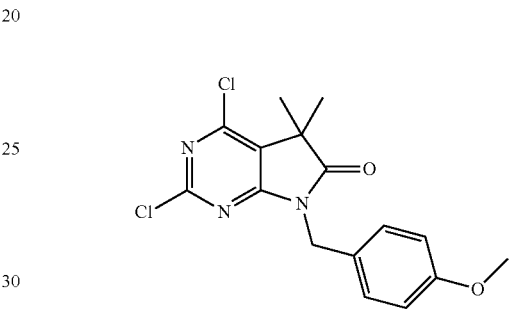

Ethyl 2-(2,4-dichloro-6-(4-methoxybenzylamino)pyrimidin-5-yl)acetate (370 mg, 1.0 mol), iodomethane (284 mg, 2.0 mmol), potassium carbonate (690 mg, 5.0 mmol) and N,N'-dimethylformamide (10 mL) were added to a sealed tube and filled with nitrogen. The mixture was stirred for 1 hour at 80° C. After cooling, the mixture was poured into water (100 mL) and extracted with ethyl acetate. The extracts were combined, washed with water and brine, dried over anhydrous sodium sulfate, filtrated and condensed. The residue was purified by silica gel column chromatography to afford the product 2,4-dichloro-7-(4-methoxybenzyl)-5,5-dimethyl-5H-pyrrolo[2,3-d]pyrimidin-6(7H)-one (270 mg, yield 77%). $^1$H NMR (400 MHz, CDCl$_3$) δ ppm 7.37-7.39 (d, 2H, J=8.8 Hz), 6.84-6.86 (d, 2H, J=8.8 Hz), 4.86 (s, 2H), 3.78 (s, 3H), 1.48 (s, 6H).

Step C/Intermediate A4

2,4-dichloro-7-(4-methoxybenzyl)-5,5-dimethyl-6,7-dihydro-5H-pyrrolo[2,3-d]pyrimidine To a solution of 2,4-dichloro-7-(4-methoxybenzyl)-5,5-dimethyl-5H-pyrrolo[2,3-d]pyrimidin-6(7H)-one (270 mg, 0.77 mol) in tetrahydrofuran (10 mL) was added diborane (1 M in tetrahydrofuran, 3.85 mL, 3.85 mmol) dropwise under nitrogen. The mixture was refluxed overnight. After cooling, methanol (2 mL) was added dropwise to decompose the excessive diborane. The solvent was removed and the residue was purified by silica gel column chromatography to afford the product 2,4-dichloro-7-(4-methoxybenzyl)-5,5-dimethyl-6,7-dihydro-5H-pyrrolo[2,3-d]pyrimidine (156 mg, yield 60%). $^1$H NMR (400 MHz, CDCl$_3$) δ ppm 7.16-7.18 (d, 2H, J=8.4 Hz), 6.86-6.88 (d, 2H, J=8.0 Hz), 4.56 (s, 2H), 3.81 (s, 3H), 3.23 (s, 2H), 1.37 (s, 6H).

Intermediate A5

(R)-2,4-dichloro-7-(4-methoxybenzyl)-5-methyl-6,7-dihydro-5H-pyrrolo[2,3-d]pyrimidine

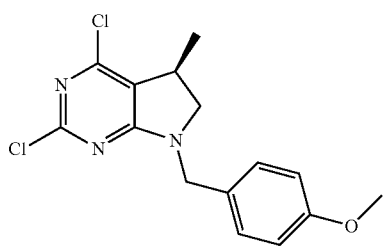 [SMILES: COc1ccc(CN2C[C@H](C)c3c(Cl)nc(Cl)nc32)cc1]

Intermediate A5 was synthesized according to the scheme as following:

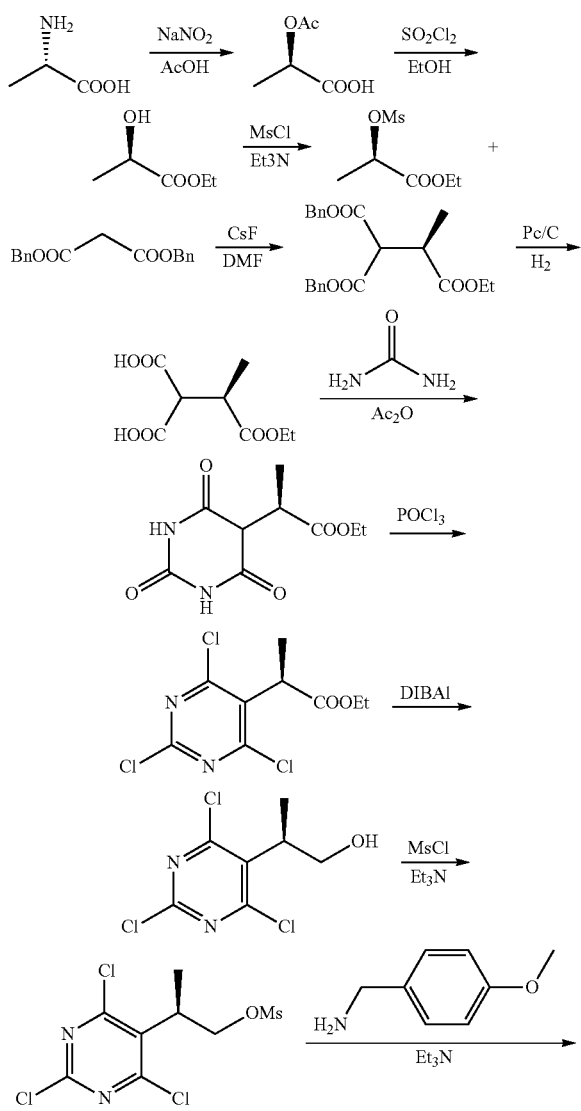

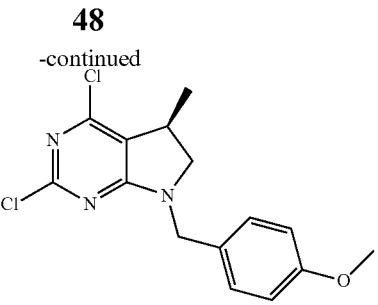

Step A: (R)-2-acetoxypropanoic acid

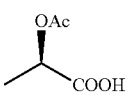

To a solution of (S)-2-aminopropanoic acid (60 g, 0.67 mol) in acetic acid (400 ml) was added NaNO₂ (93 g, 1.34 mol) several portions at 0° C. After addition, the mixture was stirred at room temperature for 4 hours. After removed the acetic acid, water added and then extracted with ether. The organic phase was collected, dried, concentrated to afford (R)-2-acetoxypropanoic acid (30 g, 35%). $^1$H NMR (400 MHz, CDCl₃) δ ppm, 11.70 (s, 2H), 5.02-5.07 (q, 1H), 2.07 (s, 3H), 1.46-1.52 (d, 3H).

Step B: (R)-ethyl 2-hydroxypropanoate

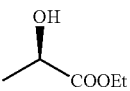

To a solution of (R)-2-acetoxypropanoic acid (30 g, 0.23 mol) in EtOH (500 ml) was added sulfuryl dichloride (54 g, 0.45 mol) dropwise below −40° C. The mixture was stirred for 48 hours at room temperature. The ethanol was removed under reduced pressure to afford sulfuryl dichloride, which was purified by silica gel chromatography (15 g, 58%). $^1$H NMR (400 MHz, CDCl₃) δ ppm, 4.22-4.27 (m, 3H), 2.87-2.87 (q, 1H), 1.41-1.43 (d, 3H, J=7.6 Hz), 1.30-1.32 (m, 3H).

Step B: (R)-ethyl 2-(methylsulfonyloxy)propanoate

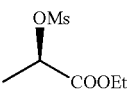

(R)-ethyl 2-hydroxypropanoate (15 g, 0.127 mol) and TEA (15.4 g, 0.15 mol) were added to THF and then cooled to 10-15° C. Then MsCl (15 g, 0.13 mol) was added to the solution dropwise with cooling while maintaining the temperature in the range of 10-15° C. at about 2 hours. The mixture was allowed to warm to about 20° C. and the solid was filtered off. The solution was washed with water and dried, concentrated to afford (R)-ethyl 2-(methylsulfonyloxy)propanoate (15 g, 60%). $^1$H NMR (400 MHz, CDCl₃)

δ ppm, 5.11-5.14 (q, 1H), 4.24-4.29 (m, 2H), 2.81-3.17 (q, 3H, J=7.2 Hz), 1.61-1.43 (d, 3H, J=7.6 Hz), 1.30-1.32 (m, 3H).

Step C: (R)-1,1-dibenzyl 2-ethyl propane-1,1,2-tricarboxylate

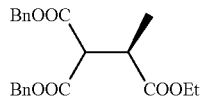

To a solution of (R)-ethyl 2-(methylsulfonyloxy)propanoate (15 g, 0.076 mol) in DMF (300 ml) was added dibenzyl malonate (21.5 g, 0.076 mol) and CsF (11.5 g, 0.076 mol). The mixture was heated to 50° C. for 2 days. After cooled to room temperature, the mixture was poured into water and then extracted with EtOAc. The organic phase was washed with brine, water and dried. Concentrated to afford (R)-1,1-dibenzyl 2-ethyl propane-1,1,2-tricarboxylate, which was purified by silica gel chromatography (11 g, 40%).

Step D: (R)-2-(1-ethoxy-1-oxopropan-2-yl)malonic acid

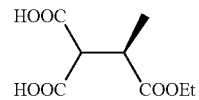

To the solution of (R)-1,1-dibenzyl 2-ethyl propane-1,1,2-tricarboxylate (11 g, 0.029 mol) in MeOH (500 ml) was added Pd/C (wet, 2 g), and then the mixture was stirred under hydrogen atmosphere at room temperature overnight. After filtered the Pd/C, the solvent was removed under reduced pressure to afford (R)-2-(1-ethoxy-1-oxopropan-2-yl)malonic acid, which was purified by silica gel chromatography (3.5 g, 60%).

Step E: (R)-ethyl 2-(2,4,6-trioxohexahydropyrimidin-5-yl)propanoate

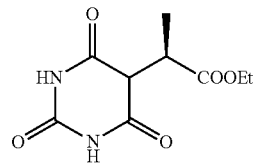 [SMILES: CCOC(=O)[C@H](C)C1C(=O)NC(=O)NC1=O]

The (R)-2-(1-ethoxy-1-oxopropan-2-yl)malonic acid (3.5 g, 0.017 mol) and the urea (1.03 g, 0.017 mol) was dissolved into Ac$_2$O (20 ml) and then added to the reaction vessel of the microwave reactor and were allowed to react under microwave irradiation at 60° C. for half an hour. After cooled to rt, added NaHCO3 aqueous and extracted with EtOAc. The organic phase was dried and concentrated to afford (R)-ethyl 2-(2,4,6-trioxohexahydropyrimidin-5-yl)propanoate, which was purified by silica gel chromatography (2.0 g, 52%).

Step F: (R)-ethyl 2-(2,4,6-trichloropyrimidin-5-yl)propanoate

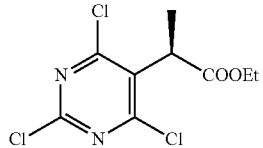 [SMILES: CCOC(=O)[C@H](C)c1c(Cl)nc(Cl)nc1Cl]

According to General Protocol I, (R)-ethyl 2-(2,4,6-trichloropyrimidin-5-yl)propanoate was prepared from (R)-ethyl 2-(2,4,6-trioxohexahydropyrimidin-5-yl)propanoate (2.0 g, 8.87 mmol), phosphoryl trichloride (20 mL) and N,N-diisopropylethylamine (5 mL) and isolated as a yellow oil (1.0 g, yield 40%). $^1$H NMR (400 MHz, CDCl$_3$) δ ppm, 4.30-4.36 (q, 1H, J=7.2 Hz), 4.17-4.24 (m, 2H), 1.54-1.56 (d, 3H, J=7.6 Hz), 1.22-1.25 (m, 3H).

Step G: (R)-2-(2,4,6-trichloropyrimidin-5-yl)propan-1-ol

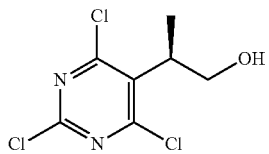

According to General Protocol I, (R)-2-(2,4,6-trichloropyrimidin-5-yl)propan-1-ol was prepared from (R)-ethyl 2-(2,4,6-trichloropyrimidin-5-yl)propanoate (1.0 g, 3.55 mmol) and diisobutylaluminium hydride (1.0 M in hexane, 10.6 mL, 10.6 mmol) and isolated as a pale yellow oil (70 mg, yield 10%). $^1$H NMR (400 MHz, CDCl3) δ ppm 4.14-4.17 (m, 1H), 3.85-3.97 (m, 2H), 1.56 (s, 1H), 1.38-1.40 (d, 3H, J=7.2 Hz).

Step H: (R)-2-(2,4,6-trichloropyrimidin-5-yl)propyl methanesulfonate

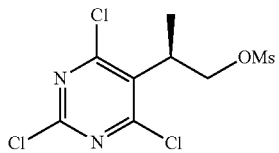 [SMILES: C[C@@H](COS(C)(=O)=O)c1c(Cl)nc(Cl)nc1Cl]

According to General Protocol I, (R)-2-(2,4,6-trichloropyrimidin-5-yl)propyl methanesulfonate was prepared from (R)-2-(2,4,6-trichloropyrimidin-5-yl)propan-1-ol (70 mg, 0.58 mmol), methanesulfonyl chloride (67 mg, 0.58 mmol) and triethyl amine (60 mg, 1.66 mmol) and isolated as a pale yellow oil (60 mg, yield 65%). $^1$H NMR (400 MHz, CDCl3) δ ppm 4.69-4.74 (t, 1H, J=9.2 Hz), 4.49-4.54 (dd, 1H, J=6.8 Hz, 10.4 Hz), 4.06-4.49 (m, 1H), 3.92 (s, 1H), 1.46-1.48 (d, 3H, J=7.2 Hz).

Step I/Intermediate A5

(R)-2,4-dichloro-7-(4-methoxybenzyl)-5-methyl-6,7-dihydro-5H-pyrrolo[2,3-d]pyrimidine

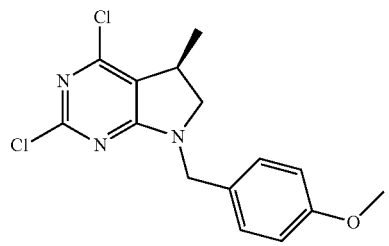 [SMILES: COc1ccc(CN2C[C@H](C)c3c(Cl)nc(Cl)nc32)cc1]

(R)-2,4-dichloro-7-(4-methoxybenzyl)-5-methyl-6,7-dihydro-5H-pyrrolo[2,3-d]pyrimidine was prepared from (R)-2-(2,4,6-trichloropyrimidin-5-yl)propyl methanesulfonate (60 mg, 0.188 mmol), (4-methoxyphenyl)methanamine (39 mg, 0.28 mmol) and triethyl amine (38 mg, 0.375 mmol), and isolated as a yellow (45 mg, yield 74%). $^1$H NMR (400 MHz, CDCl$_3$) δ ppm 7.16-7.19 (d, 2H, J=8.8 Hz), 6.86-6.88 (d, 2H, J=8.4 Hz), 4.54 (s, 2H), 3.80 (s, 3H), 3.66-3.71 (t, 1H, J=6.0 Hz), 3.33-3.36 (m, 1H), 3.08-3.12 (dd, 1H, J=4.4 Hz, 10.0 Hz), 1.29-1.31 (d, 3H, J=6.8 Hz).

Intermediate A6

2',4'-dichloro-7'-(4-methoxybenzyl)-6',7'-dihydrospiro[cyclopropane-1,5'-pyrrolo[2,3-d]pyrimidine]

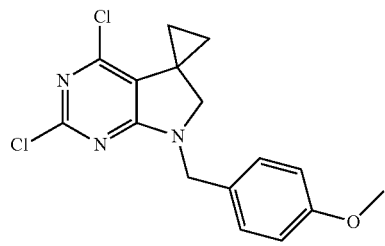 [SMILES: COc1ccc(CN2CC3(CC3)c3c(Cl)nc(Cl)nc32)cc1]

Intermediate A6 was synthesized according to the scheme as following:

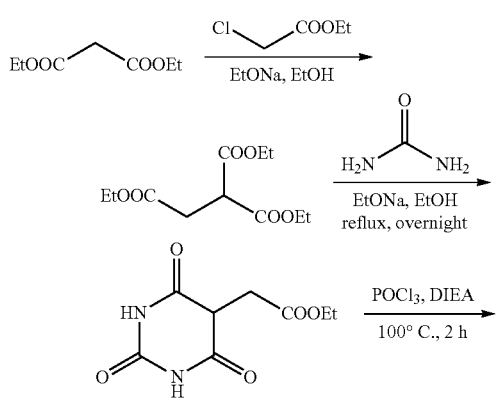

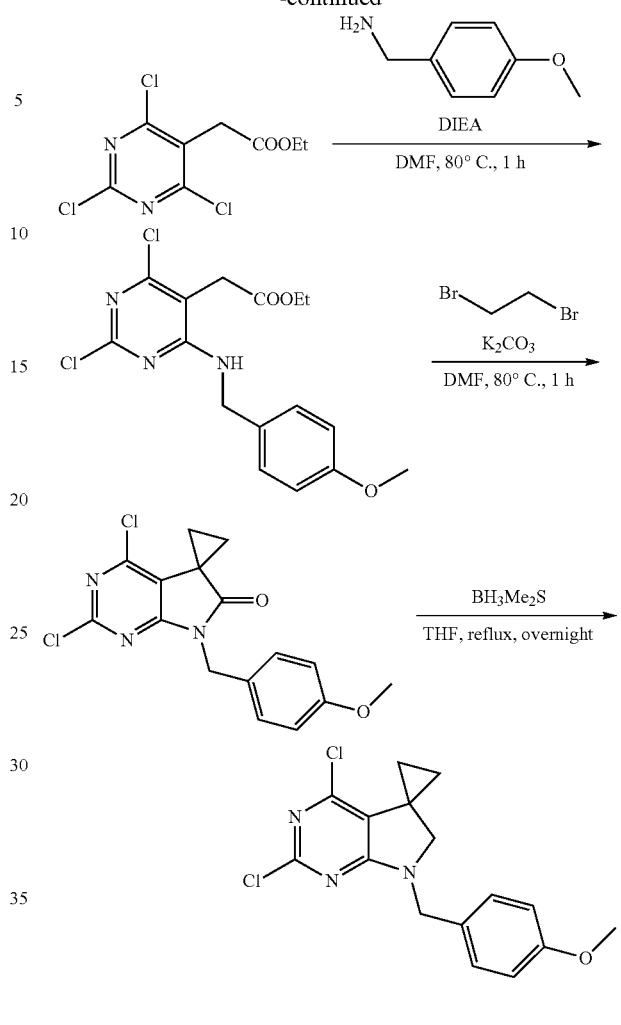

Step A: triethyl ethane-1,1,2-tricarboxylate

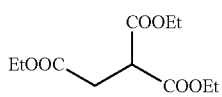

To a solution of anhydrous ethanol (1000 mL) was added sodium (23.0 g, 1 mol) in pieces. After all the sodium dissolved, the reaction mixture was cooled to 0° C. with an ice bath, diethyl malonate (160.2 g, 1 mol) was added dropwise, the reaction was allowed to warm to room temperature after stirred for 0.5 h, ethyl 2-chloroacetate (122.6 g, 1 mol) was added and stirred for another 1 h, then heated to reflux for 3 h and cooled to room temperature. Most of ethanol was removed under reduced pressure and the residue was poured into ice-water. The aqueous phase was extracted with ethyl acetate, and the organic extracts were combined, washed by brine, dried over anhydrous sodium sulfate, and evaporated to afford the product ethane-1,1,2-tricarboxylate as a pale-yellow oil (180.0 g, yield 73.1%), which was used for the next step without purification.

Step B: ethyl
2-(2,4,6-trioxohexahydropyrimidin-5-yl)acetate

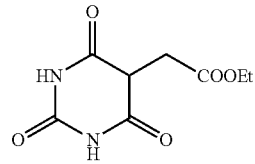 [SMILES: CCOC(=O)CC1C(=O)NC(=O)NC1=O]

To a solution of anhydrous ethanol (1500 mL) was added sodium (25.2 g, 1.1 mol) in pieces. After all the sodium dissolved, triethyl ethane-1,1,2-tricarboxylate (180.0 g, 733 mmol) and urea (43.9 g, 733 mmol) was added respectively. The reaction mixture was heated at reflux overnight and cooled to room temperature, evaporated to dryness. The residue was diluted with water and acidified by diluted hydrochloric acid (2 N). The mixture was evaporated and purified by silica gel chromatography to afford the product ethyl 2-(2,4,6-trioxohexahydropyrimidin-5-yl)acetate as a pale-yellow solid (82.8 g, yield 35.0%).

Step C: ethyl
2-(2,4,6-trichloropyrimidin-5-yl)acetate

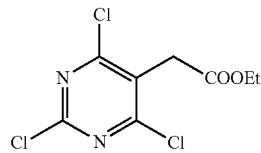

To a solution of ethyl 2-(2,4,6-trioxohexahydropyrimidin-5-yl)acetate (50.0 g, 240.0 mmol) in phosphoryl trichloride (400.0 mL) was added N,N'-diisopropylethylamine (80.0 mL) dropwise. After the addition was over, the reaction mixture was heated at 100° C. for 2 hours. Most of phosphoryl trichloride was removed under reduced pressure and the residue was basified by aqueous sodium bicarbonate. The aqueous phase was extracted with ethyl acetate, and the organic extracts were combined, washed by brine, dried over anhydrous sodium sulfate, evaporated and purified by silica gel chromatography to afford the product ethyl 2-(2,4,6-trichloropyrimidin-5-yl)acetate as a pale-yellow solid (34.4 g, yield 54.6%). $^1$H NMR (400 MHz, CDCl$_3$) δ ppm 4.24 (q, J=7.1 Hz, 2H), 3.95 (s, 2H), 1.29 (t, J=7.1 Hz, 3H).

Step D: ethyl 2-(2,4-dichloro-6-(4-methoxybenzy-lamino)pyrimidin-5-yl)acetate

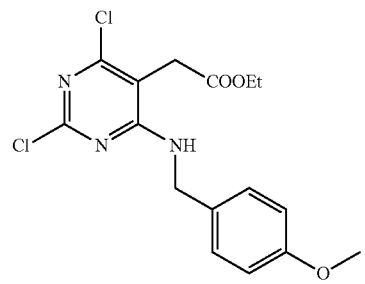 [SMILES: CCOC(=O)Cc1c(Cl)nc(Cl)nc1NCc1ccc(OC)cc1]

To a solution of ethyl 2-(2,4,6-trichloropyrimidin-5-yl) acetate (43.3 g, 160.7 mmol) in N,N-dimethylformamide (500 mL) was added 4-Methoxybenzylamine (24.2 g, 176.8 mmol) and N,N'-diisopropylethylamine (24.9 g, 192.9 mmol), the reaction mixture was heated to 60° C. for 1 h. Quenched with water, extracted with ethyl acetate, and the organic extracts were combined, washed with hydrochloride (1 N), brine, dried over anhydrous sodium sulfate, evaporated and purified by silica gel chromatography to afford the as a pale-yellow solid (27.1 g, yield 45.6%). $^1$H NMR (400 MHz, CDCl$_3$) δ ppm 7.29 (dd, J=6.0, 3.9 Hz, 1H), 6.93-6.85 (m, 1H), 6.14 (s, 1H), 4.63 (d, J=5.3 Hz, 2H), 4.15 (q, J=7.1 Hz, 2H), 3.83 (s, 3H), 3.62 (s, 2H), 1.23 (t, J=7.1 Hz, 2H).

Step E

2',4'-dichloro-7'-(4-methoxybenzyl)spiro[cyclopropane-1,5'-pyrrolo[2,3-d]pyrimidin]-6'(7'H)-one

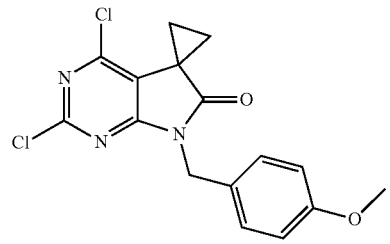 [SMILES: COc1ccc(CN2C(=O)C3(CC3)c3c(Cl)nc(Cl)nc32)cc1]

To a solution of ethyl 2-(2,4-dichloro-6-(4-methoxybenzylamino)pyrimidin-5-yl)acetate (27.1 g, 73.2 mmol) and powder potassium carbonate (101.1 g, 732.4 mmol) in N,N-dimethyllformamide (800 mL) was added 1,2-dibromoethane (27.5 g, 146.4 mmol) dropwise under nitrogen atmosphere at 40° C. After the addition was over, the reaction mixture was heated to 80° C. for 1 h. Quenched with water, extracted with ethyl acetate, and the organic extracts were combined, washed with brine, dried over anhydrous sodium sulfate, evaporated and purified by silica gel chromatography to afford the product as a snow-white solid (21.2 g, yield 82.7%). $^1$H NMR (400 MHz, CDCl$_3$) δ ppm 7.53-7.38 (m, 2H), 6.86 (dd, J=8.4, 1.3 Hz, 2H), 4.94 (d, J=0.8 Hz, 2H), 3.79 (d, J=1.6 Hz, 3H), 2.14 (qd, J=4.3, 1.6 Hz, 2H), 1.79 (qd, J=4.3, 1.6 Hz, 2H).

Step F/Intermediate A6

2',4'-dichloro-7'-(4-methoxybenzyl)-6',7'-dihydrospiro[cyclopropane-1,5'-pyrrolo[2,3-d]pyrimidine]

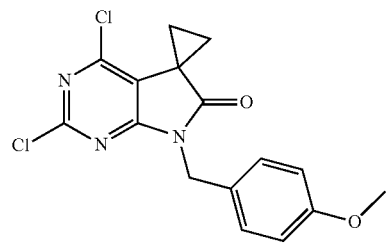 [SMILES: COc1ccc(CN2C(=O)C3(CC3)c3c(Cl)nc(Cl)nc32)cc1]

To a solution of 2',4'-dichloro-7'-(4-methoxybenzyl)spiro [cyclopropane-1,5'-pyrrolo[2,3-d]pyrimidin]-6'(7'H)-one (14.0 g, 40.0 mmol) in tetrahydrofuran (200 mL) was added 94% Borane-methyl sulfide complex (8.2 mL, 80.0 mmol) dropwise under nitrogen atmosphere. After the addition was over, the reaction mixture was heated to 60° C. overnight. When the reaction was completed, methanol was added to the reaction solution at 0° C., concentrated in vacuum and the residue was purified by silica gel chromatography to afford the product as a white solid (8.4 g, yield 62.4%). $^1$H NMR (400 MHz, CDCl$_3$) δ ppm 7.20 (d, J=8.6 Hz, 2H), 6.91-6.86 (m, 2H), 4.59 (s, 2H), 3.81 (s, 3H), 3.48 (s, 2H), 1.71 (q, J=4.9 Hz, 2H), 0.82 (q, J=4.9 Hz, 2H).

Intermediate B1

2-methoxy-4-morpholinoaniline

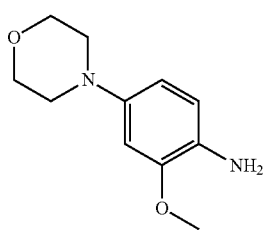 [SMILES: COc1cc(N2CCOCC2)ccc1[N+](=O)[O-]]

Step A: 4-(3-methoxy-4-nitrophenyl)morpholine

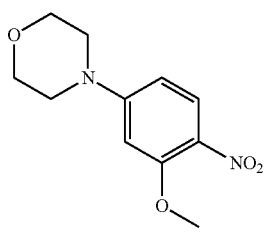

To a solution of 4-fluoro-2-methoxy-1-nitrobenzene (100 g, 0.584 mol) and morpholine (60 g, 0.689 mol) in dimethyl sulfoxide (60 mL) was added potassium carbonate (120 g, 0.870 mol). The mixture was stirred at 70° C. for 6 hours, and then poured into ice-water. The precipitate was collected by filtration and washed by water, dried to afford the product 4-(3-methoxy-4-nitrophenyl)morpholine (100 g, yield 72%).

Step B/Intermediate B1: 2-methoxy-4-morpholinoaniline

To a suspension of 4-(3-methoxy-4-nitrophenyl)morpholine (100 g, 0.42 mol) in tetrahydrofuran (2 L) was added palladium on carbon (10%, 10 g). The mixture was stirred under an atmosphere of hydrogen for 12 hours. The catalyst was removed by filtration and the filtrate was evaporated to afford the product 2-methoxy-4-morpholinoaniline (87 g, yield 100%).

Intermediate B2

2-((tert-butyldimethylsilyloxy)methyl)-4-morpholinoaniline

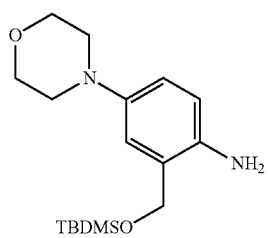

Step A: 5-chloro-2-nitrobenzaldehyde

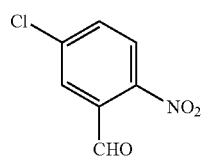 [SMILES: O=Cc1cc(Cl)ccc1[N+](=O)[O-]]

3-Chlorobenzaldehyde (15 g, 107 mmol) was added to concentrated sulfuric acid (150 mL) at −20° C., followed by addition of potassium nitrate (11.9 g, 117 mmol) in portions, keeping the temperature below −10° C. After addition, the mixture was stirred for 30 minutes and then poured into ice-water. The aqueous phase was extracted with ethyl acetate, and the organic phases were combined, washed by brine, dried over anhydrous sodium sulfate, evaporated and purified by silica gel chromatography to afford the product 5-chloro-2-nitrobenzaldehyde (12.0 g, yield 60.6%).

Step B: 2-(5-chloro-2-nitrophenyl)-1,3-dioxolane

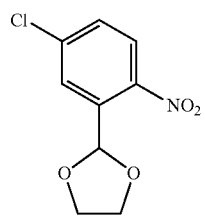 [SMILES: O=[N+]([O-])c1ccc(Cl)cc1C1OCCO1]

In a flask equipped with a Dean-Stark water separator, 5-chloro-2-nitrobenzaldehyde (12.0 g, 64.7 mmol), ethylene glycol (8.0 g, 129.3 mmol) and p-toluenesulfonic acid (0.2 g) were dissolved in toluene (150 mL). The mixture was stirred at reflux for 8 hours. Dichloromethane was added and the organic phase was washed with saturated sodium bicarbonate and brine, then dried over anhydrous sodium sulfate, evaporated and purified by silica gel chromatography to afford the product 2-(5-chloro-2-nitrophenyl)-1,3-dioxolane (13.4 g, yield 90.0%).

Step C: 4-(3-(1,3-dioxolan-2-yl)-4-nitrophenyl)morpholine

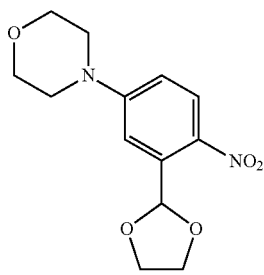 [SMILES: O=[N+]([O-])c1ccc(N2CCOCC2)cc1C1OCCO1]

2-(5-Chloro-2-nitrophenyl)-1,3-dioxolane (13.4 g, 58.4 mmol) was dissolved in morpholine (150 mL). The mixture was then heated to reflux for 16 hours. Cooling to room temperature, dichloromethane was added. The organic phase was washed with water, dried over anhydrous sodium sulfate, evaporated and purified by silica gel chromatography to afford the product 4-(3-(1,3-dioxolan-2-yl)-4-nitrophenyl)morpholine (15.9 g, yield 97.1%).

Step D: 5-morpholino-2-nitrobenzaldehyde

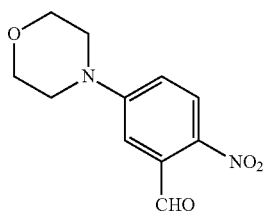 [SMILES: O=Cc1cc(N2CCOCC2)ccc1[N+](=O)[O-]]

4-(3-(1,3-Dioxolan-2-yl)-4-nitrophenyl)morpholine (15.9 g, 56.7 mmol) was dissolved in a mixture of acetone and water (100 mL/100 mL). Then p-toluenesulfonic acid (2.0 g) was added and the mixture was heated to reflux for 4 hours. Ethyl acetate was added and the organic phase was washed with saturated sodium bicarbonate and brine, and then dried over anhydrous sodium sulfate, evaporated to afford the crude product 5-morpholino-2-nitrobenzaldehyde, which was used for the next step without purification.

Step E: (5-morpholino-2-nitrophenyl)methanol

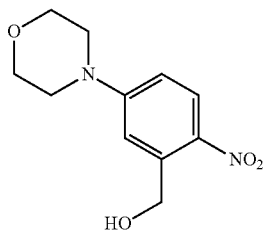 [SMILES: O=[N+]([O-])c1ccc(N2CCOCC2)cc1CO]

To a suspension of the crude 5-morpholino-2-nitrobenzaldehyde in a mixture of tetrahydrofuran and ethanol (100 mL/100 mL) was slowly added sodium borohydride (4.0 g). The mixture was stirred at room temperature for 1 hour, and then was partitioned between ether and saturated ammonium chloride. The aqueous phase was extracted with ether, and the organic phases were combined, washed by brine, dried over anhydrous sodium sulfate, evaporated and purified by silica gel chromatography to afford the product (5-morpholino-2-nitrophenyl)methanol (8.5 g, yield 62.3%, two steps).

Step F: 4-(3-((tert-butyldimethylsilyloxy)methyl)-4-nitrophenyl)morpholine

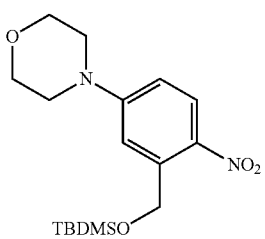 [SMILES: CC(C)(C)[Si](C)(C)OCc1cc(N2CCOCC2)ccc1[N+](=O)[O-]]

To a solution of (5-morpholino-2-nitrophenyl)methanol (3.0 g, 12.6 mmol), triethylamine (2.54 g, 25.2 mmol) and 4-dimethylaminopyridine (0.2 g) in dichloromethane (100 mL) was added tert-butylchlorodimethylsilane (2.83 g, 18.9 mmol). After the addition was over, the mixture was stirred at room temperature for 2 hours. The reaction mixture was diluted with ethyl acetate, and the organic phase was washed by saturated sodium bicarbonate, dried over anhydrous sodium sulfate, evaporated and purified by silica gel chromatography to afford the product 4-(3-((tert-butyldimethylsilyloxy)methyl)-4-nitrophenyl)morpholine (4.0 g, yield 90.9%).

Step G/Intermediate B2: 2-((tert-butyldimethylsilyloxy)methyl)-4-morpholinoaniline A mixture of 4-(3-((tert-butyldimethylsilyloxy)methyl)-4-nitrophenyl)morpholine (4.0 g, 0.11 mol), Raney Ni (1.0 g) in methanol (250 mL) was stirred under an atmosphere of hydrogenated (1.0 atm) at room temperature for 1 hour. The catalyst was removed by filtration and the filtrate was evaporated to give the product 2-((tert-butyldimethylsilyloxy)methyl)-4-morpholinoaniline (3.48 g, yield 95.1%). $^{1}$H NMR (400 MHz, CDCl$_3$) δ ppm 6.72-6.76 (m, 2H), 6.62-6.64 (d, 1H, J=8.0 Hz), 4.66 (s, 2H), 3.92 (s, 2H), 3.84-3.86 (t, 4H, J=4.4 Hz), 3.00-3.03 (t, 4H, J=4.8 Hz), 0.90-0.91 (m, 9H), 0.08-0.09 (m, 6H).

Intermediate B3

2,3-dihydrobenzo[b][1,4]dioxin-5-amine

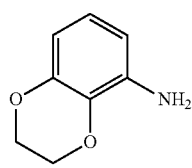 [SMILES: Nc1cccc2c1OCCO2]

Step A: 3-nitrobenzene-1,2-diol

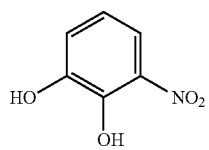 [SMILES: O=[N+]([O-])c1cccc(O)c1O]

To a solution of pyrocatechol (60 g, 0.54 mol) in ether (2000 mL) at 0° C. was added fuming nitric acid (24 mL) dropwise. After the addition was over, the reaction was allowed to stand at room temperature for 20 minutes, decanted into ice-water and the resulting solution was extracted with ether. The combined organic extracts were neutralized with aqueous sodium carbonate (10%), dried over anhydrous sodium sulfate, filtered and concentrated in vacuo. The residue obtained was purified by silica gel column chromatography (petroleum ether/ethyl acetate 5/1) to afford the product 3-nitrobenzene-1,2-diol (25 g, yield 30%). $^1$H NMR (400 MHz, CDCl$_3$) δ ppm 10.62 (s, 1H), 7.64-7.67 (dd, 1H, J=1.6 Hz, 8.8 Hz), 7.23-7.26 (m, 1H), 6.89-6.93 (t, 1H, J=8.4 Hz), 5.79 (br, 1H).

Step B: 5-nitro-2,3-dihydrobenzo[b][1,4]dioxine

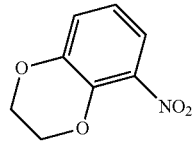 [SMILES: O=[N+]([O-])c1cccc2c1OCCO2]

To a solution of 3-nitrobenzene-1,2-diol (11 g, 0.071 mol) in N,N'-dimethylformamide (500 mL) was added potassium carbonate (29 g, 0.0.213 mol) followed by 1,2-dibromoethane (14.7 g, 0.078 mol). The mixture was heated at 110° C. for 2 hours. After cooled to room temperature, the mixture was poured into water and then extracted with ether. The organic phases were combined and dried over anhydrous sodium sulfate, filtrated and concentrated to give a crude product, which was purified by silica gel column chromatography (petroleum ether/ethyl acetate 20/1) to afford the product 5-nitro-2,3-dihydrobenzo[b][1,4]dioxine (8 g, yield 62%). $^1$H NMR (400 MHz, CDCl$_3$) δ ppm 7.48-7.50 (dd, 1H, J=1.6 Hz, 8.4 Hz), 7.09-7.12 (dd, 1H, J=1.6 Hz, 8.4 Hz), 6.88-6.92 (t, 1H, J=8.4 Hz), 4.40-4.42 (m, 2H), 4.34-4.36 (m, 2H).

Step C/Intermediate B3: 2,3-dihydrobenzo[b][1,4]dioxin-5-amine

A suspension of 5-nitro-2,3-dihydrobenzo[b][1,4]dioxine (8 g, 0.044 mol) and palladium on carbon (10%, 2 g) in methanol (250 mL) was stirred vigorously under an atmosphere of hydrogen overnight at room temperature. The mixture was filtered through a pad of Celite and then concentrated to give the crude product, which was purified by silica gel column chromatography (petroleum ether/ethyl acetate 9/1) to afford the product 2,3-dihydrobenzo[b][1,4]dioxin-5-amine (6.5 g, yield 97%). $^1$H NMR (400 MHz, CDCl$_3$) δ ppm 6.61-6.65 (t, 1H, J=8.0 Hz), 6.30-6.33 (dt, 2H, J=1.2 Hz, 2.4 Hz), 4.22-4.27 (m, 4H), 3.75 (s, 2H).

Intermediate B4

8-morpholino-2,3-dihydrobenzo[b][1,4]dioxin-5-amine

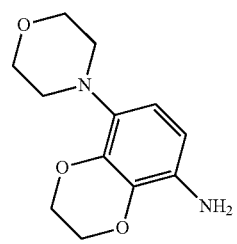 [SMILES: Nc1ccc(N2CCOCC2)c2c1OCCO2]

Step A: N-(2,3-dihydrobenzo[b][1,4]dioxin-5-yl)acetamide

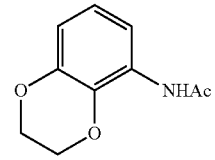 [SMILES: CC(=O)Nc1cccc2c1OCCO2]

To a solution of 2,3-dihydrobenzo[b][1,4]dioxin-5-amine (Intermediate B3, 4.5 g, 30 mmol) in ethanol (50 mL) at room temperature was slowly added acetic anhydride (3.0 g, 30 mmol). After the addition was over, the mixture was stirred at room temperature for 5 minutes. The resulting suspension was concentrated to give the crude product, which was purified by silica gel column chromatography (petroleum ether/ethyl acetate 4/1) to afford the product N-(2,3-dihydrobenzo[b][1,4]dioxin-5-yl)acetamide (5.5 g, yield 95%). $^1$H NMR (400 MHz, CDCl$_3$) δ ppm 9.12 (s, 1H), 7.44-7.46 (d, 1H, J=8.0 Hz), 6.71-6.75 (t, 1H, J=8.0 Hz), 6.59-6.61 (d, 1H, J=7.6 Hz), 4.23-4.30 (m, 4H), 2.06 (s, 3H).

Step B: N-(8-bromo-2,3-dihydrobenzo[b][1,4]dioxin-5-yl)acetamide

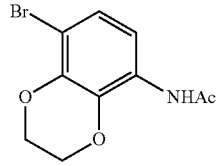

To a solution of N-(2,3-dihydrobenzo[b][1,4]dioxin-5-yl)acetamide (5.5 g, 28.5 mmol) in chloroform (20 mL) cooled at −20° C. was slowly added a solution of bromine (1.6 mL, 30 mmol) in chloroform (5 mL) so that the reaction temperature was maintained below −10° C. The reaction was stirred at 0° C. for 10 minutes, and then quenched immediately with water. The mixture was extracted with dichloromethane; the combined extracts were washed with saturated sodium bicarbonate and brine, dried over anhydrous sodium sulfate, filtered and concentrated under reduced pressure. The residue was subjected to silica gel chromatography (dichloromethane) to afford the product N-(8- bromo-2,3-dihydrobenzo[b][1,4]dioxin-5-yl)acetamide (5 g, yield 64%). ¹H NMR (400 MHz, CDCl₃) δ ppm 9.23 (s, 1H), 7.46-7.48 (d, 1H, J=8.8 Hz), 7.04-7.06 (d, 1H, J=9.2 Hz), 4.32-4.40 (m, 4H), 2.07 (s, 3H).

Step C: N-(8-morpholino-2,3-dihydrobenzo[b][1,4]dioxin-5-yl)acetamide

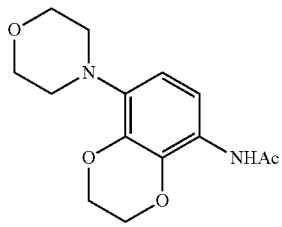 [SMILES: CC(=O)Nc1ccc(N2CCOCC2)c2c1OCCO2]

To a solution of N-(8-bromo-2,3-dihydrobenzo[b][1,4]dioxin-5-yl)acetamide (5 g, 18.4 mmol) in toluene (50 mL) was added morpholine (1.9 g, 22 mmol), Pd₂(dba)₃ (1.68 g, 1.84 mmol), X-Phos (1.75 g, 3.68 mmol) and potassium tert-butoxide (4.1 g, 36.8 mmol) in a sealed tube. The mixture was heated at 130° C. for overnight. After cooled to room temperature, the mixture was filtered and the filtrate was evaporated to give a crude product, which was purified by silica gel column chromatography (petroleum ether/ethyl acetate 4/1) to afford the product N-(8-morpholino-2,3-dihydrobenzo[b][1,4]dioxin-5-yl)acetamide (2 g, yield 40%).

Step D/Intermediate B4: 8-morpholino-2,3-dihydrobenzo[b][1,4]dioxin-5-amine

To a solution of N-(8-morpholino-2,3-dihydrobenzo[b][1,4]dioxin-5-yl)acetamide (2 g, 7.19 mmol) in methanol (100 mL) was added concentrated Hydrochloric acid (5 mL) and then the mixture was stirred at room temperature overnight. After the solvent was removed under reduce pressure, water was added and the pH was adjusted to 7-8 using aqueous sodium bicarbonate. The mixture was extracted with ethyl acetate and the combined organic phases were dried over anhydrous sodium sulfate, concentrated to give a crude product, which was purified by silica gel column chromatography (petroleum ether/ethyl acetate 2/1) to afford the product 8-morpholino-2,3-dihydrobenzo[b][1,4]dioxin-5-amine (1 g, yield 60%). ¹H NMR (400 MHz, CDCl₃) δ ppm 6.38-6.41 (d, 1H, J=8.4 Hz), 6.27-6.29 (d, 1H, J=8.4 Hz), 4.28-4.32 (m, 4H), 3.85-3.88 (t, 4H, J=4.8 Hz), 3.55 (s, 2H), 2.95-2.97 (t, 4H, J=4.8 Hz).

Intermediate B5

7-amino-1-ethyl-6-methoxy-4,5-dihydro-1H-benzo[b]azepin-2(3H)-one hydrochloride

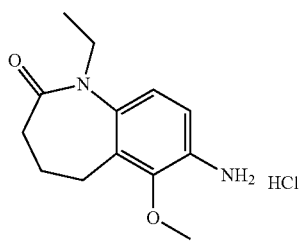 [SMILES: CCN1C(=O)CCCc2c1ccc(N)c2OC ; Cl]

Step A: 6-methoxy-4,5-dihydro-1H-benzo[b]azepin-2(3H)-one

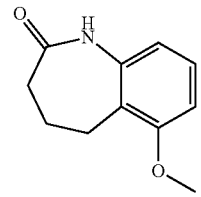

To a solution of 5-methoxy-3,4-dihydronaphthalen-1(2H)-one (8.3 g, 47.15 mmol) in polyphosphoric acid (100 mL) was added sodium azide (3.6 g, 55.4 mmol) in small portions at 0° C. within 30 minutes. Then the mixture was slowly warmed to room temperature and stirred for another 16 hours, and then poured into ice-water. The precipitate was collected and dried to afford the product 6-methoxy-4,5-dihydro-1H-benzo[b]azepin-2(3H)-one as a white solid (6.8 g, yield 75.5%). ¹H NMR (400 MHz, DMSO-d6) δ ppm 9.48 (s, 1H), 7.13-7.17 (t, 1H, J=8.0 Hz), 6.77-6.79 (d, 1H, J=7.6 Hz), 6.58-6.60 (d, 1H, J=7.6 Hz), 3.78 (s, 3H), 2.68-2.72 (t, 2H, J=6.8 Hz), 2.11-2.14 (t, 2H, J=7.2 Hz), 1.99-2.05 (m, 2H).

Step B: 6-methoxy-7-nitro-4,5-dihydro-1H-benzo[b]azepin-2(3H)-one

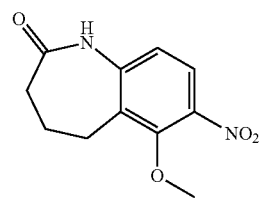 [SMILES: COc1c([N+](=O)[O-])ccc2c1CCCC(=O)N2]

To a solution of 6-methoxy-4,5-dihydro-1H-benzo[b]azepin-2(3H)-one (6.8 g, 35.6 mmol) in acetonitrile (50 ml) at −10° C. was added trifluoromethanesulfonic anhydride (15.0 mL, 106.8 mmol) dropwise. After stirring for 20 minutes, potassium nitrate (3.94 g, 39.0 mmol) was added in portions, and the mixture was slowly warmed to room temperature and stirred for another 5 hours, poured into saturated sodium bicarbonate in ice water (100 mL) and adjusted the pH to 9. The aqueous phase was extracted with ethyl acetate and the organic extracts were combined, washed with water, dried over anhydrous sodium sulfate and concentrated in vacuum. The residue was purified by silica column chromatography (petroleum ether/ethyl acetate 10/1 to 1/2) to afford the product 6-methoxy-7-nitro-4,5-dihydro-1H-benzo[b]azepin-2(3H)-one as a yellow solid (4.68 g, yield 55.7%). ¹H NMR (400 MHz, DMSO-d6) δ ppm 10.01 (s, 1H), 7.80-7.83 (d, 1H, J=8.8 Hz), 6.88-6.90 (d, 1H, J=8.8 Hz), 3.85 (s, 3H), 2.73-2.77 (t, 2H, J=7.2 Hz), 2.25-2.27 (t, 2H, J=6.8 Hz), 2.15-2.20 (m, 2H).

Step C: 1-ethyl-6-methoxy-7-nitro-4,5-dihydro-1H-benzo[b]azepin-2(3H)-one

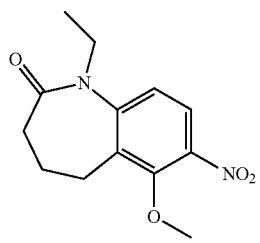 [SMILES: CCN1C(=O)CCCc2c1ccc([N+](=O)[O-])c2OC]

To a solution of 6-methoxy-7-nitro-4,5-dihydro-1H-benzo[b]azepin-2(3H)-one (4.5 g, 19.0 mmol) in dimethylformamide (30 mL) at 0° C. was added sodium hydride (60% on mineral oil, 1.15 g, 28.5 mmol) in small portions within 30 minutes. The mixture was stirred for 30 minutes at this temperature followed by adding ethyl iodide (1.84 mL, 22.9 mmol) dropwise. The mixture was warmed to room temperature and stirred for another 2 hours. Upon completion, the mixture was poured into ice-water and filtered to afford the product 1-ethyl-6-methoxy-7-nitro-4,5-dihydro-1H-benzo[b]azepin-2(3H)-one as a off-white solid (3.77 g, yield 78.5%). $^1$H NMR (400 MHz, CDCl$_3$) δ ppm 7.81-7.84 (dd, 1H, J=1.6 Hz, 8.8 Hz), 7.08-7.10 (dd, 1H, J=1.2 Hz, 8.8 Hz), 3.76-3.94 (s+m, 5H), 2.89-2.96 (m, 2H), 2.22-2.32 (m, 4H), 1.16-1.26 (m, 3H).

Step D/Intermediate B5

7-amino-1-ethyl-6-methoxy-4,5-dihydro-1H-benzo[b]azepin-2(3H)-one hydrochloride To a solution of 1-ethyl-6-methoxy-7-nitro-4,5-dihydro-1H-benzo[b]azepin-2(3H)-one (4.6 g, 18.0 mmol) in ethanol (45 mL) was added palladium on carbon (10%, 0.45 g) and hydrazine (85%, 8.78 mL, 0.18 mol). The mixture was heated to 90° C. for 6 hours. The mixture was cooled to R.T. and concentrated in vacuum. The residue was dissolved in acetone (40 mL) and was added concentrated HCl dropwise at 0° C. After removal of the solvent, the title 7-amino-1-ethyl-6-methoxy-4,5-dihydro-1H-benzo[b]azepin-2(3H)-one hydrochloride was obtained as a white solid (4.3 g, yield 87.7%). $^1$H NMR (400 MHz, CDCl$_3$) δ ppm 10.65 (br, 2H), 7.64-7.67 (d, 1H, J=8.4 Hz), 7.07-7.09 (d, 1H, J=8.4 Hz), 4.03 (s, 3H), 3.50-3.82 (m, 2H), 2.71-2.92 (m, 2H), 2.24-2.30 (m, 2H), 2.17-2.22 (m, 2H), 1.12-1.15 (t, 3H, J=7.2 Hz).

Intermediate B6

5-aminoisoindolin-1-one

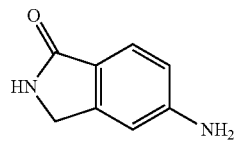 [SMILES: Nc1ccc2c(c1)CNC2=O]

Step A: methyl 2-(bromomethyl)-4-nitrobenzoate

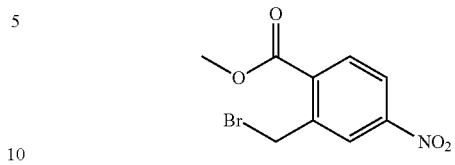

2-methyl-4-nitrobenzoic acid methyl ester (696 mg, 3.57 mmol), azobisisbutyronitrile (58.6 mg, 0.357 mmol) and N-bromosuccinimide (785 mg, 4.46 mmol) were suspended in carbon tetrachloride (35 mL) in a sealed tube. The above mixture was flushed with nitrogen for 5 minutes and heated at 80° C. for 22 hours. After cooling, the solid was filtered off and the filtrate was concentrated to dryness to obtain the crude product methyl 2-(bromomethyl)-4-nitrobenzoate as a light-brown solid, which was used for the next step without purification.

Step B: 5-nitroisoindolin-1-one

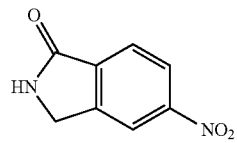

A suspension of methyl 2-(bromomethyl)-4-nitrobenzoate in ammonium solution (7 N in methanol, 5 mL) was stirred at room temperature for 2 hours and concentrated in vacuum to obtain a yellow solid. This crude solid was triturated with ethyl acetate (15 mL) and was then cooled at −20° C. The mixture was filtered to obtain the product 5-nitroisoindolin-1-one as yellow solid. $^1$H NMR (400 MHz, DMSO-d6) δ ppm 9.04 (br s, 1H), 8.48 (d, 1H, J=2.0 Hz), 8.25 (dd, 1H, J=2.0 Hz, 8.4 Hz), 7.91 (d, 1H, J=8.4 Hz), 4.51 (s, 2H).

Step C/Intermediate B6: 5-aminoisoindolin-1-one

To a solution of 5-nitroisoindolin-1-one (60 mg, 0.337 mmol) in methanol (20 mL) was added palladium on carbon (10%, 50 mg). The mixture was stirred under an atmosphere of hydrogen for 1 hour. Filtration through Celite, followed by concentration led to 5-aminoisoindolin-1-one as a tan solid (38 mg, yield 76.2%).

Intermediate B7 benzofuran-7-amine hydrochloride

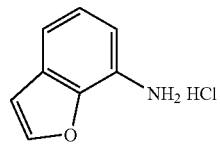

Step A: 2-hydroxy-3-nitrobenzaldehyde

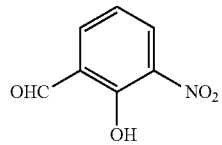 [SMILES: O=Cc1cccc([N+](=O)[O-])c1O]

To a solution of 2-hydroxybenzaldehyde (5.0 g, 41 mmol) in acetic acid (50 mL) at 0° C. was added nitric acid (65%, 4 g) dropwise. The reaction mixture was slowly warmed to room temperature for 2 hours and then heated at 40° C. for another 5 hours. The resulting mixture was poured into ice (75 g) and water (500 g). The precipitates were filtrated and purified by silica gel chromatography to afford the product 2-hydroxy-3-nitrobenzaldehyde (1.8 g, yield 26%). $^1$H NMR (400 MHz, CDCl$_3$) δ ppm 11.44 (s, 1H), 10.42 (s, 1H), 8.34-8.37 (dd, 1H, J=2.0 Hz, 8.4 Hz), 8.10-8.13 (dd, 1H, J=2.0 Hz, 7.6 Hz), 7.12-7.16 (t, 1H, J=8.0 Hz).

Step B: methyl 7-nitrobenzofuran-2-carboxylate

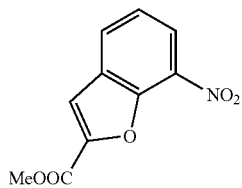 [SMILES: COC(=O)c1cc2cccc([N+](=O)[O-])c2o1]

A mixture of 2-hydroxy-3-nitrobenzaldehyde (4.3 g, 25.7 mmol), dimethyl 2-bromomalonate (5.95 g, 28.3 mmol), potassium carbonate (5.32 g, 38.6 mmol) and tetra-n-butylammonium bromide (0.8 g, 2.5 mmol) in toluene (100 mL) was heated at reflux with a Dean-Start trap for 5 hours. After cooling to room temperature, the mixture was evaporated and purified by silica gel chromatography (dichloromethane) to afford the product methyl 7-nitrobenzofuran-2-carboxylate (4.6 g, yield 81%). $^1$H NMR (400 MHz, CDCl$_3$) δ ppm 8.31-8.33 (dd, 1H, J=1.2 Hz, 8.0 Hz), 8.02-8.04 (dd, 1H, J=1.2 Hz, 8.0 Hz), 7.66 (s, 1H), 7.46-7.50 (t, 1H, J=8.0 Hz), 4.03 (s, 3H).

Step C: 7-nitrobenzofuran-2-carboxylic acid

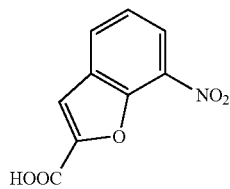 [SMILES: O=C(O)c1cc2cccc([N+](=O)[O-])c2o1]

To a suspension of methyl 7-nitrobenzofuran-2-carboxylate (4.12 g, 18.6 mmol) in ethanol (100 mL) was added potassium hydroxide (2.08 g, 37.1 mmol). The mixture was heated at reflux for 1 hour, cooled to room temperature and evaporated. The residue was diluted with water, acidified by concentrated hydrochloric acid (12 N). The suspension was stirred for another 30 minutes, and then filtrated. The precipitate was collected, washed with water and dried to afford the product 7-nitrobenzofuran-2-carboxylic acid (3.54 g, yield 92%). $^1$H NMR (400 MHz, CDCl$_3$) δ ppm 8.28-8.30 (dd, 1H, J=0.8 Hz, 8.0 Hz), 8.06-8.08 (dd, 1H, J=0.8 Hz, 7.6 Hz), 7.641-7.642 (d, 1H, J=0.4 Hz), 7.47-7.51 (m, 2H).

Step D: 7-nitrobenzofuran

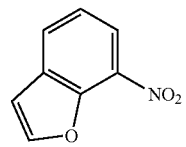 [SMILES: O=[N+]([O-])c1cccc2ccoc12]

A mixture of 7-nitrobenzofuran-2-carboxylic acid (3.54 g, 17.1 mmol) and copper(II) oxide (0.16 g, 2 mmol) in quinoline (30 mL) was heated at 170° C. for 1 hour. Cooling to room temperature, the mixture was diluted with water and extracted with ethyl acetate. The combined organic extracts were washed by brine, dried over anhydrous sodium sulfate, evaporated and purified by silica gel chromatography (petroleum ether/dichloromethane 2/3) to afford the product 7-nitrobenzofuran (2.56 g, yield 92%). $^1$H NMR (400 MHz, DMSO-d6) δ ppm 8.27-8.28 (d, 1H, J=2.0 Hz), 8.12-8.17 (m, 2H), 7.46-7.50 (t, 1H, J=8.0 Hz), 7.215-7.220 (d, 1H, J=2.0 Hz).

Step E/Intermediate B7: benzofuran-7-amine hydrochloride

To a solution of 7-nitrobenzofuran (2.56 g, 15.7 mmol) in methanol (100 mL) was added Raney Ni (ca. 200 mg) and hydrazine hydrate (2.5 g, 50 mmol) dropwise. The exothermic mixture was heated at 50° C. for 1 hour and then cooled to room temperature. The catalyst was removed by filtration and the filtrate was evaporated. The residue was diluted with ethyl acetate, and then a solution of hydrochloride in methanol (1 N) was added. The precipitate was collected and dried to afford the product benzofuran-7-amine hydrochloride (2.025 g, yield 76%). $^1$H NMR (400 MHz, DMSO-d6) δ ppm 8.12-8.13 (d, 1H, J=2.0 Hz), 7.57-7.59 (dd, 1H, J=1.2 Hz, 8.0 Hz), 7.35-7.37 (m, 1H), 7.24-7.28 (t, 1H, J=8.0 Hz), 7.047-7.053 (d, 1H, J=2.4 Hz).

Intermediate B8

1,3-dimethyl-1H-pyrazol-5-amine

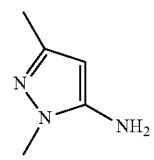

To a solution of 3-aminocrotononitrile (16.5 g, 0.2 mol) in n-pentanol (40 mL) was added methylhydrazine (12.9 g, 0.28 mol). The solution was maintained at reflux for 3 hours. The n-pentanol and the excess methylhydrazine were subsequently distilled off under reduced pressure. The beige precipitate obtained was taken up in heptanes (150 mL), filtered on a sinter funnel and then dried under vacuum at a temperature of 40° C. to afford the product 1,3-dimethyl-1H-pyrazol-5-amine as a beige solid (13.5 g, yield 60.4%).

Intermediate B9

3,4,5-trimethoxyaniline

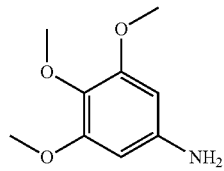

Step A: 1,2,3-trimethoxy-5-nitrobenzene

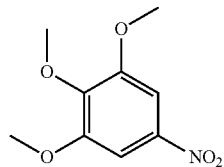

To a solution of nitric acid (20.0 mL) and acetic acid (40.0 mL) under 10° C. was added 3,4,5-trimethoxybenzoic acid (10.0 g, 47.0 mmol) in portions. The mixture was stirred at room temperature for 30 minutes. The reaction mixture was then poured into ice-water. The resulting precipitate was collected by filtration and washed with water, which was then recrystallized from ethanol to afford the product 1,2,3-trimethoxy-5-nitrobenzene (6.64 g, yield 66.1%). $^1$H NMR (400 MHz, DMSO-d6) δ ppm 7.51 (s, 2H), 3.87 (s, 6H), 3.77 (s, 3H).

Step B/Intermediate B9: 3,4,5-trimethoxyaniline

To a solution of 1,2,3-trimethoxy-5-nitrobenzene (6.64 g, 31.2 mmol) in ethanol (250 mL) was added palladium on carbon (10%, 300 mg) and hydrazine hydrate (85%, 5.7 mL). After emission of gas has ceased, the reaction mixture was heated at refluxed for 1 hour, cooling to room temperature, filtered and evaporated to afford the product 3,4,5-trimethoxyaniline as a white solid (5.5 g, yield 96.4%). $^1$H NMR (400 MHz, DMSO-d6) δ ppm 5.86 (s, 2H), 4.82 (br, 2H), 3.64 (s, 6H), 3.50 (s, 3H).

Intermediate B10

1-(3-morpholinopropyl)-1H-indol-4-amine

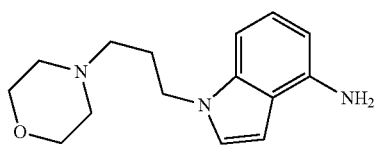

Step A: 1-(3-bromopropyl)-4-nitro-1H-indole

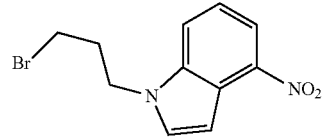 [SMILES: O=[N+]([O-])c1cccc2c1ccn2CCCBr]

To a solution of 4-nitroindole (5 g, 31 mmol) in anhydrous N,N'-dimethylformamide (200 mL) was added grounded potassium hydroxide (1.74 g, 31 mmol) in portions. Then a solution of 1,3-dibromopropane (18 g, 89 mmol) in N,N'-dimethylformamide was added dropwise. The mixture was stirred at room temperature for 12 hours, diluted with water and extracted with ethyl acetate. The organic phases were combined, washed by brine, dried over anhydrous sodium sulfate, filtrated and evaporated. The residue was purified by silica gel chromatography to afford the product 1-(3-bromopropyl)-4-nitro-1H-indole as brown-red oil (8.18 g, yield 94%).

Step B: 4-(3-(4-nitro-1H-indol-1-yl)propyl)morpholine

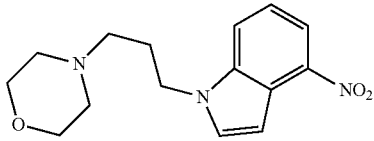 [SMILES: O=[N+]([O-])c1cccc2c1ccn2CCCN1CCOCC1]

To a solution of 1-(3-bromopropyl)-4-nitro-1H-indole (8.18 g, 28.9 mmol) in anhydrous N,N'-dimethylformamide (200 mL) was added grounded potassium carbonate (12 g, 87 mmol) in portions. Then a solution of morpholine (12.6 g, 144.8 mmol) in N,N'-dimethylformamide was added dropwise. The mixture was stirred at 80° C. for 12 hours, diluted with water and extracted with ethyl acetate. The organic phases were combined, washed by brine, dried over anhydrous sodium sulfate, filtrated and evaporated to afford the product 4-(3-(4-nitro-1H-indol-1-yl)propyl)morpholine, which was used for the next step without purification.

Step C/Intermediate B10:1-(3-morpholinopropyl)-1H-indol-4-amine

To a solution of crude 4-(3-(4-nitro-1H-indol-1-yl)propyl)morpholine in methanol (100 mL) was added palladium on carbon (10%). The mixture was stirred under an atmosphere of hydrogen for 12 hours. The catalyst was removed by filtration and the filtrate was evaporated. The residue was purified by silica gel chromatography to afford the product 1-(3-morpholinopropyl)-1H-indol-4-amine (5 g, yield 67%, two steps) as a brown solid. $^1$H NMR (400 MHz, DMSO-d6) δ ppm 8.12, J=2.4 Hz).

Intermediate C1

2-amino-N-methyl benzamide

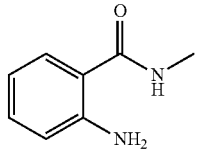

Isatoic anhydride (10 g, 61.3 mmol) was suspended in tetrahydrofuran (200 ml) and treated dropwise with methylamine in methanol (40%, 10 mL) with stirring. After stirring at room temperature for 16 hours, the solvent was distilled off under reduced pressure to afford the product 2-amino-N-methylbenzamide (9 g, yield 97.8%). $^1$H NMR (400 MHz, CDCl$_3$) δ ppm 7.14-7.32 (m, 2H), 6.60-6.72 (m, 2H), 6.05 (br s, 1H), 2.97 (d, 3H, J=5.0 Hz).

Intermediate C2

4-amino-N-methylbenzo[d][1,3]dioxole-5-carboxamide

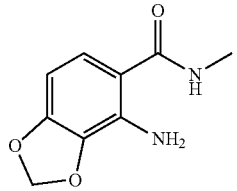

Step A: 4-nitrobenzo[d][1,3]dioxole

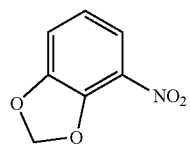 [SMILES: O=[N+]([O-])c1cccc2c1OCO2]

To a suspension of sodium hydride (60%, 1.0 g, 25 mmol) in hexamethylphosphorous triamide (100 mL) was added a solution of 3-nitrobenzene-1,2-diol (from Intermediate B3, 1.55 g, 10 mmol) in hexamethylphosphorous triamide (20 mL) during 10 minutes. Then diiodomethane (0.94 mL, 11.6 mmol) was added and the solution was stirred for another 30 minutes, quenched by ice-water and extracted with ether. The combined organic extracts were dried over anhydrous sodium sulfate, concentrated to afford the product 4-nitrobenzo[d][1,3]dioxole (1.32 g, yield 79%). $^1$H NMR (400 MHz, CDCl$_3$) δ ppm 7.59-7.62 (dd, 1H, J=1.2 Hz, 8.8 Hz), 7.06-7.09 (dd, 1H, J=0.8 Hz, 8.0 Hz), 6.91-6.96 (dt, 1H, J=0.8 Hz, 8.4 Hz), 6.219-6.221 (d, 2H, J=0.8 Hz).

Step B: benzo[d][1,3]dioxol-4-amine

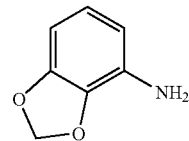

To a solution of 4-nitrobenzo[d][1,3]dioxole (2.0 g, 12 mmol) in ethanol (80 mL) was added Raney Ni (ca. 0.5 g). The mixture was stirred under an atmosphere of hydrogen for 4 hours. The catalyst was removed by filtration and the filtrate was concentrated. The residue was purified by silica gel chromatography (dichloromethane) to afford the product benzo[d][1,3]dioxol-4-amine (1.04 g, yield 63%). $^1$H NMR (400 MHz, CDCl$_3$) δ ppm 6.64-6.68 (t, 1H, J=8.0 Hz), 6.29-6.35 (dt, 2H, J=0.8 Hz, 6.4 Hz), 5.90 (s, 2H), 3.52 (br, 2H).

Step C: [1,3]dioxolo[4',5':5,6]benzo[1,2-b]azet-6(7H)-one

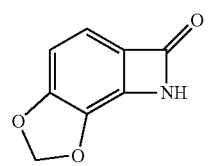 [SMILES: O=C1Nc2c1ccc1c2OCO1]

To a slurry of chloral hydrate (1.39 g, 8.4 mmol) and sodium sulfate (6.91 g, 48.7 mmol) in water (23.1 mL) was added benzo[d][1,3]dioxol-4-amine (1.0 g, 7.3 mmol), hydroxylamine sulfate (6.24 g, 38 mmol) and diluted hydrochloric acid (1.2 N, 7.7 mL). After stirring at 60° C. for 1.5 hours, the reaction mixture was kept at 25° C. overnight. The brown solid was collected by filtration and washed with water. After drying under vacuum, the solid was taken up in methane sulfonic acid and the solution was heated at 45° C. for 30 minutes. The mixture was cooled to 0° C. and then poured into ice (200 g). A dark red solid was precipitated and collected by filtration, dried to afford the product (635 mg, yield 53%). $^1$H NMR (400 MHz, CDCl$_3$) δ ppm 7.68 (br s, 1H), 7.35-7.37 (d, 1H, J=8.0 Hz), 6.59-6.61 (d, 1H, J=8.0 Hz), 6.13 (s, 2H).

Step D: 4-aminobenzo[d][1,3]dioxole-5-carboxylic acid

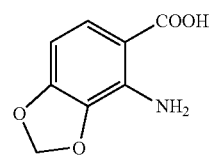

To a solution of sodium hydroxide (4.6 g, 115 mmol) in water (35 mL) was added the Intermediate from Step C (2.35 g, 14.4 mmol). A solution of hydrogen peroxide (30%, 21 mL) was then added over 30 minutes. The reaction was neutralized to pH 7 by the addition of diluted hydrochloric acid (1N). The precipitate was collected and dried to afford the product 4-aminobenzo[d][1,3]dioxole-5-carboxylic acid (1.68 g, yield 64%). ¹H NMR (400 MHz, DMSO-d6) δ ppm 7.40-7.42 (d, 1H, J=8.4 Hz), 6.25-6.27 (d, 1H, J=8.4 Hz), 6.04 (s, 2H).

Step E/Intermediate C2:
4-amino-N-methylbenzo[d][1,3]dioxole-5-carboxamide

To a solution of methylamine (0.43 g, 13.9 mmol, prepared from 33% aqueous solution and sodium hydroxide) in acetonitrile (20 mL) was added 4-aminobenzo[d][1,3]dioxole-5-carboxylic acid (1.68 g, 9.3 mmol), N,N'-diisopropylethylamine (3.24 mL, 18.6 mmol) and O-(7-azabenzotriazol-1-yl)-N,N,N',N'''-tetramethyluronium hexafluorophosphate (HATU, 4.28 g, 11.2 mmol). The mixture was stirred at room temperature for 12 hours, and then evaporated. The residue was diluted with dichloromethane, washed by water, dried over anhydrous sodium sulfate, concentrated and purified by silica gel chromatography to afford the product 4-amino-N-methylbenzo[d][1,3]dioxole-5-carboxamide (1.48 g, yield 82%). ¹H NMR (400 MHz, CDCl₃) δ ppm 6.95-6.98 (d, 1H, J=8.4 Hz), 6.24-6.26 (d, 1H, J=8.0 Hz), 5.97 (s, 2H), 2.94-2.95 (m, 3H).

Intermediate C3

(2-aminophenyl)(pyrrolidin-1-yl)methanone

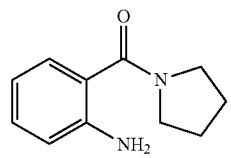 [SMILES: Nc1ccccc1C(=O)N1CCCC1]

To a solution of 2-aminobenzoic acid (5.0 g, 36.5 mol) in tetrahydrofuran (50 mL) was added N,N'-carbonyldiimidazole (6.5 g, 40.1 mol) at 25° C., the resulting mixture was stirred for 1 hour at this temperature. Then pyrrolidine (3.5 g, 40.1 mmol) was added and the mixture was stirred overnight. The solvent was removed under the reduced pressure and the residue was washed with water and extracted with dichloromethane, the organic phase was dried over anhydrous sodium sulfate, concentrated to afford the product (2-aminophenyl)(pyrrolidin-1-yl)methanone (5.4 g, yield 66%), which was used for the next step without further purification. ¹H NMR (400 MHz, CDCl₃) δ ppm 7.12-7.21 (m, 2H), 6.66-6.71 (m, 2H), 4.62 (br s, 2H), 3.63 (br s, 2H), 3.47 (br s, 2H), 1.87-1.94 (m, 4H).

Intermediate C4

2-amino-N-methyl benzenesulfonamide

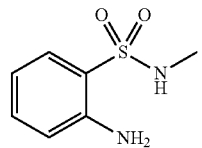

Step A: N-methyl-2-nitrobenzenesulfonamide

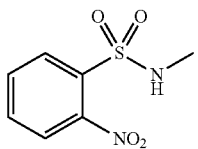

To a solution of 2-nitrobenzene-1-sulfonyl chloride (30 g, 0.14 mol) in dichloromethane (500 mL) was slowly added a solution of methylamine in water (30%, 15.3 g) and triethylamine (38 mL, 0.27 mol) respectively. The mixture was stirred at room temperature for 1 hour and then evaporated. The residue was subjected to silica gel chromatography to afford the product N-methyl-2-nitrobenzenesulfonamide (26 g, yield 90%).

Step B/Intermediate C4:
2-amino-N-methylbenzenesulfonamide

To a solution of N-methyl-2-nitrobenzenesulfonamide (26 g, 0.12 mol) in methanol (500 mL) was added palladium on carbon (10%, 2 g). The mixture was stirred under an atmosphere of hydrogen at room temperature for 3 hours. The catalyst was filtrated and the filtrate was evaporated to afford the product 2-amino-N-methylbenzenesulfonamide (22 g, yield 98%). ¹H NMR (400 MHz, CDCl₃) δ ppm 7.45-7.48 (dd, 1H, J=1.6 Hz, 8.0 Hz), 7.24-7.31 (m, 2H), 6.81-6.83 (dd, 1H, J=0.6 Hz, 8.0 Hz), 6.60-6.65 (m, 1H), 5.89 (s, 2H), 2.370-2.374 (d, 3H, J=1.6 Hz).

Intermediate C5

2-amino-N-propylbenzenesulfonamide hydrochloride

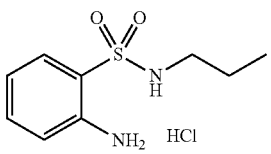

Step A: 2-nitro-N-propylbenzenesulfonamide

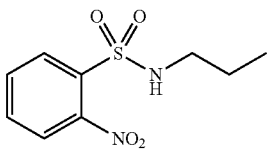 [SMILES: CCCNS(=O)(=O)c1ccccc1[N+](=O)[O-]]

To a solution of propan-1-amine (2.36 g, 0.04 mol) in tetrahydrofuran (100 mL) at 0° C. was added triethylamine (4.05 g, 0.04 mol) and 2-nitrobenzene-1-sulfonyl chloride (8.88 g, 0.04 mol) in several portions over 10-15 minutes. The reaction mixture was stirred at room temperature for 4 hours, filtered and concentrated to afford the product 2-nitro-N-propylbenzenesulfonamide (9.18 g, yield 93.9%). ¹H NMR (400 MHz, CDCl₃) δ ppm 8.11-8.16 (m, 1H), 7.84-7.89 (m, 1H), 7.74-7.79 (m, 2H), 5.26 (s, 1H), 3.05-3.10 (t, 2H, J=6.4 Hz), 1.51-1.60 (m, 2H), 0.89-0.92 (t, 3H, J=7.6 Hz).

Step B/Intermediate C5: 2-amino-N-propylbenzenesulfonamide hydrochloride

To a solution of 2-nitro-N-propylbenzenesulfonamide (8.64 g, 0.035 mol) in methanol (100 mL) was added palladium on carbon (10%, 3.5 g). The mixture was stirred under an atmosphere of hydrogen for 12 hours. The catalyst was removed by filtration and the filtrate was evaporated. The solid residue was washed with ether to afford 2-amino-N-propylbenzenesulfonamide (7.45 g, yield 98.3%), which was dissolved in ether, and bubbled in hydrochloride (gas) to afford the product 2-amino-N-propylbenzenesulfonamide hydrochloride (8.61 g, yield 98.4%). ¹H NMR (400 MHz, DMSO-d6) δ ppm 8.14 (br s, 3H), 7.50-7.62 (m, 2H), 7.26-7.30 (dt, 1H, J=1.6 Hz, 7.6 Hz), 6.88-6.90 (d, 1H, J=8.0 Hz), 6.67-6.71 (m, 1H), 2.61-2.65 (t, 2H, J=7.2 Hz), 1.28-1.37 (sext, 2H, J=7.2 Hz), 0.72-0.76 (t, 3H, J=7.6 Hz).

Intermediate C6

2-amino-N-cyclobutylbenzenesulfonamide

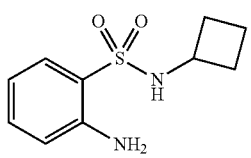 [SMILES: Nc1ccccc1S(=O)(=O)NC1CCC1]

Step A: N-cyclobutyl-2-nitrobenzenesulfonamide

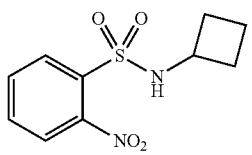 [SMILES: O=[N+]([O-])c1ccccc1S(=O)(=O)NC1CCC1]

To a solution of 2-nitrobenzene-1-sulfonyl chloride (6.8 g, 30.8 mol) in dichloromethane (100 mL) at 0° C. was added triethylamine (14 g, 138.6 mol) and cyclobutanamine (2.2 g, 31 mmol) in several portions over 10-15 minutes. The reaction mixture was stirred at room temperature for 4 hours, concentrated and purified by silica gel chromatography to afford the product N-cyclobutyl-2-nitrobenzenesulfonamide (7 g, yield 88.9%). ¹H NMR (400 MHz, CDCl₃) δ ppm 8.14-8.16 (m, 1H), 7.84-7.87 (m, 1H), 7.72-7.74 (m, 2H), 5.45-5.47 (d, 1H, J=8.8 Hz), 3.93-3.99 (m, 1H), 2.11-2.18 (m, 2H), 1.84-1.90 (m, 2H), 1.59-1.69 (m, 2H).

Step B/Intermediate C6: 2-amino-N-cyclobutylbenzenesulfonamide

To a solution of N-cyclobutyl-2-nitrobenzenesulfonamide (7 g, 27.3 mmol) in methanol (100 mL) was added palladium on carbon (10%). The mixture was stirred under an atmosphere of hydrogen for 12 hours. The catalyst was removed by filtration and the filtrate was evaporated to afford the product 2-amino-N-cyclobutylbenzenesulfonamide (6 g, yield 97.1%). ¹H NMR (400 MHz, CDCl₃) δ ppm 7.68-7.71 (dd, 1H, J=1.6 Hz, 8.0 Hz), 7.27-7.33 (m, 1H), 6.74-6.82 (m, 2H), 5.30 (s, 1H), 5.08 (s, 2H), 3.70-3.73 (m, 1H), 1.96-2.04 (m, 2H), 1.67-1.75 (m, 2H), 1.48-1.62 (m, 2H).

Intermediate C7

2-amino-N-cyclopentylbenzenesulfonamide

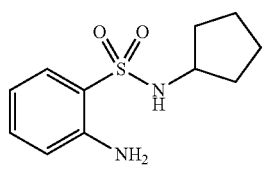

Step A: N-cyclopentyl-2-nitrobenzenesulfonamide

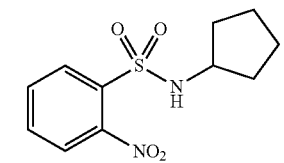 [SMILES: O=[N+]([O-])c1ccccc1S(=O)(=O)NC1CCCC1]

To a solution of 2-nitrobenzene-1-sulfonyl chloride (22.1 g, 100 mol) in dichloromethane (500 mL) at 0° C. was added triethylamine (14 g, 138.6 mol) and cyclopentanamine (9 g, 105.9 mmol) in several portions over 10-15 minutes. The reaction mixture was stirred at room temperature for 4 hours, concentrated and purified by silica gel chromatography to afford the product N-cyclopentyl-2-nitrobenzenesulfonamide (23 g, yield 85.2%). ¹H NMR (400 MHz, CDCl₃) δ ppm 8.16-8.18 (m, 1H), 7.84-7.87 (m, 1H), 7.40-7.78 (m, 2H), 5.25-5.27 (d, 1H, J=7.6 Hz), 3.76-3.81 (m, 1H), 1.79-1.87 (m, 2H), 1.62-1.70 (m, 2H), 1.39-1.58 (m, 4H).

Step B/Intermediate C7: 2-amino-N-cyclopentylbenzenesulfonamide

To a solution of N-cyclopentyl-2-nitrobenzenesulfonamide (23 g, 85.2 mmol) in methanol (500 mL) was added palladium on carbon (10%). The mixture was stirred under an atmosphere of hydrogen for 12 hours. The catalyst was removed by filtration and the filtrate was evaporated to afford the product 2-amino-N-cyclopentylbenzenesulfonamide (20 g, yield 97.8%). ¹H NMR (400 MHz, CDCl₃) δ ppm 7.71-7.74 (dd, 1H, J=1.2 Hz, 8.0 Hz), 7.30-7.34 (m, 1H), 6.75-6.82 (m, 2H), 4.86 (br s, 3H), 3.50-3.53 (m, 1H), 1.67-1.69 (m, 2H), 1.55-1.62 (m, 2H), 1.42-1.50 (m, 2H), 1.22-1.36 (m, 2H).

Intermediate C8

2-amino-N-cyclohexylbenzenesulfonamide

Step A: N-cyclohexyl-2-nitrobenzenesulfonamide

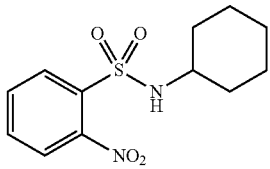

To a solution of 2-nitrobenzene-1-sulfonyl chloride (22.1 g, 100 mol) in dichloromethane (500 mL) at 0° C. was added triethylamine (14 g, 138.6 mol) and cyclohexanamine (11.9 g, 120.2 mmol) in several portions over 10-15 minutes. The reaction mixture was stirred at room temperature for 4 hours, concentrated and purified by silica gel chromatography to afford the product N-cyclohexyl-2-nitrobenzenesulfonamide (25.7 g, yield 90.5%). $^1$H NMR (400 MHz, CDCl$_3$) δ ppm 8.16-8.19 (m, 1H), 7.85-7.87 (m, 1H), 7.72-7.78 (m, 2H), 5.24-5.26 (d, 1H, J=7.6 Hz), 3.34-3.36 (m, 1H), 1.77-1.81 (m, 2H), 1.63-1.69 (m, 2H), 1.52-1.56 (m, 1H), 1.17-1.30 (m, 5H).

Step B/Intermediate C8:
2-amino-N-cyclohexylbenzenesulfonamide

To a solution of N-cyclohexyl-2-nitrobenzenesulfonamide (25.7 g, 90.5 mmol) in methanol (500 mL) was added palladium on carbon (10%). The mixture was stirred under an atmosphere of hydrogen for 12 hours. The catalyst was removed by filtration and the filtrate was evaporated to afford the product 2-amino-N-cyclohexylbenzenesulfonamide (22 g, yield 95.7%). $^1$H NMR (400 MHz, CDCl$_3$) δ ppm 7.72-7.74 (dd, 1H, J=1.2 Hz, 8.0 Hz), 7.27-7.33 (m, 1H), 6.75-6.82 (m, 2H), 4.84 (s, 3H), 3.05-3.07 (m, 1H), 1.59-1.70 (m, 4H), 1.46-1.50 (m, 1H), 1.08-1.22 (m, 5H).

Intermediate C9

N-(2-aminophenyl)acetamide

To a solution of benzene-1,2-diamine (100 g, 0.93 mol) in dichloromethane (1 L) at 0° C. was added acetic anhydride (87 mL, 0.92 mol). After stirring at 0° C. for 2 hours, the mixture was stand at 0° C. for 12 hours and the precipitate was collected by filtration, washed by dichloromethane and ether, dried in air to afford the product N-(2-aminophenyl)acetamide (25 g, yield 18%). $^1$H NMR (400 MHz, CDCl$_3$) δ ppm 7.14-7.26 (m, 2H), 7.04-7.08 (m, 1H), 6.78-6.81 (m, 2H), 3.86 (br s, 2H), 2.20 (s, 3H).

Intermediate C10

N-(2-aminophenyl)-N-methylmethanesulfonamide

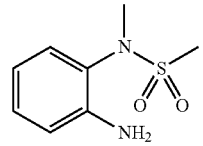

Step A:
N-methyl-N-(2-nitrophenyl)methanesulfonamide

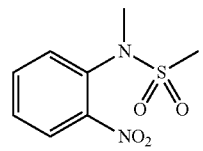

To a suspension of cesium carbonate (20.2 g, 0.065 mol) in acetonitrile (500 mL) at room temperature was added N-methylmethanesulfonamide (5.33 g, 0.049 mol) and 1-fluoro-2-nitrobenzene (4.59 g, 0.033 mol) dropwise over 10-15 minutes. The reaction was stirred at room temperature for 12 hours. Upon completion, the mixture was filtered and then concentrated. The residue was purified by silica gel chromatography (dichloromethane) to afford the product N-methyl-N-(2-nitrophenyl)methanesulfonamide (4.2 g, yield 56.1%). $^1$H NMR (400 MHz, DMSO-d6) δ ppm 7.92-7.94 (dd, 1H, J=1.2 Hz, 8.0 Hz), 7.74-7.81 (m, 2H), 7.57-7.62 (m, 1H), 3.27 (s, 3H), 3.03 (s, 3H).

Step B/Intermediate C10:
N-(2-aminophenyl)-N-methylmethanesulfonamide

To a solution of N-methyl-N-(2-nitrophenyl)methanesulfonamide (3.90 g, 0.017 mol) in a mixture of methanol and dichloromethane (100 mL) was added palladium on carbon (10%, 1.5 g). The mixture was stirred under an atmosphere of hydrogen for 8 hours. The catalyst was removed by filtration and the filtrate was evaporated. The solid residue was washed with ether to afford the product N-(2-(aminomethyl)phenyl)-N-methylmethanesulfonamide (3.3 g, yield 97.4%). $^1$H NMR (400 MHz, DMSO-d6) δ ppm 7.16-7.18 (dd, 1H, J=1.2 Hz, 7.6 Hz), 6.99-7.04 (m, 1H), 6.72-6.75 (dd, 1H, J=1.2 Hz, 8.0 Hz), 6.53-6.57 (m, 1H), 5.09 (br, 2H), 3.06 (s, 3H), 3.02 (s, 3H).

Intermediate C11

N-(2-(aminomethyl)phenyl)-N-methylmethanesulfonamide hydrochloride

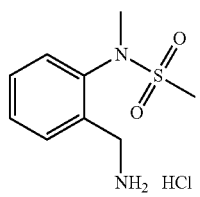

Step A: N-(2-cyanophenyl)-N-methylmethanesulfonamide

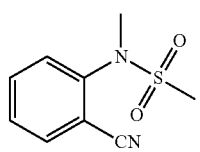

To a solution of cesium carbonate (55.78 g, 171 mmol) in acetonitrile (500 mL) at room temperature was added N-methylmethane-sulfonamide (14.0 g, 0.128 mol). 2-Fluoro-benzonitrile (10.37 g, 86 mmol) was then added in portions over 10-15 minutes. The reaction mixture was stirred at room temperature for 12 hours. Upon completion, the mixture was filtered and then concentrated. The residue diluted with water and extracted by dichloromethane. The organic phases were combined, washed by brine, dried over anhydrous sodium sulfate and evaporated to afford the product N-(2-cyanophenyl)-N-methylmethane-sulfonamide (16.0 g, yield 88.9%). $^1$H NMR (400 MHz, CDCl$_3$) δ ppm 7.62-7.73 (m, 2H), 7.54-7.56 (m, 1H), 7.45-7.50 (m, 1H), 3.40 (s, 3H), 3.14 (s, 3H).

Step B/Intermediate C11: N-(2-(aminomethyl)phenyl)-N-methylmethanesulfonamide hydrochloride To a solution of N-(2-cyanophenyl)-N-methylmethanesulfonamide (16.0 g, 76 mmol) in a solution of ammonia in ethanol (500 mL, 4 mol·L$^{-1}$) was added palladium on carbon (10%, 4 g). The mixture was stirred under an atmosphere of hydrogen for 24 hours. The catalyst was removed by filtration and the filtrate was evaporated. The residue was washed with ether to give N-(2-(aminomethyl)phenyl)-N-methylmethanesulfonamide (14.2 g, yield 87.1%). $^1$H NMR (400 MHz, CDCl$_3$) δ ppm 7.53-7.55 (m, 1H), 7.36-7.40 (m, 1H), 7.29-7.33 (m, 1H), 7.23-7.25 (m, 1H), 3.97-3.99 (br d, 2H, J=8.0 Hz), 3.27 (s, 3H), 3.00 (s, 3H). N-(2-(aminomethyl)phenyl)-N-methylmethanesulfonamide was dissolved in ether and bubbled in hydrochloride (gas) to afford the product N-(2-(aminomethyl)phenyl)-N-methylmethanesulfonamide hydrochloride (15.0 g, yield 90.4%). $^1$H NMR (400 MHz, CDCl$_3$) δ ppm 7.54-7.55 (m, 1H), 7.35-7.40 (m, 1H), 7.28-7.33 (m, 1H), 7.24-7.26 (m, 1H), 3.99 (br s, 2H), 3.25 (s, 3H), 2.98 (s, 3H).

General Protocol II: Synthesis of 6,7-dihydro-5H-pyrrolo[2,3-d]pyrimidine-2,4-diamines

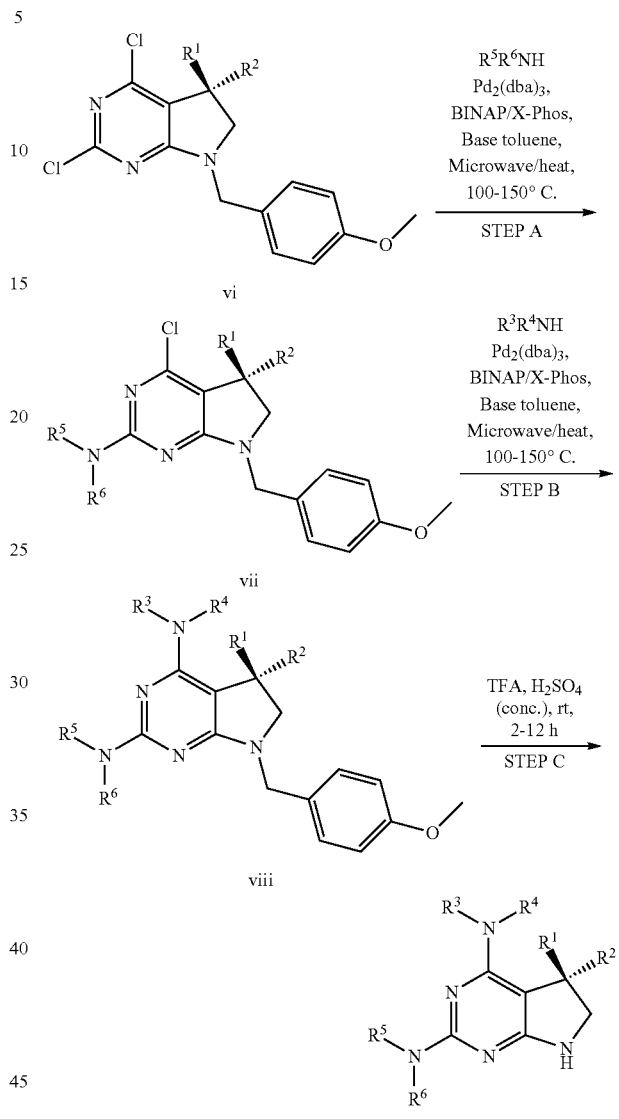

Step A: To a solution of 2,4-dichloro-7-(4-methoxybenzyl)-6,7-dihydro-5H-pyrrolo[2,3-d]pyrimidines (vi, Intermediates A1-A4, 1.0 eq.) in anhydrous toluene was added R$^5$R$^6$NH (Intermediates B1-B10, 1.0-1.2 eq.), Pd$_2$(dba)$_3$ (5-20 mol %), (±)-BINAP/X-Phos (10-20 mol %) and cesium carbonate/sodium (potassium) tert-butoxide/potassium carbonate (1.5-4.0 eq.) respectively. The mixture was heated at 100-150° C. under microwave or in a sealed tube for several hours. Cooling to room temperature, the reaction mixture was evaporated and diluted with ethyl acetate, washed by brine, dried over anhydrous sodium sulfate, evaporated and subjected to silica gel chromatography to afford the product 4-chloro-7-(4-methoxybenzyl)-6,7-dihydro-5H-pyrrolo[2,3-d]pyrimidin-2-amines (vii).

Step B: To a solution of 4-chloro-7-(4-methoxybenzyl)-6,7-dihydro-5H-pyrrolo[2,3-d]pyrimidin-2-amines (vii, 1.0 eq.) in anhydrous toluene was added R$^3$R$^4$NH (Intermediates C1-C11, 1.0-1.2 eq.), Pd$_2$(dba)$_3$ (5-20 mol %), (±)-

BINAP/X-Phos (10-20 mol %) and cesium carbonate/sodium (potassium) tert-butoxide//potassium carbonate (1.5-4.0 eq.) respectively. The mixture was heated at 100-150° C. under microwave or in a sealed tube for several hours. Cooling to room temperature, the reaction mixture was evaporated and diluted with ethyl acetate, washed by brine, dried over anhydrous sodium sulfate, evaporated and subjected to silica gel chromatography to afford the product 7-(4-methoxybenzyl)-6,7-dihydro-5H-pyrrolo[2,3-d]pyrimidine-2,4-diamine (viii).

Step C: To a solution of 7-(4-methoxybenzyl)-6,7-dihydro-5H-pyrrolo[2,3-d]pyrimidine-2,4-diamine (viii) in anhydrous trifluoroacetic acid was added several drops of concentrated sulfuric acid. The mixture was stirred at room temperature for 2-12 hours, and then quenched by aqueous sodium bicarbonate. The aqueous phase was extracted with ethyl acetate and the organic phases were combined, washed by brine, dried over anhydrous sodium sulfate, evaporated and subjected to silica gel chromatography to afford the product 6,7-dihydro-5H-pyrrolo[2,3-d]pyrimidine-2,4-diamines (ix, Examples 1-37).

Example 1

2-(2-(2-methoxy-4-morpholinophenylamino)-6,7-dihydro-5H-pyrrolo[2,3-d]pyrimidin-4-ylamino)-N-methyl benzamide

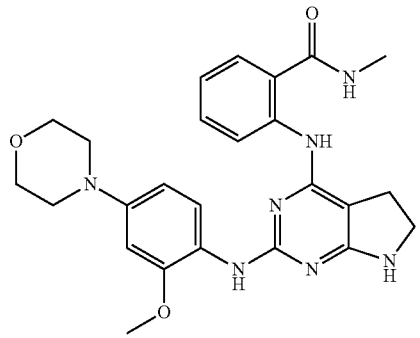

Step A 4-chloro-N-(2-methoxy-4-morpholinophenyl)-7-(4-methoxybenzyl)-6,7-dihydro-5H-pyrrolo[2,3-d]pyrimidin-2-amine

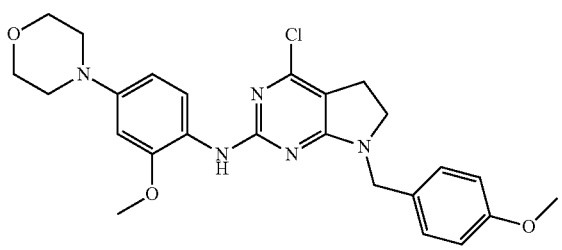 [SMILES: COc1ccc(CN2CCc3c(Cl)nc(Nc4ccc(N5CCOCC5)cc4OC)nc32)cc1]

According to General Protocol II, 4-chloro-N-(2-methoxy-4-morpholinophenyl)-7-(4-methoxybenzyl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 200 mg, 0.65 mmol), 2-methoxy-4-morpholinoaniline (Intermediate B1, 160 mg, 0.77 mmol), Pd$_2$(dba)$_3$ (30 mg, 0.033 mmol), (±)-BINAP (40 mg, 0.064 mmol) and cesium carbonate (315 mg, 0.97 mmol), and isolated as a yellow solid (100 mg, yield 32%). $^1$H NMR (400 MHz, CDCl$_3$) δ ppm 8.37-8.39 (d, 1H, J=9.6 Hz), 7.38 (s, 1H), 7.21-7.26 (m, 2H), 6.86-6.88 (dd, 2H, J=2.0 Hz, 6.8 Hz), 6.50-6.52 (m, 2H), 4.54 (s, 2H), 3.85-3.87 (t+s, 7H), 3.80 (s, 3H), 3.45-3.49 (t, 2H, J=8.4 Hz), 3.08-3.11 (t, 4H, J=4.8 Hz), 2.90-2.94 (t, 2H, J=8.4 Hz).

Step B 2-(2-(2-methoxy-4-morpholinophenylamino)-7-(4-methoxybenzyl)-6,7-dihydro-5H-pyrrolo[2,3-d]pyrimidin-4-ylamino)-N-methylbenzamide

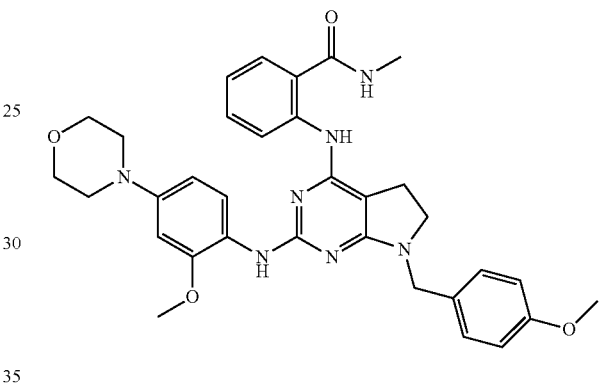

According to General Protocol II, 2-(2-(2-methoxy-4-morpholinophenylamino)-7-(4-methoxybenzyl)-6,7-dihydro-5H-pyrrolo[2,3-d]pyrimidin-4-ylamino)-N-methylbenzamide was prepared from 4-chloro-N-(2-methoxy-4-morpholinophenyl)-7-(4-methoxybenzyl)-6,7-dihydro-5H-pyrrolo[2,3-d]pyrimidin-2-amine (100 mg, 0.21 mmol), 2-amino-N-methylbenzamide (Intermediate C1, 40 mg, 0.27 mmol), Pd$_2$(dba)$_3$ (10 mg, 0.011 mmol), (±)-BINAP (15 mg, 0.024 mmol) and cesium carbonate (105 mg, 0.322 mmol), and isolated as a yellow solid (60 mg, yield 48%). $^1$H NMR (400 MHz, CDCl$_3$) δ ppm 10.00 (s, 1H), 8.63-8.65 (d, 1H, J=8.0 Hz), 8.39-8.41 (d, 1H, J=8.8 Hz), 7.38-7.40 (m, 2H), 7.24-7.26 (m, 1H), 7.19 (s, 1H), 6.85-6.90 (m, 3H), 6.526-6.532 (d, 1H, J=2.4 Hz), 6.47-6.49 (dd, 1H, J=2.4 Hz, 8.8 Hz), 6.22 (s, 1H), 4.52 (s, 2H), 3.86-3.88 (t+s, 7H), 3.80 (s, 3H), 3.40-3.45 (t, 2H, J=8.8 Hz), 3.09-3.11 (t, 4H, J=4.8 Hz), 2.96-2.98 (d, 3H, J=5.2 Hz), 2.89-2.93 (t, 2H, J=8.8 Hz).

Step C 2-(2-(2-methoxy-4-morpholinophenylamino)-6,7-dihydro-5H-pyrrolo[2,3-d]pyrimidin-4-ylamino)-N-methylbenzamide According to General Protocol II, 2-(2-(2-methoxy-4-morpholinophenylamino)-6,7-dihydro-5H-pyrrolo[2,3-d]pyrimidin-4-ylamino)-N-methylbenzamide was prepared from 2-(2-(2-methoxy-4-morpholinophenylamino)-7-(4-methoxybenzyl)-6,7-dihydro-5H-pyrrolo[2,3-d]pyrimidin-4-ylamino)-N-methylbenzamide (20 mg, 0.034 mmol), trifluoroacetic acid (1 mL) and two drops of concentrated sulfuric acid, and isolated as a yellow solid (14 mg, yield 88%). ¹H NMR (400 MHz, DMSO-d6) δ ppm 10.64 (s, 1H), 8.61-8.63 (d, 1H, J=4.8 Hz), 8.55-8.57 (d, 1H, J=8.0 Hz), 7.83-7.85 (d, 1H, J=8.8 Hz), 7.65-7.67 (dd, 1H, J=1.2 Hz, 8.0 Hz), 7.31-7.35 (dt, 1H, J=1.2 Hz, 8.4 Hz), 7.14 (s, 1H), 6.88-6.92 (dt, 1H, J=0.8 Hz, 8.0 Hz), 6.605-6.611 (d, 1H, J=2.4 Hz), 6.56 (s, 1H), 6.42-6.45 (dd, 1H, J=2.4 Hz, 8.8 Hz), 3.80 (s, 3H), 3.72-3.74 (t, 4H, J=4.8 Hz), 3.48-3.53 (t, 2H, J=8.8 Hz), 3.05-3.07 (t, 4H, J=4.8 Hz), 2.76-2.81 (s+t, 5H).

Example 2

4-(2-(2-methoxy-4-morpholinophenylamino)-6,7-dihydro-5H-pyrrolo[2,3-d]pyrimidin-4-ylamino)-N-methylbenzo[d][1,3]dioxole-5-carboxamide

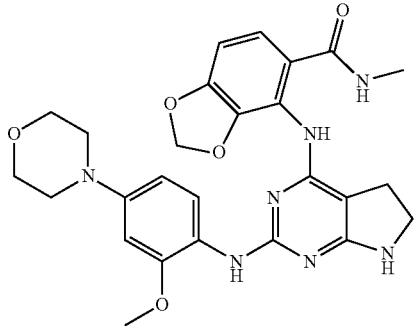 [SMILES: CNC(=O)c1ccc2c(c1Nc1nc(Nc3ccc(N4CCOCC4)cc3OC)nc3c1CCN3)OCO2]

Step A 4-(2-(2-methoxy-4-morpholinophenylamino)-7-(4-methoxybenzyl)-6,7-dihydro-5H-pyrrolo[2,3-d]pyrimidin-4-ylamino)-N-methylbenzo[d][1,3]dioxole-5-carboxamide

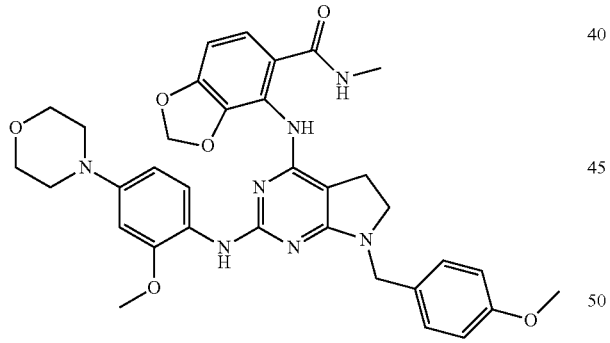

According to General Protocol II, 4-(2-(2-methoxy-4-morpholinophenylamino)-7-(4-methoxybenzyl)-6,7-dihydro-5H-pyrrolo[2,3-d]pyrimidin-4-ylamino)-N-methylbenzo[d][1,3]dioxole-5-carboxamide was prepared from 4-chloro-N-(2-methoxy-4-morpholinophenyl)-7-(4-methoxybenzyl)-6,7-dihydro-5H-pyrrolo[2,3-d]pyrimidin-2-amine (80 mg, 0.166 mmol), 4-amino-N-methylbenzo[d][1,3]dioxole-5-carboxamide (Intermediate C2, 39 mg, 0.201 mmol), Pd₂(dba)₃ (30 mg, 0.033 mmol), X-Phos (16 mg, 0.034 mmol) and cesium carbonate (108 mg, 0.331 mmol) heated at 130° C. in a sealed tube for 12 hours, and isolated as a yellow solid (20 mg, yield 19%). ¹H NMR (400 MHz, CDCl₃) δ ppm 8.27-8.29 (d, 1H, J=8.8 Hz), 7.22-7.27 (m, 3H), 7.09-7.11 (d, 1H, J=8.4 Hz), 6.84-6.87 (m, 2H), 6.65-6.67 (d, 1H, J=8.4 Hz), 6.48 (s, 1H), 6.34-6.36 (m, 2H), 5.90 (s, 2H), 4.49 (s, 2H), 3.81-3.87 (m, 7H), 3.78-3.80 (m, 3H), 3.37-3.41 (t, 2H, J=8.0 Hz), 3.07-3.08 (m, 4H), 2.888-2.891 (d, 3H, J=1.2 Hz), 2.79-2.83 (t, 3H, J=8.0 Hz).

Step B 4-(2-(2-methoxy-4-morpholinophenylamino)-6,7-dihydro-5H-pyrrolo[2,3-d]pyrimidin-4-ylamino)-N-methylbenzo[d][1,3]dioxole-5-carboxamide According to General Protocol II, 4-(2-(2-methoxy-4-morpholinophenylamino)-6,7-dihydro-5H-pyrrolo[2,3-d]pyrimidin-4-ylamino)-N-methylbenzo[d][1,3]dioxole-5-carboxamide was prepared from 4-(2-(2-methoxy-4-morpholinophenylamino)-7-(4-methoxybenzyl)-6,7-dihydro-5H-pyrrolo[2,3-d]pyrimidin-4-ylamino)-N-methylbenzo[d][1,3]dioxole-5-carboxamide (20 mg, 0.031 mmol), trifluoroacetic acid (5 mL) and four drops of concentrated sulfuric acid, and isolated as a white solid (6.3 mg, yield 39%). ¹H NMR (400 MHz, CDCl₃) δ ppm 8.29 (s, 1H), 8.15-8.17 (d, 1H, J=8.8 Hz), 7.12 (s, 1H), 7.07-7.09 (d, 1H, J=8.0 Hz), 6.67-6.69 (d, 1H, J=8.0 Hz), 6.46-6.47 (d, 1H, J=2.4 Hz), 6.30-6.33 (dd, 1H, J=1.6 Hz, 8.4 Hz), 6.21-6.22 (d, 1H, J=4.4 Hz), 5.87 (s, 2H), 4.41 (s, 1H), 3.85-3.87 (t, 4H, J=4.8 Hz), 3.82 (s, 3H), 3.61-3.65 (t, 2H, J=8.4 Hz), 3.04-3.07 (t, 4H, J=4.8 Hz), 2.90-2.97 (m, 5H).

Example 3

(2-(2-(2-methoxy-4-morpholinophenylamino)-6,7-dihydro-5H-pyrrolo[2,3-d]pyrimidin-4-ylamino)phenyl)(pyrrolidin-1-yl)methanone

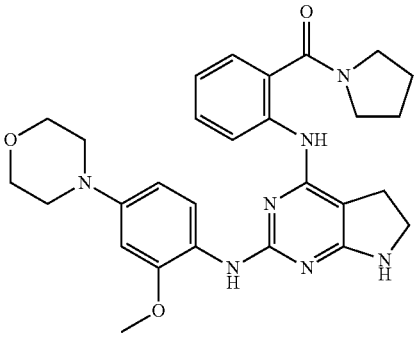 [SMILES: COc1cc(N2CCOCC2)ccc1Nc1nc2c(c(Nc3ccccc3C(=O)N3CCCC3)n1)CCN2]

Step A (2-(2-(2-methoxy-4-morpholinophenylamino)-7-(4-methoxybenzyl)-6,7-dihydro-5H-pyrrolo[2,3-d]pyrimidin-4-ylamino)phenyl)(pyrrolidin-1-yl)methanone

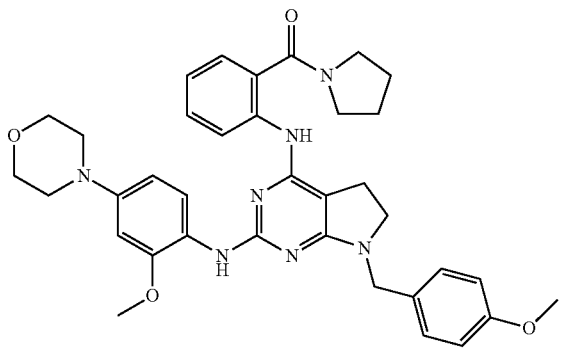 [SMILES: COc1ccc(CN2CCc3c(Nc4ccccc4C(=O)N4CCCC4)nc(Nc4ccc(N5CCOCC5)cc4OC)nc32)cc1]

According to General Protocol II, (2-(2-(2-methoxy-4-morpholinophenylamino)-7-(4-methoxybenzyl)-6,7-dihydro-5H-pyrrolo[2,3-d]pyrimidin-4-ylamino)phenyl)(pyrrolidin-1-yl)methanone was prepared from 4-chloro-N-(2-methoxy-4-morpholinophenyl)-7-(4-methoxybenzyl)-6,7-dihydro-5H-pyrrolo[2,3-d]pyrimidin-2-amine (120 mg, 0.25 mmol), (2-aminophenyl)(pyrrolidin-1-yl)methanone hydrochloride (Intermediate C3, 68 mg, 0.30 mmol), Pd$_2$(dba)$_3$ (92 mg, 0.101 mmol), (±)-BINAP (62 mg, 0.10 mmol) and cesium carbonate (325 mg, 1.0 mmol) heated at 130° C. in a sealed tube for 12 hours, and isolated as a yellow solid (60 mg, yield 38%). $^1$H NMR (400 MHz, CDCl$_3$) δ ppm 8.61 (s, 1H), 8.45-8.47 (d, 1H, J=8.4 Hz), 8.37-8.39 (d, 1H, J=8.8 Hz), 7.32-7.38 (m, 2H), 7.23-7.24 (m, 2H), 6.92-6.95 (t, 1H, J=7.2 Hz), 6.85-6.87 (d, 2H, J=8.4 Hz), 6.525-6.531 (d, 1H, J=2.4 Hz), 6.46-6.49 (dd, 1H, J=2.4 Hz, 8.4 Hz), 4.52 (s, 2H), 3.86-3.88 (s+m, 7H), 3.80 (s, 3H), 3.61-3.64 (t, 2H, J=7.2 Hz), 3.52-3.53 (m, 2H), 3.39-3.43 (t, 2H, J=7.6 Hz), 3.09-3.11 (t, 4H, J=4.8 Hz), 2.80-2.84 (t, 2H, J=8.4 Hz), 1.94-1.96 (m, 2H), 1.85-1.86 (m, 2H).

Step B (2-(2-(2-methoxy-4-morpholinophenylamino)-6,7-dihydro-5H-pyrrolo[2,3-d]pyrimidin-4-ylamino) phenyl)(pyrrolidin-1-yl)methanone According to General Protocol II, (2-(2-(2-methoxy-4-morpholinophenylamino)-6,7-dihydro-5H-pyrrolo[2,3-d] pyrimidin-4-ylamino) phenyl)(pyrrolidin-1-yl)methanone was prepared from (2-(2-(2-methoxy-4-morpholinophenylamino)-7-(4-methoxybenzyl)-6,7-dihydro-5H-pyrrolo[2,3-d]pyrimidin-4-ylamino)phenyl)(pyrrolidin-1-yl)methanone (80 mg, 0.126 mmol), trifluoroacetic acid (6 mL) and five drops of concentrated sulfuric acid, and isolated as a white solid (56 mg, yield 86%). $^1$H NMR (400 MHz, DMSO-d6) δ ppm 8.58 (s, 1H), 8.08-8.10 (d, 1H, J=8.0 Hz), 7.89-7.91 (d, 1H, J=8.8 Hz), 7.39-7.41 (d, 1H, J=7.6 Hz), 7.30-7.32 (m, 1H), 7.06 (s, 1H), 6.96-6.99 (t, 1H, J=7.6 Hz), 6.59-6.60 (d, 1H, J=2.0 Hz), 6.55 (s, 1H), 6.37-6.40 (dd, 1H, J=2.4 Hz, 8.8 Hz), 3.79 (s, 3H), 3.71-3.73 (t, 4H, J=4.4 Hz), 3.44-3.49 (m, 6H), 3.02-3.05 (t, 4H, J=4.4 Hz), 2.67-2.71 (t, 2H, J=8.4 Hz), 1.74-1.83 (m, 4H).

Example 4

2-(2-(2-methoxy-4-morpholinophenylamino)-6,7-dihydro-5H-pyrrolo[2,3-d]pyrimidin-4-ylamino)-N-methylbenzenesulfonamide

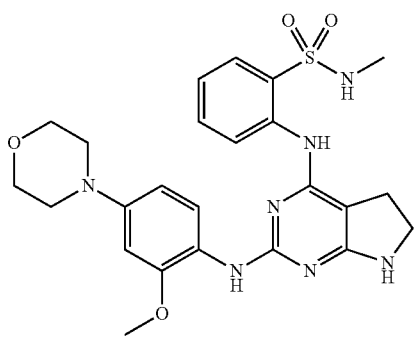 [SMILES: CNS(=O)(=O)c1ccccc1Nc1nc(Nc2ccc(N3CCOCC3)cc2OC)nc2c1CCN2]

Step A: 2-(2-(2-methoxy-4-morpholinophenylamino)-7-(4-methoxybenzyl)-6,7-dihydro-5H-pyrrolo[2,3-d]pyrimidin-4-ylamino)-N-methylbenzenesulfonamide

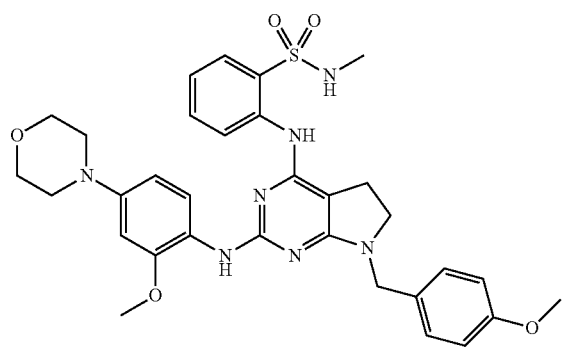 [SMILES: CNS(=O)(=O)c1ccccc1Nc1nc(Nc2ccc(N3CCOCC3)cc2OC)nc2c1CCN2Cc1ccc(OC)cc1]

According to General Protocol II, 2-(2-(2-methoxy-4-morpholinophenylamino)-7-(4-methoxybenzyl)-6,7-dihydro-5H-pyrrolo[2,3-d]pyrimidin-4-ylamino)-N-methylbenzenesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (100 mg, 0.208 mmol), 2-amino-N-methylbenzenesulfonamide (Intermediate C4, 46 mg, 0.25 mmol), Pd$_2$(dba)$_3$ (38 mg, 0.042 mmol), (±)-BINAP (26 mg, 0.042 mmol) and cesium carbonate (136 mg, 0.416 mmol) heated at 130° C. in a sealed tube for 24 hours, and isolated as a solid (94 mg, yield 72%).

Step B: 2-(2-(2-methoxy-4-morpholinophenylamino)-6,7-dihydro-5H-pyrrolo[2,3-d]pyrimidin-4-ylamino)-N-methylbenzenesulfonamide According to General Protocol II, 2-(2-(2-methoxy-4-morpholinophenylamino)-6,7-dihydro-5H-pyrrolo[2,3-d] pyrimidin-4-ylamino) -N-methylbenzenesulfonamide was prepared from 2-(2-(2-methoxy-4-morpholinophenylamino)-7-(4-methoxybenzyl)-6,7-dihydro-5H-pyrrolo[2,3-d]pyrimidin-4-ylamino)-N-methylbenzenesulfonamide (94 mg, 0.149 mmol), trifluoroacetic acid (10 mL) and six drops of concentrated sulfuric acid, and isolated as a white solid (65 mg, yield 70%). $^1$H NMR (400 MHz, DMSO-d6) δ ppm 8.49 (m, 1H), 8.32 (s, 1H), 7.75-7.78 (m, 2H), 7.69-7.71 (d, 1H, J=8.0 Hz), 7.47-7.51 (t, 1H, J=7.6 Hz), 7.27 (s, 1H), 7.07 (m, 1H), 6.75 (s, 1H), 6.63-6.64 (d, 1H, J=2.8 Hz), 6.43-6.46 (dd, 1H, J=2.4 Hz, 8.8 Hz), 3.81 (s, 3H), 3.74-3.76 (m, 4H), 3.51-3.55 (t, 2H, J=8.4 Hz), 3.07-3.09 (t, 4H, J=4.8 Hz), 2.77-2.81 (t, 2H, J=8.0 Hz), 2.42-2.43 (d, 3H, J=5.2 Hz).

Example 5

2-(2-(2-methoxy-4-morpholinophenylamino)-6,7-dihydro-5H-pyrrolo[2,3-d]pyrimidin-4-ylamino)-N-propylbenzenesulfonamide

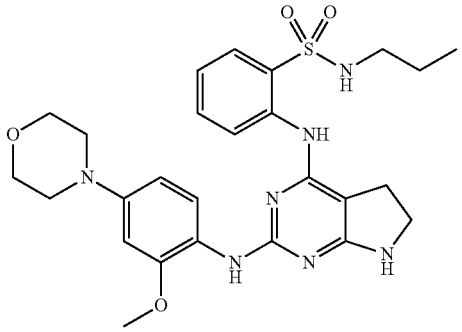 [SMILES: CCCNS(=O)(=O)c1ccccc1Nc1nc(Nc2ccc(N3CCOCC3)cc2OC)nc2c1CCN2]

Step A: 2-(2-(2-methoxy-4-morpholinophenylamino)-7-(4-methoxybenzyl)-6,7-dihydro-5H-pyrrolo[2,3-d]pyrimidin-4-ylamino)-N-propylbenzenesulfonamide

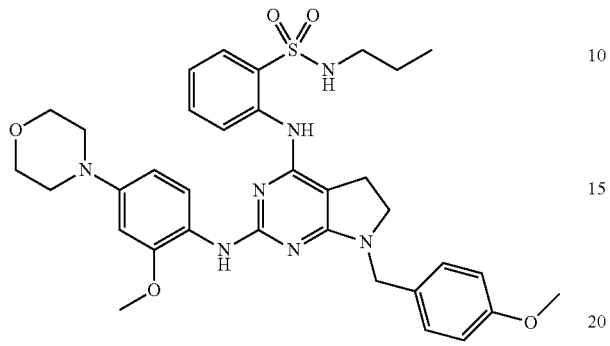

According to General Protocol II, 2-(2-(2-methoxy-4-morpholinophenylamino)-7-(4-methoxybenzyl)-6,7-dihydro-5H-pyrrolo[2,3-d]pyrimidin-4-ylamino)-N-propyl-benzenesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (100 mg, 0.207 mmol), 2-amino-N-propylbenzenesulfonamide hydrochloride (Intermediate C5, 62 mg, 0.247 mmol), Pd$_2$(dba)$_3$ (38 mg, 0.042 mmol), (±)-BINAP (26 mg, 0.042 mmol) and cesium carbonate (271 mg, 0.831 mmol) heated at 130° C. in a sealed tube for 12 hours, and isolated as a yellow solid (40 mg, yield 29%). $^1$H NMR (400 MHz, CDCl$_3$) δ ppm 8.31-8.35 (m, 2H), 7.92 (s, 1H), 7.84-7.86 (dd, 1H, J=1.2 Hz, 8.0 Hz), 7.49-7.53 (m, 1H), 7.23-7.26 (m, 3H), 7.05-7.09 (m, 1H), 6.85-6.88 (m, 2H), 6.52-6.53 (d, 1H, J=2.8 Hz), 6.40-6.43 (dd, 1H, J=2.8 Hz, 8.8 Hz), 4.60-4.63 (t, 1H, J=6.0 Hz), 4.52 (s, 2H), 3.86-3.89 (m, 7H), 3.80 (s, 3H), 3.41-3.45 (t, 2H, J=8.4 Hz), 3.08-3.11 (m, 4H), 2.78-2.87 (m, 4H), 1.37-1.43 (m, 2H), 0.75-0.79 (t, 3H, J=7.2 Hz).

Step B: 2-(2-(2-methoxy-4-morpholinophenylamino)-6,7-dihydro-5H-pyrrolo[2,3-d]pyrimidin-4-ylamino)-N-propylbenzenesulfonamide According to General Protocol II, 2-(2-(2-methoxy-4-morpholinophenylamino)-6,7-dihydro-5H-pyrrolo[2,3-d]pyrimidin-4-ylamino)-N-propylbenzenesulfonamide was prepared from 2-(2-(2-methoxy-4-morpholinophenylamino)-7-(4-methoxybenzyl)-6,7-dihydro-5H-pyrrolo[2,3-d]pyrimidin-4-ylamino)-N-propylbenzenesulfonamide (40 mg, 0.061 mmol), trifluoroacetic acid (4 mL) and three drops of concentrated sulfuric acid, and isolated as a white solid (16 mg, yield 48%). $^1$H NMR (400 MHz, DMSO-d6) δ ppm 8.42-8.44 (d, 1H, J=8.8 Hz), 8.28 (s, 1H), 7.84-7.85 (m, 1H), 7.77-7.79 (d, 1H, J=8.8 Hz), 7.68-7.70 (d, 1H, J=7.6 Hz), 7.43-7.45 (m, 1H), 7.22 (s, 1H), 7.02-7.06 (t, 1H, J=7.6 Hz), 6.71 (s, 1H), 6.60-6.61 (d, 1H, J=2.4 Hz), 6.40-6.42 (dd, 1H, J=2.4 Hz, 8.8 Hz), 3.79 (s, 3H), 3.71-3.74 (m, 4H), 3.49-3.53 (m, 2H), 3.04-3.06 (m, 4H), 2.76-2.80 (t, 2H, J=8.4 Hz), 2.68-2.73 (m, 2H), 1.30-1.35 (m, 2H), 0.70-0.73 (t, 3H, J=7.6 Hz).

Example 6

N-cyclobutyl-2-(2-(2-methoxy-4-morpholinophenylamino)-6,7-dihydro-5H-pyrrolo[2,3-d]pyrimidin-4-ylamino)benzenesulfonamide

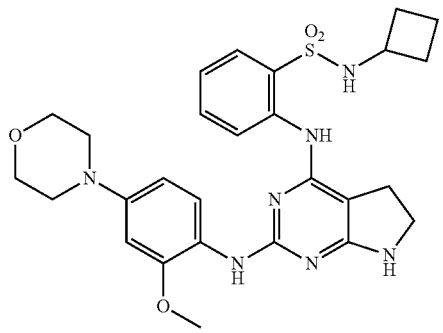 [SMILES: COc1cc(N2CCOCC2)ccc1Nc1nc2c(c(Nc3ccccc3S(=O)(=O)NC3CCC3)n1)CCN2]

Step A: N-cyclobutyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide

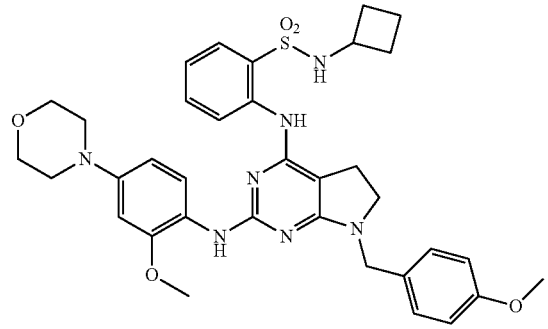 [SMILES: COc1ccc(CN2CCc3c(Nc4ccccc4S(=O)(=O)NC4CCC4)nc(Nc4ccc(N5CCOCC5)cc4OC)nc32)cc1]

According to General Protocol II, N-cyclobutyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (100 mg, 0.208 mmol), 2-amino-N-cyclobutylbenzenesulfonamide (Intermediate C6, 56 mg, 0.248 mmol), Pd$_2$(dba)$_3$ (38 mg, 0.042 mmol), X-Phos (20 mg, 0.042 mmol) and cesium carbonate (136 mg, 0.416 mmol) heated at 130° C. in a sealed tube for 12 hours, and isolated as a white solid (100 mg, yield 71%). $^1$H NMR (400 MHz, CDCl$_3$) δ ppm 8.28-8.35 (dd, 2H, J=8.8 Hz, 19.2 Hz), 7.83-7.89 (m, 2H), 7.48-7.52 (t, 1H, J=8.0 Hz), 7.25-7.27 (m, 3H), 7.04-7.08 (t, 1H, J=7.6 Hz), 6.86-6.88 (m, 2H), 6.53 (s, 1H), 6.38-6.40 (d, 1H, J=8.8 Hz), 4.87-4.89 (d, 1H, J=8.8 Hz), 4.54 (s, 2H), 3.86-3.89 (m, 7H), 3.80 (s, 3H), 3.71-3.73 (m, 1H), 3.43-3.47 (t, 2H, J=8.4 Hz), 3.08-3.10 (m, 4H), 2.80-2.84 (t, 2H, J=8.0 Hz), 1.95-2.02 (m, 2H), 1.69-1.76 (m, 2H), 1.45-1.52 (m, 2H).

Step B: N-cyclobutyl-2-(2-(2-methoxy-4-morpholinophenylamino)-6,7-dihydro-5H-pyrrolo[2,3-d]pyrimidin-4-ylamino)benzenesulfonamide According to General Protocol II, N-cyclobutyl-2-(2-(2-methoxy-4-morpholinophenylamino)-6,7-dihydro-5H-pyrrolo[2,3-d]pyrimidin-4-ylamino)benzenesulfonamide was prepared from N-cyclobutyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide (100 mg, 0.181 mmol), trifluoroacetic acid (6 mL) and five drops of concentrated sulfuric acid, and isolated as a white solid (39.8 mg, yield 49%). $^1$H NMR (400 MHz, DMSO-d6) δ ppm 8.42-8.44 (d, 1H, J=8.4 Hz), 8.30 (s, 1H), 8.18-8.20 (d, 1H, J=8.8 Hz), 7.80-7.82 (d, 1H, J=8.4 Hz), 7.70-7.72 (dd, 1H, J=1.6 Hz, 8.0 Hz), 7.44-7.48 (m, 1H), 7.02-7.06 (m, 1H), 6.75 (s, 1H), 6.62-6.63 (d, 1H, J=2.4 Hz), 6.40-6.43 (dd, 1H, J=2.4 Hz, 9.2 Hz), 3.81 (s, 3H), 3.73-3.76 (t, 4H, J=4.4 Hz), 3.52-3.61 (m, 3H), 3.06-3.08 (t, 4H, J=4.8 Hz), 2.78-2.83 (t, 2H, J=8.8 Hz), 1.87-1.90 (m, 2H), 1.73-1.87 (m, 2H), 1.45-1.49 (m, 2H).

Example 7

N-cyclopentyl-2-(2-(2-methoxy-4-morpholinophenylamino)-6,7-dihydro-5H-pyrrolo[2,3-d]pyrimidin-4-ylamino)benzenesulfonamide

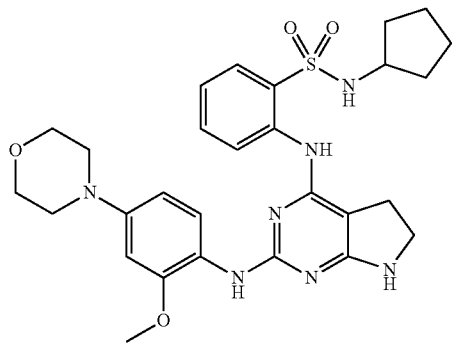 [SMILES: COc1cc(N2CCOCC2)ccc1Nc1nc2c(c(Nc3ccccc3S(=O)(=O)NC3CCCC3)n1)CCN2]

Step A: N-cyclopentyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide

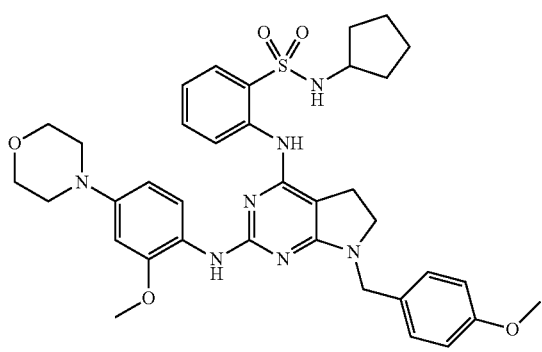 [SMILES: COc1ccc(CN2CCc3c(Nc4ccccc4S(=O)(=O)NC4CCCC4)nc(Nc4ccc(N5CCOCC5)cc4OC)nc32)cc1]

According to General Protocol II, N-cyclopentyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (80 mg, 0.166 mmol), 2-amino-N-cyclopentylbenzenesulfonamide (Intermediate C7, 48 mg, 0.20 mmol), Pd$_2$(dba)$_3$ (30 mg, 0.033 mmol), X-Phos (16 mg, 0.034 mmol) and cesium carbonate (108 mg, 0.331 mmol) heated at 130° C. in a sealed tube for 12 hours, and isolated as a white solid (90 mg, yield 79%). $^1$H NMR (400 MHz, CDCl$_3$) δ ppm 8.32-8.34 (d, 1H, J=8.8 Hz), 8.23-8.25 (d, 1H, J=8.4 Hz), 7.87-7.89 (dd, 1H, J=1.2 Hz, 8.0 Hz), 7.82 (s, 1H), 7.49-7.53 (t, 1H, J=8.0 Hz), 7.25-7.26 (m, 3H), 7.07-7.11 (t, 1H, J=8.0 Hz), 6.86-6.88 (m, 2H), 6.52 (s, 1H), 6.38-6.40 (d, 1H, J=8.8 Hz), 4.53-4.57 (m, 3H), 3.86-3.89 (m, 7H), 3.80 (s, 3H), 3.53-3.54 (m, 1H), 3.42-3.46 (t, 2H, J=8.4 Hz), 3.08-3.10 (t, 4H, J=3.6 Hz), 2.79-2.83 (t, 2H, J=8.4 Hz), 1.65-1.71 (m, 2H), 1.49-1.50 (m, 2H), 1.36-1.40 (m, 2H), 1.24-1.31 (m, 2H).

Step B: N-cyclopentyl-2-(2-(2-methoxy-4-morpholinophenylamino)-6,7-dihydro-5H-pyrrolo[2,3-d]pyrimidin-4-ylamino)benzenesulfonamide According to General Protocol II, N-cyclopentyl-2-(2-(2-methoxy-4-morpholinophenylamino)-6,7-dihydro-5H-pyrrolo[2,3-d]pyrimidin-4-ylamino)benzenesulfonamide was prepared from N-cyclopentyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide (100 mg, 0.146 mmol), trifluoroacetic acid (6 mL) and five drops of concentrated sulfuric acid, and isolated as a white solid (19.6 mg, yield 24%). $^1$H NMR (400 MHz, DMSO-d6) δ ppm 8.39-8.41 (d, 1H, J=8.4 Hz), 8.29 (s, 1H), 7.87-7.89 (d, 1H, J=8.0 Hz), 7.80-7.82 (d, 1H, J=8.8 Hz), 7.73-7.75 (dd, 1H, J=1.6 Hz, 8.0 Hz), 7.46-7.47 (m, 1H), 7.24 (s, 1H), 7.03-7.07 (t, 1H, J=7.6 Hz), 6.75 (s, 1H), 6.62-6.63 (d, 1H, J=2.4 Hz), 6.40-6.43 (dd, 1H, J=2.4 Hz, 8.8 Hz), 3.81 (s, 3H), 3.73-3.76 (t, 4H, J=5.2 Hz), 3.51-3.55 (t, 2H, J=8.4 Hz), 3.43-3.44 (m, 1H), 3.05-3.08 (t, 4H, J=4.8 Hz), 2.77-2.81 (t, 2H, J=8.4 Hz), 1.48-1.60 (m, 4H), 1.24-1.35 (m, 4H).

Example 8

N-cyclohexyl-2-(2-(2-methoxy-4-morpholinophenylamino)-6,7-dihydro-5H-pyrrolo[2,3-d]pyrimidin-4-ylamino)benzenesulfonamide

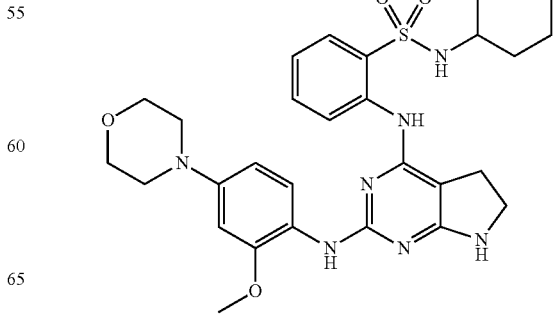

Step A: N-cyclohexyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide

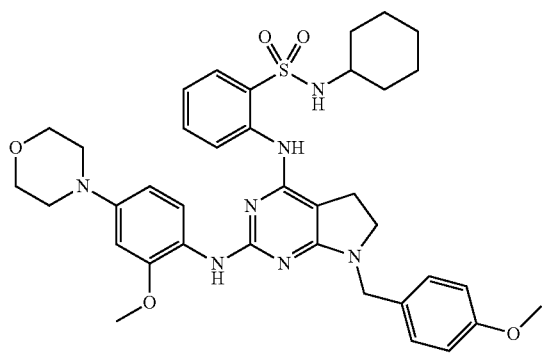 [SMILES: COc1ccc(CN2CCc3c(Nc4ccccc4S(=O)(=O)NC4CCCCC4)nc(Nc4ccc(N5CCOCC5)cc4OC)nc32)cc1]

According to General Protocol II, N-cyclohexyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (80 mg, 0.166 mmol), 2-amino-N-cyclohexylbenzenesulfonamide (Intermediate C8, 51 mg, 0.201 mmol), Pd$_2$(dba)$_3$ (30 mg, 0.033 mmol), X-Phos (16 mg, 0.034 mmol) and cesium carbonate (108 mg, 0.331 mmol) heated at 130° C. in a sealed tube for 12 hours, and isolated as a white solid (100 mg, yield 86%). $^1$H NMR (400 MHz, CDCl$_3$) δ ppm 8.31-8.33 (d, 1H, J=8.0 Hz), 8.20-8.21 (m, 1H), 7.87-7.89 (dd, 1H, J=1.6 Hz, 8.0 Hz), 7.81 (s, 1H), 7.48-7.52 (dt, 1H, J=1.2 Hz, 8.8 Hz), 7.24-7.26 (m, 3H), 7.06-7.10 (m, 1H), 6.85-6.88 (dd, 1H, J=2.0 Hz, 6.8 Hz), 6.516-6.523 (d, 1H, J=2.8 Hz), 6.36-6.39 (dd, 1H, J=2.8 Hz, 8.8 Hz), 4.58-4.60 (d, 1H, J=7.6 Hz), 4.53 (s, 2H), 3.85-3.88 (m, 7H), 3.80 (s, 3H), 3.41-3.45 (t, 2H, J=8.4 Hz), 3.07-3.10 (m, 5H), 2.79-2.83 (t, 2H, J=8.4 Hz), 1.66-1.68 (m, 2H), 1.50-1.53 (m, 2H), 1.24-1.29 (m, 1H), 1.00-1.14 (m, 5H).

Step B: N-cyclohexyl-2-(2-(2-methoxy-4-morpholinophenylamino)-6,7-dihydro-5H-pyrrolo[2,3-d]pyrimidin-4-ylamino)benzenesulfonamide According to General Protocol II, N-cyclohexyl-2-(2-(2-methoxy-4-morpholinophenylamino)-6,7-dihydro-5H-pyrrolo[2,3-d]pyrimidin-4-ylamino)benzenesulfonamide was prepared from N-cyclohexyl-2-(2-(2-methoxy-4-morpholinophenylamino)-7-(4-methoxybenzyl)-6,7-dihydro-5H-pyrrolo[2,3-d]pyrimidin-4-ylamino)benzenesulfonamide (90 mg, 0.129 mmol), trifluoroacetic acid (5 mL) and four drops of concentrated sulfuric acid, and isolated as a white solid (20.1 mg, yield 27%). $^1$H NMR (400 MHz, DMSO-d6) δ ppm 8.32-8.34 (d, 1H, J=7.6 Hz), 8.23 (s, 1H), 7.82-7.88 (m, 2H), 7.75-7.77 (m, 1H), 7.46-7.48 (m, 1H), 7.22 (s, 1H), 7.05-7.09 (t, 1H, J=7.6 Hz), 6.75 (s, 1H), 6.63 (s, 1H), 6.39-6.42 (d, 1H, J=8.8 Hz), 3.81 (s, 3H), 3.75-3.76 (m, 4H), 3.51-3.55 (t, 2H, J=8.4 Hz), 3.07-3.08 (m, 4H), 2.95-2.96 (m, 1H), 2.78-2.82 (t, 2H, J=8.0 Hz), 1.52-1.54 (m, 4H), 1.40-1.42 (m, 1H), 0.99-1.08 (m, 4H), 0.84-0.86 (m, 1H).

Example 9

N-(2-(2-(2-methoxy-4-morpholinophenylamino)-6,7-dihydro-5H-pyrrolo[2,3-d]pyrimidin-4-ylamino)phenyl)acetamide

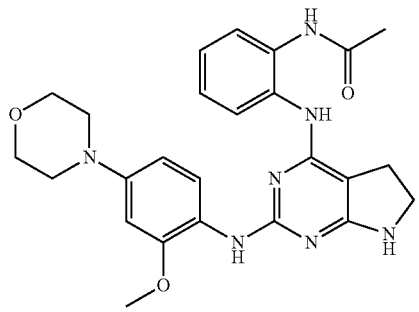 [SMILES: COc1cc(N2CCOCC2)ccc1Nc1nc2c(c(Nc3ccccc3NC(C)=O)n1)CCN2]

Step A: N-(2-(2-(2-methoxy-4-morpholinophenylamino)-7-(4-methoxybenzyl)-6,7-dihydro-5H-pyrrolo[2,3-d]pyrimidin-4-ylamino)phenyl)acetamide

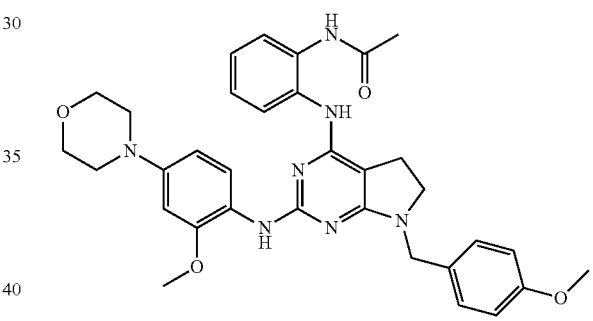

According to General Protocol II, N-(2-(2-(2-methoxy-4-morpholinophenylamino)-7-(4-methoxybenzyl)-6,7-dihydro-5H-pyrrolo[2,3-d]pyrimidin-4-ylamino)phenyl)acetamide was prepared from 4-chloro-N-(2-methoxy-4-morpholinophenyl)-7-(4-methoxybenzyl)-6,7-dihydro-5H-pyrrolo[2,3-d]pyrimidin-2-amine (120 mg, 0.25 mmol), N-(2-aminophenyl)acetamide (Intermediate C9, 41 mg, 0.27 mmol), Pd$_2$(dba)$_3$ (46 mg, 0.05 mmol), (±)-BINAP (31 mg, 0.05 mmol) and cesium carbonate (163 mg, 0.5 mmol) heated at 130° C. in a sealed tube for 24 hours, and isolated as a solid (108 mg, yield 51%).

Step B: N-(2-(2-(2-methoxy-4-morpholinophenylamino)-6,7-dihydro-5H-pyrrolo[2,3-d]pyrimidin-4-ylamino)phenyl)acetamide According to General Protocol II, N-(2-(2-(2-methoxy-4-morpholinophenylamino)-6,7-dihydro-5H-pyrrolo[2,3-d]pyrimidin-4-ylamino)phenyl)acetamide was prepared from N-(2-(2-(2-methoxy-4-morpholinophenylamino)-7-(4-methoxybenzyl)-6,7-dihydro-5H-pyrrolo[2,3-d]pyrimidin-4-ylamino)phenyl)acetamide (60 mg, 0.1 mmol), trifluoroacetic acid (10 mL) and five drops of concentrated sulfuric acid, and isolated as a white solid (10 mg, yield 21%). $^1$H NMR (400 MHz, DMSO-d6) δ ppm 9.75 (s, 1H), 7.72-7.76

(br, 1H), 7.42-7.54 (m, 3H), 7.20 (m, 3H), 6.63 (s, 1H), 6.38 (br s, 1H), 3.81 (s, 3H), 3.73-3.74 (m, 5H), 3.52 (s, 3H), 3.08 (m, 4H), 2.06 (s, 3H).

Example 10

N-(2-(2-(2-methoxy-4-morpholinophenylamino)-6,7-dihydro-5H-pyrrolo[2,3-d]pyrimidin-4-ylamino)phenyl)-N-methylmethanesulfonamide

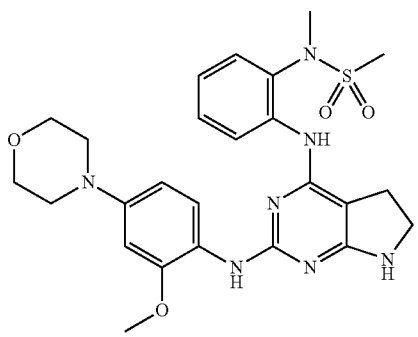 [SMILES: COc1cc(N2CCOCC2)ccc1Nc1nc2c(c(Nc3ccccc3N(C)S(C)(=O)=O)n1)CCN2]

Step A: N-(2-(2-(2-methoxy-4-morpholinophenylamino)-7-(4-methoxybenzyl)-6,7-dihydro-5H-pyrrolo[2,3-d]pyrimidin-4-ylamino)phenyl)-N-methylmethanesulfonamide

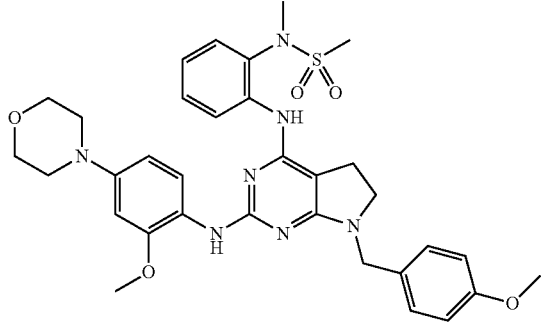 [SMILES: COc1ccc(CN2CCc3c(Nc4ccccc4N(C)S(C)(=O)=O)nc(Nc4ccc(N5CCOCC5)cc4OC)nc32)cc1]

According to General Protocol II, N-(2-(2-(2-methoxy-4-morpholinophenylamino)-7-(4-methoxybenzyl)-6,7-dihydro-5H-pyrrolo[2,3-d]pyrimidin-4-ylamino)phenyl)-N-methylmethanesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (100 mg, 0.208 mmol), N-(2-aminophenyl)-N-methylmethanesulfonamide (Intermediate C10, 50 mg, 0.25 mmol), Pd$_2$(dba)$_3$ (38 mg, 0.042 mmol), (±)-BINAP (26 mg, 0.042 mmol) and cesium carbonate (271 mg, 0.831 mmol) heated at 130° C. in a sealed tube for 12 hours, and isolated as a white solid (70 mg, yield 52%). $^1$H NMR (400 MHz, CDCl$_3$) δ ppm 8.36-8.41 (dd, 2H, J=8.4 Hz, 13.2 Hz), 7.31-7.33 (m, 2H), 7.27-7.28 (m, 3H), 7.15 (s, 1H), 6.99-7.02 (m, 1H), 6.86-6.88 (m, 2H), 6.53 (s, 1H), 6.45-6.47 (d, 1H, J=8.8 Hz), 4.52 (s, 2H), 3.87-3.88 (m, 7H), 3.79 (s, 3H), 3.40-3.45 (t, 2H, J=8.8 Hz), 3.26-3.27 (d, 3H, J=1.6 Hz), 3.09-3.11 (m, 4H), 2.969-2.973 (d, 3H, J=1.6 Hz), 2.82-2.86 (t, 2H, J=8.0 Hz).

Step B: N-(2-(2-(2-methoxy-4-morpholinophenylamino)-6,7-dihydro-5H-pyrrolo[2,3-d]pyrimidin-4-ylamino)phenyl)-N-methylmethanesulfonamide According to General Protocol II, N-(2-(2-(2-methoxy-4-morpholinophenylamino)-6,7-dihydro-5H-pyrrolo[2,3-d]pyrimidin-4-ylamino)phenyl)-N-methylmethanesulfonamide was prepared from N-(2-(2-(2-methoxy-4-morpholinophenylamino)-7-(4-methoxybenzyl)-6,7-dihydro-5H-pyrrolo[2,3-d]pyrimidin-4-ylamino)phenyl)-N-methylmethanesulfonamide (70 mg, 0.108 mmol), trifluoroacetic acid (6 mL) and five drops of concentrated sulfuric acid, and isolated as a white solid (36.4 mg, yield 64%). $^1$H NMR (400 MHz, DMSO-d6) δ ppm 8.13 (m, 1H), 7.79 (m, 1H), 7.51 (m, 1H), 7.04-7.29 (m, 4H), 6.61-6.63 (m, 2H), 6.22 (m, 1H), 3.81 (s, 3H), 3.73-3.76 (t, 4H, J=4.8 Hz), 3.50-3.54 (t, 2H, J=7.6 Hz), 3.17 (s, 3H), 3.07-3.08 (m, 7H), 2.71-2.72 (m, 3H).

Example 11

N-(2-((2-(2-methoxy-4-morpholinophenylamino)-6,7-dihydro-5H-pyrrolo[2,3-d]pyrimidin-4-ylamino)phenyl)-N-methylmethanesulfonamide

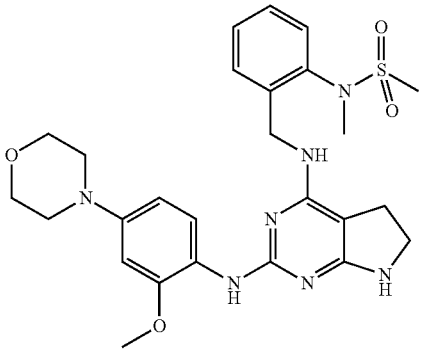 [SMILES: COc1cc(N2CCOCC2)ccc1Nc1nc2c(c(NCc3ccccc3N(C)S(C)(=O)=O)n1)CCN2]

Step A: N-(2-((2-(2-methoxy-4-morpholinophenylamino)-7-(4-methoxybenzyl)-6,7-dihydro-5H-pyrrolo[2,3-d]pyrimidin-4-ylamino)methyl)phenyl)-N-methylmethanesulfonamide

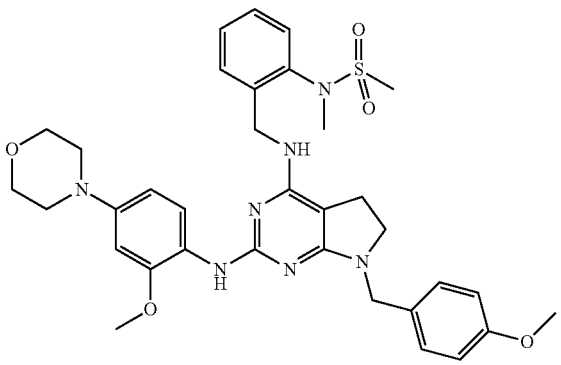 [SMILES: COc1ccc(CN2CCc3c(NCc4ccccc4N(C)S(C)(=O)=O)nc(Nc4ccc(N5CCOCC5)cc4OC)nc32)cc1]

According to General Protocol II, N-(2-((2-(2-methoxy-4-morpholinophenylamino)-7-(4-methoxybenzyl)-6,7-dihydro-5H-pyrrolo[2,3-d]pyrimidin-4-ylamino)methyl)phenyl)-N-methylmethanesulfonamide was prepared from 4-chloro-N-(2-methoxy-4-morpholinophenyl)-7-(4-methoxybenzyl)-6,7-dihydro-5H-pyrrolo[2,3-d]pyrimidin-2-amine (120 mg, 0.25 mmol), N-(2-(aminomethyl)phenyl)-N-methylmethanesulfonamide hydrochloride (Intermediate C11, 62 mg, 0.25 mmol), Pd$_2$(dba)$_3$ (23 mg, 0.025 mmol), X-Phos (31 mg, 0.05 mmol) and cesium carbonate (325 mg, 1.0 mmol) heated at 130° C. in a sealed tube for 24 hours, and isolated as a solid (20 mg, yield 12%).

Step B: N-(2-((2-(2-methoxy-4-morpholinophenylamino)-6,7-dihydro-5H-pyrrolo[2,3-d]pyrimidin-4-ylamino)methyl)phenyl)-N-methylmethanesulfonamide According to General Protocol II, N-(2-((2-(2-methoxy-4-morpholinophenylamino)-6,7-dihydro-5H-pyrrolo[2,3-d]pyrimidin-4-ylamino)methyl)phenyl)-N-methylmethanesulfonamide was prepared from N-(2-((2-(2-methoxy-4-morpholinophenylamino)-7-(4-methoxybenzyl)-6,7-dihydro-5H-pyrrolo[2,3-d]pyrimidin-4-ylamino)methyl)phenyl)-N-methylmethanesulfonamide (20 mg, 0.303 mmol), trifluoroacetic acid (4 mL) and one drops of concentrated sulfuric acid, and isolated as a white solid (0.63 mg, yield 4%). $^1$H NMR (400 MHz, CD$_3$OD) δ ppm 7.92-7.94 (d, 1H, J=8.0 Hz), 7.78-7.81 (m, 1H), 7.58-7.62 (m, 1H), 7.46-7.53 (m, 2H), 7.33-7.35 (m, 2H), 6.58-6.60 (m, 1H), 6.35-6.37 (d, 1H, J=8.8 Hz), 4.56 (s, 1H), 3.81-3.85 (m, 7H), 3.56-3.63 (m, 3H), 3.18 (m, 2H), 3.04-3.05 (m, 7H), 2.80-2.84 (t, 2H, J=8.4 Hz).

Example 12

N$^2$-(2-methoxy-4-morpholinophenyl)-N$^4$-(6-methylpyridin-2-yl)-6,7-dihydro-5H-pyrrolo[2,3-d]pyrimidine-2,4-diamine

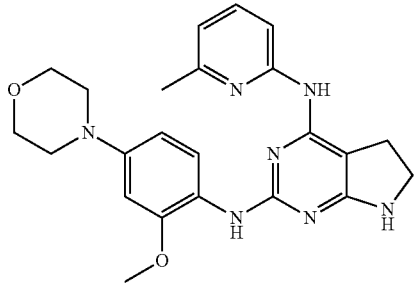 [SMILES: COc1cc(N2CCOCC2)ccc1Nc1nc2c(c(Nc3cccc(C)n3)n1)CCN2]

Step A: N$^2$-(2-methoxy-4-morpholinophenyl)-7-(4-methoxybenzyl)-N$^4$-(6-methylpyridin-2-yl)-6,7-dihydro-5H-pyrrolo[2,3-d]pyrimidine-2,4-diamine

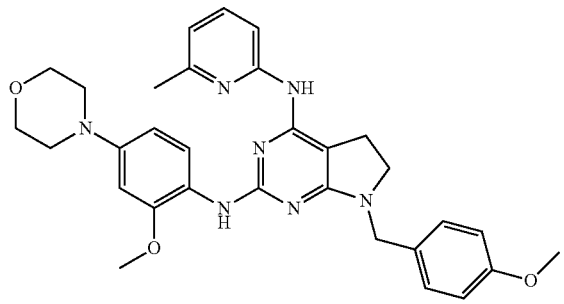 [SMILES: COc1ccc(CN2CCc3c(Nc4cccc(C)n4)nc(Nc4ccc(N5CCOCC5)cc4OC)nc32)cc1]

According to General Protocol II, N$^2$-(2-methoxy-4-morpholinophenyl)-7-(4-methoxybenzyl)-N$^4$-(6-methylpyridin-2-yl)-6,7-dihydro-5H-pyrrolo[2,3-d]pyrimidine-2,4-diamine was prepared from 4-chloro-N-(2-methoxy-4-morpholinophenyl)-7-(4-methoxybenzyl)-6,7-dihydro-5H-pyrrolo[2,3-d]pyrimidin-2-amine (100 mg, 0.208 mmol), 6-methylpyridin-2-amine (commercial available, 29 mg, 0.266 mmol), Pd$_2$(dba)$_3$ (21 mg, 0.022 mmol), (±)-BINAP (28 mg, 0.044 mmol) and cesium carbonate (144 mg, 0.44 mmol) heated at 125° C. in a sealed tube under microwave for 4 hours, and isolated as a solid (40 mg, yield 33%). $^1$H NMR (400 MHz, CDCl$_3$) δ ppm 7.98-8.00 (d, 1H, J=8.4 Hz), 7.84 (br, 1H), 7.47-7.51 (t, 1H, J=8.0 Hz), 7.39-7.43 (t, 1H, J=8.0 Hz), 7.20-7.22 (m, 3H), 6.86-6.88 (m, 2H), 6.65-6.67 (m, 1H), 6.59-6.61 (m, 1H), 6.46-6.52 (m, 3H), 5.89 (br s, 2H), 4.52 (s, 2H), 3.86-3.89 (m, 6H), 3.80 (s, 3H), 3.48-3.53 (m, 3H), 3.14-3.16 (m, 6H), 2.07-2.11 (m, 3H).

Step B: N$^2$-(2-methoxy-4-morpholinophenyl)-N$^4$-(6-methylpyridin-2-yl)-6,7-dihydro-5H-pyrrolo[2,3-d]pyrimidine-2,4-diamine According to General Protocol II, N$^2$-(2-methoxy-4-morpholinophenyl)-N$^4$-(6-methylpyridin-2-yl)-6,7-dihydro-5H-pyrrolo[2,3-d]pyrimidine-2,4-diamine was prepared from N$^2$-(2-methoxy-4-morpholinophenyl)-7-(4-methoxybenzyl)-N$^4$-(6-methylpyridin-2-yl)-6,7-dihydro-5H-pyrrolo[2,3-d]pyrimidine-2,4-diamine (40 mg, 72.3 mmol), trifluoroacetic acid (5 mL) and two drops of concentrated sulfuric acid, and isolated as a white solid (3.6 mg, yield 11.5%). $^1$H NMR (400 MHz, CDCl$_3$) δ ppm 8.02-8.04 (d, 2H, J=8.4 Hz), 7.50-7.51 (m, 1H), 7.19 (br s, 1H), 6.71-6.73 (d, 1H, J=7.2 Hz), 6.48-6.51 (m, 3H), 3.84-3.88 (m, 7H), 3.64-3.68 (t, 2H, J=8.0 Hz), 3.05-3.12 (m, 6H), 2.31 (br, 3H).

Example 13

N$^4$-(3,4-difluorophenyl)-N$^2$-(2-methoxy-4-morpholinophenyl)-6,7-dihydro-5H-pyrrolo[2,3-d]pyrimidine-2,4-diamine

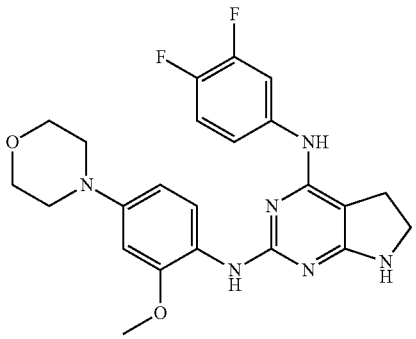 [SMILES: COc1cc(N2CCOCC2)ccc1Nc1nc2c(c(Nc3ccc(F)c(F)c3)n1)CCN2]

Step A: N$^4$-(3,4-difluorophenyl)-N$^2$-(2-methoxy-4-morpholinophenyl)-7-(4-methoxybenzyl)-6,7-dihydro-5H-pyrrolo[2,3-d]pyrimidine-2,4-diamine

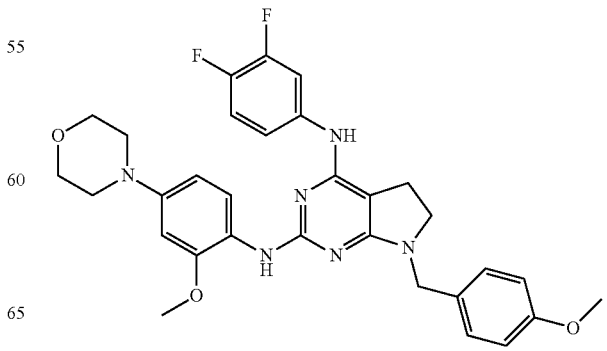

According to General Protocol II, N⁴-(3,4-difluorophenyl)-N²-(2-methoxy-4-morpholinophenyl)-7-(4-methoxybenzyl)-6,7-dihydro-5H-pyrrolo[2,3-d]pyrimidine-2,4-diamine was prepared from 4-chloro-N-(2-methoxy-4-morpholinophenyl)-7-(4-methoxybenzyl)-6,7-dihydro-5H-pyrrolo[2,3-d]pyrimidin-2-amine (90 mg, 0.187 mmol), 3,4-difluoroaniline (commercial available, 29 mg, 0.225 mmol), Pd₂(dba)₃ (34 mg, 0.037 mmol), (±)-BINAP (23 mg, 0.037 mmol) and cesium carbonate (122 mg, 0.374 mmol) heated at 130° C. in a sealed tube for 12 hours, and isolated as a yellow solid (46 mg, yield 43%). ¹H NMR (400 MHz, CDCl₃) δ ppm 8.29-8.31 (d, 1H, J=8.8 Hz), 7.57-7.58 (m, 1H), 7.23-7.26 (m, 2H), 7.15 (s, 1H), 7.01-7.06 (m, 1H), 6.92-6.94 (m, 1H), 6.85-6.87 (m, 2H), 6.49-6.53 (dt, 2H, J=2.4 Hz, 8.4 Hz), 5.82 (s, 1H), 4.52 (s, 2H), 3.86-3.89 (m, 7H), 3.80 (s, 3H), 3.37-3.42 (t, 2H, J=8.8 Hz), 3.10-3.12 (t, 4H, J=4.8 Hz), 2.66-2.71 (t, 2H, J=8.4 Hz).

Step B: N⁴-(3,4-difluorophenyl)-N²-(2-methoxy-4-morpholinophenyl)-6,7-dihydro-5H-pyrrolo[2,3-d]pyrimidine-2,4-diamine According to General Protocol II, N⁴-(3,4-difluorophenyl)-N²-(2-methoxy-4-morpholinophenyl)-6,7-dihydro-5H-pyrrolo[2,3-d]pyrimidine-2,4-diamine was prepared from N⁴-(3,4-difluorophenyl)-N²-(2-methoxy-4-morpholinophenyl)-7-(4-methoxybenzyl)-6,7-dihydro-5H-pyrrolo[2,3-d]pyrimidine-2,4-diamine (46 mg, 0.080 mmol), trifluoroacetic acid (5 mL) and three drops of concentrated sulfuric acid, and isolated as a white solid (2.9 mg, yield 8%). ¹H NMR (400 MHz, DMSO-d6) δ ppm 8.27 (s, 1H), 7.82-7.87 (m, 1H), 7.72-7.74 (d, 1H, J=8.8 Hz), 7.19-7.25 (m, 2H), 7.12 (s, 1H), 6.596-6.603 (d, 1H, J=2.8 Hz), 6.40-6.41 (d, 1H, J=2.4 Hz), 6.38-6.41 (dd, 1H, J=2.4 Hz, 8.8 Hz), 3.78 (s, 3H), 3.71-3.74 (m, 4H), 3.43-3.47 (m, 2H), 3.03-3.05 (t, 4H, J=4.8 Hz), 2.79-2.83 (t, 2H, J=8.4 Hz).

Example 14

2-(2-(2-(hydroxymethyl)-4-morpholinophenylamino)-6,7-dihydro-5H-pyrrolo[2,3-d]pyrimidin-4-ylamino)-N-methylbenzamide

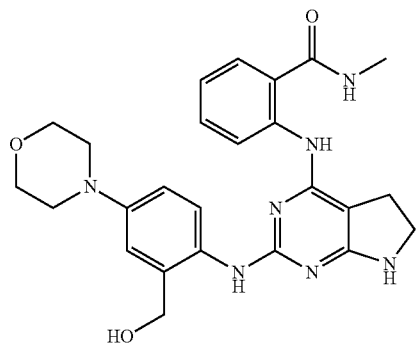 [SMILES: CNC(=O)c1ccccc1Nc1nc(Nc2ccc(N3CCOCC3)cc2CO)nc2c1CCN2]

Step A: N-(2-((tert-butyldimethylsilyloxy)methyl)-4-morpholinophenyl)-4-chloro-7-(4-methoxybenzyl)-6,7-dihydro-5H-pyrrolo[2,3-d]pyrimidin-2-amine

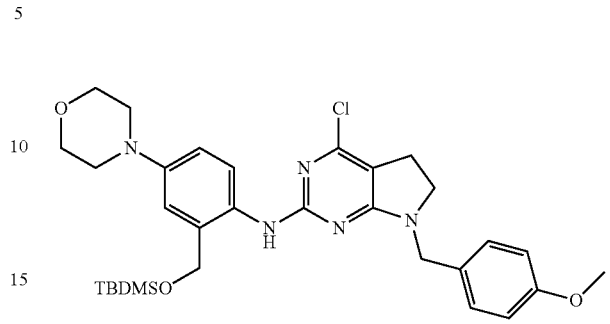

According to General Protocol II, N-(2-((tert-butyldimethylsilyloxy)methyl)-4-morpholinophenyl)-4-chloro-7-(4-methoxybenzyl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 1 g, 3.2 mmol), 2-((tert-butyldimethylsilyloxy)methyl)-4-morpholinoaniline (Intermediate B2, 1.14 g, 3.5 mmol), Pd₂(dba)₃ (146 mg, 0.16 mmol), (±)-BINAP (200 mg, 0.32 mmol) and cesium carbonate (2.08 g, 6.2 mmol), and isolated as a solid (0.5 g, yield 26.3%).

Step B: 2-(2-(2-((tert-butyldimethylsilyloxy)methyl)-4-morpholinophenylamino)-7-(4-methoxybenzyl)-6,7-dihydro-5H-pyrrolo[2,3-d]pyrimidin-4-ylamino)-N-methylbenzamide

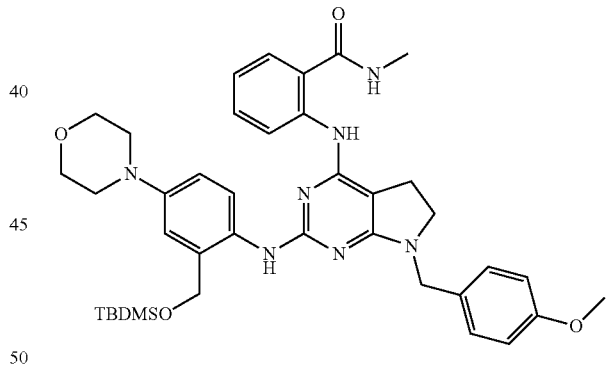

According to General Protocol II, 2-(2-(2-((tert-butyldimethylsilyloxy)methyl)-4-morpholinophenylamino)-7-(4-methoxybenzyl)-6,7-dihydro-5H-pyrrolo[2,3-d]pyrimidin-4-ylamino)-N-methylbenzamide was prepared from N-(2-((tert-butyldimethylsilyloxy)methyl)-4-morpholinophenyl)-4-chloro-7-(4-methoxybenzyl)-6,7-dihydro-5H-pyrrolo[2,3-d]pyrimidin-2-amine (500 mg, 0.84 mmol), 2-amino-N-methylbenzamide (Intermediate C1, 151 mg, 1 mmol), Pd₂(dba)₃ (192 mg, 0.21 mmol), X-Phos (200 mg, 0.42 mmol) and cesium carbonate (546 mg, 1.7 mmol), and isolated as a solid (417 mg, yield 68.8%). ¹H NMR (400 MHz, DMSO-d6) δ ppm 10.79 (s, 1H), 8.57-8.61 (m, 2H), 8.02 (s, 1H), 7.63-7.71 (m, 2H), 7.21-7.23 (m, 3H), 6.96-6.97 (d, 1H, J=2.8 Hz), 6.85-6.91 (m, 4H), 4.72 (s, 2H), 4.41 (s, 2H), 3.74-3.77 (s+m, 7H), 3.32-3.42 (m, 2H), 3.05-3.07 (t, 4H, J=4.8 Hz), 2.75-2.79 (s+m, 5H), 0.89 (s, 9H), 0.06 (s, 6H).

Step C: 2-(2-(2-(hydroxymethyl)-4-morpholinophenylamino)-6,7-dihydro-5H-pyrrolo[2,3-d]pyrimidin-4-ylamino)-N-methylbenzamide According to General Protocol II, 2-(2-(2-(hydroxymethyl)-4-morpholinophenylamino)-6,7-dihydro-5H-pyrrolo[2,3-d]pyrimidin-4-ylamino)-N-methylbenzamide was prepared from 2-(2-(2-((tert-butyldimethylsilyloxy)methyl)-4-morpholinophenylamino)-7-(4-methoxybenzyl)-6,7-dihydro-5H-pyrrolo[2,3-d]pyrimidin-4-ylamino)-N-methylbenzamide (200 mg, 0.282 mmol), trifluoroacetic acid (2 mL) and four drops of concentrated sulfuric acid, and isolated as a solid (30 mg, yield 22.4%). $^1$H NMR (400 MHz, DMSO-d6) δ ppm 10.69 (s, 1H), 8.56-8.58 (m, 2H), 7.94 (s, 1H), 7.61-7.63 (d, 1H, J=6.0 Hz), 7.54-7.57 (d, 1H, J=8.8 Hz), 7.20-7.22 (m, 1H), 6.92-6.93 (d, 1H, J=2.8 Hz), 6.80-6.88 (m, 2H), 6.51 (s, 1H), 5.21-5.23 (t, 1H, J=5.6 Hz), 4.45-4.46 (d, 2H, J=5.2 Hz), 3.73-3.75 (t, 4H, J=4.8 Hz), 3.45-3.51 (m, 2H), 3.03-3.06 (t, 4H, J=4.8 Hz), 2.76-2.80 (m, 5H).

Example 15

2-(2-(2,3-dihydrobenzo[b][1,4]dioxin-5-ylamino)-6,7-dihydro-5H-pyrrolo[2,3-d]pyrimidin-4-ylamino)-N-methylbenzamide

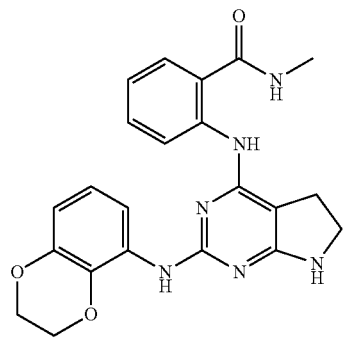 [SMILES: CNC(=O)c1ccccc1Nc1nc(Nc2cccc3c2OCCO3)nc2c1CCN2]

Step A: 4-chloro-N-(2,3-dihydrobenzo[b][1,4]dioxin-5-yl)-7-(4-methoxybenzyl)-6,7-dihydro-5H-pyrrolo[2,3-d]pyrimidin-2-amine

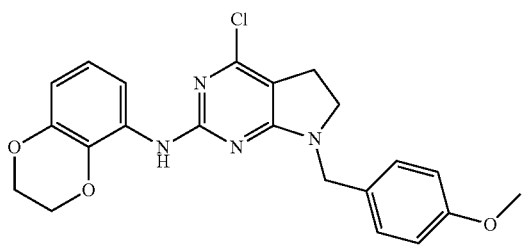 [SMILES: COc1ccc(CN2CCc3c(Cl)nc(Nc4cccc5c4OCCO5)nc32)cc1]

According to General Protocol II, 4-chloro-N-(2,3-dihydrobenzo[b][1,4]dioxin-5-yl)-7-(4-methoxybenzyl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 310 mg, 1.0 mmol), 2,3-dihydrobenzo[b][1,4]dioxin-5-amine (Intermediate B3, 151 mg, 1.0 mmol), Pd$_2$(dba)$_3$ (183 mg, 0.2 mmol), (±)-BINAP (124 mg, 0.2 mmol) and sodium tert-butoxide (192 mg, 2.0 mmol) in a microwave tube at 100° C. for 10 minutes, and isolated as a yellow solid (100 mg, yield 24%). $^1$H NMR (400 MHz, CDCl$_3$) δ ppm 8.10-8.12 (dd, 1H, J=1.2 Hz, 8.4 Hz), 7.22-7.24 (d, 2H, J=8.8 Hz), 6.86-6.88 (dd, 2H, J=2.0 Hz, 6.8 Hz), 6.78-6.83 (t, 1H, J=8.4 Hz), 6.51-6.53 (dd, 1H, J=1.2 Hz, 8.0 Hz), 6.31-6.33 (d, 1H, J=8.0 Hz), 4.54 (s, 2H), 4.25-4.32 (m, 7H), 3.80 (s, 3H), 3.47-3.51 (t, 2H, J=8.4 Hz), 2.91-2.96 (t, 2H, J=8.4 Hz).

Step B: 2-(2-(2,3-dihydrobenzo[b][1,4]dioxin-5-ylamino)-7-(4-methoxybenzyl)-6,7-dihydro-5H-pyrrolo[2,3-d]pyrimidin-4-ylamino)-N-methylbenzamide

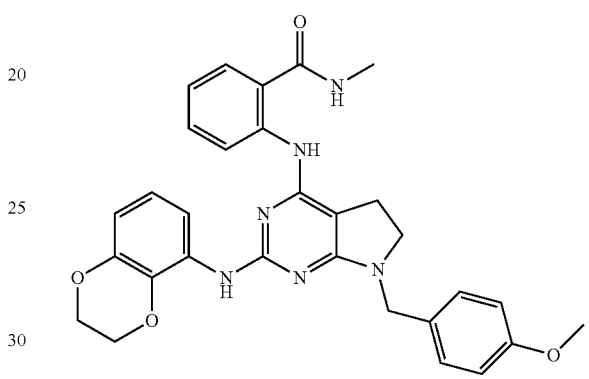

According to General Protocol II, 2-(2-(2,3-dihydrobenzo[b][1,4]dioxin-5-ylamino)-7-(4-methoxybenzyl)-6,7-dihydro-5H-pyrrolo[2,3-d]pyrimidin-4-ylamino)-N-methylbenzamide was prepared from 4-chloro-N-(2,3-dihydrobenzo[b][1,4]dioxin-5-yl)-7-(4-methoxybenzyl)-6,7-dihydro-5H-pyrrolo[2,3-d]pyrimidin-2-amine (100 mg, 0.236 mmol), 2-amino-N-methylbenzamide (Intermediate C1, 42 mg, 0.280 mmol), Pd$_2$(dba)$_3$ (43 mg, 0.047 mmol), X-Phos (22 mg, 0.046 mmol) and cesium carbonate (154 mg, 0.472 mmol) heated at 130° C. for 12 hours, and isolated as a yellow solid (50 mg, yield 39%). $^1$H NMR (400 MHz, CDCl$_3$) δ ppm 10.03 (s, 1H), 8.62-8.64 (d, 1H, J=8.4 Hz), 8.12-8.14 (dd, 1H, J=0.8 Hz, 8.0 Hz), 7.39-7.42 (m, 2H), 7.22-7.26 (m, 2H), 6.85-6.91 (m, 3H), 6.74-6.79 (t, 1H, J=8.4 Hz), 6.48-6.50 (dd, 1H, J=1.6 Hz, 8.4 Hz), 6.21-6.22 (m, 1H), 4.52 (s, 2H), 4.33-4.35 (m, 2H), 4.26-4.28 (m, 2H), 3.78 (s, 3H), 3.42-3.46 (t, 2H, J=8.4 Hz), 2.971-2.974 (d, 3H, J=1.2 Hz), 2.90-2.94 (t, 2H, J=8.4 Hz).

Step C: 2-(2-(2,3-dihydrobenzo[b][1,4]dioxin-5-ylamino)-6,7-dihydro-5H-pyrrolo[2,3-d]pyrimidin-4-ylamino)-N-methylbenzamide According to General Protocol II, 2-(2-(2,3-dihydrobenzo[b][1,4]dioxin-5-ylamino)-6,7-dihydro-5H-pyrrolo[2,3-d]pyrimidin-4-ylamino)-N-methylbenzamide was prepared from 2-(2-(2,3-dihydrobenzo[b][1,4]dioxin-5-ylamino)-7-(4-methoxybenzyl)-6,7-dihydro-5H-pyrrolo[2,3-d]pyrimidin-4-ylamino)-N-methylbenzamide (60 mg, 0.115 mmol), trifluoroacetic acid (6 mL) and four drops of concentrated sulfuric acid, and isolated as a solid (27 mg, yield 69%). $^1$H NMR (400 MHz, DMSO-d6) δ ppm 9.18 (s, 1H), 8.67 (s, 1H), 7.68-7.70 (d, 1H, J=7.6 Hz), 7.36-7.38 (m, 2H), 7.15-7.16 (m, 1H), 6.78-6.85 (m, 2H), 6.74-6.76 (m, 1H), 6.21-6.32 (m, 4H), 2.78-2.79 (d, 3H, J=4.4 Hz), some signals (—CH$_2$CH$_2$—) was overlapped with solvent residual peak.

Example 16

N-methyl-2-(2-(8-morpholino-2,3-dihydrobenzo[b][1,4]dioxin-5-ylamino)-6,7-dihydro-5H-pyrrolo[2,3-d]pyrimidin-4-ylamino)benzamide

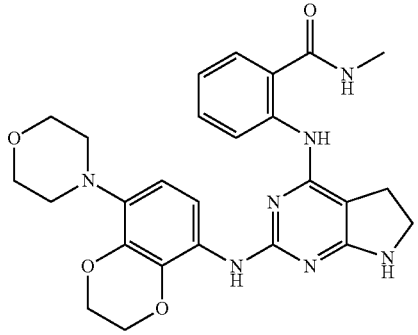 [SMILES: CNC(=O)c1ccccc1Nc1nc(Nc2ccc(N3CCOCC3)c3c2OCCO3)nc2c1CCN2]

Step A: 4-chloro-7-(4-methoxybenzyl)-N-(8-morpholino-2,3-dihydrobenzo[b][1,4]dioxin-5-yl)-6,7-dihydro-5H-pyrrolo[2,3-d]pyrimidin-2-amine

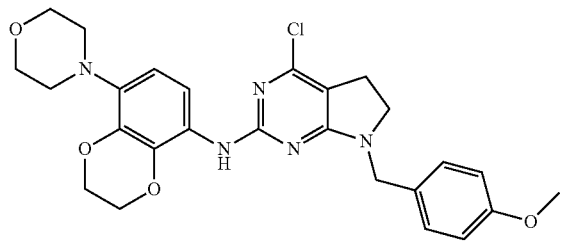 [SMILES: COc1ccc(CN2CCc3c(Cl)nc(Nc4ccc(N5CCOCC5)c5c4OCCO5)nc32)cc1]

According to General Protocol II, 4-chloro-7-(4-methoxybenzyl)-N-(8-morpholino-2,3-dihydrobenzo[b][1,4]dioxin-5-yl)-6,7-dihydro-5H-pyrrolo[2,3-c]pyrimidin-2-amine was prepared from 2,4-dichloro-7-(4-methoxybenzyl)-6,7-dihydro-5H-pyrrolo[2,3-d]pyrimidine (Intermediate A1, 200 mg, 0.645 mmol), 8-morpholino-2,3-dihydrobenzo[b][1,4]dioxin-5-amine (Intermediate B4, 152 mg, 0.644 mmol), Pd$_2$(dba)$_3$ (118 mg, 0.129 mmol), (±)-BINAP (80 mg, 0.129 mmol) and sodium tert-butoxide (124 mg, 1.292 mmol) in a microwave tube at 100° C. for 10 minutes, and isolated as a yellow solid (200 mg, yield 61%). $^1$H NMR (400 MHz, CDCl$_3$) δ ppm 8.01-8.03 (d, 1H, J=8.8 Hz), 7.21-7.24 (d, 2H, J=8.4 Hz), 6.86-6.88 (d, 2H, J=8.8 Hz), 6.51-6.54 (d, 1H, J=8.8 Hz), 4.54 (s, 2H), 4.30-4.34 (m, 4H), 3.86-3.89 (m, 4H), 3.80 (s, 3H), 3.46-3.50 (m, 2H), 3.00-3.03 (m, 4H), 2.91-2.95 (m, 2H).

Step B: 2-(7-(4-methoxybenzyl)-2-(8-morpholino-2,3-dihydrobenzo[b][1,4]dioxin-5-ylamino)-6,7-dihydro-5H-pyrrolo[2,3-d]pyrimidin-4-ylamino)-N-methylbenzamide

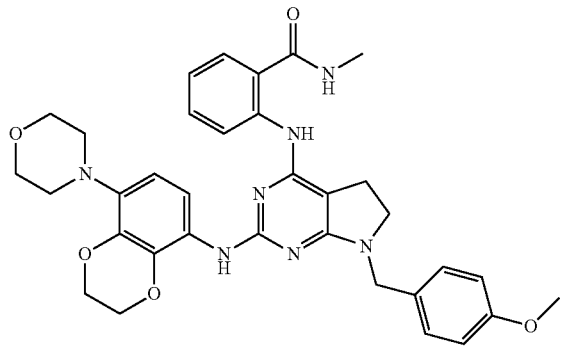 [SMILES: CNC(=O)c1ccccc1Nc1nc(Nc2ccc(N3CCOCC3)c3c2OCCO3)nc2c1CCN2Cc1ccc(OC)cc1]

According to General Protocol II, 2-(7-(4-methoxybenzyl)-2-(8-morpholino-2,3-dihydrobenzo[b][1,4]dioxin-5-ylamino)-6,7-dihydro-5H-pyrrolo[2,3-d]pyrimidin-4-ylamino)-N-methylbenzamide was prepared from 4-chloro-7-(4-methoxybenzyl)-N-(8-morpholino-2,3-dihydrobenzo[b][1,4]dioxin-5-yl)-6,7-dihydro-5H-pyrrolo[2,3-d]pyrimidin-2-amine (200 mg, 0.39 mmol), 2-amino-N-methylbenzamide (Intermediate C1, 71 mg, 0.47 mmol), Pd$_2$(dba)$_3$ (72 mg, 0.079 mmol), X-Phos (37 mg, 0.078 mmol) and cesium carbonate (274 mg, 0.840 mmol) in a microwave tube at 130° C. for 2 hours, and isolated as a white solid (75 mg, yield 31%). $^1$H NMR (400 MHz, CDCl$_3$) δ ppm 10.03 (s, 1H), 8.62-8.64 (d, 1H, J=8.4 Hz), 8.02-8.04 (d, 1H, J=8.8 Hz), 7.38-7.42 (m, 2H), 7.23-7.25 (m, 2H), 7.09 (s, 1H), 6.85-6.92 (m, 3H), 6.47-6.50 (d, 1H, J=8.8 Hz), 6.27-6.29 (d, 1H, J=8.4 Hz), 4.52 (s, 2H), 4.27-4.34 (m, 4H), 3.85-3.90 (m, 4H), 3.80 (s, 3H), 3.41-3.45 (t, 2H, J=8.4 Hz), 3.01-3.03 (m, 3H), 2.95-2.97 (m, 4H), 2.89-2.93 (t, 2H, J=8.4 Hz).

Step C: N-methyl-2-(2-(8-morpholino-2,3-dihydrobenzo[b][1,4]dioxin-5-ylamino)-6,7-dihydro-5H-pyrrolo[2,3-d]pyrimidin-4-ylamino)benzamide According to General Protocol II, N-methyl-2-(2-(8-morpholino-2,3-dihydrobenzo[b][1,4]dioxin-5-ylamino)-6,7-dihydro-5H-pyrrolo[2,3-d]pyrimidin-4-ylamino)benzamide was prepared from 2-(7-(4-methoxybenzyl)-2-(8-morpholino-2,3-dihydrobenzo[b][1,4]dioxin-5-ylamino)-6,7-dihydro-5H-pyrrolo[2,3-d]pyrimidin-4-ylamino)-N-methylbenzamide (75 mg, 0.120 mmol), trifluoroacetic acid (6 mL) and five drops of concentrated sulfuric acid, and isolated as a solid (60 mg, yield 99%). $^1$H NMR (400 MHz, DMSO-d6) δ ppm 11.98 (s, 1H), 10.68 (s, 1H), 8.63-8.64 (m, 2H), 7.66-7.67 (d, 1H, J=7.6 Hz), 7.47-7.49 (d, 1H, J=6.8 Hz), 7.33-7.37 (t, 1H, J=8.0 Hz), 6.93-6.97 (t, 1H, J=7.6 Hz), 6.72 (br s, 1H), 6.42-6.44 (d, 1H, J=8.8 Hz), 4.25-4.28 (m, 4H), 3.71-3.73 (t, 4H, J=4.4 Hz), 3.53-3.57 (t, 2H, J=8.4 Hz), 2.92-2.94 (t, 4H, J=4.4 Hz), 2.78-2.81 (m, 5H).

Example 17

2-(2-(1-ethyl-6-methoxy-2-oxo-2,3,4,5-tetrahydro-1H-benzo[b]azepin-7-ylamino)-6,7-dihydro-5H-pyrrolo[2,3-d]pyrimidin-4-ylamino)-N-methylbenzamide

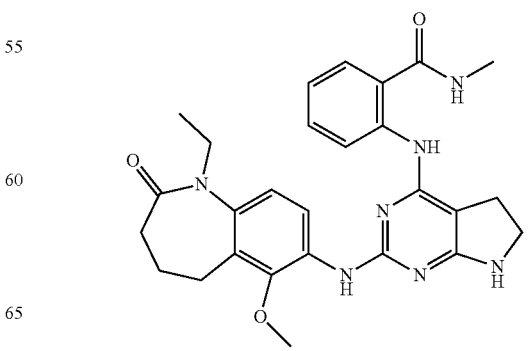

Step A: 7-(4-chloro-7-(4-methoxybenzyl)-6,7-dihydro-5H-pyrrolo[2,3-d]pyrimidin-2-ylamino)-1-ethyl-6-methoxy-4,5-dihydro-1H-benzo[b]azepin-2(3H)-one

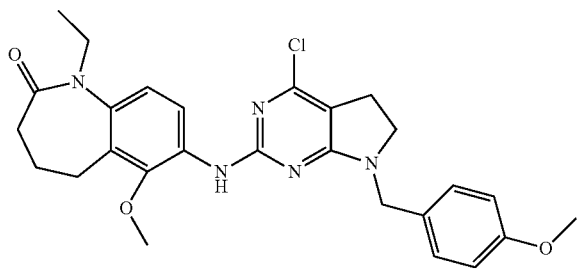 [SMILES: CCN1C(=O)CCCc2c1ccc(Nc1nc(Cl)c3c(n1)N(Cc1ccc(OC)cc1)CC3)c2OC]

According to General Protocol II, 7-(4-chloro-7-(4-methoxybenzyl)-6,7-dihydro-5H-pyrrolo[2,3-d]pyrimidin-2-ylamino)-1-ethyl-6-methoxy-4,5-dihydro-1H-benzo[b]azepin-2(3H)-one was prepared from 2,4-dichloro-7-(4-methoxybenzyl)-6,7-dihydro-5H-pyrrolo[2,3-d]pyrimidine (Intermediate A1, 310 mg, 1.0 mmol), 7-amino-1-ethyl-6-methoxy-4,5-dihydro-1H-benzo[b]azepin-2(3H)-one hydrochloride (Intermediate B5, 271 mg, 1.0 mmol), Pd$_2$(dba)$_3$ (183 mg, 0.2 mmol), (±)-BINAP (124 mg, 0.2 mmol) and cesium carbonate (1.304 g, 4.0 mmol) in a microwave tube at 130° C. for 2 hours, and isolated as a yellow solid (100 mg, yield 20%). $^1$H NMR (400 MHz, CDCl$_3$) δ ppm 8.45-8.48 (dd, 1H, J=2.0 Hz, 9.2 Hz), 7.48 (s, 1H), 7.23-7.27 (m, 2H), 6.96-6.99 (d, 1H, J=8.8 Hz), 6.88-6.90 (t, 2H, J=2.4 Hz), 4.57 (s, 2H), 3.79-3.81 (m, 6H), 3.50-3.54 (t, 3H, J=8.4 Hz), 2.94-2.98 (t, 2H, J=8.4 Hz), 2.29 (s, 3H), 1.11-1.17 (m, 4H), some signals (—CH$_2$CH$_2$CH$_2$—) were overlapped with residual impurity peak.

Step B: 2-(2-(1-ethyl-6-methoxy-2-oxo-2,3,4,5-tetrahydro-1H-benzo[b]azepin-7-ylamino)-7-(4-methoxy benzyl)-6,7-dihydro-5H-pyrrolo[2,3-d]pyrimidin-4-ylamino)-N-methylbenzamide

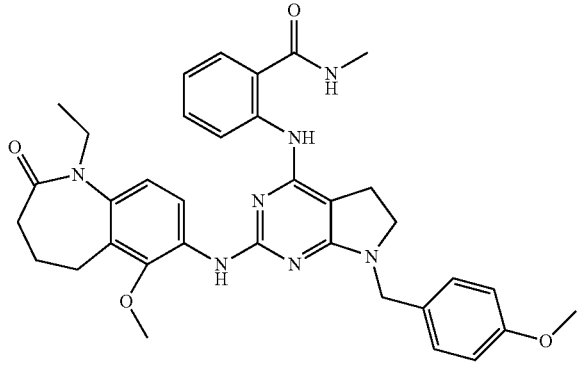 [SMILES: CCN1C(=O)CCCc2c1ccc(Nc1nc(Nc3ccccc3C(=O)NC)c3c(n1)N(Cc1ccc(OC)cc1)CC3)c2OC]

According to General Protocol II, 2-(2-(1-ethyl-6-methoxy-2-oxo-2,3,4,5-tetrahydro-1H-benzo[b]azepin-7-ylamino)-7-(4-methoxy benzyl)-6,7-dihydro-5H-pyrrolo[2,3-d]pyrimidin-4-ylamino)-N-methylbenzamide was prepared from 7-(4-chloro-7-(4-methoxybenzyl)-6,7-dihydro-5H-pyrrolo[2,3-d]pyrimidin-2-ylamino)-1-ethyl-6-methoxy-4,5-dihydro-1H-benzo[b]azepin-2(3H)-one (100 mg, 0.197 mmol), 2-amino-N-methylbenzamide (Intermediate C1, 35 mg, 0.233 mmol), Pd$_2$(dba)$_3$ (36 mg, 0.039 mmol), (±)-BINAP (24 mg, 0.039 mmol) and cesium carbonate (128 mg, 0.393 mmol) heated at 130° C. for 12 hours, and isolated as a white solid (30 mg, yield 25%). $^1$H NMR (400 MHz, CDCl$_3$) δ ppm 10.09 (s, 1H), 8.58-8.61 (d, 1H, J=8.4 Hz), 8.48-8.51 (d, 1H, J=9.2 Hz), 7.52-7.53 (m, 1H), 7.41-7.42 (m, 2H), 7.27-7.30 (m, 1H), 7.24-7.26 (m, 1H), 6.86-6.96 (m, 3H), 4.54 (s, 2H), 3.80-3.82 (m, 6H), 3.45-3.49 (t, 2H, J=8.4 Hz), 2.92-3.00 (m, 5H), 2.29-2.30 (m, 2H), 1.59-1.61 (m, 2H), 1.11-1.15 (t, 3H, J=7.2 Hz), 0.94-0.98 (t, 2H, J=7.6 Hz).

Step C: 2-(2-(1-ethyl-6-methoxy-2-oxo-2,3,4,5-tetrahydro-1H-benzo[b]azepin-7-ylamino)-6,7-dihydro-5H-pyrrolo[2,3-d]pyrimidin-4-ylamino)-N-methylbenzamide According to General Protocol II, 2-(2-(1-ethyl-6-methoxy-2-oxo-2,3,4,5-tetrahydro-1H-benzo[b]azepin-7-ylamino)-6,7-dihydro-5H-pyrrolo[2,3-d]pyrimidin-4-ylamino)-N-methylbenzamide was prepared from 2-(2-(1-ethyl-6-methoxy-2-oxo-2,3,4,5-tetrahydro-1H-benzo[b]azepin-7-ylamino)-7-(4-methoxy benzyl)-6,7-dihydro-5H-pyrrolo[2,3-d]pyrimidin-4-ylamino)-N-methylbenzamide (30 mg, 0.048 mmol), trifluoroacetic acid (6 mL) and three drops of concentrated sulfuric acid, and isolated as a solid (4.7 mg, yield 20%). $^1$H NMR (400 MHz, CD$_3$OD) δ ppm 8.37-8.39 (d, 1H, J=8.4 Hz), 8.27-8.29 (m, 1H), 7.60-7.62 (d, 1H, J=7.6 Hz), 7.37-7.39 (m, 1H), 6.97-6.99 (m, 2H), 3.77-3.78 (m, 3H), 3.64-3.68 (t, 2H, J=8.0 Hz), 2.90-2.96 (m, 5H), 2.20-2.24 (m, 8H), 1.09-1.12 (m, 3H).

Example 18

N-methyl-2-(2-(1-oxoisoindolin-5-ylamino)-6,7-dihydro-5H-pyrrolo[2,3-d]pyrimidin-4-ylamino)benzamide

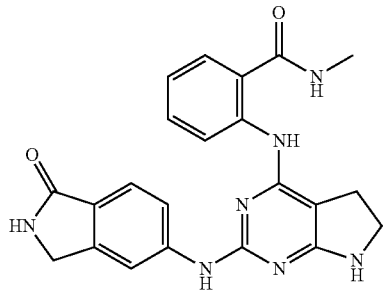 [SMILES: CNC(=O)c1ccccc1Nc1nc(Nc2ccc3c(c2)CNC3=O)nc2c1CCN2]

Step A: 5-(4-chloro-7-(4-methoxybenzyl)-6,7-dihydro-5H-pyrrolo[2,3-d]pyrimidin-2-ylamino)isoindolin-1-one

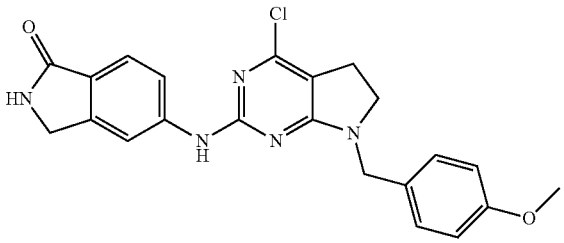 [SMILES: COc1ccc(CN2CCc3c(Cl)nc(Nc4ccc5c(c4)CNC5=O)nc32)cc1]

According to General Protocol II, 5-(4-chloro-7-(4-methoxybenzyl)-6,7-dihydro-5H-pyrrolo[2,3-d]pyrimidin-2-ylamino)isoindolin-1-one was prepared from 2,4-dichloro-7-(4-methoxybenzyl)-6,7-dihydro-5H-pyrrolo[2,3-d]pyrimidine (Intermediate A1, 310 mg, 1.0 mmol), 5-aminoisoindolin-1-one (Intermediate B6, 148 mg, 1.0 mmol), Pd$_2$(dba)$_3$ (183 mg, 0.2 mmol), (±)-BINAP (124 mg, 0.2 mmol) and cesium carbonate (654 mg, 2.01 mmol) in a microwave vessel at 130° C. for 3 hours, and isolated as a yellow solid (80 mg, yield 19%). $^1$H NMR (400 MHz, CDCl$_3$) δ ppm 8.05 (s, 1H), 7.72-7.73 (m, 1H), 7.46-7.48 (d, 2H, J=8.4 Hz), 7.22-7.24 (m, 2H), 6.87-6.89 (d, 2H, J=6.8 Hz), 6.09 (s, 1H), 4.54 (s, 2H), 4.41 (s, 2H), 3.805-3.809 (d, 3H, J=1.6 Hz), 3.54-3.55 (m, 2H), 2.96-2.97 (m, 2H).

Step B: 2-(7-(4-methoxybenzyl)-2-(1-oxoisoindolin-5-ylamino)-6,7-dihydro-5H-pyrrolo[2,3-d]pyrimidin-4-ylamino)-N-methylbenzamide

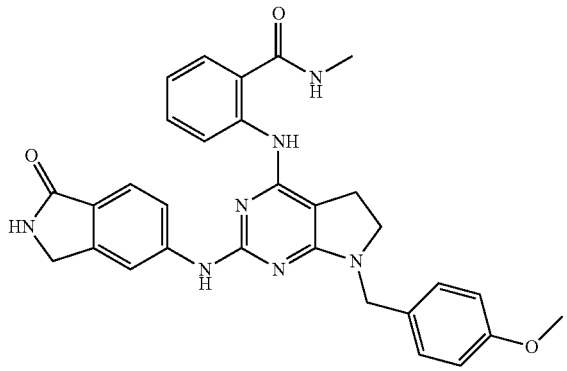 [SMILES: CNC(=O)c1ccccc1Nc1nc(Nc2ccc3c(c2)CNC3=O)nc2c1CCN2Cc1ccc(OC)cc1]

According to General Protocol II, 2-(7-(4-methoxybenzyl)-2-(1-oxoisoindolin-5-ylamino)-6,7-dihydro-5H-pyrrolo[2,3-d]pyrimidin-4-ylamino)-N-methylbenzamide was prepared from 5-(4-chloro-7-(4-methoxybenzyl)-6,7-dihydro-5H-pyrrolo[2,3-d]pyrimidin-2-ylamino)isoindolin-1-one (80 mg, 0.190 mmol), 2-amino-N-methylbenzamide (Intermediate C1, 34 mg, 0.227 mmol), Pd$_2$(dba)$_3$ (35 mg, 0.038 mmol), X-Phos (18 mg, 0.038 mmol) and cesium carbonate (124 mg, 0.380 mmol) heated in a sealed tube at 130° C. for 12 hours, and isolated as a yellow solid (10 mg, yield 10%).

Step C: N-methyl-2-(2-(1-oxoisoindolin-5-ylamino)-6,7-dihydro-5H-pyrrolo[2,3-d]pyrimidin-4-ylamino)benzamide According to General Protocol II, N-methyl-2-(2-(1-oxoisoindolin-5-ylamino)-6,7-dihydro-5H-pyrrolo[2,3-d]pyrimidin-4-ylamino)benzamide was prepared from 2-(7-(4-methoxybenzyl)-2-(1-oxoisoindolin-5-ylamino)-6,7-dihydro-5H-pyrrolo[2,3-d]pyrimidin-4-ylamino)-N-methylbenzamide (10 mg, 0.019 mmol), trifluoroacetic acid (3 mL) and two drops of concentrated sulfuric acid, and isolated as a white solid (1.9 mg, yield 26%). $^1$H NMR (400 MHz, CD$_3$OD) δ ppm 8.45-8.47 (d, 1H, J=8.8 Hz), 8.12 (s, 1H), 7.55-7.63 (m, 3H), 7.40-7.44 (t, 1H, J=8.4 Hz), 7.00-7.04 (t, 1H, J=8.0 Hz), 4.34 (s, 2H), 3.65-3.69 (t, 2H, J=8.4 Hz), 2.94-2.98 (t, 2H, J=8.0 Hz), 2.90 (s, 3H).

Example 19

2-(2-(benzofuran-7-ylamino)-6,7-dihydro-5H-pyrrolo[2,3-d]pyrimidin-4-ylamino)-N-methylbenzamide

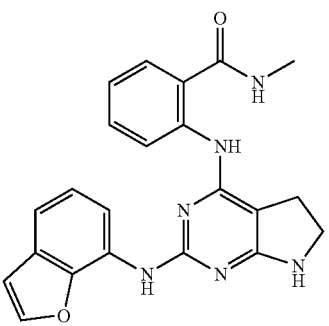 [SMILES: CNC(=O)c1ccccc1Nc1nc(Nc2cccc3ccoc23)nc2c1CCN2]

Step A: N-(benzofuran-7-yl)-4-chloro-7-(4-methoxybenzyl)-6,7-dihydro-5H-pyrrolo[2,3-d]pyrimidin-2-amine

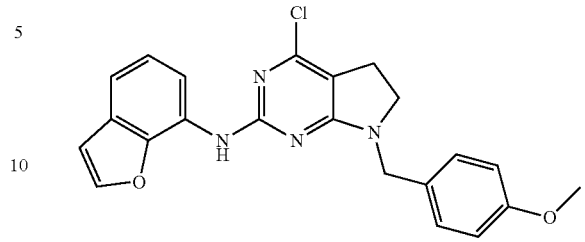

According to General Protocol II, N-(benzofuran-7-yl)-4-chloro-7-(4-methoxybenzyl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 310 mg, to mmol), benzofuran-7-amine hydrochloride (Intermediate B7, 169.6 mg, 1.0 mmol), Pd$_2$(dba)$_3$ (183 mg, 0.2 mmol), (±)-BINAP (124 mg, 0.2 mmol) and cesium carbonate (1.304 g, 4.0 mmol), and isolated as a solid (200 mg, yield 49%). $^1$H NMR (400 MHz, CDCl$_3$) δ ppm 8.35-8.37 (dd, 1H, J=2.8 Hz, 6.4 Hz), 7.596-7.601 (d, 1H, J=2.0 Hz), 7.46 (s, 1H), 7.20-7.26 (m, 3H), 6.86-6.88 (dd, 2H, J=2.0 Hz, 6.4 Hz), 6.768-6.774 (d, 1H, J=2.4 Hz), 4.56 (s, 2H), 3.80 (s, 3H), 3.49-3.54 (t, 2H, J=8.4 Hz), 2.94-2.98 (t, 2H, J=8.4 Hz).

Step B: 2-(2-(benzofuran-7-ylamino)-7-(4-methoxybenzyl)-6,7-dihydro-5H-pyrrolo[2,3-d]pyrimidin-4-ylamino)-N-methylbenzamide

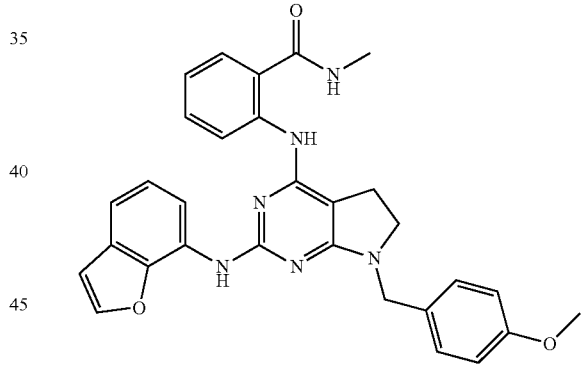

According to General Protocol II, 2-(2-(benzofuran-7-ylamino)-7-(4-methoxybenzyl)-6,7-dihydro-5H-pyrrolo[2,3-d]pyrimidin-4-ylamino)-N-methylbenzamide was prepared from N-(benzofuran-7-yl)-4-chloro-7-(4-methoxybenzyl)-6,7-dihydro-5H-pyrrolo[2,3-d]pyrimidin-2-amine (100 mg, 0.25 mmol), 2-amino-N-methylbenzamide (Intermediate C1, 44 mg, 0.293 mmol), Pd$_2$(dba)$_3$ (10 mg, 0.011 mmol), (±)-BINAP (15 mg, 0.049 mmol) and potassium-tert-butoxide (47 mg, 0.489 mmol) heated at 130° C. for 12 hours, and isolated as a solid (60 mg, yield 47%).

Step C: 2-(2-(benzofuran-7-ylamino)-6,7-dihydro-5H-pyrrolo[2,3-d]pyrimidin-4-ylamino)-N-methylbenzamide According to General Protocol II, 2-(2-(benzofuran-7-ylamino)-6,7-dihydro-5H-pyrrolo[2,3-d]pyrimidin-4-ylamino)-N-methylbenz amide was prepared from 2-(2-(benzofuran-7-ylamino)-7-(4-methoxybenzyl)-6,7-dihydro- 5H-pyrrolo[2,3-d]pyrimidin-4-ylamino)-N-methylbenzamide (60 mg, 0.115 mmol), trifluoroacetic acid (8 mL) and four drops of concentrated sulfuric acid, and isolated as a solid (10 mg, yield 22%). ¹H NMR (400 MHz, DMSO-d6) δ ppm 10.73 (s, 1H), 8.58-8.59 (d, 1H, J=4.4 Hz), 8.36-8.39 (m, 2H), 7.94-7.95 (d, 1H, J=2.4 Hz), 7.61-7.63 (t, 2H, J=7.6 Hz), 7.32-7.34 (d, 1H, J=7.6 Hz), 7.10-7.18 (m, 2H), 6.956-9.962 (d, 1H, J=2.4 Hz), 6.83-6.87 (t, 1H, J=7.6 Hz), 6.65 (s, 1H), 3.52-3.57 (t, 2H, J=8.8 Hz), 2.81-2.85 (t, 2H, J=8.8 Hz), 2.77-2.78 (d, 3H, J=4.4 Hz).

Example 20

2-(2-(1,3-dimethyl-1H-pyrazol-5-ylamino)-6,7-dihydro-5H-pyrrolo[2,3-d]pyrimidin-4-ylamino)-N-methylbenzamide

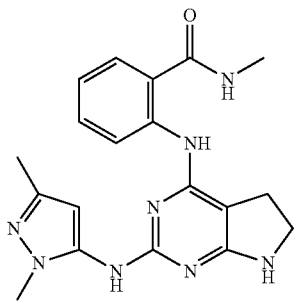 [SMILES: CNC(=O)c1ccccc1Nc1nc(Nc2cc(C)nn2C)nc2c1CCN2]

Step A: 4-chloro-N-(1,3-dimethyl-1H-pyrazol-5-yl)-7-(4-methoxybenzyl)-6,7-dihydro-5H-pyrrolo[2,3-d]pyrimidin-2-amine

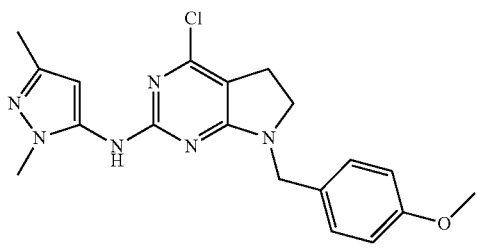 [SMILES: COc1ccc(CN2CCc3c(Cl)nc(Nc4cc(C)nn4C)nc32)cc1]

According to General Protocol II, 4-chloro-N-(1,3-dimethyl-1H-pyrazol-5-yl)-7-(4-methoxybenzyl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 130 mg, 0.421 mmol), 1,3-dimethyl-1H-pyrazol-5-amine (Intermediate B8, 56 mg, 0.505 mmol), Pd₂(dba)₃ (20 mg, 0.022 mmol), (±)-BINAP (26 mg, 0.042 mmol) and cesium carbonate (206 mg, 0.632 mmol) in a microwave at 130° C. for 2.5 hours, and isolated as a solid (20 mg, yield 9.8%). ¹H NMR (400 MHz, DMSO-d6) δ ppm 9.16 (s, 1H), 6.25-6.27 (d, 2H, J=8.4 Hz), 6.95-6.98 (d, 2H, J=8.8 Hz), 6.02 (s, 1H), 4.50 (s, 2H), 3.79 (s, 3H), 3.62 (s, 3H), 3.53-3.57 (t, 2H, J=8.4 Hz), 2.92-2.96 (t, 2H, J=8.4 Hz), 2.14 (s, 3H).

Step B: 2-(2-(1,3-dimethyl-1H-pyrazol-5-ylamino)-7-(4-methoxybenzyl)-6,7-dihydro-5H-pyrrolo[2,3-d]pyrimidin-4-ylamino)-N-methylbenzamide

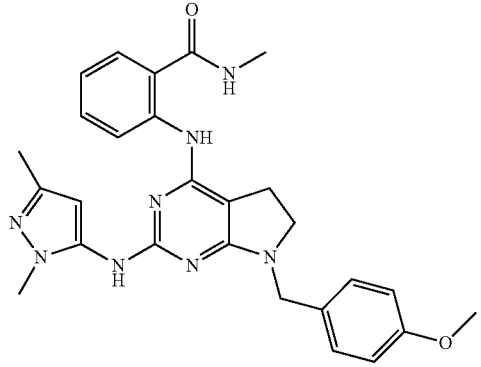 [SMILES: CNC(=O)c1ccccc1Nc1nc(Nc2cc(C)nn2C)nc2c1CCN2Cc1ccc(OC)cc1]

According to General Protocol II, 2-(2-(1,3-dimethyl-1H-pyrazol-5-ylamino)-7-(4-methoxybenzyl)-6,7-dihydro-5H-pyrrolo[2,3-d]pyrimidin-4-ylamino)-N-methylbenzamide was prepared from 4-chloro-N-(1,3-dimethyl-1H-pyrazol-5-yl)-7-(4-methoxybenzyl)-6,7-dihydro-5H-pyrrolo[2,3-d]pyrimidin-2-amine (75 mg, 0.155 mmol), 2-amino-N-methylbenzamide (Intermediate C1, 28 mg, 0.185 mmol), Pd₂(dba)₃ (28 mg, 0.031 mmol), (±)-BINAP (19 mg, 0.031 mmol) and cesium carbonate (76 mg, 0.233 mmol) in a microwave tube heated at 130° C., and isolated as a solid (50 mg, yield 65%). ¹H NMR (400 MHz, CDCl₃) δ ppm 10.23 (s, 1H), 8.47-8.49 (d, 1H, J=8.4 Hz), 7.36-7.38 (d, 1H, J=8.0 Hz), 7.30-7.34 (t, 1H, J=8.0 Hz), 7.19-7.21 (d, 2H, J=8.4 Hz), 6.85-6.89 (m, 3H), 6.37 (s, 1H), 6.20-6.21 (d, 1H, J=3.2 Hz), 6.08 (s, 1H), 4.46 (s, 2H), 3.801 (s, 3H), 3.799 (s, 3H), 3.43-3.47 (t, 2H, J=8.4 Hz), 2.97-2.98 (d, 3H, J=4.8 Hz), 2.89-2.93 (t, 2H, J=8.4 Hz).

Step C: 2-(2-(1,3-dimethyl-1H-pyrazol-5-ylamino)-6,7-dihydro-5H-pyrrolo[2,3-d]pyrimidin-4-ylamino)-N-methylbenzamide According to General Protocol II, 2-(2-(1,3-dimethyl-1H-pyrazol-5-ylamino)-6,7-dihydro-5H-pyrrolo[2,3-d]pyrimidin-4-ylamino)-N-methylbenzamide was prepared from 2-(2-(1,3-dimethyl-1H-pyrazol-5-ylamino)-7-(4-methoxybenzyl)-6,7-dihydro-5H-pyrrolo[2,3-d]pyrimidin-4-ylamino)-N-methylbenzamide (50 mg, 0.1 mmol), trifluoroacetic acid (5 mL) and three drops of concentrated sulfuric acid, and isolated as a solid (3.8 mg, yield 10%). ¹H NMR (400 MHz, DMSO-d6) δ ppm 10.83 (s, 1H), 8.67-8.69 (d, 2H, J=8.0 Hz), 8.54 (s, 1H), 7.71-7.73 (m, 1H), 7.31-7.32 (m, 1H), 6.95-6.97 (m, 1H), 6.72 (s, 1H), 5.98 (s, 1H), 3.57-3.60 (m, 5H), 2.84-2.89 (m, 5H), 2.05 (s, 3H).

Example 21

N-methyl-2-(2-(3,4,5-trimethoxyphenylamino)-6,7-dihydro-5H-pyrrolo[2,3-d]pyrimidin-4-ylamino)benzamide

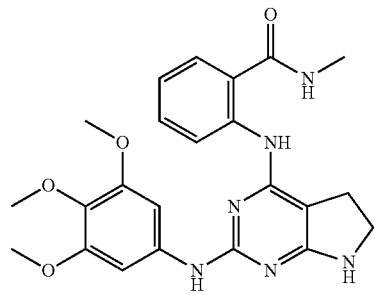 [SMILES: CNC(=O)c1ccccc1Nc1nc(Nc2cc(OC)c(OC)c(OC)c2)nc2c1CCN2]

Step A: 4-chloro-7-(4-methoxybenzyl)-N-(3,4,5-trimethoxyphenyl)-6,7-dihydro-5H-pyrrolo[2,3-d]pyrimidin-2-amine

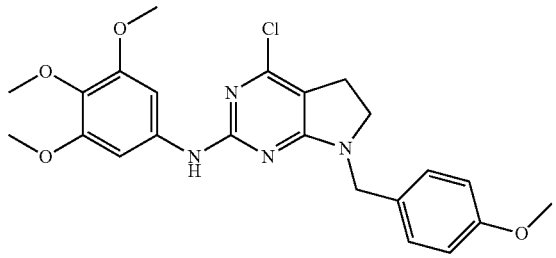

According to General Protocol II, 4-chloro-7-(4-methoxybenzyl)-N-(3,4,5-trimethoxyphenyl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 200 mg, 0.645 mmol), 3,4,5-trimethoxyaniline (Intermediate B9, 118 mg, 0.645 mmol), Pd$_2$(dba)$_3$ (118 mg, 0.129 mmol), (±)-BINAP (80 mg, 0.129 mmol) and cesium carbonate (421 mg, 1.291 mmol) in a microwave tube at 130° C. for 2 hours, and isolated as a white solid (100 mg, yield 68%). $^1$H NMR (400 MHz, CDCl$_3$) δ ppm 7.19-7.21 (d, 2H, J=8.4 Hz), 6.97 (s, 2H), 6.83-6.87 (m, 3H), 4.54 (s, 2H), 3.79-3.80 (s+s, 12H), 3.39-3.53 (t, 2H, J=8.4 Hz), 2.93-2.97 (t, 2H, J=8.4 Hz).

Step B: 2-(7-(4-methoxybenzyl)-2-(3,4,5-trimethoxyphenylamino)-6,7-dihydro-5H-pyrrolo[2,3-d]pyrimidin-4-ylamino)-N-methylbenzamide

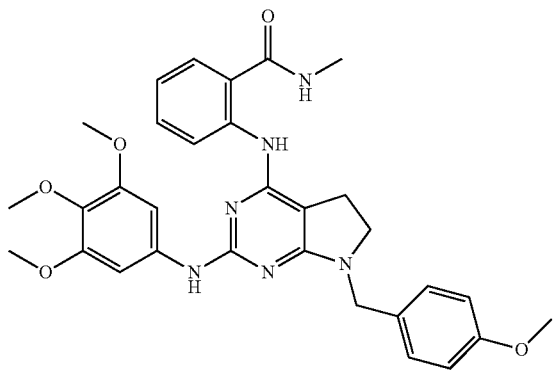

According to General Protocol II, 2-(7-(4-methoxybenzyl)-2-(3,4,5-trimethoxyphenylamino)-6,7-dihydro-5H-pyrrolo[2,3-d]pyrimidin-4-ylamino)-N-methylbenzamide was prepared from 4-chloro-7-(4-methoxybenzyl)-N-(3,4,5-trimethoxyphenyl)-6,7-dihydro-5H-pyrrolo[2,3-d]pyrimidin-2-amine (100 mg, 0.219 mmol), 2-amino-N-methylbenzamide (Intermediate C1, 39 mg, 0.26 mmol), Pd$_2$(dba)$_3$ (40 mg, 0.044 mmol), (±)-BINAP (27 mg, 0.043 mmol) and cesium carbonate (143 mg, 0.439 mmol) heated at 130° C. for 12 hours, and isolated as a yellow solid (30 mg, yield 24%). $^1$H NMR (400 MHz, CDCl$_3$) δ ppm 10.11 (s, 1H), 8.63-8.65 (d, 1H, J=8.4 Hz), 7.37-7.40 (m, 1H), 7.17-7.30 (m, 3H), 6.96 (s, 2H), 6.85-6.88 (m, 2H), 6.62-6.69 (m, 2H), 6.19 (s, 1H), 6.04 (s, 1H), 4.53 (s, 2H), 3.79-3.80 (m, 6H), 3.72 (s, 6H), 3.45-3.49 (t, 2H, J=8.4 Hz), 2.92-2.98 (m, 5H).

Step C: N-methyl-2-(2-(3,4,5-trimethoxyphenylamino)-6,7-dihydro-5H-pyrrolo[2,3-d]pyrimidin-4-ylamino)benzamide According to General Protocol II, N-methyl-2-(2-(3,4,5-trimethoxyphenylamino)-6,7-dihydro-5H-pyrrolo[2,3-d]pyrimidin-4-ylamino)benzamide was prepared from 2-(7-(4-methoxybenzyl)-2-(3,4,5-trimethoxyphenylamino)-6,7-dihydro-5H-pyrrolo[2,3-d]pyrimidin-4-ylamino)-N-methylbenzamide (30 mg, 0.053 mmol), trifluoroacetic acid (6 mL) and three drops of concentrated sulfuric acid, and isolated as a solid (5.8 mg, yield 24%). $^1$H NMR (400 MHz, DMSO-d6) δ ppm 10.60 (s, 1H), 8.60-8.69 (m, 3H), 7.64-7.66 (d, 1H, J=8.0 Hz), 7.30-7.34 (t, 1H, J=8.0 Hz), 7.08 (s, 2H), 6.89-6.93 (t, 1H, J=7.6 Hz), 6.65 (s, 1H), 3.64 (s, 6H), 3.58 (s, 3H), 3.51-3.55 (t, 2H, J=8.4 Hz), 2.77-2.84 (m, 5H).

Example 22

N-methyl-2-(2-(1-(3-morpholinopropyl)-1H-indol-4-ylamino)-6,7-dihydro-5H-pyrrolo[2,3-d]pyrimidin-4-ylamino)benzamide

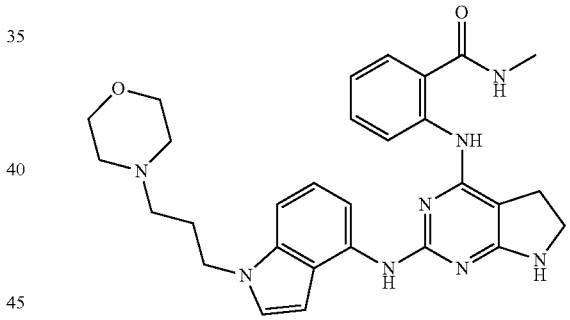

Step A: 4-chloro-7-(4-methoxybenzyl)-N-(1-(3-morpholinopropyl)-1H-indol-4-yl)-6,7-dihydro-5H-pyrrolo[2,3-d]pyrimidin-2-amine

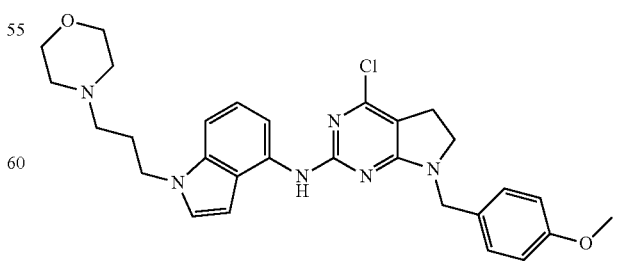

According to General Protocol II, 4-chloro-7-(4-methoxybenzyl)-N-(1-(3-morpholinopropyl)-1H-indol-4- yl)-6,7-dihydro-5H-pyrrolo[2,3-d]pyrimidin-2-amine was prepared from 2,4-dichloro-7-(4-methoxybenzyl)-6,7-dihydro-5H-pyrrolo[2,3-d]pyrimidine (Intermediate A1, 309 mg, 1.0 mmol), 1-(3-morpholinopropyl)-1H-indol-4-amine (Intermediate B10, 259 mg, 1.0 mmol), Pd$_2$(dba)$_3$ (183 mg, 0.2 mmol), (±)-BINAP (124 mg, 0.2 mmol) and cesium carbonate (652 mg, 2.0 mmol) heated in a microwave tube at 140° C. for 3 hours, and isolated as a solid (135 mg, yield 25.4%).

Step B: 2-(7-(4-methoxybenzyl)-2-(1-(3-morpholinopropyl)-1H-indol-4-ylamino)-6,7-dihydro-5H-pyrrolo[2,3-d]pyrimidin-4-ylamino)-N-methylbenzamide

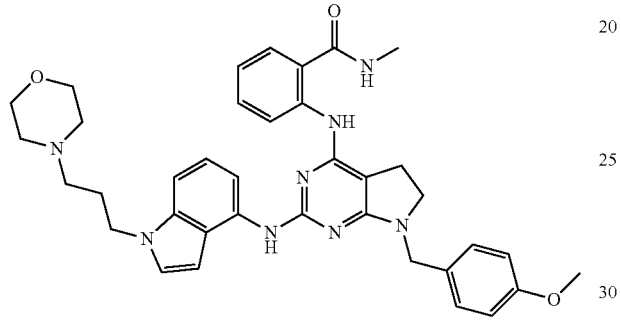

According to General Protocol II, 2-(7-(4-methoxybenzyl)-2-(1-(3-morpholinopropyl)-1H-indol-4-ylamino)-6,7-dihydro-5H-pyrrolo[2,3-d]pyrimidin-4-ylamino)-N-methylbenzamide was prepared from 4-chloro-7-(4-methoxybenzyl)-N-(1-(3-morpholinopropyl)-1H-indol-4-yl)-6,7-dihydro-5H-pyrrolo[2,3-d]pyrimidin-2-amine (135 mg, 0.254 mmol), 2-amino-N-methylbenzamide (Intermediate C1, 38 mg, 0.253 mmol), Pd$_2$(dba)$_3$ (46 mg, 0.050 mmol), X-Phos (24 mg, 0.050 mmol) and cesium carbonate (124 mg, 0.380 mmol) heated in a microwave tube at 140° C. for 3.5 hours, and isolated as a solid (100 mg, yield 61%). $^1$H NMR (400 MHz, CDCl$_3$) δ ppm 10.06 (s, 1H), 8.68-8.70 (d, 1H, J=8.4 Hz), 8.09-8.10 (d, 1H, J=6.8 Hz), 7.40-7.42 (m, 2H), 7.14-7.18 (m, 1H), 7.02-7.06 (m, 2H), 6.86-6.93 (m, 3H), 6.58 (s, 1H), 6.16 (s, 1H), 4.55 (s, 2H), 4.19-4.22 (m, 2H), 3.80 (s, 3H), 3.72-3.80 (m, 5H), 3.44-3.49 (m, 3H), 2.94-2.99 (m, 5H), 2.40-2.42 (m, 4H), 2.22-2.28 (m, 2H), 1.99-2.04 (m, 4H).

Step C: N-methyl-2-(2-(1-(3-morpholinopropyl)-1H-indol-4-ylamino)-6,7-dihydro-5H-pyrrolo[2,3-d]pyrimidin-4-ylamino)benzamide According to General Protocol II, N-methyl-2-(2-(1-(3-morpholinopropyl)-1H-indol-4-ylamino)-6,7-dihydro-5H-pyrrolo[2,3-d]pyrimidin-4-ylamino)benzamide was prepared from 2-(7-(4-methoxybenzyl)-2-(1-(3-morpholinopropyl)-1H-indol-4-ylamino)-6,7-dihydro-5H-pyrrolo[2,3-d]pyrimidin-4-ylamino)-N-methylbenzamide (100 mg, 0.155 mmol), trifluoroacetic acid (5 mL) and four drops of concentrated sulfuric acid, and isolated as a solid (10 mg, yield 12%). $^1$H NMR (400 MHz, CDCl$_3$) δ ppm 10.18 (s, 1H), 8.69-8.72 (d, 1H, J=8.4 Hz), 7.95-7.97 (d, 1H, J=7.6 Hz), 7.37-7.42 (m, 2H), 7.13-7.17 (m, 1H), 7.03-7.05 (m, 2H), 6.82-6.94 (m, 2H), 6.51-6.52 (d, 1H, J=2.8 Hz), 6.19-6.20 (d, 1H, J=4.8 Hz), 4.49 (s, 1H), 4.18-4.21 (t, 2H, J=6.8 Hz), 3.65-3.74 (m, 7H), 2.99-3.07 (m, 5H), 2.39-2.40 (m, 4H), 2.17-2.19 (m, 2H), 1.95-1.99 (m, 3H).

Example 23

(±)-2-(2-(2-methoxy-4-morpholinophenylamino)-5-methyl-6,7-dihydro-5H-pyrrolo[2,3-d]pyrimidin-4-ylamino)-N-methylbenzamide

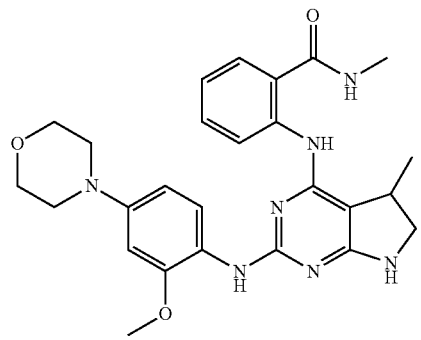 [SMILES: CNC(=O)c1ccccc1Nc1nc(Nc2ccc(N3CCOCC3)cc2OC)nc2c1C(C)CN2]

Step A: (±)-4-chloro-N-(2-methoxy-4-morpholinophenyl)-7-(4-methoxybenzyl)-5-methyl-6,7-dihydro-5H-pyrrolo[2,3-d]pyrimidin-2-amine

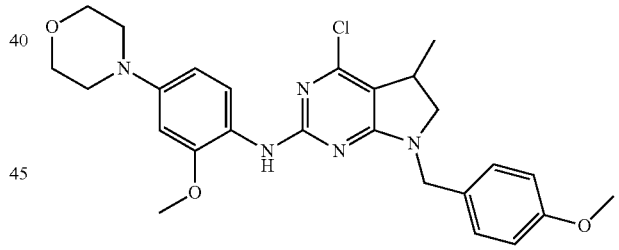

According to General Protocol II, (±)-4-chloro-N-(2-methoxy-4-morpholinophenyl)-7-(4-methoxybenzyl)-5-methyl-6,7-dihydro-5H-pyrrolo[2,3-d]pyrimidin-2-amine was prepared from (±)-2,4-dichloro-7-(4-methoxybenzyl)-5-methyl-6,7-dihydro-5H-pyrrolo[2,3-d]pyrimidine (Intermediate A2, 190 mg, 0.586 mmol), 2-methoxy-4-morpholinoaniline (Intermediate B1, 146 mg, 0.702 mmol), Pd$_2$(dba)$_3$ (27 mg, 0.03 mmol), (±)-BINAP (36 mg, 0.058 mmol) and cesium carbonate (287 mg, 0.88 mmol), and isolated as a yellow solid (100 mg, yield 35%). $^1$H NMR (400 MHz, CDCl$_3$) δ ppm 8.37-8.39 (d, 1H, J=9.2 Hz), 7.39 (s, 1H), 7.20-7.22 (dd, 2H, J=2.0 Hz, 6.8 Hz), 6.86-6.88 (m, 2H), 6.49-6.52 (m, 2H), 4.54 (s, 2H), 3.85-3.87 (t+s, 7H), 3.80 (s, 3H), 3.57-3.62 (t, 1H, J=9.6 Hz), 3.29-3.31 (m, 1H), 3.08-3.11 (m, 4H), 3.00-3.03 (dd, 1H, J=4.0 Hz, 9.6 Hz), 1.24-1.28 (m, 3H).

Step B: (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzamide

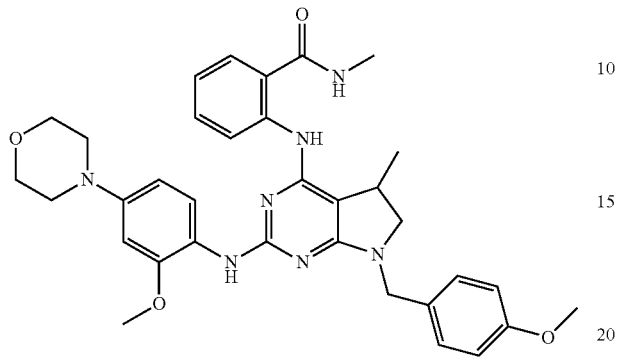

According to General Protocol II, (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (65 mg, 0.131 mmol), 2-amino-N-methylbenzamide (Intermediate C1, 24 mg, 0.16 mmol), Pd$_2$(dba)$_3$ (6 mg, 0.007 mmol), (±)-BINAP (9 mg, 0.014 mmol) and cesium carbonate (64 mg, 0.196 mmol), and isolated as a yellow solid (55 mg, yield 45%). $^1$H NMR (400 MHz, CDCl$_3$) δ ppm 9.98 (s, 1H), 8.61-8.63 (d, 1H, J=8.4 Hz), 8.38-8.40 (d, 1H, J=8.8 Hz), 7.38-7.42 (m, 2H), 7.23-7.25 (m, 2H), 7.18 (s, 1H), 6.85-6.92 (m, 3H), 6.52 (s, 1H), 6.46-6.48 (d, 1H, J=8.8 Hz), 6.15-6.16 (d, 1H, J=4.8 Hz), 4.46-4.60 (dd, 2H, J=14.8 Hz, 42.8 Hz), 3.86-3.88 (t+s, 7H), 3.798-3.802 (d, 3H, J=1.6 Hz), 3.51-3.53 (m, 1H), 3.35-3.38 (m, 1H), 3.09-3.11 (t, 4H), 2.97-3.00 (s+m, 4H), 1.28-1.32 (m, 3H).

Step C: (±)-2-(2-(2-methoxy-4-morpholinophenylamino)-5-methyl-6,7-dihydro-5H-pyrrolo[2,3-d]pyrimidin-4-ylamino)-N-methylbenzamide According to General Protocol II, (±)-2-(2-(2-methoxy-4-morpholinophenylamino)-5-methyl-6,7-dihydro-5H-pyrrolo[2,3-d]pyrimidin-4-ylamino)-N-methylbenzamide was prepared from (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzamide (55 mg, 0.09 mmol), trifluoroacetic acid (4 mL) and four drops of concentrated sulfuric acid, and isolated as a yellow solid (5 mg, yield 11%). $^1$H NMR (400 MHz, DMSO-d6) δ ppm 10.62 (br s, 1H), 8.63-8.64 (d, 1H, J=4.8 Hz), 8.40 (br s, 1H), 7.71-7.73 (d, 1H, J=8.4 Hz), 7.62-7.65 (dd, 2H, J=1.2 Hz, 8.0 Hz), 7.31-7.35 (t, 1H, J=7.6 Hz), 6.94-6.97 (t, 1H, J=7.6 Hz), 6.62-6.63 (d, 1H, J=2.4 Hz), 6.43-6.45 (dd, 1H, J=2.4 Hz, 8.8 Hz), 3.80 (s, 3H), 3.68-3.74 (m, 5H), 3.31 (m, 2H), 3.09-3.11 (m, 5H), 2.76-2.77 (d, 3H, J=4.4 Hz), 1.20-1.21 (m, 3H).

(±)-2-(2-(2-methoxy-4-morpholinophenylamino)-5-methyl-6,7-dihydro-5H-pyrrolo[2,3-d]pyrimidin-4-ylamino)-N-methylbenzamide was resolved on Chiralcel AD-H (4.6×150 mm, Chiral Technologies) eluted with 0.025% diethylamine in ethanol/hexane (1/1). Two enantiomers were separated with retention time of 7.213 minutes and 10.835 minutes, respectively.

Example 24

(±)-(2-(2-(2-methoxy-4-morpholinophenylamino)-5-methyl-6,7-dihydro-5H-pyrrolo[2,3-d]pyrimidin-4-ylamino)phenyl)(pyrrolidin-1-yl)methanone

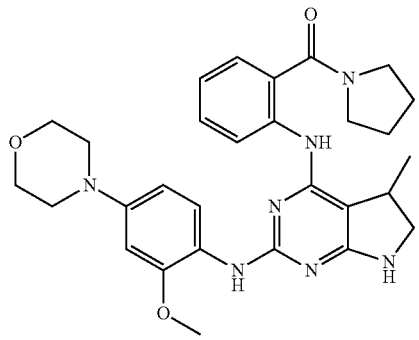 [SMILES: COc1cc(N2CCOCC2)ccc1Nc1nc2c(c(Nc3ccccc3C(=O)N3CCCC3)n1)C(C)CN2]

Step A: (±)-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)(pyrrolidin-1-yl)methanone

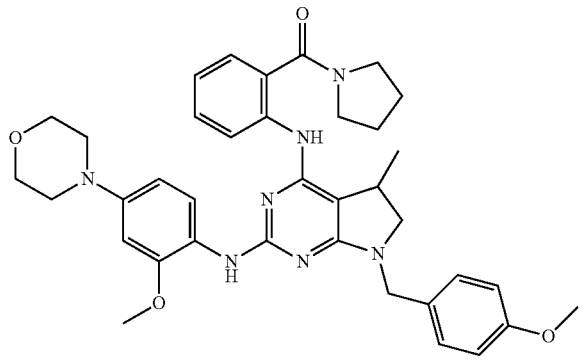 [SMILES: COc1ccc(CN2CC(C)c3c(Nc4ccccc4C(=O)N4CCCC4)nc(Nc4ccc(N5CCOCC5)cc4OC)nc32)cc1]

According to General Protocol II, (±)-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)(pyrrolidin-1-yl)methanone was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (, 70 mg, 0.141 mmol), (2-aminophenyl)(pyrrolidin-1-yl)methanone hydrochloride (Intermediate C3, 39 mg, 0.172 mmol), Pd$_2$(dba)$_3$ (13 mg, 0.014 mmol), (±)-BINAP (18 mg, 0.029 mmol) and cesium carbonate (92 mg, 0.282 mmol) heated in a sealed tube at 130° C. for 12 hours, and isolated as a solid (90 mg, yield 98%). $^1$H NMR (400 MHz, CDCl$_3$) δ ppm 8.63 (s, 1H), 8.40-8.44 (t, 2H, J=8.8 Hz), 7.31-7.38 (m, 2H), 7.19-7.24 (m, 3H), 6.93-6.95 (dd, 1H, J=0.8 Hz, 7.2 Hz), 6.86-6.92 (dd, 2H, J=1.6 Hz, 20.4 Hz), 6.518-6.524 (d, 1H, J=2.4 Hz), 6.45-6.47 (dd, 1H, J=2.0 Hz, 8.8 Hz), 4.47-4.58 (dd, 2H, J=14.8 Hz, 23.6 Hz), 3.86-3.88 (m, 7H), 3.80 (s, 3H), 3.62-3.63 (m, 2H), 3.50-3.54 (m, 3H), 3.27-3.28 (m, 1H), 3.09-3.11 (t, 4H, J=4.8 Hz), 2.94-2.98 (dd, 2H, J=4.4 Hz, 9.6 Hz), 1.84-1.95 (m, 4H), 1.24-1.27 (m, 3H).

Step B: (±)-(2-(2-(2-methoxy-4-morpholinophenylamino)-5-methyl-6,7-dihydro-5H-pyrrolo[2,3-d]pyrimidin-4-ylamino)phenyl)(pyrrolidin-1-yl)methanone According to General Protocol II, (±)-(2-(2-(2-methoxy-4-morpholinophenylamino)-5-methyl-6,7-dihydro-5H-pyrrolo[2,3-d]pyrimidin-4-ylamino)phenyl)(pyrrolidin-1-yl)methanone was prepared from (±)-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)(pyrrolidin-1-yl)methanone (90 mg, 0.138 mmol), trifluoroacetic acid (8 mL) and four drops of concentrated sulfuric acid, and isolated as a yellow solid (44.4 mg, yield 60%). $^1$H NMR (400 MHz, DMSO-d6) δ ppm 8.67 (s, 1H), 8.21-8.23 (d, 1H, J=8.8 Hz), 7.86-7.88 (d, 1H, J=8.0 Hz), 7.42-7.44 (d, 1H, J=7.6 Hz), 7.31-7.35 (t, 1H, J=8.0 Hz), 7.13 (s, 1H), 6.97-7.01 (t, 1H, J=7.6 Hz), 6.61-6.62 (m, 2H), 6.39-6.42 (dd, 1H, J=2.0 Hz, 8.4 Hz), 3.81 (s, 3H), 3.73-3.76 (t, 4H, J=4.4 Hz), 3.62-3.67 (t, 1H, J=9.2 Hz), 3.35-3.52 (m, 5H), 3.01-3.05 (m, 5H), 1.75-1.87 (m, 4H), 1.16-1.18 (d, 3H, J=6.4 Hz).

Example 25

(±)-2-(2-(2-methoxy-4-morpholinophenylamino)-5-methyl-6,7-dihydro-5H-pyrrolo[2,3-d]pyrimidin-4-ylamino)-N-methylbenzenesulfonamide

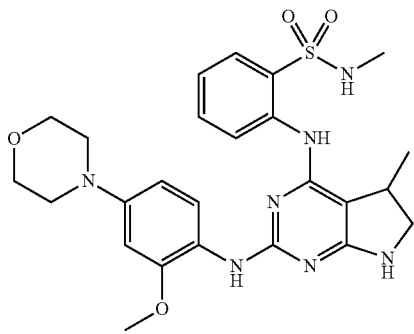 [SMILES: CNS(=O)(=O)c1ccccc1Nc1nc(Nc2ccc(N3CCOCC3)cc2OC)nc2c1C(C)CN2]

Step A: (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzenesulfonamide According to General Protocol II, (±)-2-(2-(2-methoxy-4-morpholinophenylamino)-7-(4-methoxybenzyl)-5-methyl-6,7-dihydro-5H-pyrrolo[2,3-a]pyrimidin-4-ylamino)-N-methylbenzenesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (80 mg, 0.161 mmol), 2-amino-N-methylbenzenesulfonamide (Intermediate C4, 36 mg, 0.194 mmol), Pd$_2$(dba)$_3$ (15 mg, 0.016 mmol), (±)-BINAP (20 mg, 0.032 mmol) and cesium carbonate (105 mg, 0.322 mmol) heated at 130° C. in a sealed tube for 12 hours, and isolated as a solid (95 mg, yield 91%). $^1$H NMR (400 MHz, CDCl$_3$) δ ppm 8.32-8.38 (dd, 2H, J=8.4 Hz, 15.2 Hz), 8.00 (s, 1H), 7.85-7.87 (dd, 1H, J=1.6 Hz, 8.0 Hz), 7.50-7.54 (m, 1H), 7.22-7.27 (m, 3H), 7.07-7.10 (t, 1H, J=8.0 Hz), 6.86-6.88 (m, 2H), 6.52-6.53 (d, 1H, J=2.4 Hz), 6.40-6.43 (dd, 1H, J=1.2 Hz, 8.8 Hz), 4.49-4.60 (m, 2H), 4.44-4.46 (m, 1H), 3.87-3.89 (m, 7H), 3.81 (s, 3H), 3.54-3.59 (m, 1H), 3.27-3.28 (m, 1H), 3.09-3.11 (t, 4H, J=4.4 Hz), 2.99-3.02 (dd, 1H, J=4.0 Hz, 9.6 Hz 2.59-2.61 (d, 3H, J=5.6 Hz), 1.22-1.28 (m, 3H).

Step B: (±)-2-(2-(2-methoxy-4-morpholinophenylamino)-5-methyl-6,7-dihydro-5H-pyrrolo[2,3-d]pyrimidin-4-ylamino)-N-methylbenzenesulfonamide According to General Protocol II, (±)-2-(2-(2-methoxy-4-morpholinophenylamino)-5-methyl-6,7-dihydro-5H-pyrrolo[2,3-d]pyrimidin-4-ylamino)-N-methylbenzenesulfonamide was prepared from (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzenesulfonamide (95 mg, 0.147 mmol), trifluoroacetic acid (8 mL) and four drops of concentrated sulfuric acid, and isolated as a solid (54 mg, yield 70%). $^1$H NMR (400 MHz, DMSO-d6) δ ppm 8.48-8.50 (d, 1H, J=8.0 Hz), 8.36 (s, 1H), 7.74-7.79 (m, 2H), 7.68-7.71 (dd, 1H, J=1.6 Hz, 7.6 Hz), 7.46-7.48 (m, 1H), 7.26 (s, 1H), 7.05-7.09 (m, 1H), 6.74 (s, 1H), 6.62-6.63 (d, 1H, J=2.8 Hz), 6.42-6.45 (dd, 1H, J=2.4 Hz, 8.8 Hz), 3.81 (s, 3H), 3.74-3.76 (t, 4H, J=4.8 Hz), 3.66-3.67 (t, 1H), 3.30-3.31 (m, 1H), 3.05-3.09 (m, 5H), 2.43-2.45 (d, 3H, J=5.2 Hz), 1.16-1.18 (d, 3H, J=7.2 Hz).

Example 26

(±)-2-(2-(2-methoxy-4-morpholinophenylamino)-5-methyl-6,7-dihydro-5H-pyrrolo[2,3-d]pyrimidin-4-ylamino)-N-propylbenzenesulfonamide

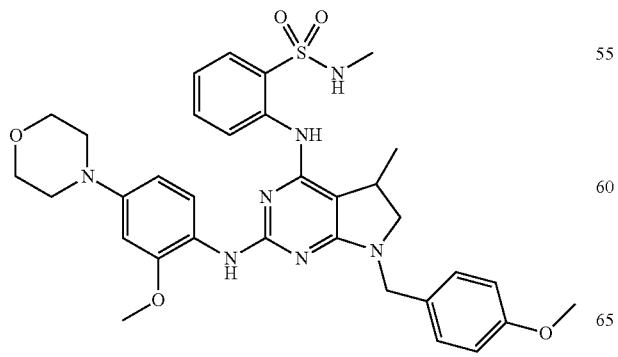

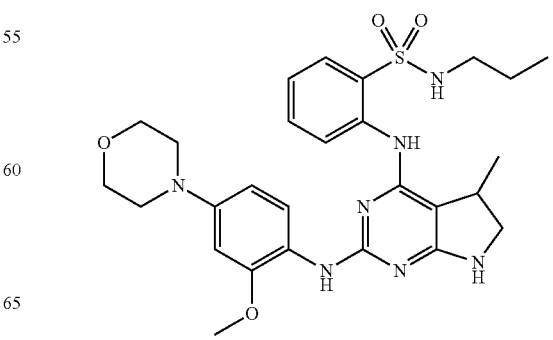

Step A: (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-propylbenzenesulfonamide

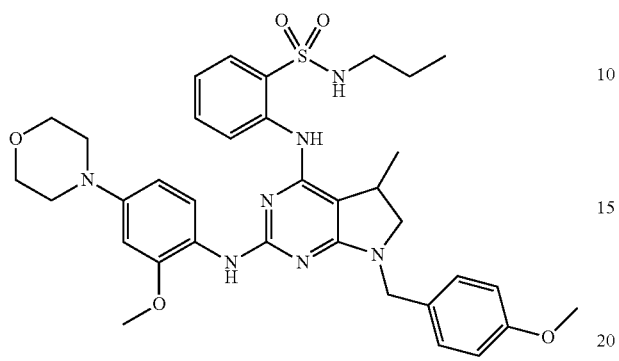

According to General Protocol II, (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-propylbenzenesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (70 mg, 0.141 mmol), 2-amino-N-propylbenzenesulfonamide hydrochloride (Intermediate C5, 43 mg, 0.171 mmol), Pd$_2$(dba)$_3$ (13 mg, 0.014 mmol), (±)-BINAP (18 mg, 0.029 mmol) and cesium carbonate (138 mg, 0.423 mmol) heated at 130° C. in a sealed tube for 12 hours, and isolated as a solid (60 mg, yield 63%). $^1$H NMR (400 MHz, CDCl$_3$) δ ppm 8.30-8.34 (dd, 2H, J=4.8 Hz, 10.4 Hz), 7.96 (s, 1H), 7.85-7.88 (dd, 1H, J=1.2 Hz, 8.0 Hz), 7.49-7.54 (t, 1H, J=7.6 Hz), 7.23-7.25 (m, 2H), 7.07-7.11 (t, 1H, J=7.6 Hz), 6.86-6.88 (d, 2H, J=8.4 Hz), 6.518-6.524 (d, 1H, J=2.4 Hz), 6.38-6.41 (dd, 1H, J=2.4 Hz, 8.8 Hz), 4.45-4.60 (m, 3H), 3.86-3.89 (m, 7H), 3.81 (s, 3H), 3.54-3.59 (t, 1H, J=9.2 Hz), 3.26-3.29 (m, 1H), 3.08-3.11 (t, 4H, J=4.8 Hz), 2.99-3.02 (dd, 1H, J=4.0 Hz, 9.6 Hz), 2.82-2.90 (m, 2H), 1.36-1.43 (m, 2H), 1.23-1.26 (m, 3H), 0.75-0.79 (t, 3H, J=7.2 Hz).

Step B: (±)-2-(2-(2-methoxy-4-morpholinophenylamino)-5-methyl-6,7-dihydro-5H-pyrrolo[2,3-d]pyrimidin-4-ylamino)-N-propylbenzenesulfonamide According to General Protocol II, (±)-2-(2-(2-methoxy-4-morpholinophenylamino)-5-methyl-6,7-dihydro-5H-pyrrolo[2,3-d]pyrimidin-4-ylamino)-N-propylbenzenesulfonamide was prepared from (±)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-propylbenzenesulfonamide (60 mg, 0.089 mmol), trifluoroacetic acid (5 mL) and four drops of concentrated sulfuric acid, and isolated as a solid (24.5 mg, yield 49.7%). $^1$H NMR (400 MHz, DMSO-d6) δ ppm 8.42-8.44 (d, 1H, J=8.4 Hz), 8.35 (s, 1H), 7.85-7.88 (t, 1H, J=6.0 Hz), 7.76-7.78 (d, 1H, J=8.8 Hz), 7.68-7.70 (dd, 1H, J=1.2 Hz, 8.0 Hz), 7.42-7.46 (m, 1H), 7.24 (s, 1H), 7.02-7.05 (m, 1H), 6.73 (s, 1H), 6.60-6.61 (d, 1H, J=2.4 Hz), 6.38-6.41 (dd, 1H, J=2.4 Hz, 8.8 Hz), 3.79 (s, 3H), 3.71-3.74 (t, 4H, J=4.8 Hz), 3.63-3.68 (t, 1H, J=9.2 Hz), 3.25-3.27 (m, 1H), 3.04-3.06 (m, 5H), 2.68-2.76 (m, 2H), 1.32-1.37 (q, 2H, J=7.2 Hz), 1.14-1.16 (d, 3H, J=6.4 Hz), 0.71-0.74 (t, 3H, J=7.6 Hz).

Example 27

(±)-N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide

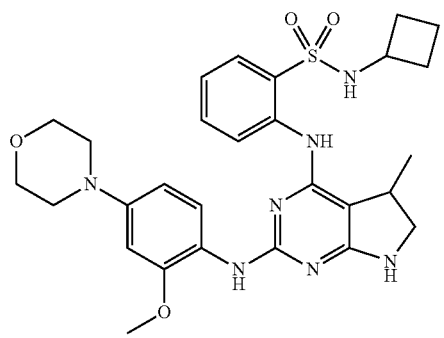 [SMILES: COc1cc(N2CCOCC2)ccc1Nc1nc2c(c(Nc3ccccc3S(=O)(=O)NC3CCC3)n1)C(C)CN2]

Step A: (±)-N-cyclobutyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide

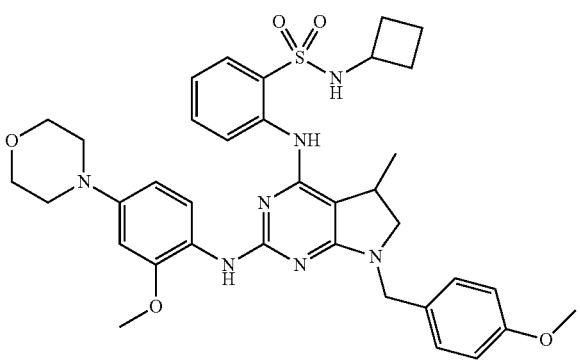 [SMILES: COc1ccc(CN2CC(C)c3c(Nc4ccccc4S(=O)(=O)NC4CCC4)nc(Nc4ccc(N5CCOCC5)cc4OC)nc32)cc1]

According to General Protocol II, (±)-N-cyclobutyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (50 mg, 0.101 mmol), 2-amino-N-cyclobutylbenzenesulfonamide (Intermediate C6, 28 mg, 0.124 mmol), Pd$_2$(dba)$_3$ (10 mg, 0.011 mmol), (±)-BINAP (13 mg, 0.021 mmol) and cesium carbonate (66 mg, 0.202 mmol) heated in a sealed tube at 130° C. for 12 hours, and isolated as a solid (55 mg, yield 79.4%). $^1$H NMR (400 MHz, CDCl$_3$) δ ppm 8.29-8.32 (d, 2H, J=8.8 Hz), 7.90 (s, 1H), 7.84-7.86 (d, 1H, J=6.4 Hz), 7.48-7.52 (t, 1H, J=8.0 Hz), 7.24-7.26 (m, 2H), 7.05-7.09 (t, 1H, J=7.6 Hz), 6.87-6.90 (m, 2H), 6.51-6.52 (d, 1H, J=2.4 Hz), 6.33-6.36 (dd, 1H, J=2.8 Hz, 8.8 Hz), 4.66-4.68 (d, 1H, J=5.2 Hz), 4.49-4.60 (dd, 2H, J=14.8 Hz, 29.6 Hz), 3.86-3.89 (m, 7H), 3.81 (s, 3H), 3.71-3.73 (m, 1H), 3.55-3.60 (t, 1H, J=9.2 Hz), 3.27-3.30 (m, 1H), 3.07-3.10 (t, 4H, J=4.4 Hz), 2.99-3.03 (dd, 1H, J=4.0 Hz, 9.6 Hz), 1.96-2.05 (m, 2H), 1.66-1.75 (m, 2H), 1.30-1.52 (m, 2H), 1.25-1.27 (m, 3H).

Step B: (±)-N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide According to General Protocol II, (±)-N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide was prepared from (±)-N-cyclobutyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide (55 mg, 0.08 mmol), trifluoroacetic acid (5 mL) and four drops of concentrated sulfuric acid, and isolated as a yellow solid (41.1 mg, yield 90.8%). $^1$H NMR (400 MHz, DMSO-d6) δ ppm 8.51-8.53 (d, 1H, J=8.4 Hz), 8.42 (s, 1H), 8.27-8.29 (d, 1H, J=8.8 Hz), 7.84-7.86 (d, 1H, J=8.8 Hz), 7.75-7.78 (dd, 1H, J=1.6 Hz, 8.4 Hz), 7.49-7.52 (t, 1H, J=7.2 Hz), 7.32 (s, 1H), 7.08-7.12 (m, 1H), 6.83 (s, 1H), 6.68-6.69 (d, 1H, J=2.0 Hz), 6.45-6.48 (dd, 1H, J=1.6 Hz, 8.8 Hz), 3.87 (s, 3H), 3.79-3.81 (t, 4H, J=4.4 Hz), 3.65-3.77 (m, 2H), 3.33-3.35 (m, 1H), 3.12-3.15 (m, 5H), 2.02-2.06 (m, 1H), 1.87-1.92 (m, 2H), 1.77-1.81 (m, 1H), 1.48-1.55 (m, 2H), 1.23-1.25 (d, 3H, J=6.4 Hz).

Example 28

(±)-N-cyclopentyl-2-(2-(2-methoxy-4-morpholinophenylamino)-5-methyl-6,7-dihydro-5H-pyrrolo[2,3-d]pyrimidin-4-ylamino)benzenesulfonamide

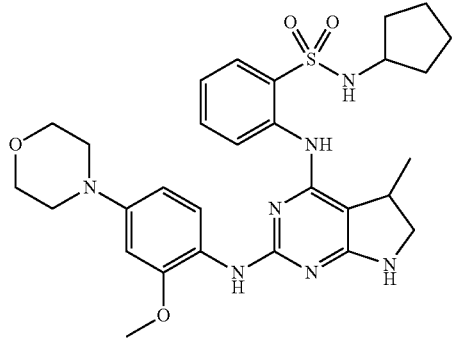 [SMILES: COc1cc(N2CCOCC2)ccc1Nc1nc2c(c(Nc3ccccc3S(=O)(=O)NC3CCCC3)n1)C(C)CN2]

Step A: (±)-N-cyclopentyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide

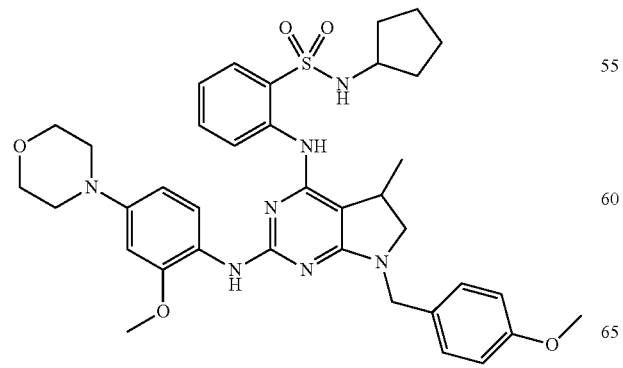

According to General Protocol II, (±)-N-cyclopentyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (50 mg, 0.101 mmol), 2-amino-N-cyclopentylbenzenesulfonamide (Intermediate C7, 29 mg, 0.121 mmol), Pd$_2$(dba)$_3$ (10 mg, 0.011 mmol), (±)-BINAP (13 mg, 0.021 mmol) and cesium carbonate (66 mg, 0.202 mmol) heated in a sealed tube at 130° C. for 12 hours, and isolated as a solid (55 mg, yield 77.9%). $^1$H NMR (400 MHz, CDCl$_3$) δ ppm 8.27-8.30 (dd, 2H, J=4.8 Hz, 7.6 Hz), 7.86-7.89 (m, 2H), 7.50-7.53 (t, 1H, J=7.6 Hz), 7.23-7.25 (m, 2H), 7.07-7.11 (t, 1H, J=7.6 Hz), 6.86-6.88 (dd, 2H, J=2.0 Hz, 6.4 Hz), 6.51-6.52 (d, 1H, J=2.4 Hz), 6.34-6.37 (dd, 1H, J=2.8 Hz, 8.4 Hz), 4.49-4.59 (dd, 2H, J=14.8 Hz, 26.8 Hz), 4.41-4.43 (d, 1H, J=7.6 Hz), 3.86-3.89 (m, 7H), 3.81 (s, 3H), 3.52-3.59 (m, 2H), 3.28-3.30 (m, 1H), 3.07-3.10 (t, 4H, J=4.8 Hz), 2.99-3.02 (dd, 1H, J=4.4 Hz, 9.6 Hz), 1.66-1.71 (m, 2H), 1.47-1.50 (m, 2H), 1.22-1.39 (7H).

Step B: (±)-N-cyclopentyl-2-(2-(2-methoxy-4-morpholinophenylamino)-5-methyl-6,7-dihydro-5H-pyrrolo[2,3-d]pyrimidin-4-ylamino)benzenesulfonamide According to General Protocol II, (±)-N-cyclopentyl-2-(2-(2-methoxy-4-morpholinophenylamino)-5-methyl-6,7-dihydro-5H-pyrrolo[2,3-d]pyrimidin-4-ylamino)benzenesulfonamide was prepared from (±)-N-cyclopentyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide (55 mg, 0.079 mmol), trifluoroacetic acid (5 mL) and four drops of concentrated sulfuric acid, and isolated as a solid (47 mg, yield 100%). $^1$H NMR (400 MHz, DMSO-d6) δ ppm 8.43-8.45 (d, 1H, J=8.8 Hz), 8.38 (s, 1H), 7.89-7.91 (d, 1H, J=7.6 Hz), 7.78-7.81 (d, 1H, J=8.8 Hz), 7.72-7.75 (dd, 1H, J=1.2 Hz, 8.0 Hz), 7.43-7.47 (m, 1H), 7.26 (s, 1H), 7.03-7.07 (t, 1H, J=7.6 Hz), 6.76 (s, 1H), 6.62-6.63 (d, 1H, J=2.4 Hz), 6.39-6.42 (dd, 1H, J=2.4 Hz, 8.8 Hz), 3.81 (s, 3H), 3.73-3.76 (t, 4H, J=4.8 Hz), 3.65-3.69 (t, 1H, J=9.2 Hz), 3.43-3.45 (m, 1H), 3.26-3.30 (m, 1H), 3.06-3.08 (m, 5H), 1.64-1.66 (m, 1H), 1.51-1.56 (m, 4H), 1.16-1.39 (m, 3H), 0.83-0.85 (d, 3H, J=8.0 Hz).

Example 29

(±)-N-cyclohexyl-2-(2-(2-methoxy-4-morpholinophenylamino)-5-methyl-6,7-dihydro-5H-pyrrolo[2,3-d]pyrimidin-4-ylamino)benzenesulfonamide

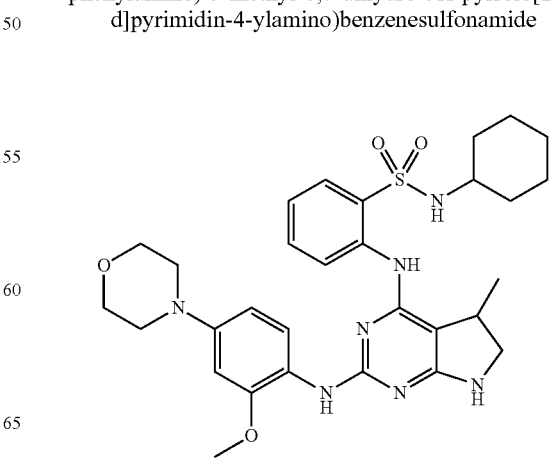

Step A: (±)-N-cyclohexyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide

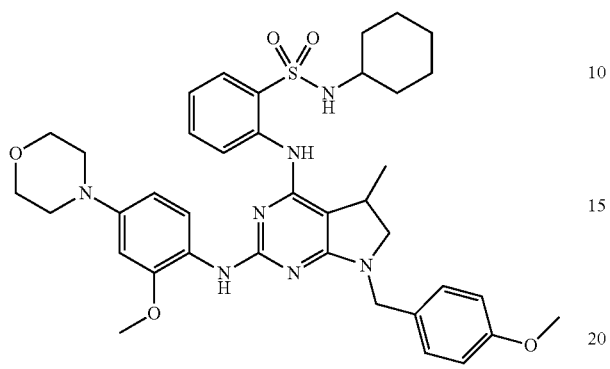

According to General Protocol II, (±)-N-cyclohexyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (50 mg, 0.101 mmol), 2-amino-N-cyclohexylbenzenesulfonamide (Intermediate C8, 31 mg, 0.121 mmol), Pd$_2$(dba)$_3$ (10 mg, 0.011 mmol), (±)-BINAP (13 mg, 0.021 mmol) and cesium carbonate (66 mg, 0.202 mmol) heated in a sealed tube at 130° C. for 12 hours, and isolated as a solid (55 mg, yield 97.4%). $^1$H NMR (400 MHz, CDCl$_3$) δ ppm 8.25-8.29 (t, 2H, J=7.6 Hz), 7.88-7.90 (dd, 1H, J=1.6 Hz, 8.0 Hz), 7.85 (s, 1H), 7.49-7.53 (m, 1H), 7.23-7.27 (m, 3H), 7.08-7.12 (t, 1H, J=7.6 Hz), 6.86-6.88 (m, 2H), 6.508-6.514 (d, 1H, J=2.4 Hz), 6.32-6.35 (dd, 1H, J=2.4 Hz, 8.8 Hz), 4.49-4.59 (dd, 2H, J=14.8 Hz, 24.0 Hz), 4.37-4.39 (d, 1H, J=7.6 Hz), 3.86-3.88 (m, 7H), 3.81 (s, 3H), 3.54-3.59 (t, 1H, J=9.6 Hz), 3.28-3.31 (m, 1H), 3.07-3.09 (m, 5H), 2.99-3.02 (dd, 1H, J=4.0 Hz, 9.2 Hz), 1.68-1.70 (m, 2H), 1.49-1.50 (m, 2H), 1.39-1.43 (m, 1H), 1.26-1.28 (m, 3H), 0.98-1.11 (m, 5H).

Step B: (±)-N-cyclohexyl-2-(2-(2-methoxy-4-morpholinophenylamino)-5-methyl-6,7-dihydro-5H-pyrrolo[2,3-d]pyrimidin-4-ylamino)benzenesulfonamide According to General Protocol II, (±)-N-cyclohexyl-2-(2-(2-methoxy-4-morpholinophenylamino)-5-methyl-6,7-dihydro-5H-pyrrolo[2,3-d]pyrimidin-4-ylamino)benzenesulfonamide was prepared from (±)-N-cyclohexyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide (70 mg, 0.098 mmol), trifluoroacetic acid (5 mL) and four drops of concentrated sulfuric acid, and isolated as a solid (38.3 mg, yield 65.4%). $^1$H NMR (400 MHz, DMSO-d6) δ ppm 8.32-8.36 (m, 2H), 7.83-7.85 (d, 1H, J=8.0 Hz), 7.78-7.80 (d, 1H, J=8.8 Hz), 7.72-7.74 (m, 1H), 7.42-7.44 (m, 1H), 7.21 (s, 1H), 7.03-7.07 (t, 1H, J=8.0 Hz), 6.73 (s, 1H), 6.597-6.603 (d, 1H, J=2.4 Hz), 6.35-6.37 (dd, 1H, J=2.0 Hz, 8.8 Hz), 3.79 (s, 3H), 3.71-3.73 (t, 4H, J=4.8 Hz), 3.63-3.68 (t, 1H, J=9.2 Hz), 3.05-3.07 (m, 5H), 3.03-3.04 (m, 1H), 1.21-1.61 (m, 4H), 0.94-1.18 (m, 7H), 0.81-0.83 (m, 2H).

Example 30

(±)-N-(2-(2-(2-methoxy-4-morpholinophenylamino)-5-methyl-6,7-dihydro-5H-pyrrolo[2,3-d]pyrimidin-4-ylamino)phenyl)acetamide

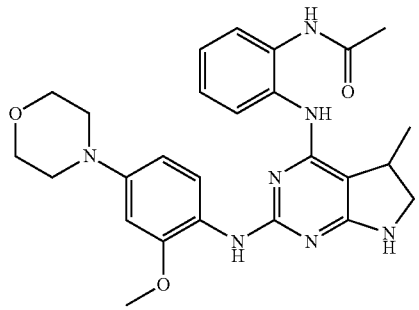 [SMILES: COc1cc(N2CCOCC2)ccc1Nc1nc2c(c(Nc3ccccc3NC(C)=O)n1)C(C)CN2]

Step A: (±)-N-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)acetamide

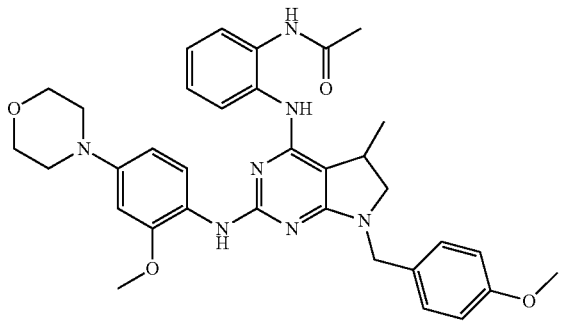 [SMILES: COc1ccc(CN2CC(C)c3c(Nc4ccccc4NC(C)=O)nc(Nc4ccc(N5CCOCC5)cc4OC)nc32)cc1]

According to General Protocol II, (±)-N-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)acetamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (70 mg, 0.141 mmol), N-(2-aminophenyl)acetamide (Intermediate C9, 26 mg, 0.173 mmol), Pd$_2$(dba)$_3$ (15 mg, 0.016 mmol), (±)-BINAP (20 mg, 0.032 mmol) and cesium carbonate (105 mg, 0.322 mmol) heated in a sealed tube at 130° C. for 12 hours, and isolated as a yellow solid (80 mg, yield 93%). $^1$H NMR (400 MHz, CDCl$_3$) δ ppm 8.75 (s, 1H), 8.11-8.13 (d, 1H, J=8.4 Hz), 7.74-7.76 (d, 1H, J=8.0 Hz), 7.31-7.33 (m, 1H), 7.13-7.26 (m, 5H), 6.86-6.88 (d, 2H, J=8.4 Hz), 6.49-6.50 (d, 1H, J=2.4 Hz), 6.37-6.39 (dd, 1H, J=2.4 Hz, 8.8 Hz), 4.48-4.58 (dd, 2H, J=15.2 Hz, 28.4 Hz), 3.86-3.89 (m, 7H), 3.80 (s, 3H), 3.51-3.55 (t, 1H, J=9.2 Hz), 3.07-3.10 (m, 5H), 2.95-2.98 (dd, 1H, J=4.0 Hz, 9.6 Hz), 2.02 (s, 3H), 0.86-0.89 (m, 3H).

Step B: (±)-N-(2-(2-(2-methoxy-4-morpholinophenylamino)-5-methyl-6,7-dihydro-5H-pyrrolo[2,3-d]pyrimidin-4-ylamino)phenyl)acetamide According to General Protocol II, (±)-N-(2-(2-(2-methoxy-4-morpholinophenylamino)-5-methyl-6,7-dihydro-5H-pyrrolo[2,3-d]pyrimidin-4-ylamino)phenyl)acetamide was prepared from (±)-N-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)acetamide (80 mg, 0.131 mmol), trifluoroacetic acid (8 mL) and three drops of concentrated sulfuric acid, and isolated as a yellow solid (45 mg, yield 70%). $^1$H NMR (400 MHz, DMSO-d6) δ ppm 10.00 (s, 1H), 7.97-7.99 (d, 1H, J=8.8 Hz), 7.68-7.69 (d, 1H, J=7.2 Hz), 7.59 (s, 1H), 7.36-7.38 (d, 1H, J=8.0 Hz), 7.24-7.27 (t, 1H, J=7.2 Hz), 7.08-7.15 (m, 2H), 6.65-6.66 (d, 2H, J=2.4 Hz), 6.35-6.37 (d, 1H, J=7.6 Hz), 3.86 (s, 3H), 3.78-3.81 (t, 4H, J=4.4 Hz), 3.67-3.71 (t, 1H, J=9.2 Hz), 3.23 (m, 1H), 3.08-3.10 (m, 5H), 2.12 (s, 3H), 1.12-1.14 (d, 3H, J=6.4 Hz).

Example 31

(±)-N-(2-(2-(2-methoxy-4-morpholinophenylamino)-5-methyl-6,7-dihydro-5H-pyrrolo[2,3-d]pyrimidin-4-ylamino)phenyl)-N-methylmethanesulfonamide

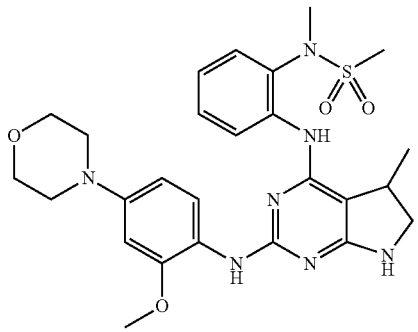

Step A: (±)-N-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)-N-methylmethanesulfonamide

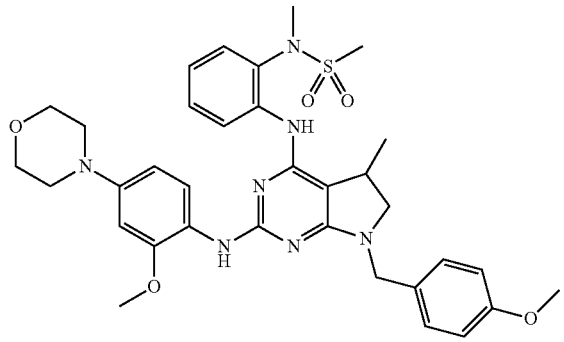 [SMILES: COc1ccc(CN2CC(C)c3c(Nc4ccccc4N(C)S(C)(=O)=O)nc(Nc4ccc(N5CCOCC5)cc4OC)nc32)cc1]

According to General Protocol II, (±)-N-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)-N-methylmethanesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (80 mg, 0.161 mmol), N-(2-aminophenyl)-N-methylmethanesulfonamide (Intermediate 010, 39 mg, 0.195 mmol), Pd$_2$(dba)$_3$ (15 mg, 0.016 mmol), (±)-BINAP (20 mg, 0.032 mmol) and cesium carbonate (105 mg, 0.322 mmol) heated at 130° C. in a sealed tube for 12 hours, and isolated as a solid (80 mg, yield 75%). $^1$H NMR (400 MHz, CDCl$_3$) δ ppm 8.38-8.40 (d, 2H, J=8.8 Hz), 7.32-7.36 (t, 1H, J=8.4 Hz), 7.20-7.26 (m, 4H), 7.00-7.04 (m, 1H), 6.86-6.88 (d, 2H, J=8.8 Hz), 6.518-6.524 (d, 1H, J=2.4 Hz), 6.44-6.46 (dd, 1H, J=2.8 Hz, 8.8 Hz), 4.46-4.60 (dd, 2H, J=14.8 Hz, 41.6 Hz), 3.86-3.89 (m, 7H), 3.80 (s, 3H), 3.52-3.56 (t, 1H, J=9.6 Hz), 3.27-3.28 (m, 1H), 3.27 (s, 3H), 3.09-3.11 (t, 4H, J=4.4 Hz), 2.97-3.00 (m, 4H), 1.26-1.27 (m, 3H).

Step B: (±)-N-(2-(2-(2-methoxy-4-morpholinophenylamino)-5-methyl-6,7-dihydro-5H-pyrrolo[2,3-d]pyrimidin-4-ylamino)phenyl)-N-methylmethanesulfonamide According to General Protocol II, (±)-N-(2-(2-(2-methoxy-4-morpholinophenylamino)-5-methyl-6,7-dihydro-5H-pyrrolo[2,3-d]pyrimidin-4-ylamino)phenyl)-N-methylmethanesulfonamide was prepared from (±)-N-(2-(2-(2-methoxy-4-morpholinophenylamino)-7-(4-methoxybenzyl)-5-methyl-6,7-dihydro-5H-pyrrolo[2,3-d]pyrimidin-4-ylamino)phenyl)-N-methylmethanesulfonamide (80 mg, 0.121 mmol), trifluoroacetic acid (8 mL) and three drops of concentrated sulfuric acid, and isolated as a solid (28.4 mg, yield 43%). $^1$H NMR (400 MHz, DMSO-d6) δ ppm 8.26-8.28 (d, 1H, J=8.0 Hz), 7.80-7.82 (d, 1H, J=8.8 Hz), 7.51-7.53 (d, 1H, J=8.4 Hz), 7.25-7.26 (m, 2H), 7.17 (s, 1H), 7.03-7.04 (m, 1H), 6.61-6.62 (m, 2H), 6.41-6.43 (d, 1H, J=8.0 Hz), 3.81 (s, 3H), 3.74-3.75 (m, 4H), 3.66-3.67 (m, 1H), 3.16-3.17 (m, 1H), 3.10 (s, 3H), 3.03-3.07 (m, 8H), 1.20-1.23 (t, 3H, J=6.4 Hz).

Example 32

(±)-N-(2-((2-(2-methoxy-4-morpholinophenylamino)-5-methyl-6,7-dihydro-5H-pyrrolo[2,3-d]pyrimidin-4-ylamino)methyl)phenyl)-N-methylmethanesulfonamide

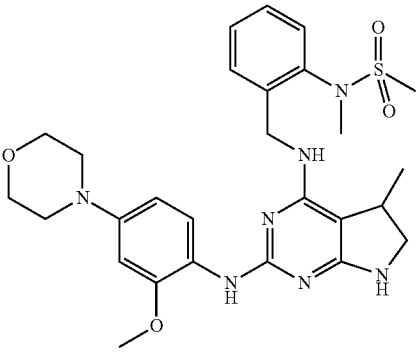 [SMILES: COc1cc(N2CCOCC2)ccc1Nc1nc(NCc2ccccc2N(C)S(C)(=O)=O)c2c(n1)NCC2C]

Step A: (±)-N-(2-((2-(2-methoxy-4-morpholinophenylamino)-7-(4-methoxybenzyl)-5-methyl-6,7-dihydro-5H-pyrrolo[2,3-d]pyrimidin-4-ylamino)methyl)phenyl)-N-methylmethanesulfonamide

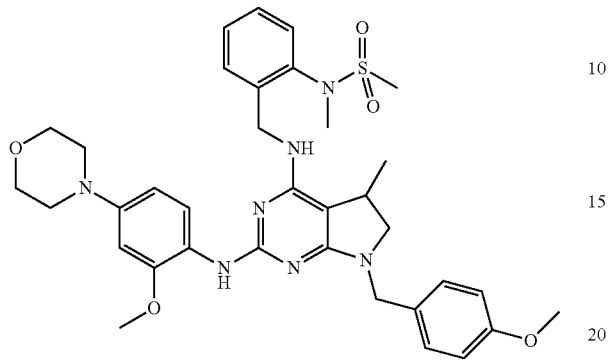

According to General Protocol II, (±)-N-(2-((2-(2-methoxy-4-morpholinophenylamino)-7-(4-methoxybenzyl)-5-methyl-6,7-dihydro-5H-pyrrolo[2,3-d]pyrimidin-4-ylamino)methyl)phenyl)-N-methylmethanesulfonamide was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (60 mg, 0.121 mmol), N-(2-(aminomethyl)phenyl)-N-methylmethanesulfonamide hydrochloride (Intermediate C11, 37 mg, 0.147 mmol), Pd$_2$(dba)$_3$ (13 mg, 0.014 mmol), (±)-BINAP (15 mg, 0.024 mmol) and cesium carbonate (118 mg, 0.362 mmol) heated at 130° C. in a sealed tube for 24 hours, and isolated as a solid (50 mg, yield 60.8%). $^1$H NMR (400 MHz, CDCl$_3$) δ ppm 8.49-8.51 (m, 1H), 7.65-7.68 (t, 1H, J=4.4 Hz), 7.32-7.34 (m, 2H), 7.18-7.24 (m, 3H), 6.84-6.86 (m, 2H), 6.516-6.522 (d, 1H, J=1.6 Hz), 6.44-6.46 (d, 1H, J=8.8 Hz), 5.19 (br, 1H), 4.87 (br s, 1H), 4.41-4.54 (dd, 2H, J=14.4 Hz, 40.0 Hz), 3.85-3.88 (m, 7H), 3.80 (s, 3H), 3.40-3.41 (m, 1H), 3.30 (s, 2H), 3.06-3.09 (m, 4H), 3.00 (s, 3H), 2.86-2.89 (dd, 1H, J=4.0 Hz, 8.8 Hz), 1.26-1.28 (m, 3H).

Step B: (±)-N-(2-((2-(2-methoxy-4-morpholinophenylamino)-5-methyl-6,7-dihydro-5H-pyrrolo[2,3-d]pyrimidin-4-ylamino)methyl)phenyl)-N-methylmethanesulfonamide According to General Protocol II, (±)-N-(2-((2-(2-methoxy-4-morpholinophenylamino)-5-methyl-6,7-dihydro-5H-pyrrolo[2,3-d]pyrimidin-4-ylamino)methyl)phenyl)-N-methylmethanesulfonamide was prepared from (±)-N-(2-((2-(2-methoxy-4-morpholinophenylamino)-7-(4-methoxybenzyl)-5-methyl-6,7-dihydro-5H-pyrrolo[2,3-a]pyrimidin-4-ylamino)methyl)phenyl)-N-methylmethanesulfonamide (50 mg, 0.074 mmol), trifluoroacetic acid (4 mL) and one drops of concentrated sulfuric acid, and isolated as a solid (18.3 mg, yield 44.5%). $^1$H NMR (400 MHz, DMSO-d6) δ ppm 7.83 (s, 1H), 7.48-7.50 (m, 1H), 7.29-7.36 (m, 3H), 6.89 (br, 1H), 6.54-6.58 (m, 2H), 6.22-6.23 (m, 2H), 4.44-4.78 (m, 2H), 3.77 (s, 3H), 3.69-3.71 (t, 4H, J=4.8 Hz), 3.55-3.59 (t, 1H, J=4.8 Hz), 3.20-3.23 (m, 4H), 3.09 (s, 3H), 2.96-2.98 (m, 5H), 1.12-1.14 (d, 3H, J=6.0 Hz).

Example 33

(±)-N$^2$-(2-methoxy-4-morpholinophenyl)-5-methyl-N$^4$-(6-methylpyridin-2-yl)-6,7-dihydro-5H-pyrrolo[2,3-d]pyrimidine-2,4-diamine

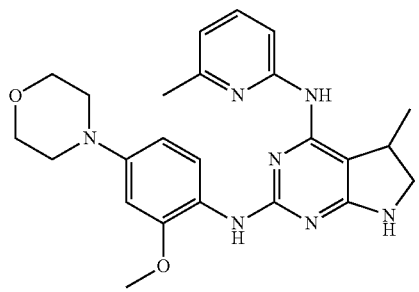 [SMILES: COc1cc(N2CCOCC2)ccc1Nc1nc2c(c(Nc3cccc(C)n3)n1)C(C)CN2]

Step A: (±)-N$^2$-(2-methoxy-4-morpholinophenyl)-7-(4-methoxybenzyl)-5-methyl-N$^4$-(6-methylpyridin-2-yl)-6,7-dihydro-5H-pyrrolo[2,3-d]pyrimidine-2,4-diamine

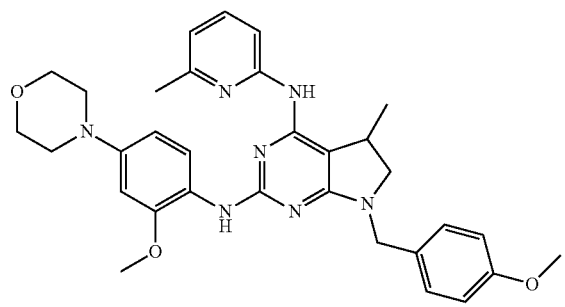 [SMILES: COc1ccc(CN2CC(C)c3c(Nc4cccc(C)n4)nc(Nc4ccc(N5CCOCC5)cc4OC)nc32)cc1]

According to General Protocol II, (±)-N$^2$-(2-methoxy-4-morpholinophenyl)-7-(4-methoxybenzyl)-5-methyl-N$^4$-(6-methylpyridin-2-yl)-6,7-dihydro-5H-pyrrolo[2,3-d]pyrimidine-2,4-diamine was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (70 mg, 0.141 mmol), 6-methylpyridin-2-amine (commercial available, 19 mg, 0.176 mmol), Pd$_2$(dba)$_3$ (13 mg, 0.014 mmol), (±)-BINAP (18 mg, 0.029 mmol) and cesium carbonate (92 mg, 0.282 mmol) heated at 130° C. in a sealed tube for 12 hours, and isolated as a solid (70 mg, yield 87%). $^1$H NMR (400 MHz, CDCl$_3$) δ ppm 8.08-8.10 (d, 1H, J=8.4 Hz), 7.48-7.52 (t, 1H, J=8.0 Hz), 7.33-7.38 (m, 2H), 7.22-7.25 (m, 2H), 7.12 (s, 1H), 6.86-6.88 (d, 2H, J=8.4 Hz), 6.70-6.72 (d, 1H, J=7.2 Hz), 6.50-6.54 (m, 2H), 4.61 (s, 1H), 4.46-4.61 (dd, 2H, J=14.8 Hz, 44.4 Hz), 3.87-3.88 (m, 7H), 3.80 (s, 3H), 3.54-3.59 (t, 1H, J=9.2 Hz), 3.11-3.14 (t, 4H, J=4.4 Hz), 2.99-3.02 (dd, 1H, J=2.0 Hz, 9.2 Hz), 2.33 (m, 4H), 1.23-1.26 (m, 3H).

Step B: (±)-N$^2$-(2-methoxy-4-morpholinophenyl)-5-methyl-N$^4$-(6-methylpyridin-2-yl)-6,7-dihydro-5H-pyrrolo[2,3-d]pyrimidine-2,4-diamine According to General Protocol II, (±)-N$^2$-(2-methoxy-4-morpholinophenyl)-5-methyl-N$^4$-(6-methylpyridin-2-yl)-6, 7-dihydro-5H-pyrrolo[2,3-d]pyrimidine-2,4-diamine was prepared from (±)-N²-(2-methoxy-4-morpholinophenyl)-7-(4-methoxybenzyl)-5-methyl-N⁴-(6-methylpyridin-2-yl)-6,7-dihydro-5H-pyrrolo[2,3-d]pyrimidine-2,4-diamine (70 mg, 0.123 mmol), trifluoroacetic acid (5 mL) and four drops of concentrated sulfuric acid, and isolated as a solid (43.2 mg, yield 78.5%). ¹H NMR (400 MHz, DMSO-d6) δ ppm 8.46 (s, 1H), 7.82-7.83 (m, 1H), 7.70-7.71 (m, 1H), 7.44-7.45 (m, 1H), 7.10-7.11 (m, 1H), 6.61-6.73 (m, 2H), 6.40-6.41 (m, 1H), 3.72-3.79 (m, 7H), 3.49-3.51 (m, 3H), 2.97-3.15 (m, 7H), 2.20 (m, 4H), 0.87-0.91 (m, 3H).

Example 34

(±)-N⁴-(3,4-difluorophenyl)-N²-(2-methoxy-4-morpholinophenyl)-5-methyl-6,7-dihydro-5H-pyrrolo[2,3-d]pyrimidine-2,4-diamine

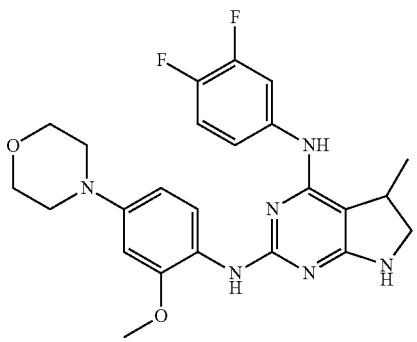 [SMILES: COc1cc(N2CCOCC2)ccc1Nc1nc2c(c(Nc3ccc(F)c(F)c3)n1)C(C)CN2]

Step A: (±)-N⁴-(3,4-difluorophenyl)-N²-(2-methoxy-4-morpholinophenyl)-7-(4-methoxybenzyl)-5-methyl-6,7-dihydro-5H-pyrrolo[2,3-d]pyrimidine-2,4-diamine

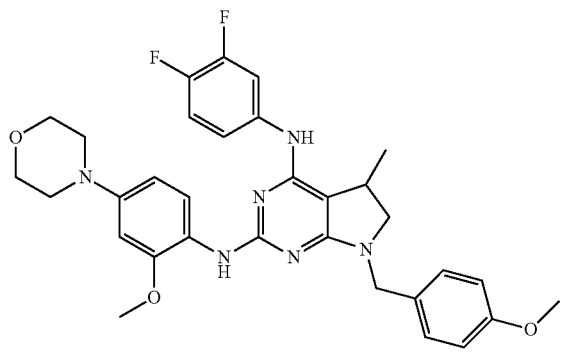 [SMILES: COc1ccc(CN2CC(C)c3c(Nc4ccc(F)c(F)c4)nc(Nc4ccc(N5CCOCC5)cc4OC)nc32)cc1]

According to General Protocol II, (±)-N⁴-(3,4-difluorophenyl)-N²-(2-methoxy-4-morpholinophenyl)-7-(4-methoxybenzyl)-5-methyl-6,7-dihydro-5H-pyrrolo[2,3-d]pyrimidine-2,4-diamine was prepared from (±)-4-chloro-N-(2-methoxy-4-morpholinophenyl)-7-(4-methoxybenzyl)-5-methyl-6,7-dihydro-5H-pyrrolo[2,3-d]pyrimidin-2-amine (90 mg, 0.181 mmol), 3,4-difluoroaniline (commercial available, 28 mg, 0.217 mmol), Pd₂(dba)₃ (17 mg, 0.019 mmol), (±)-BINAP (23 mg, 0.037 mmol) and cesium carbonate (120 mg, 0.368 mmol) heated in a sealed tube at 130° C. for 12 hours, and isolated as a solid (70 mg, yield 66%).

¹H NMR (400 MHz, CDCl₃) δ ppm 8.27-8.29 (d, 1H, J=8.4 Hz), 7.58-7.61 (m, 1H), 7.22-7.25 (m, 2H), 7.15 (s, 1H), 7.04-7.06 (m, 1H), 6.93-6.94 (m, 1H), 6.86-6.88 (dd, 2H, J=2.0 Hz, 6.8 Hz), 6.48-6.53 (dt, 2H, J=2.8 Hz, 8.8 Hz), 5.84 (s, 1H), 4.52-4.58 (dd, 2H, J=14.4 Hz, 24.0 Hz), 3.86-3.89 (m, 7H), 3.80 (s, 3H), 3.50-3.55 (t, 1H, J=9.2 Hz), 3.10-3.12 (m, 5H), 2.94-2.97 (dd, 1H, J=4.0 Hz, 9.6 Hz), 1.13-1.15 (d, 3H, J=6.8 Hz).

Step B: (±)-N⁴-(3,4-difluorophenyl)-N²-(2-methoxy-4-morpholinophenyl)-5-methyl-6,7-dihydro-5H-pyrrolo[2,3-d]pyrimidine-2,4-diamine According to General Protocol II, (±)-N⁴-(3,4-difluorophenyl)-N²-(2-methoxy-4-morpholinophenyl)-5-methyl-6,7-dihydro-5H-pyrrolo[2,3-d]pyrimidine-2,4-diamine was prepared from (±)-N⁴-(3,4-difluorophenyl)-N²-(2-methoxy-4-morpholinophenyl)-7-(4-methoxybenzyl)-5-methyl-6,7-dihydro-5H-pyrrolo[2,3-d]pyrimidine-2,4-diamine (70 mg, 0.119 mmol), trifluoroacetic acid (5 mL) and four drops of concentrated sulfuric acid, and isolated as a solid (51.7 mg, yield 93%). ¹H NMR (400 MHz, DMSO-d6) δ ppm 8.20 (s, 1H), 7.82-7.88 (m, 1H), 7.73-7.75 (d, 1H, J=8.8 Hz), 7.21-7.24 (m, 2H), 7.16 (s, 1H), 6.615-6.622 (d, 1H, J=2.8 Hz), 6.55 (s, 1H), 6.40-6.42 (dd, 1H, J=2.0 Hz, 8.8 Hz), 3.80 (s, 3H), 3.73-3.76 (t, 4H, J=4.4 Hz), 3.57-3.62 (t, 1H, J=8.4 Hz), 3.02-3.07 (m, 5H), 1.10-1.12 (d, 3H, J=6.8 Hz).

Example 35

(S)-2-(2-(2-methoxy-4-morpholinophenylamino)-5-methyl-6,7-dihydro-5H-pyrrolo[2,3-d]pyrimidin-4-ylamino)-N-methylbenzamide

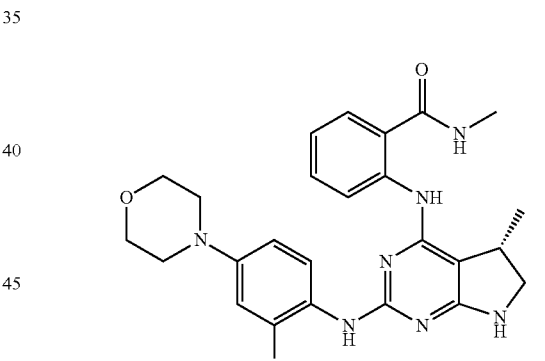

Step A: (S)-4-chloro-N-(2-methoxy-4-morpholinophenyl)-7-(4-methoxybenzyl)-5-methyl-6,7-dihydro-5H-pyrrolo[2,3-d]pyrimidin-2-amine

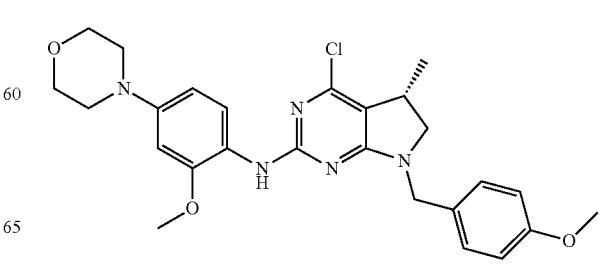

According to General Protocol II, (S)-4-chloro-N-(2-methoxy-4-morpholinophenyl)-7-(4-methoxybenzyl)-5-methyl-6,7-dihydro-5H-pyrrolo[2,3-d]pyrimidin-2-amine was prepared from (S)-2,4-dichloro-7-(4-methoxybenzyl)-5-methyl-6,7-dihydro-5H-pyrrolo[2,3-d]pyrimidine (Intermediate A3, 120 mg, 0.37 mmol), 2-methoxy-4-morpholinoaniline (Intermediate B1, 85 mg, 0.41 mmol), Pd$_2$(dba)$_3$ (34 mg, 0.04 mmol), (±)-BINAP (46 mg, 0.74 mmol) and cesium carbonate (181 mg, 0.56 mmol), and isolated as a solid (88 mg, yield 48%). $^1$H NMR (400 MHz, CDCl$_3$) δ ppm 8.37-8.40 (d, 1H, J=9.6 Hz), 7.40 (s, 1H), 7.20-7.25 (m, 2H), 6.83-6.88 (m, 2H), 6.49-6.52 (dd, 2H, J=2.8 Hz, 6.0 Hz), 4.55 (s, 2H), 3.85-3.88 (s+m, 7H), 3.80 (s, 3H), 3.58-3.62 (t, 1H, J=9.6 Hz), 3.28-3.30 (m, 1H), 3.08-3.11 (t, 4H, J=4.8 Hz), 3.00-3.03 (dd, 1H, J=4.0 Hz, 9.6 Hz), 1.24-1.27 (m, 3H).

Step B: (S)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzamide

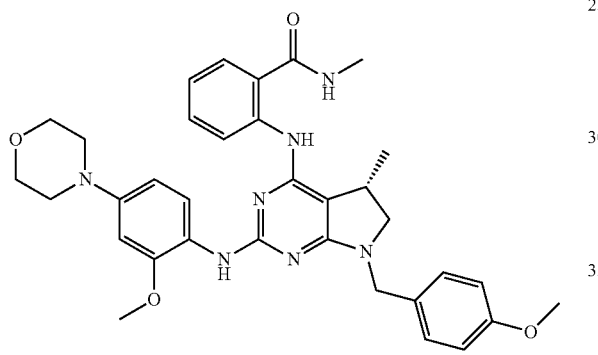

According to General Protocol II, (S)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzamide was prepared from (S)-4-chloro-N-(2-methoxy-4-morpholinophenyl)-7-(4-methoxybenzyl)-5-methyl-6,7-dihydro-5H-pyrrolo[2,3-d]pyrimidin-2-amine (88 mg, 0.18 mmol), 2-amino-N-methylbenzamide (Intermediate C1, 27 mg, 0.18 mmol), Pd$_2$(dba)$_3$ (16 mg, 0.02 mmol), (±)-BINAP (22 mg, 0.04 mmol) and cesium carbonate (87 mg, 0.27 mmol) heated at 130° C. for overnight, and isolated as a solid (50 mg, yield 46%). $^1$H NMR (400 MHz, CDCl$_3$) δ ppm 10.00 (s, 1H), 8.61-8.63 (d, 1H, J=8.4 Hz), 8.39-7.42 (d, 1H, J=8.8 Hz), 7.38-7.43 (m, 2H), 7.20-7.27 (m, 3H), 6.86-6.93 (m, 3H), 6.46-6.49 (m, 2H), 6.22 (s, 1H), 4.46-4.61 (dd, 2H, J=10.8 Hz, 43.2 Hz), 3.87-3.88 (s+m, 7H), 3.81 (s, 3H), 3.51-3.54 (m, 1H), 3.36 (s, 1H), 3.10-3.12 (t, 4H, J=3.2 Hz), 2.97-3.01 (m, 4H), 1.27-1.33 (m, 3H).

Step C: (S)-2-(2-(2-methoxy-4-morpholinophenylamino)-5-methyl-6,7-dihydro-5H-pyrrolo[2,3-d]pyrimidin-4-ylamino)-N-methylbenzamide According to General Protocol II, (S)-2-(2-(2-methoxy-4-morpholinophenylamino)-5-methyl-6,7-dihydro-5H-pyrrolo[2,3-d]pyrimidin-4-ylamino)-N-methylbenzamide was prepared from (S)-2-(2-(2-methoxy-4-morpholinophenylamino)-7-(4-methoxybenzyl)-5-methyl-6,7-dihydro-5H-pyrrolo[2,3-d]pyrimidin-4-ylamino)-N-methylbenzamide (50 mg, 0.082 mmol), trifluoroacetic acid (10 mL) and four drops of concentrated sulfuric acid, and isolated as a solid (20 mg, yield 50%). $^1$H NMR (400 MHz, DMSO-d6) δ ppm 10.08 (s, 1H), 8.60-8.63 (dd, 1H, J=1.2 Hz, 8.4 Hz), 8.24-8.26 (d, 1H, J=8.8 Hz), 7.38-7.42 (m, 2H), 7.10 (s, 1H), 6.91-6.95 (m, 1H), 6.51-6.52 (d, 1H, J=2.4 Hz), 6.45-6.48 (dd, 1H, J=3.2 Hz, 8.8 Hz), 6.18-6.19 (d, 1H, J=4.4 Hz), 4.49 (s, 1H), 3.85-3.89 (s+m, 7H), 3.76-3.81 (t, 1H, J=9.2 Hz), 3.47-3.49 (m, 1H), 3.20-3.23 (dd, 1H, J=4.4 Hz, 8.8 Hz), 3.09-3.11 (t, 4H, J=4.8 Hz), 2.98-2.99 (d, 3H, J=4.8 Hz), 1.38-1.40 (d, 3H, J=6.4 Hz). e.e. 92.70%, determined by HPLC analysis (Chiralcel AD-H, 0.025% diethylamino in ethanol/hexane (1/1) at x mL·min$^{-1}$; λ=220 nm; T=30° C., t$_R$=7.200 minutes for the (R)-enantiomer (minor) and 10.798 minutes for the (S)-enantiomer (major)).

Example 36

(S)—N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide

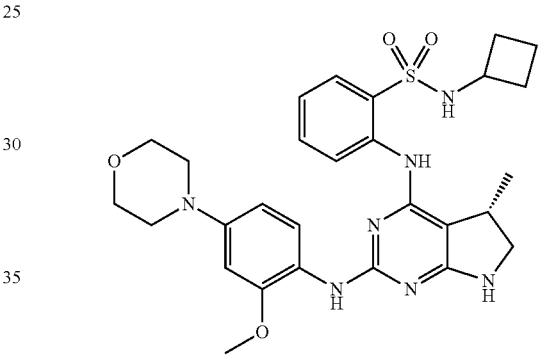

Step A: (S)—N-cyclobutyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide

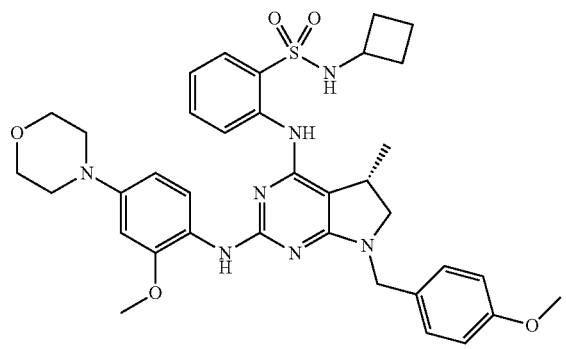

According to General Protocol II, (S)—N-cyclobutyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide was prepared from (S)-4-chloro-N-(2-methoxy-4-morpholinophenyl)-7-(4-methoxybenzyl)-5-methyl-6,7-dihydro-5H-pyrrolo[2,3-d]

pyrimidin-2-amine (32 mg, 0.065 mmol), 2-amino-N-cyclobutylbenzenesulfonamide (Intermediate C6, 17 mg, 0.077 mmol), Pd₂(dba)₃ (12 mg, 0.013 mmol), X-Phos (6 mg, 0.013 mmol) and cesium carbonate (42 mg, 0.129 mmol) heated in a sealed tube at 130° C. for 12 hours, and isolated as a solid (20 mg, yield 45%). ¹H NMR (400 MHz, CDCl₃) δ ppm 8.30-8.32 (d, 2H, J=8.4 Hz), 7.90 (s, 1H), 7.84-7.86 (m, 1H), 7.48-7.52 (t, 1H, J=7.6 Hz), 7.24-7.26 (m, 2H), 7.05-7.09 (t, 1H, J=7.6 Hz), 6.87-6.89 (d, 2H, J=8.4 Hz), 6.51-6.52 (d, 1H, J=2.4 Hz), 6.34-6.36 (dd, 1H, J=2.4 Hz, 8.4 Hz), 4.66-4.68 (d, 1H, J=9.2 Hz), 4.49-4.60 (dd, 2H, J=14.8 Hz, 29.2 Hz), 3.86-3.89 (m, 7H), 3.81 (s, 3H), 3.71-3.74 (m, 1H), 3.55-3.60 (t, 1H, J=9.6 Hz), 3.28-3.31 (m, 1H), 3.07-3.10 (t, 4H, J=4.8 Hz), 3.00-3.03 (dd, 1H, J=4.0 Hz, 9.2 Hz), 1.96-2.02 (m, 2H), 1.66-1.75 (m, 2H), 1.45-1.52 (m, 2H), 1.22-1.24 (m, 3H).

Step B: (S)—N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide According to General Protocol II, (S)—N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide was prepared from ti (S)—N-cyclobutyl-2-(2-(2-methoxy-4-morpholinophenylamino)-7-(4-methoxybenzyl)-5-methyl-6,7-dihydro-5H-pyrrolo[2,3-d]pyrimidin-4-ylamino)benzenesulfonamide (20 mg, 0.029 mmol), trifluoroacetic acid (10 mL) and three drops of concentrated sulfuric acid, and isolated as a solid (14 mg, yield 85%). ¹H NMR (400 MHz, CDCl₃) δ ppm 8.29-8.31 (d, 1H, J=8.4 Hz), 8.15-8.17 (d, 1H, J=8.8 Hz), 8.02 (s, 1H), 7.86-7.88 (d, 1H, J=8.0 Hz), 7.48-7.52 (t, 1H, J=8.0 Hz), 7.18 (s, 1H), 7.08-7.12 (t, 1H, J=7.6 Hz), 6.496-6.501 (d, 1H, J=2.0 Hz), 6.32-6.35 (dd, 1H, J=2.0 Hz, 8.8 Hz), 4.89-4.90 (d, 1H, J=8.8 Hz), 4.69 (s, 1H), 3.70-3.88 (m, 8H), 3.38-3.43 (m, 1H), 3.21-3.24 (dd, 1H, J=4.0 Hz, 8.8 Hz), 3.07-3.09 (t, 4H, J=4.4 Hz), 1.97-2.01 (m, 2H), 1.64-1.75 (m, 2H), 1.42-1.51 (m, 2H), 1.26-1.33 (m, 3H).

Example 37

2-(2-(2-methoxy-4-morpholinophenylamino)-5,5-dimethyl-6,7-dihydro-5H-pyrrolo[2,3-d]pyrimidin-4-ylamino)-N-methylbenzamide

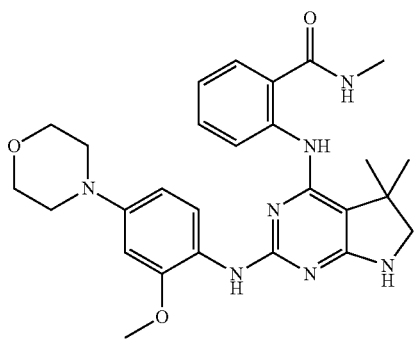 [SMILES: CNC(=O)c1ccccc1Nc1nc(Nc2ccc(N3CCOCC3)cc2OC)nc2c1C(C)(C)CN2]

Step A: 4-chloro-N-(2-methoxy-4-morpholinophenyl)-7-(4-methoxybenzyl)-5,5-dimethyl-6,7-dihydro-5H-pyrrolo[2,3-d]pyrimidin-2-amine

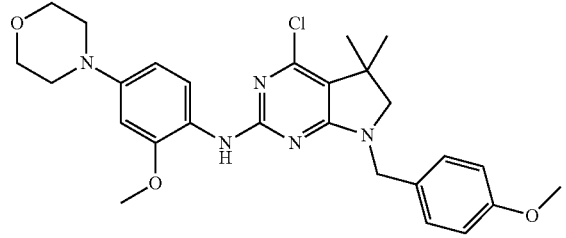 [SMILES: COc1ccc(CN2CC(C)(C)c3c(Cl)nc(Nc4ccc(N5CCOCC5)cc4OC)nc32)cc1]

According to General Protocol II, 4-chloro-N-(2-methoxy-4-morpholinophenyl)-7-(4-methoxybenzyl)-5,5-dimethyl-6,7-dihydro-5H-pyrrolo[2,3-d]pyrimidin-2-amine was prepared from 2,4-dichloro-7-(4-methoxybenzyl)-5,5-dimethyl-6,7-dihydro-5H-pyrrolo[2,3-d]pyrimidine (Intermediate A4, 156 mg, 0.46 mmol), 2-methoxy-4-morpholinoaniline (Intermediate B1, 115 mg, 0.55 mmol), Pd₂(dba)₃ (42 mg, 0.046 mmol), (±)-BINAP (57 mg, 0.092 mmol) and potassium carbonate (225 mg, 0.69 mmol) heated at 130° C. under microwave for 3 hours, and isolated as a white solid (86 mg, yield 37%). ¹H NMR (400 MHz, CDCl₃) δ ppm 8.36-8.38 (d, 1H, J=9.2 Hz), 7.39 (s, 1H), 7.20-7.22 (d, 2H, J=8.4 Hz), 6.86-6.88 (d, 2H, J=8.8 Hz), 6.50-6.51 (m, 2H), 4.57 (s, 2H), 3.85-3.87 (m, 7H), 3.80 (s, 3H), 3.16 (s, 2H), 3.08-3.11 (t, 4H, J=4.8 Hz), 1.35 (s, 6H).

Step B: 2-(2-(2-methoxy-4-morpholinophenylamino)-7-(4-methoxybenzyl)-5,5-dimethyl-6,7-dihydro-5H-pyrrolo[2,3-d]pyrimidin-4-ylamino)-N-methylbenzamide

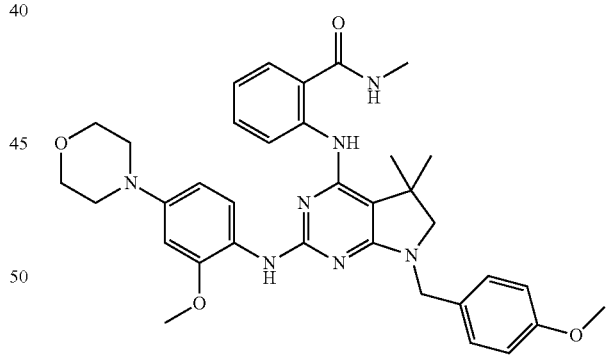

According to General Protocol II, 2-(2-(2-methoxy-4-morpholinophenylamino)-7-(4-methoxybenzyl)-5,5-dimethyl-6,7-dihydro-5H-pyrrolo[2,3-d]pyrimidin-4-ylamino)-N-methylbenzamide was prepared from 4-chloro-N-(2-methoxy-4-morpholinophenyl)-7-(4-methoxybenzyl)-5,5-dimethyl-6,7-dihydro-5H-pyrrolo[2,3-d]pyrimidin-2-amine (86 mg, 0.169 mol), 2-amino-N-methylbenzamide (Intermediate C1, 51 mg, 0.338 mmol), Pd₂(dba)₃ (16 mg, 0.017 mmol), (±)-BINAP (22 mg, 0.035 mmol) and potassium carbonate (110 mg, 0.338 mmol) heated at 150° C. under microwave for 3 hours, and isolated as a white solid (70 mg, yield 67%). ¹H NMR (400 MHz, CDCl₃) δ ppm 9.76 (s, 1H), 8.52-8.54 (d, 1H, J=8.0 Hz), 8.36-8.38 (d, 1H, J=8.8 Hz), 7.37-7.41 (t, 2H, J=7.6 Hz), 7.23-7.25 (m, 2H), 7.17 (s, 1H), 6.90-6.94 (t, 1H, J=6.8 Hz), 6.86-6.90 (m, 2H), 6.51-6.52 (d, 1H, J=2.8 Hz), 6.42-6.44 (dd, 1H, J=2.0 Hz, 8.8 Hz), 6.19 (m, 1H), 4.54 (s, 2H), 3.86-3.88 (m, 7H), 3.80 (s, 3H), 3.08-3.10 (m, 6H), 2.97-2.98 (d, 3H, J=4.8 Hz), 1.46 (s, 6H).

Step C: 2-(2-(2-methoxy-4-morpholinophenylamino)-5,5-dimethyl-6,7-dihydro-5H-pyrrolo[2,3-d]pyrimidin-4-ylamino)-N-methylbenzamide According to General Protocol II, 2-(2-(2-methoxy-4-morpholinophenylamino)-5,5-dimethyl-6,7-dihydro-5H-pyrrolo[2,3-d]pyrimidin-4-ylamino)-N-methylbenzamide was prepared from 2-(2-(2-methoxy-4-morpholinophenylamino)-7-(4-methoxybenzyl)-5,5-dimethyl-6,7-dihydro-5H-pyrrolo[2,3-d]pyrimidin-4-ylamino)-N-methylbenzamide (70 mg, 0.112 mmol), trifluoroacetic acid (3 mL) and five drops of concentrated sulfuric acid, and isolated as a yellow solid (30 mg, yield 53.3%). $^1$H NMR (400 MHz, CDCl$_3$) δ ppm 9.84 (s, 1H), 8.52-8.54 (dd, 1H, J=1.2 Hz, 8.8 Hz), 8.23-8.25 (d, 1H, J=8.8 Hz), 7.37-7.41 (m, 2H), 7.09 (s, 1H), 6.96-7.00 (m, 1H), 6.50-6.51 (d, 1H, J=2.8 Hz), 6.41-6.44 (dd, 1H, J=2.8 Hz, 8.8 Hz), 6.11 (s, 1H), 4.43 (s, 1H), 3.85-3.89 (m, 7H), 3.336-3.339 (d, 3H, J=1.2 Hz), 3.08-3.11 (t, 4H, J=4.8 Hz), 2.99-3.00 (d, 3H, J=4.8 Hz), 1.52 (s, 6H).

Compounds in Example 38-163 were synthesized according to the synthetic method described in the invention.

Example 38

2-(2-(2-methoxy-4-morpholinophenylamino)-6,7-dihydro-5H-pyrrolo[2,3-d]pyrimidin-4-ylamino)-N,N-dimethylbenzenesulfonamide

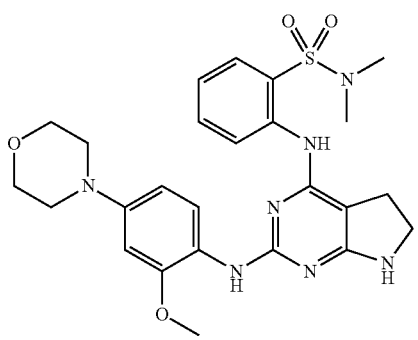 [SMILES: COc1cc(N2CCOCC2)ccc1Nc1nc2c(c(Nc3ccccc3S(=O)(=O)N(C)C)n1)CCN2]

$^1$H NMR (400 MHz, DMSO-d$_6$) δ ppm 8.53-8.55 (dd, 1H, J=0.8 Hz, 8.0 Hz), 8.41 (s, 1H), 7.74-7.76 (d, 1H, J=8.4 Hz), 7.66-7.68 (m, 1H), 7.54-7.55 (m, 1H), 7.28 (s, 1H), 7.10-7.14 (t, 1H, J=7.2 Hz), 6.79 (s, 1H), 6.625-6.631 (d, 1H, J=2.4 Hz), 6.43-6.46 (dd, 1H, J=6.4 Hz, 8.8 Hz), 3.82 (s, 3H), 3.74-3.76 (m, 4H), 3.47-3.55 (m, 2H), 3.07-3.09 (m, 4H), 2.78-2.82 (t, 2H, J=8.4 Hz), 2.64 (s, 6H)

$^1$H NMR (400 MHz, DMSO-d$_6$) δ ppm 8.53-8.55 (dd, 1H, J=0.8 Hz, 8.0 Hz), 8.41 (s, 1H), 7.74-7.76 (d, 1H, J=8.4 Hz), 7.66-7.68 (m, 1H), 7.54-7.55 (m, 1H), 7.28 (s, 1H), 7.10-7.14 (t, 1H, J=7.2 Hz), 6.79 (s, 1H), 6.625-6.631 (d, 1H, J=2.4 Hz), 6.43-6.46 (dd, 1H, J=6.4 Hz, 8.8 Hz), 3.82 (s, 3H), 3.74-3.76 (m, 4H), 3.47-3.55 (m, 2H), 3.07-3.09 (m, 4H), 2.78-2.82 (t, 2H, J=8.4 Hz), 2.64 (s, 6H).

Example 39

N-butyl-2-(2-(2-methoxy-4-morpholinophenylamino)-6,7-dihydro-5H-pyrrolo[2,3-d]pyrimidin-4-ylamino)benzenesulfonamide

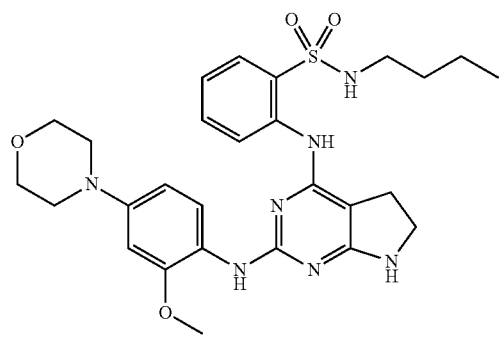 [SMILES: CCCCNS(=O)(=O)c1ccccc1Nc1nc(Nc2ccc(N3CCOCC3)cc2OC)nc2c1CCN2]

$^1$H NMR (400 MHz, DMSO-d$_6$) δ ppm 8.41-8.43 (d, 1H, J=8.0 Hz), 8.27 (s, 1H), 7.79-7.82 (m, 2H), 7.69-7.71 (d, 1H, J=8.0 Hz), 7.45-7.46 (m, 1H), 7.21 (s, 1H), 7.04-7.06 (m, 1H), 6.72 (s, 1H), 6.61 (s, 1H), 6.40-6.42 (d, 1H, J=8.8 Hz), 3.79 (s, 3H), 3.72-3.73 (m, 4H), 3.49-3.53 (t, 2H, J=8.4 Hz), 3.05-3.06 (m, 4H), 2.72-2.80 (m, 4H), 1.27-1.30 (m, 2H), 1.11-1.17 (m, 2H), 0.69-0.73 (t, 3H, J=6.8 Hz).

Example 40

N-isopropyl-2-(2-(2-methoxy-4-morpholinophenylamino)-6,7-dihydro-5H-pyrrolo[2,3-d]pyrimidin-4-ylamino)benzenesulfonamide

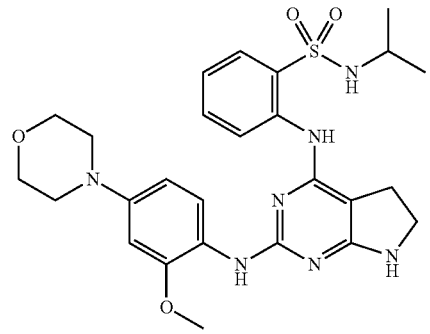 [SMILES: COc1cc(N2CCOCC2)ccc1Nc1nc2c(c(Nc3ccccc3S(=O)(=O)NC(C)C)n1)CCN2]

$^1$H NMR (400 MHz, DMSO-d6) δ ppm 8.38-8.40 (d, 1H, J=8.4 Hz), 8.23 (s, 1H), 7.78-7.83 (m, 2H), 7.72-7.74 (d, 1H, J=8.0 Hz), 7.43-7.47 (t, 1H, J=7.6 Hz), 7.23 (s, 1H), 7.01-7.05 (t, 1H, J=7.6 Hz), 6.73 (s, 1H), 6.61 (s, 1H), 6.39-6.41 (d, 1H, J=8.8 Hz), 3.788-3.791 (d, 3H, J=1.2 Hz), 3.72-3.73 (m, 4H), 3.49-3.53 (t, 2H, J=8.4 Hz), 3.23-3.28 (m, 1H), 3.05-3.06 (m, 4H), 2.76-2.80 (t, 2H, J=8.0 Hz), 0.91-0.93 (m, 6H).

Example 41

2-(2-(2-methoxy-4-morpholinophenylamino)-6,7-dihydro-5H-pyrrolo[2,3-d]pyrimidin-4-ylamino)benzenesulfonamide

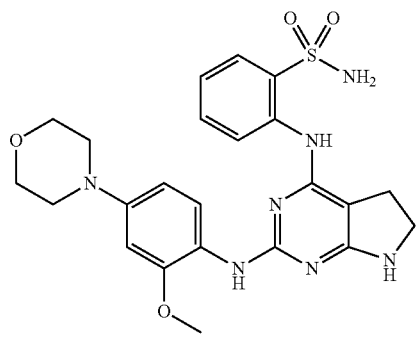 [SMILES: COc1cc(N2CCOCC2)ccc1Nc1nc2c(c(Nc3ccccc3S(N)(=O)=O)n1)CCN2]

$^1$H NMR (400 MHz, DMSO-d6) δ ppm 8.51-8.53 (d, 1H, J=8.4 Hz), 8.39 (s, 1H), 7.89-7.91 (d, 1H, J=8.8 Hz), 7.82-7.84 (dd, 1H, J=1.2 Hz, 8.0 Hz), 7.68 (s, 2H), 7.49-7.53 (m, 1H), 7.29 (s, 1H), 7.09-7.13 (m, 1H), 6.78 (s, 1H), 6.69-6.70 (d, 1H, J=2.4 Hz), 6.48-6.51 (dd, 1H, J=2.4 Hz, 8.8 Hz), 3.88 (s, 3H), 3.80-3.82 (t, 4H, J=4.8 Hz), 3.57-3.61 (t, 2H, J=8.4 Hz), 3.13-3.15 (t, 4H, J=4.8 Hz), 2.83-2.88 (t, 2H, J=8.4 Hz).

Example 42

N-cyclopropyl-2-(2-(2-methoxy-4-morpholinophenylamino)-6,7-dihydro-5H-pyrrolo[2,3-d]pyrimidin-4-ylamino)benzenesulfonamide

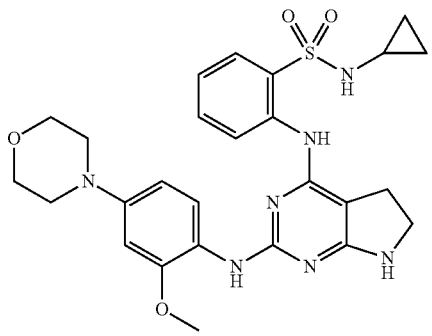 [SMILES: COc1cc(N2CCOCC2)ccc1Nc1nc2c(c(Nc3ccccc3S(=O)(=O)NC3CC3)n1)CCN2]

$^1$H NMR (400 MHz, DMSO-d6) δ ppm 8.49-8.51 (d, 1H, J=8.0 Hz), 8.19 (s, 1H), 8.14 (s, 1H), 7.79-7.81 (d, 1H, J=8.8 Hz), 7.73-7.76 (dd, 1H, J=1.6 Hz, 8.0 Hz), 7.47-7.50 (t, 1H, J=7.6 Hz), 7.25 (s, 1H), 7.05-7.09 (t, 1H, J=8.0 Hz), 6.75 (s, 1H), 6.627-6.634 (d, 1H, J=2.8 Hz), 6.42-6.45 (dd, 1H, J=2.4 Hz, 8.8 Hz), 3.81 (s, 3H), 3.74-3.76 (t, 4H, J=4.8 Hz), 3.50-3.55 (t, 2H, J=8.4 Hz), 3.07-3.09 (t, 4H, J=4.8 Hz), 2.78-2.82 (t, 2H, J=8.4 Hz), 2.07-2.11 (m, 1H), 0.43-0.46 (m, 2H), 0.38-0.39 (m, 2H).

Example 43

N-ethyl-2-(2-(2-methoxy-4-morpholinophenylamino)-6,7-dihydro-5H-pyrrolo[2,3-d]pyrimidin-4-ylamino)benzenesulfonamide

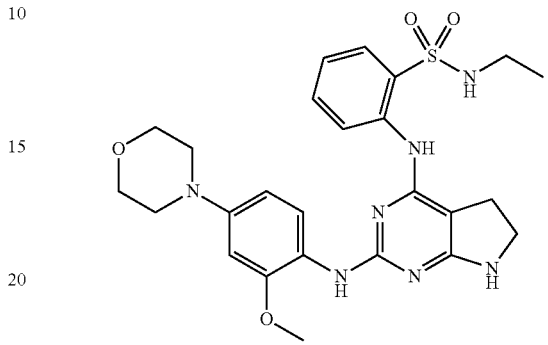

$^1$H NMR (400 MHz, CDCl$_3$) δ ppm 8.32 (s, 1H), 8.18 (d, J=8.6 Hz, 1H), 8.05 (s, 1H), 7.88 (d, J=7.8 Hz, 1H), 7.52 (t, J=7.8 Hz, 1H), 7.21-7.05 (m, 2H), 6.51 (d, J=2.5 Hz, 1H), 6.42 (d, J=9.0 Hz, 1H), 4.63 (s, 1H), 4.56 (s, 1H), 3.92-3.82 (m, 7H), 3.67 (t, J=8.2 Hz, 2H), 3.15-3.06 (m, 4H), 3.01-2.83 (m, 4H), 1.04 (t, J=7.2 Hz, 3H).

Example 44

N-sec-butyl-2-(2-(2-methoxy-4-morpholinophenylamino)-6,7-dihydro-5H-pyrrolo[2,3-d]pyrimidin-4-ylamino)benzenesulfonamide

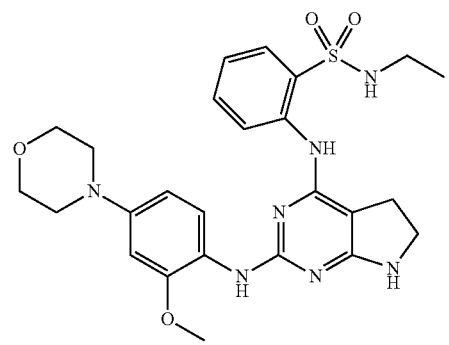 [SMILES: CCNS(=O)(=O)c1ccccc1Nc1nc(Nc2ccc(N3CCOCC3)cc2OC)nc2c1CCN2]

$^1$H NMR (400 MHz, CDCl$_3$) δ ppm 8.27 (d, J=8.0 Hz, 1H), 8.20 (d, J=8.2 Hz, 1H), 7.97 (s, 1H), 7.90 (d, J=7.8 Hz, 1H), 7.51 (s, 1H), 7.17 (s, 1H), 7.11 (t, J=7.9 Hz, 1H), 6.51 (s, 1H), 6.37 (d, J=9.3 Hz, 1H), 4.52 (s, 1H), 4.38 (d, J=7.9 Hz, 1H), 3.86 (s, 7H), 3.68 (t, J=8.1 Hz, 2H), 3.18 (s, 1H), 3.09 (s, 4H), 2.94 (t, J=8.5 Hz, 2H), 1.35-1.30 (m, 2H), 0.97 (d, J=6.2 Hz, 3H), 0.71 (t, J=7.0 Hz, 3H).

Example 45

N-isobutyl-2-(2-(2-methoxy-4-morpholinophenylamino)-6,7-dihydro-5H-pyrrolo[2,3-d]pyrimidin-4-ylamino)benzenesulfonamide

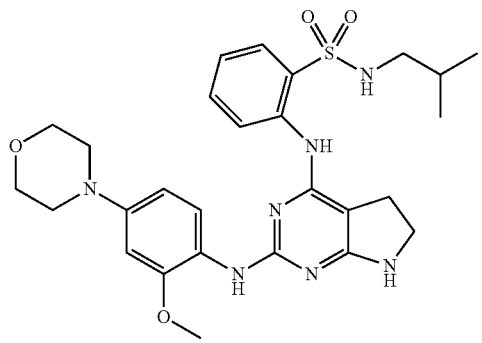 [SMILES: COc1cc(N2CCOCC2)ccc1Nc1nc2c(c(Nc3ccccc3S(=O)(=O)NCC(C)C)n1)CCN2]

$^1$H NMR (400 MHz, DMSO-d$_6$) δ ppm 8.48 (s, 1H), 7.86 (t, J=6.4 Hz, 1H), 7.76 (d, J=6.8 Hz, 1H), 7.48-7.60 (m, 2H), 7.14-7.47 (m, 2H), 6.64 (s, 1H), 6.49-6.51 (m, 1H), 3.79 (s, 3H), 3.72-3.74 (m, 4H), 3.51-3.61 (m, 2H), 3.24-3.31 (m, 2H), 3.05-3.14 (m, 2H), 2.53 (t, J=6.4 Hz, 2H), 1.54-1.61 (m, 1H), 0.75 (d, J=5.2 Hz, 6H).

Example 46

N-isopropyl-2-(2-(2-methoxy-4-morpholinophenylamino)-6,7-dihydro-5H-pyrrolo[2,3-d]pyrimidin-4-ylamino)benzenesulfonamide

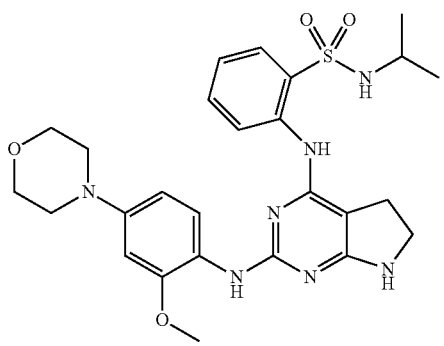 [SMILES: COc1cc(N2CCOCC2)ccc1Nc1nc2c(c(Nc3ccccc3S(=O)(=O)NC(C)C)n1)CCN2]

$^1$H NMR (400 MHz, DMSO-d$_6$) δ ppm 8.46 (d, J=8.6 Hz, 1H), 8.36 (s, 1H), 7.84 (d, J=7.8 Hz, 1H), 7.79 (d, J=8.8 Hz, 1H), 7.74 (dd, J=8.0, 1.5 Hz, 1H), 7.44 (t, J=7.9 Hz, 1H), 7.25 (s, 1H), 7.04 (t, J=7.2 Hz, 1H), 6.75 (s, 1H), 6.62 (d, J=2.5 Hz, 1H), 6.40 (dd, J=8.7, 2.5 Hz, 1H), 3.80 (s, 3H), 3.76-3.71 (m, 4H), 3.67 (t, J=9.1 Hz, 1H), 3.31-3.25 (m, 2H), 3.11-3.01 (m, 4H), 1.17 (d, J=6.7 Hz, 3H), 1.01 (d, J=6.5 Hz, 3H), 0.90 (d, J=6.5 Hz, 3H).

Example 47

N-tert-butyl-2-(2-(2-methoxy-4-morpholinophenylamino)-6,7-dihydro-5H-pyrrolo[2,3-d]pyrimidin-4-ylamino)benzenesulfonamide

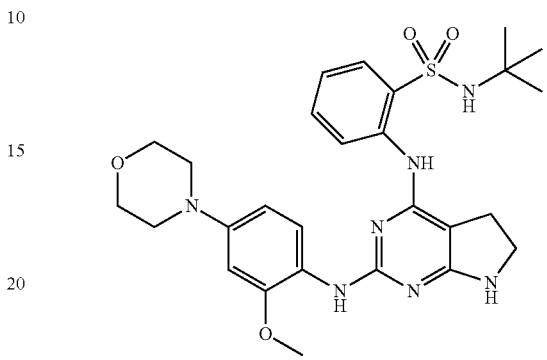

$^1$H NMR (400 MHz, CDCl$_3$) δ ppm 8.18 (dd, J=13.6, 8.8 Hz, 2H), 7.93 (d, J=7.9 Hz, 1H), 7.81 (s, 1H), 7.51 (t, J=7.7 Hz, 1H), 7.14 (dd, J=18.7, 11.1 Hz, 2H), 6.51 (s, 1H), 6.37 (d, J=8.6 Hz, 1H), 4.56 (d, J=13.0 Hz, 2H), 3.92-3.79 (m, 7H), 3.68 (t, J=8.4 Hz, 2H), 3.10 (d, J=4.8 Hz, 4H), 2.92 (t, J=8.2 Hz, 2H), 1.16 (s, 9H).

Example 48

2-(2-(2-methoxy-4-morpholinophenylamino)-6,7-dihydro-5H-pyrrolo[2,3-d]pyrimidin-4-ylamino)-N-(3-methoxypropyl)benzenesulfonamide $^1$H NMR (400 MHz, DMSO-d$_6$) δ ppm 8.43 (d, J=8.8 Hz, 1H), 8.25 (s, 1H), 7.85 (t, J=5.8 Hz, 1H), 7.78 (d, J=8.7 Hz, 1H), 7.69 (dd, J=8.0, 1.3 Hz, 1H), 7.46 (t, J=7.3 Hz, 1H), 7.23 (s, 1H), 7.05 (t, J=7.6 Hz, 1H), 6.73 (s, 1H), 6.61 (d, J=2.3 Hz, 1H), 6.41 (dd, J=8.7, 2.3 Hz, 1H), 3.79 (s, 3H), 3.75-3.68 (m, 4H), 3.51 (t, J=8.5 Hz, 2H), 3.18 (t, J=6.1 Hz, 2H), 3.09-3.00 (m, 7H), 2.79 (dd, J=13.2, 6.5 Hz, 4H), 1.59-1.46 (m, 2H).

Example 49

N-(2-(dimethylamino)ethyl)-2-(2-(2-methoxy-4-morpholinophenylamino)-6,7-dihydro-5H-pyrrolo[2,3-d]pyrimidin-4-ylamino)benzenesulfonamide

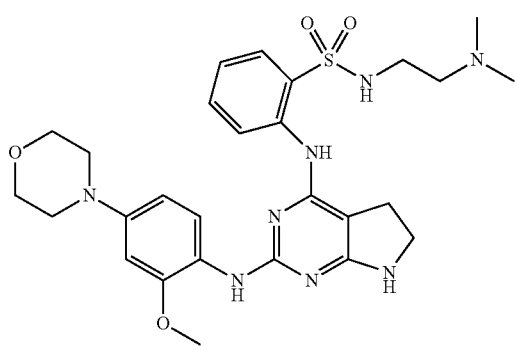 [SMILES: COc1cc(N2CCOCC2)ccc1Nc1nc2c(c(Nc3ccccc3S(=O)(=O)NCCN(C)C)n1)CCN2]

$^1$H NMR (400 MHz, DMSO-d$_6$) δ ppm 8.41 (d, J=8.6 Hz, 1H), 8.24 (s, 1H), 7.79 (d, J=8.7 Hz, 1H), 7.72 (d, J=6.5 Hz, 1H), 7.47 (t, J=7.2 Hz, 1H), 7.22 (s, 1H), 7.06 (t, J=7.5 Hz, 1H), 6.73 (s, 1H), 6.61 (d, J=2.4 Hz, 1H), 6.40 (dd, J=8.8, 2.5 Hz, 1H), 3.79 (s, 3H), 3.76-3.66 (m, 4H), 3.51 (t, J=8.1 Hz, 2H), 3.12-3.00 (m, 4H), 2.89 (s, 2H), 2.78 (t, J=8.5 Hz, 2H), 2.14 (s, 6H).

Example 50

2-(2-(2-methoxy-4-morpholinophenylamino)-6,7-dihydro-5H-pyrrolo[2,3-d]pyrimidin-4-ylamino)-N-(2-methoxyethyl)benzenesulfonamide

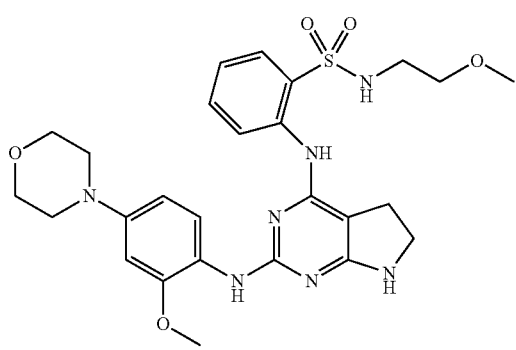 [SMILES: COCCNS(=O)(=O)c1ccccc1Nc1nc(Nc2ccc(N3CCOCC3)cc2OC)nc2c1CCN2]

$^1$H NMR (400 MHz, DMSO-d$_6$) δ ppm 8.44 (d, J=8.5 Hz, 1H), 8.26 (s, 1H), 8.08 (d, J=5.9 Hz, 1H), 7.80 (d, J=8.6 Hz, 1H), 7.71 (d, J=7.6 Hz, 1H), 7.46 (s, 1H), 7.23 (s, 1H), 7.05 (d, J=7.7 Hz, 1H), 6.72 (s, 1H), 6.62 (s, 1H), 6.42 (d, J=8.4 Hz, 1H), 3.80 (s, 3H), 3.74 (m, 4H), 3.51 (t, J=8.2 Hz, 2H), 3.25 (t, J=5.6 Hz, 2H), 3.10 (s, 2H), 3.06 (s, 3H), 2.96-2.87 (m, 2H), 2.79 (t, J=8.6 Hz, 2H).

Example 51

2-(2-(2-methoxy-4-morpholinophenylamino)-6,7-dihydro-5H-pyrrolo[2,3-d]pyrimidin-4-ylamino)-N-phenylbenzenesulfonamide

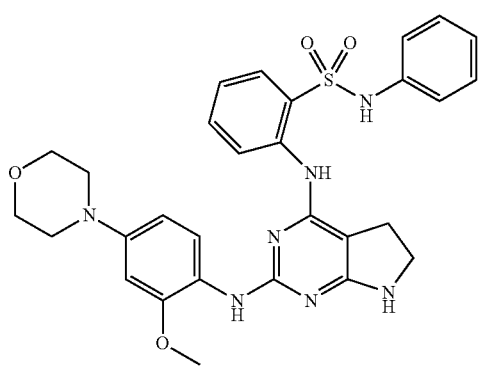 [SMILES: COc1cc(N2CCOCC2)ccc1Nc1nc2c(c(Nc3ccccc3S(=O)(=O)Nc3ccccc3)n1)CCN2]

$^1$H NMR (400 MHz, CDCl$_3$) δ ppm 8.14 (d, J=8.7 Hz, 1H), 8.04 (d, J=8.5 Hz, 1H), 7.80 (s, 1H), 7.73 (d, J=7.7 Hz, 1H), 7.47 (t, J=7.8 Hz, 1H), 7.23 (s, 1H), 7.11-6.99 (m, 5H), 6.51 (d, J=2.2 Hz, 1H), 6.34 (d, J=8.7 Hz, 1H), 4.57 (s, 1H), 3.91-3.83 (m, 7H), 3.61 (t, J=8.3 Hz, 2H), 3.13-3.05 (m, 4H), 2.78 (t, J=8.4 Hz, 2H).

Example 52

N-isopropyl-2-(2-(4-morpholinophenylamino)-6,7-dihydro-5H-pyrrolo[2,3-d]pyrimidin-4-ylamino)benzenesulfonamide

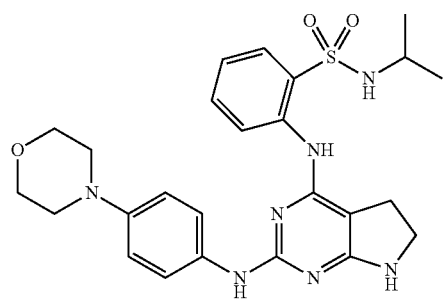 [SMILES: CC(C)NS(=O)(=O)c1ccccc1Nc1nc(Nc2ccc(N3CCOCC3)cc2)nc2c1CCN2]

$^1$H NMR (400 MHz, DMSO-d$_6$) δ ppm 8.61 (s, 1H), 8.45 (d, J=8.5 Hz, 1H), 8.23 (s, 1H), 7.83 (d, J=8.0 Hz, 1H), 7.73 (dd, J=8.0, 1.6 Hz, 1H), 7.49 (dd, J=11.2, 8.1 Hz, 3H), 7.03 (t, J=7.1 Hz, 1H), 6.79 (d, J=9.1 Hz, 2H), 6.71 (s, 1H), 3.75-3.64 (m, 4H), 3.51 (t, J=8.6 Hz, 2H), 3.29-3.20 (m, 1H), 3.02-2.91 (m, 4H), 2.78 (t, J=8.6 Hz, 2H), 0.92 (d, J=6.5 Hz, 6H).

Example 53

4-(4-(2-(N-isopropylsulfamoyl)phenylamino)-6,7-dihydro-5H-pyrrolo[2,3-d]pyrimidin-2-ylamino)-N-methylbenzamide

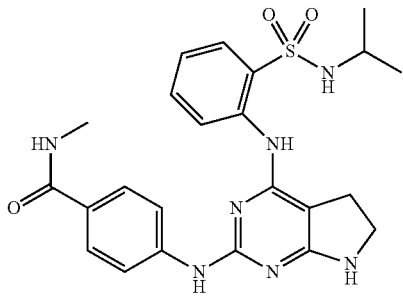 [SMILES: CNC(=O)c1ccc(Nc2nc3c(c(Nc4ccccc4S(=O)(=O)NC(C)C)n2)CCN3)cc1]

$^1$H NMR (400 MHz, DMSO-d$_6$) δ ppm 9.18 (s, 1H), 8.33 (d, J=8.6 Hz, 1H), 8.23-8.10 (m, 2H), 7.85 (d, J=7.7 Hz, 1H), 7.81-7.70 (m, 3H), 7.64 (d, J=8.8 Hz, 2H), 7.55 (t, J=7.7 Hz, 1H), 7.10 (t, J=7.7 Hz, 1H), 6.89 (s, 1H), 3.55 (t, J=8.4 Hz, 2H), 2.82 (t, J=8.6 Hz, 2H), 2.74 (d, J=4.5 Hz, 3H), 1.98 (d, J=7.9 Hz, 1H), 0.92 (d, J=6.5 Hz, 6H).

Example 54

2-(2-(4-(hydroxymethyl)phenylamino)-6,7-dihydro-5H-pyrrolo[2,3-d]pyrimidin-4-ylamino)-N-isopropylbenzenesulfonamide

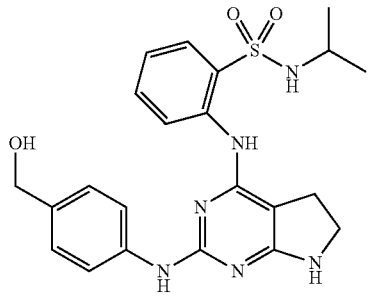 [SMILES: CC(C)NS(=O)(=O)c1ccccc1Nc1nc(Nc2ccc(CO)cc2)nc2c1CCN2]

$^1$H NMR (400 MHz, CDCl$_3$) δ ppm 8.14 (d, J=8.4 Hz, 1H), 7.88 (s, 1H), 7.81 (d, J=7.8 Hz, 1H), 7.42 (t, J=6.9 Hz, 3H), 7.12 (d, J=8.4 Hz, 2H), 7.03 (t, J=7.6 Hz, 1H), 6.77 (s, 1H), 4.52 (s, 2H), 4.40 (d, J=8.0 Hz, 1H), 3.65 (t, 2H), 3.34-3.21 (m, 1H), 2.85 (t, J=8.4 Hz, 2H), 0.91 (d, J=6.5 Hz, 6H).

Example 55

2-(2-(2-fluoro-4-morpholinophenylamino)-6,7-dihydro-5H-pyrrolo[2,3-d]pyrimidin-4-ylamino)-N-isopropylbenzenesulfonamide

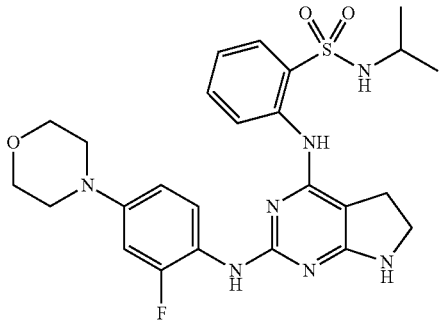 [SMILES: CC(C)NS(=O)(=O)c1ccccc1Nc1nc(Nc2ccc(N3CCOCC3)cc2F)nc2c1CCN2]

$^1$H NMR (400 MHz, DMSO-d$_6$) δ ppm 8.46 (d, J=8.3 Hz, 1H), 8.31 (s, 1H), 8.01 (s, 1H), 7.82 (d, J=7.9 Hz, 1H), 7.48-7.28 (m, 2H), 6.98 (t, J=7.6 Hz, 1H), 6.80 (dd, J=14.0, 2.5 Hz, 1H), 6.72-6.61 (m, 2H), 3.83-3.66 (m, 4H), 3.50 (t, J=8.6 Hz, 2H), 3.30-3.24 (m, 1H), 3.16-3.00 (m, 4H), 2.74 (dd, J=31.1, 22.6 Hz, 2H), 0.87 (dd, J=38.0, 6.7 Hz, 6H).

Example 56

N-isopropyl-2-(2-(2-methoxy-6-morpholino-3-ylamino)-6,7-dihydro-5H-pyrrolo[2,3-d]pyrimidin-4-ylamino)benzenesulfonamide

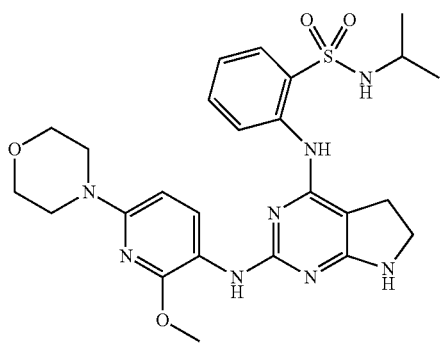 [SMILES: COc1nc(N2CCOCC2)ccc1Nc1nc2c(c(Nc3ccccc3S(=O)(=O)NC(C)C)n1)CCN2]

$^1$H NMR (400 MHz, CDCl$_3$) δ ppm 8.39 (d, 1H, J=8.4 Hz), 8.25 (s, 1H), 7.85 (d, 1H, J=8.4 Hz), 7.82 (d, 1H, J=8.0 Hz), 7.71 (dd, 1H, J=8.0 Hz, 1.2 Hz), 7.40 (t, 1H, J=7.6 Hz), 7.33 (s, 1H), 7.01 (t, 1H, J=7.6 Hz), 6.72 (s, 1H), 6.27 (d, 1H, J=8.4 Hz), 3.80 (s, 1H), 3.69-3.71 (m, 4H), 3.50 (t, 2H, J=8.4 Hz), 3.33-3.36 (m, 4H), 3.21-3.27 (m, 1H), 2.77 (t, 2H, J=8.8 Hz), 0.94 (d, 1H, J=6.8 Hz).

Example 57

N-isopropyl-2-(2-(6-morpholinopyridin-3-ylamino)-6,7-dihydro-5H-pyrrolo[2,3-d]pyrimidin-4-ylamino)benzenesulfonamide

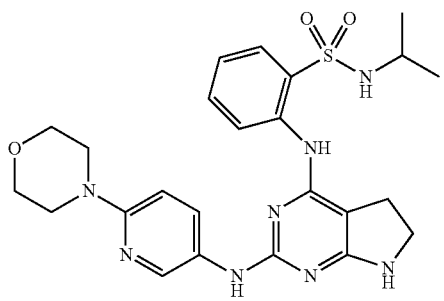 [SMILES: CC(C)NS(=O)(=O)c1ccccc1Nc1nc(Nc2ccc(N3CCOCC3)nc2)nc2c1CCN2]

$^1$H NMR (400 MHz, CDCl$_3$) δ ppm 8.66 (s, 1H), 8.40 (d, 1H, J=8.4 Hz), 8.36 (d, 1H, J=2.4 Hz), 8.23 (s, 1H), 7.84-7.87 (m, 2H), 7.33 (dd, 1H, J=8.0 Hz, 1.2 Hz), 7.46 (t, 1H, J=7.2 Hz), 7.03 (t, 1H, J=7.6 Hz), 6.78 (s, 1H), 6.74 (d, 1H, J=9.2 Hz), 3.67-3.70 (m, 4H), 3.52 (t, 2H, J=8.8 Hz), 3.26-3.31 (m, 5H), 2.78 (t, 2H, J=8.4 Hz), 0.92 (d, 1H, J=6.4 Hz).

Example 58

N-isopropyl-2-(2-(5-morpholinopyridin-2-ylamino)-6,7-dihydro-5H-pyrrolo[2,3-d]pyrimidin-4-ylamino)benzenesulfonamide

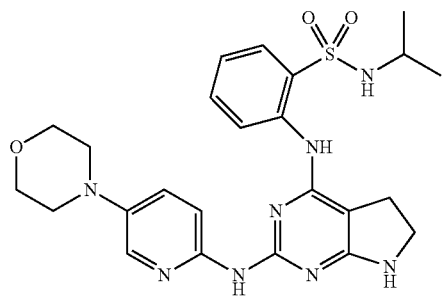 [SMILES: CC(C)NS(=O)(=O)c1ccccc1Nc1nc(Nc2ccc(N3CCOCC3)cn2)nc2c1CCN2]

$^1$H NMR (400 MHz, CDCl$_3$) δ ppm 8.99 (s, 1H), 8.11 (m, 2H), 8.03-7.74 (m, 3H), 7.50 (t, J=7.0 Hz, 1H), 7.12 (d, J=8.2 Hz, 2H), 6.54 (s, 1H), 4.49 (s, 1H), 4.07-3.78 (m, 4H), 3.72 (s, 2H), 3.42 (d, J=5.6 Hz, 1H), 3.13-2.95 (m, 4H), 2.92 (s, 2H), 1.01 (d, J=6.5 Hz, 6H).

Example 59

2-(2-(2-ethoxy-4-morpholinophenylamino)-6,7-dihydro-5H-pyrrolo[2,3-d]pyrimidin-4-ylamino)-N-isopropylbenzenesulfonamide

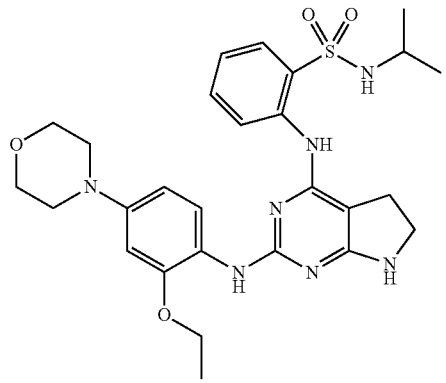 [SMILES: CCOc1cc(N2CCOCC2)ccc1Nc1nc2c(c(Nc3ccccc3S(=O)(=O)NC(C)C)n1)CCN2]

$^1$H NMR (400 MHz, CDCl$_3$) δ ppm 8.21 (d, J=9.3 Hz, 2H), 7.91 (d, J=6.6 Hz, 2H), 7.52 (t, J=7.3 Hz, 1H), 7.21 (s, 1H), 7.13 (d, J=7.3 Hz, 1H), 6.50 (d, J=2.5 Hz, 1H), 6.37 (d, J=9.0 Hz, 1H), 4.57 (s, 1H), 4.40 (s, 1H), 4.08 (q, J=7.0 Hz, 2H), 3.91-3.83 (m, 4H), 3.68 (t, J=8.2 Hz, 2H), 3.41 (d, J=7.1 Hz, 1H), 3.14-3.01 (m, 4H), 2.93 (s, 2H), 1.45 (t, J=7.0 Hz, 3H), 1.01 (d, J=6.5 Hz, 6H).

Example 60

N-isopropyl-2-(2-(4-morpholino-2-(trifluoromethyl)phenylamino)-6,7-dihydro-5H-pyrrolo[2,3-d]pyrimidin-4-ylamino)benzenesulfonamide

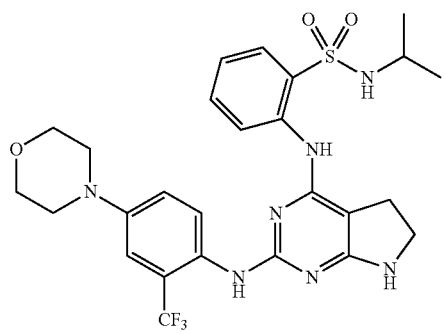 [SMILES: CC(C)NS(=O)(=O)c1ccccc1Nc1nc(Nc2ccc(N3CCOCC3)cc2C(F)(F)F)nc2c1CCN2]

$^1$H NMR (400 MHz, CDCl$_3$) δ ppm 8.11 (d, J=8.3 Hz, 1H), 7.95 (s, 1H), 7.88 (d, J=9.0 Hz, 1H), 7.77 (dd, J=8.0, 1.6 Hz, 1H), 7.30 (td, J=8.4, 4.0 Hz, 1H), 7.08-6.92 (m, 2H), 6.89 (dd, J=9.1, 2.9 Hz, 1H), 6.61 (s, 1H), 4.55 (s, 1H), 4.38 (d, J=7.7 Hz, 1H), 3.98-3.71 (m, 4H), 3.57 (t, J=8.5 Hz, 2H), 3.31 (dq, J=13.2, 6.6 Hz, 1H), 3.13-2.86 (m, 4H), 2.82 (t, J=8.5 Hz, 2H), 0.97-0.82 (m, 6H).

Example 61

N-isopropyl-2-(2-(4-(trifluoromethyl)phenylamino)-6,7-dihydro-5H-pyrrolo[2,3-d]pyrimidin-4-ylamino)benzenesulfonamide

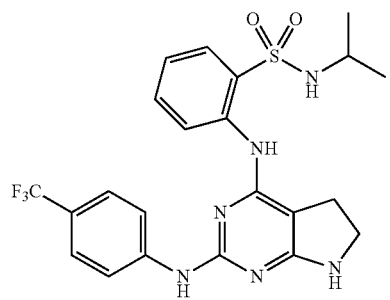 [SMILES: CC(C)NS(=O)(=O)c1ccccc1Nc1nc(Nc2ccc(C(F)(F)F)cc2)nc2c1CCN2]

$^1$H NMR (400 MHz, DMSO-d$_6$) δ ppm 9.35 (s, 1H), 8.29 (d, J=8.2 Hz, 1H), 8.19 (s, 1H), 7.89 (d, J=8.7 Hz, 2H), 7.84 (d, J=8.1 Hz, 1H), 7.77 (dd, J=8.0, 1.4 Hz, 1H), 7.56 (t, J=7.8 Hz, 1H), 7.47 (d, J=8.7 Hz, 2H), 7.10 (t, J=7.6 Hz, 1H), 6.93 (s, 1H), 3.56 (t, J=8.5 Hz, 2H), 3.28-3.14 (m, 1H), 2.83 (t, J=8.5 Hz, 2H), 0.92 (d, J=6.5 Hz, 6H).

Example 62

4-(4-(2-(N-isopropylsulfamoyl)phenylamino)-6,7-dihydro-5H-pyrrolo[2,3-d]pyrimidin-2-ylamino)-N,N-dimethylbenzamide

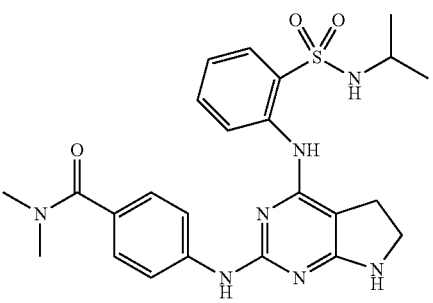 [SMILES: CC(C)NS(=O)(=O)c1ccccc1Nc1nc(Nc2ccc(C(=O)N(C)C)cc2)nc2c1CCN2]

$^1$H NMR (400 MHz, CDCl$_3$) δ ppm 8.11 (dd, J=8.3, 0.8 Hz, 1H), 7.90 (s, 1H), 7.84 (dd, J=8.0, 1.5 Hz, 1H), 7.54-7.41 (m, 3H), 7.26-7.21 (m, 2H), 7.06 (dd, J=11.2, 4.0 Hz, 2H), 4.67 (d, J=7.8 Hz, 1H), 4.59 (s, 1H), 3.59 (t, J=8.5 Hz, 2H), 3.35 (dq, J=13.2, 6.5 Hz, 1H), 2.99 (s, 6H), 2.86 (t, J=8.5 Hz, 2H), 0.91 (dd, J=18.9, 6.6 Hz, 6H).

Example 63

N-(4-(4-(2-(N-isopropylsulfamoyl)phenylamino)-6,7-dihydro-5H-pyrrolo[2,3-d]pyrimidin-2-ylamino)phenyl)acetamide

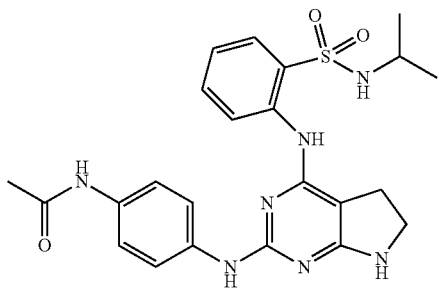 [SMILES: CC(=O)Nc1ccc(Nc2nc3c(c(Nc4ccccc4S(=O)(=O)NC(C)C)n2)CCN3)cc1]

$^1$H NMR (400 MHz, DMSO-d$_6$) δ ppm 9.70 (s, 1H), 8.76 (s, 1H), 8.40 (d, J=8.4 Hz, 1H), 8.20 (s, 1H), 7.82 (d, J=7.8 Hz, 1H), 7.75 (dd, J=8.0, 1.5 Hz, 1H), 7.55 (d, J=9.0 Hz, 2H), 7.47 (t, J=7.1 Hz, 1H), 7.35 (d, J=9.0 Hz, 2H), 7.05 (t, J=7.6 Hz, 1H), 6.75 (s, 1H), 3.52 (dd, J=16.0, 7.5 Hz, 2H), 3.29-3.21 (m, 1H), 2.80 (1, J=8.5 Hz, 2H), 1.97 (d, J=3.2 Hz, 3H), 0.92 (d, J=6.5 Hz, 6H).

Example 64

N-isopropyl-2-(2-(4-(N-methylsulfamoyl)phenylamino)-6,7-dihydro-5H-pyrrolo[2,3-d]pyrimidin-4-ylamino)benzenesulfonamide

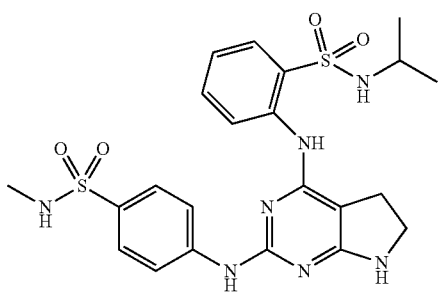 [SMILES: CNS(=O)(=O)c1ccc(Nc2nc3c(c(Nc4ccccc4S(=O)(=O)NC(C)C)n2)CCN3)cc1]

$^1$H NMR (400 MHz, DMSO-d$_6$) δ ppm 8.14 (d, J=8.3 Hz, 1H), 8.00 (s, 1H), 7.94 (d, J=7.9 Hz, 1H), 7.75-7.61 (m, 4H), 7.56 (t, J=7.8 Hz, 1H), 7.18 (dd, J=14.2, 6.3 Hz, 2H), 4.71 (s, 1H), 4.65 (d, J=7.7 Hz, 1H), 4.37 (t, J=17.6 Hz, 1H), 3.71 (t, J=8.5 Hz, 2H), 3.45 (dd, J=13.4, 6.7 Hz, 1H), 2.96 (t, J=8.5 Hz, 2H), 2.62 (t, J=16.5 Hz, 3H), 0.99 (dd, J=24.1, 7.1 Hz, 6H).

Example 65

N-isopropyl-2-(2-(4-(morpholine-4-carbonyl)phenylamino)-6,7-dihydro-5H-pyrrolo[2,3-d]pyrimidin-4-ylamino)benzenesulfonamide

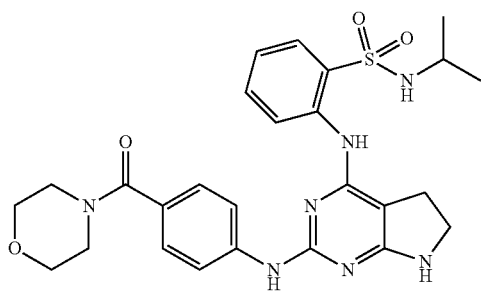 [SMILES: CC(C)NS(=O)(=O)c1ccccc1Nc1nc(Nc2ccc(C(=O)N3CCOCC3)cc2)nc2c1CCN2]

$^1$H NMR (400 MHz, DMSO-d$_6$) δ ppm 9.14 (s, 1H), 8.33 (d, J=8.2 Hz, 1H), 8.20 (s, 1H), 7.83 (d, J=8.0 Hz, 1H), 7.79-7.73 (m, 3H), 7.57-7.49 (m, 1H), 7.23 (d, J=8.7 Hz, 2H), 7.09 (t, J=7.6 Hz, 1H), 6.86 (s, 1H), 3.62-3.52 (m, 6H), 3.48 (s, 4H), 3.24 (dd, J=13.8, 7.1 Hz, 1H), 2.82 (t, J=8.6 Hz, 2H), 0.92 (d, J=6.5 Hz, 6H).

Example 66

N-isopropyl-2-(2-(2-methyl-4-morpholinophenylamino)-6,7-dihydro-5H-pyrrolo[2,3-d]pyrimidin-4-ylamino)benzenesulfonamide

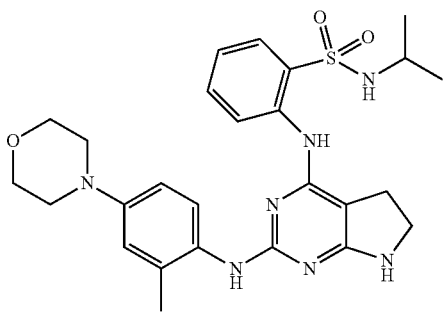 [SMILES: Cc1cc(N2CCOCC2)ccc1Nc1nc2c(c(Nc3ccccc3S(=O)(=O)NC(C)C)n1)CCN2]

$^1$H NMR (400 MHz, CDCl$_3$) δ ppm 8.27 (d, J=8.4 Hz, 1H), 8.16 (s, 1H), 7.85 (d, J=8.0 Hz, 1H), 7.66 (d, J=8.4 Hz, 1H), 7.37 (t, J=8.0 Hz, 1H), 7.04 (t, J=7.6 Hz, 1H), 6.77 (s, 1H), 6.72 (d, J=8.8 Hz, 1H), 6.38 (s, 1H), 4.58 (s, 1H), 4.44 (d, J=6.8 Hz, 1H), 3.87-3.89 (m, 4H), 3.66 (t, J=8.4 Hz, 2H), 3.44-3.38 (m, 1H), 3.11-3.13 (m, 4H), 2.90 (t, J=8.4 Hz, 2H), 2.26 (s, 3H), 1.02 (d, J=6.8 Hz, 6H).

Example 67

N-isopropyl-2-(2-(2-methoxy-4-(pyrrolidin-1-yl)phenylamino)-6,7-dihydro-5H-pyrrolo[2,3-d]pyrimidin-4-ylamino)benzenesulfonamide

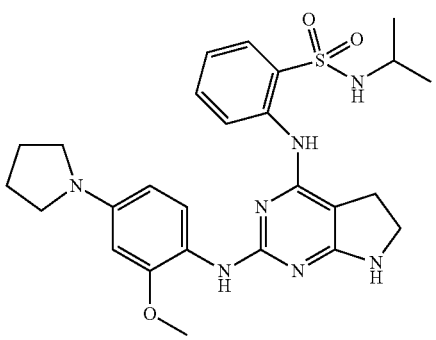 [SMILES: COc1cc(N2CCCC2)ccc1Nc1nc2c(c(Nc3ccccc3S(=O)(=O)NC(C)C)n1)CCN2]

$^1$H NMR (400 MHz, DMSO-d$_6$) δ ppm 8.48 (d, J=8.0 Hz, 1H), 8.27 (s, 1H), 7.83 (d, J=8.0 Hz, 1H), 7.73 (dd, J=8.0, 1.6 Hz, 1H), 7.58 (d, J=8.8 Hz, 1H), 7.41 (t, J=8.4 Hz, 1H), 7.17 (s, 1H), 7.02 (t, J=8.0 Hz, 1H), 6.66 (s, 1H), 6.20 (d, J=2.4 Hz, 1H), 6.06 (dd, J=8.8 Hz, 2.4 Hz, 1H), 3.78 (s, 3H), 3.51 (t, J=8.8 Hz, 2H), 3.25-3.32 (m, 1H), 3.21-3.24 (m, 4H), 2.78 (t, J=8.4 Hz, 2H), 1.94-1.97 (m, 4H), 0.94 (d, J=6.4 Hz, 6H).

Example 68

N-isopropyl-2-(2-(2-methoxy-4-(piperidin-1-yl)phenylamino)-6,7-dihydro-5H-pyrrolo[2,3-d]pyrimidin-4-ylamino)benzenesulfonamide

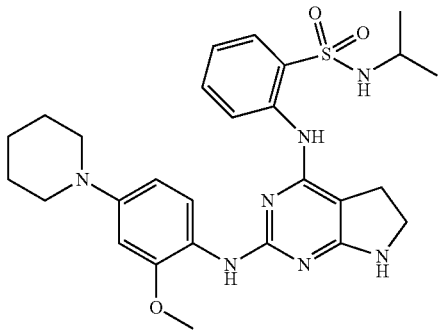 [SMILES: COc1cc(N2CCCCC2)ccc1Nc1nc2c(c(Nc3ccccc3S(=O)(=O)NC(C)C)n1)CCN2]

¹H NMR (400 MHz, DMSO-d₆) δ ppm 8.41 (d, J=8.4 Hz, 1H), 8.25 (s, 1H), 7.83 (d, J=8.0 Hz, 1H), 7.77 (d, J=8.8 Hz, 1H), 7.74 (dd, J=8.8 Hz, 1.6 Hz, 1H), 7.46 (t, J=8.8 Hz, 1H), 7.22 (s, 1H), 7.05 (t, J=8.0 Hz, 1H), 6.73 (s, 1H), 6.59 (d, J=2.4 Hz, 1H), 6.41 (dd, J=8.8 Hz, 2.4 Hz, 1H), 3.80 (s, 3H), 3.53 (t, J=8.4 Hz, 2H), 3.24-3.31 (m, 1H), 3.05-3.08 (m, 4H), 2.79 (t, J=8.4 Hz, 2H), 1.61-1.67 (m, 4H), 1.51-1.54 (m, 2H), 0.94 (d, J=6.4 Hz, 6H).

Example 69

2-(2-(4-(1-hydroxyethyl)phenylamino)-6,7-dihydro-5H-pyrrolo[2,3-d]pyrimidin-4-ylamino)-N-isopropylbenzenesulfonamide

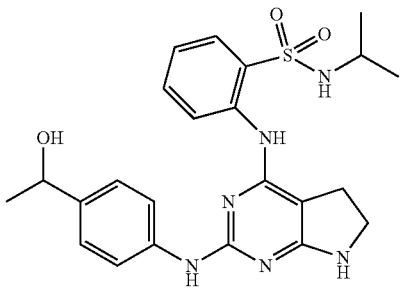 [SMILES: CC(C)NS(=O)(=O)c1ccccc1Nc1nc(Nc2ccc(C(C)O)cc2)nc2c1CCN2]

¹H NMR (400 MHz, CDCl₃) δ ppm 8.25 (d, J=8.1 Hz, 1H), 7.98 (s, 1H), 7.90 (dd, J=8.0, 1.5 Hz, 1H), 7.69-7.39 (m, 3H), 7.31-7.22 (m, 2H), 7.12 (t, J=7.1 Hz, 1H), 6.77 (s, 1H), 4.86 (q, J=6.4 Hz, 1H), 4.55 (s, 1H), 4.45 (d, J=7.2 Hz, 1H), 3.69 (t, J=8.5 Hz, 2H), 3.42 (dd, J=14.0, 6.6 Hz, 1H), 2.94 (t, J=8.5 Hz, 2H), 1.47 (t, J=13.5 Hz, 3H), 1.01 (d, J=6.5 Hz, 6H).

Example 70

N-isopropyl-2-(2-(2-methoxy-4-(2-morpholinoethoxy)phenylamino)-6,7-dihydro-5H-pyrrolo[2,3-d]pyrimidin-4-ylamino)benzenesulfonamide

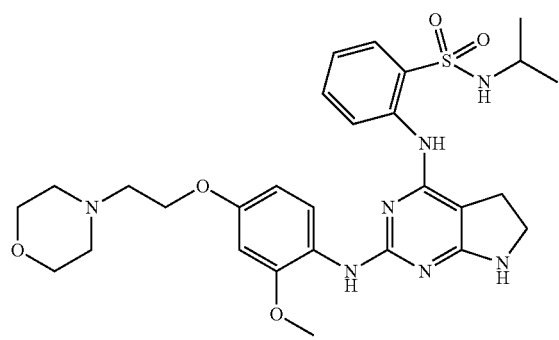 [SMILES: COc1cc(OCCN2CCOCC2)ccc1Nc1nc2c(c(Nc3ccccc3S(=O)(=O)NC(C)C)n1)CCN2]

¹H NMR (400 MHz, CDCl₃) δ ppm 8.24 (d, J=8.4 Hz, 1H), 8.18 (d, J=8.9 Hz, 1H), 7.96-7.74 (m, 2H), 7.57-7.43 (m, 1H), 7.08 (dd, J=29.7, 22.6 Hz, 2H), 6.52 (t, J=10.3 Hz, 1H), 6.34 (dd, J=8.9, 2.6 Hz, 1H), 4.55 (s, 1H), 4.47 (d, J=7.7 Hz, 1H), 4.08 (t, J=5.8 Hz, 2H), 3.94-3.79 (m, 3H), 3.79-3.70 (m, 4H), 3.67 (t, J=8.5 Hz, 2H), 3.41 (dq, J=13.2, 6.6 Hz, 1H), 2.93 (t, J=8.4 Hz, 2H), 2.80 (t, J=5.8 Hz, 2H), 2.66-2.49 (m, 4H), 0.99 (t, J=11.8 Hz, 6H).

Example 71

N-isopropyl-2-(2-(4-(trifluoromethoxy)phenylamino)-6,7-dihydro-5H-pyrrolo[2,3-d]pyrimidin-4-ylamino)benzenesulfonamide

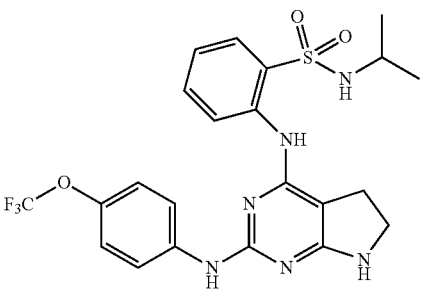 [SMILES: CC(C)NS(=O)(=O)c1ccccc1Nc1nc(Nc2ccc(OC(F)(F)F)cc2)nc2c1CCN2]

¹H NMR (400 MHz, DMSO-d₆) δ ppm 9.11 (s, 1H), 8.33 (d, J=8.4 Hz, 1H), 8.22 (s, 1H), 7.85 (d, J=8.0 Hz, 1H), 7.76-7.79 (m, 3H), 7.54 (t, J=8.8 Hz, 1H), 7.16 (d, J=8.8 Hz, 2H), 7.09 (t, J=8.0 Hz, 1H), 6.87 (s, 1H), 3.56 (t, J=8.4 Hz, 2H), 3.28-3.31 (m, 1H), 2.83 (t, J=8.4 Hz, 2H), 0.94 (d, J=6.4 Hz, 6H).

Example 72

N-isopropyl-2-(2-(4-(1-(isopropylamino)ethyl)phenylamino)-6,7-dihydro-5H-pyrrolo[2,3-d]pyrimidin-4-ylamino)benzenesulfonamide

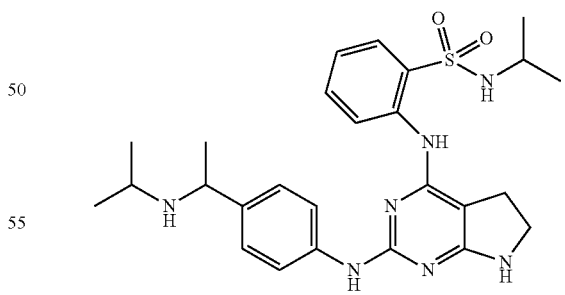

¹H NMR (400 MHz, DMSO-d₆) δ ppm 9.17-9.23 (brs, 2H), 8.86-8.89 (brs, 1H), 8.32-8.38 (brs, 1H), 8.28 (s, 1H), 7.86 (d, J=7.6 Hz, 1H), 7.78 (d, J=7.6 Hz, 1H), 7.73 (d, J=8.8 Hz, 2H), 7.56 (t, J=7.6 Hz, 1H), 7.43 (d, J=8.8 Hz, 2H), 7.12 (t, J=7.6 Hz, 1H), 4.36-4.40 (m, 1H), 3.57 (t, J=8.4 Hz, 2H), 3.26-3.31 (m, 1H), 2.87-2.92 (m, 1H), 2.82 (t, J=8.0 Hz, 2H), 1.55 (d, J=6.8 Hz, 3H), 1.22 (d, J=6.8 Hz, 6H), 0.94 (d, J=6.4 Hz, 6H).

Example 73

N-isopropyl-2-(2-(3-(methylsulfonamido)phenylamino)-6,7-dihydro-5H-pyrrolo[2,3-d]pyrimidin-4-ylamino)benzenesulfonamide

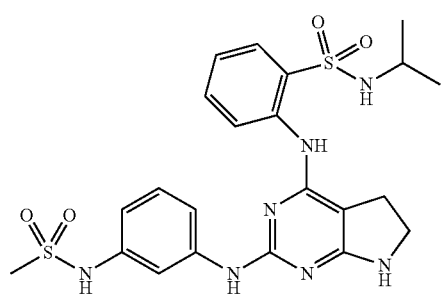 [SMILES: CC(C)NS(=O)(=O)c1ccccc1Nc1nc(Nc2cccc(NS(C)(=O)=O)c2)nc2c1CCN2]

$^1$H NMR (400 MHz, CDCl$_3$) δ ppm 8.21 (d, J=8.3 Hz, 1H), 8.01 (d, J=7.8 Hz, 2H), 7.73 (s, 1H), 7.64 (t, J=7.8 Hz, 1H), 7.30-7.14 (m, 3H), 6.91 (d, J=8.7 Hz, 2H), 6.32 (s, 1H), 4.73 (s, 1H), 4.59 (d, J=7.8 Hz, 1H), 3.77 (t, J=8.5 Hz, 2H), 3.51 (dd, J=13.0, 6.6 Hz, 1H), 3.06 (d, J=1.4 Hz, 3H), 3.00 (d, J=9.1 Hz, 2H), 1.09 (dd, J=6.5, 1.3 Hz, 6H).

Example 74

3-(4-(2-(N-isopropylsulfamoyl)phenylamino)-6,7-dihydro-5H-pyrrolo[2,3-d]pyrimidin-2-ylamino)-N-methylbenzamide

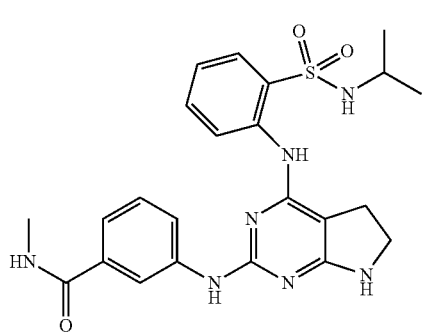 [SMILES: CNC(=O)c1cccc(Nc2nc3c(c(Nc4ccccc4S(=O)(=O)NC(C)C)n2)CCN3)c1]

$^1$H NMR (400 MHz, DMSO-d$_6$) δ ppm 8.99 (s, 1H), 8.47 (d, J=8.4 Hz, 1H), 8.31 (s, 1H), 8.20 (q, J=4.8 Hz, 1H), 7.99 (s, 1H), 7.83-7.88 (m, 2H), 7.75 (dd, J=8.4 Hz, 1.6 Hz, 1H), 7.46 (t, J=8.4 Hz, 1H), 7.23-7.29 (m, 2H), 7.06 (t, J=8.4 Hz, 1H), 6.82 (s, 1H), 3.56 (t, J=8.4 Hz, 2H), 3.25-3.31 (m, 1H), 2.83 (t, J=8.0 Hz, 2H), 2.74 (d, J=4.4 Hz, 3H), 0.94 (d, J=6.4 Hz, 6H).

Example 75

N-(3-(4-(2-(N-isopropylsulfamoyl)phenylamino)-6,7-dihydro-5H-pyrrolo[2,3-d]pyrimidin-2-ylamino)phenyl)acetamide

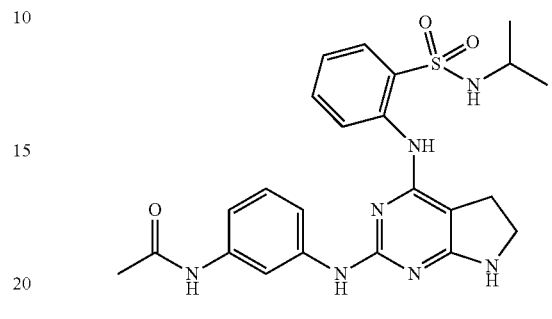

$^1$H NMR (400 MHz, DMSO-d$_6$) δ ppm 9.80 (s, 1H), 8.90-9.00 (brs, 1H), 8.41-8.50 (brs, 1H), 8.34 (s, 1H), 7.84 (d, J=8.0 Hz, 1H), 7.76 (d, J=7.2 Hz, 1H), 7.66 (s, 1H), 7.46-7.49 (m, 2H), 7.00-7.19 (m, 3H), 6.84-6.89 (brs, 1H), 3.56 (t, J=8.4 Hz, 2H), 3.24-3.33 (m, 1H), 2.70-2.89 (brs, 1H), 2.02 (s, 3H), 0.95 (d, J=6.8 Hz, 6H).

Example 76

2-(2-(4-(4-(dimethylamino)piperidin-1-yl)-2-methoxyphenylamino)-6,7-dihydro-5H-pyrrolo[2,3-d]pyrimidin-4-ylamino)-N-isopropylbenzenesulfonamide

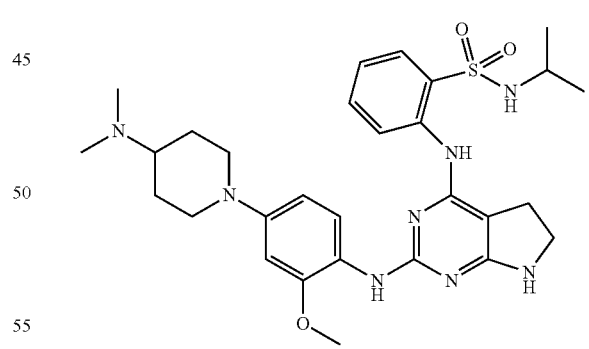

$^1$H NMR (400 MHz, DMSO-d$_6$) δ ppm 8.39 (d, J=8.4 Hz, 1.6 Hz, 1H), 8.25 (s, 1H), 7.83 (d, J=8.0 Hz, 1H), 7.81 (d, J=8.8 Hz, 1H), 7.74 (dd, J=8.8 Hz, 1H), 7.46 (t, J=8.8 Hz, 1H), 7.24 (s, 1H), 7.05 (t, J=8.0 Hz, 1H), 6.73 (s, 1H), 6.63 (d, J=2.4 Hz, 1H), 6.45 (dd, J=8.8 Hz, 2.4 Hz, 1H), 3.81 (s, 3H), 3.76 (d, J=12.8 Hz, 2H), 3.53 (t, J=8.8 Hz, 2H), 3.23-3.31 (m, 1H), 3.05-3.19 (m, 1H), 2.79 (t, J=8.8 Hz, 2H), 2.62-2.75 (m, 8H), 2.03 (d, J=12.8 Hz, 2H), 1.64-1.72 (m, 2H), 0.94 (d, J=6.8 Hz, 6H).

Example 77

2-(2-(4-(1H-imidazol-1-yl)-2-methoxyphenylamino)-6,7-dihydro-5H-pyrrolo[2,3-d]pyrimidin-4-ylamino)-N-isopropylbenzenesulfonamide

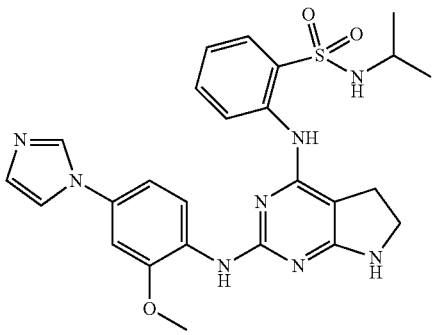 [SMILES: COc1cc(-n2ccnc2)ccc1Nc1nc2c(c(Nc3ccccc3S(=O)(=O)NC(C)C)n1)CCN2]

$^1$H NMR (400 MHz, DMSO-d$_6$) δ ppm 8.30 (d, J=8.8 Hz, 1H), 8.27 (d, J=6.4 Hz, 1H), 8.21 (d, J=6.8 Hz, 2H), 7.84 (d, J=8.4 Hz, 1H), 7.75 (d, J=8.0 Hz, 1H), 7.71 (s, 1H), 7.55 (t, J=8.0 Hz, 1H), 7.44 (s, 1H), 7.24 (s, 1H), 7.04-7.09 (m, 3H), 6.90 (s, 1H), 3.93 (s, 3H), 3.55 (t, J=8.4 Hz, 2H), 3.21-3.31 (m, 1H), 2.81 (t, J=8.8 Hz, 2H), 0.92 (d, J=6.8 Hz, 6H).

Example 78

N-isopropyl-2-(2-(4-(pyrrolidine-1-carbonyl)phenylamino)-6,7-dihydro-5H-pyrrolo[2,3-d]pyrimidin-4-ylamino)benzenesulfonamide

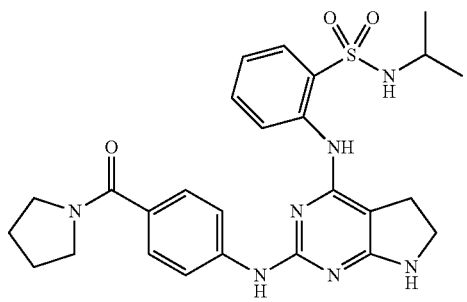 [SMILES: CC(C)NS(=O)(=O)c1ccccc1Nc1nc(Nc2ccc(C(=O)N3CCCC3)cc2)nc2c1CCN2]

$^1$H NMR (400 MHz, CDCl$_3$) δ ppm 8.15 (d, J=8.5 Hz, 1H), 8.02 (s, 1H), 7.91 (d, J=8.0 Hz, 1H), 7.62-7.50 (m, 3H), 7.42 (d, J=8.6 Hz, 2H), 7.14 (t, J=7.6 Hz, 1H), 4.79 (m, 2H), 3.67 (dd, J=17.5, 8.4 Hz, 4H), 3.53-3.35 (m, 3H), 2.91 (t, J=8.3 Hz, 2H), 2.01-1.79 (m, 4H), 1.00 (t, J=8.1 Hz, 6H).

Example 79

2-(2-(4-(4-(hydroxymethyl)piperidin-1-yl)-2-methoxyphenylamino)-6,7-dihydro-5H-pyrrolo[2,3-d]pyrimidin-4-ylamino)-N-isopropylbenzenesulfonamide

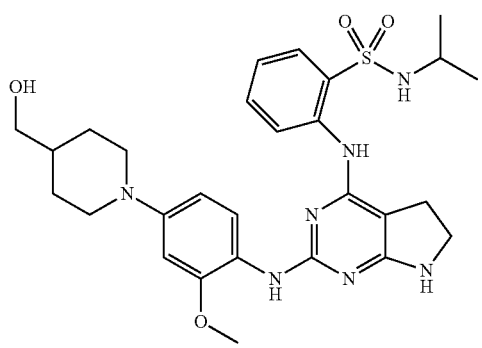 [SMILES: COc1cc(N2CCC(CO)CC2)ccc1Nc1nc2c(c(Nc3ccccc3S(=O)(=O)NC(C)C)n1)CCN2]

$^1$H NMR (400 MHz, CDCl$_3$) δ ppm 8.26 (d, J=8.2 Hz, 1H), 8.15 (d, J=8.8 Hz, 1H), 8.00-7.78 (m, 2H), 7.52 (t, J=7.9 Hz, 1H), 7.12 (dd, J=15.7, 7.6 Hz, 2H), 6.54 (d, J=2.5 Hz, 1H), 6.41 (dd, J=8.8, 2.5 Hz, 1H), 4.54 (s, 1H), 4.44 (d, J=7.6 Hz, 1H), 3.84 (d, J=6.7 Hz, 3H), 3.67 (t, J=8.5 Hz, 2H), 3.63-3.48 (m, 4H), 3.40 (dq, J=13.0, 6.6 Hz, 1H), 2.92 (t, J=8.5 Hz, 2H), 2.67 (dd, J=12.0, 9.7 Hz, 2H), 1.86 (d, J=11.6 Hz, 2H), 1.56-1.38 (m, 2H), 1.02 (dd, J=12.2, 6.6 Hz, 6H).

Example 80

2-(2-(4-(3-hydroxypyrrolidin-1-yl)-2-methoxyphenylamino)-6,7-dihydro-5H-pyrrolo[2,3-d]pyrimidin-4-ylamino)-N-isopropylbenzenesulfonamide

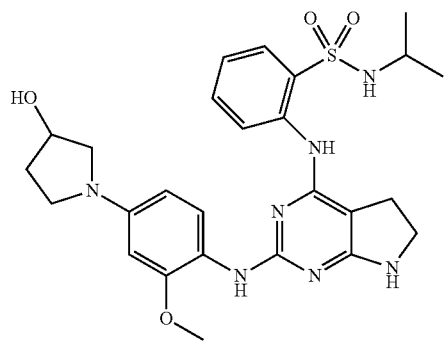 [SMILES: COc1cc(N2CCC(O)C2)ccc1Nc1nc2c(c(Nc3ccccc3S(=O)(=O)NC(C)C)n1)CCN2]

$^1$H NMR (400 MHz, CDCl$_3$) δ ppm 8.26 (s, 1H), 7.97-8.05 (m, 2H), 7.88 (d, J=8.3 Hz, 1H), 7.50-7.55 (m, 2H), 7.26 (s, 5H), 7.09 (m, 2H), 6.14 (s, 1H), 6.05 (d, J=8.8 Hz, 1H), 3.84 (s, 3H), 3.64 (t, J=8.0 Hz, 2H), 3.56-3.19 (m, 5H), 2.87 (s, 2H), 2.27-2.10 (m, 2H), 2.07-1.94 (m, 4H), 1.00 (d, J=6.5 Hz, 6H).

Example 81

2-(2-(4-(3-hydroxypiperidin-1-yl)-2-methoxyphenylamino)-6,7-dihydro-5H-pyrrolo[2,3-d]pyrimidin-4-ylamino)-N-isopropylbenzenesulfonamide

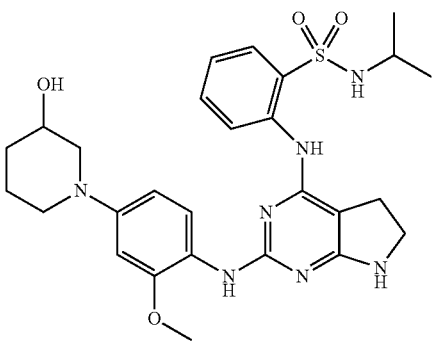 [SMILES: COc1cc(N2CCCC(O)C2)ccc1Nc1nc2c(c(Nc3ccccc3S(=O)(=O)NC(C)C)n1)CCN2]

$^1$H NMR (400 MHz, DMSO-d$_6$) δ ppm 8.34 (s, 1H), 7.79 (d, J=7.6 Hz, 1H), 7.73-7.75 (m, 1H), 7.45-7.53 (m, 1H), 7.05-7.11 (m, 1H), 6.61 (s, 1H), 6.37-6.42 (m, 1H), 4.13-4.21 (m, 1H), 3.78 (s, 3H), 3.62-3.71 (m, 1H), 3.52 (t, J=8.0

Hz, 2H), 3.34-3.45 (m, 2H), 2.63-2.85 (m, 4H), 1.88-1.94 (m, 1H), 1.68-1.74 (m, 1H), 1.38-1.58 (m, 2H), 0.92 (d, J=6.4 Hz, 6H).

Example 82

N-isopropyl-2-(2-(4-(1-(piperidin-1-yl)ethyl)phenylamino)-6,7-dihydro-5H-pyrrolo[2,3-d]pyrimidin-4-ylamino)benzenesulfonamide

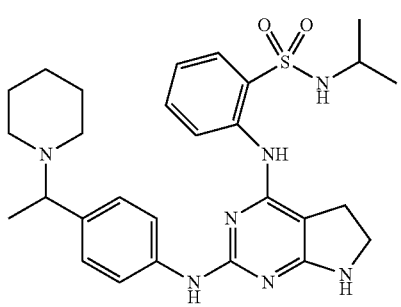 [SMILES: CC(C)NS(=O)(=O)c1ccccc1Nc1nc(Nc2ccc(C(C)N3CCCCC3)cc2)nc2c1CCN2]

$^1$H NMR (400 MHz, CDCl$_3$) δ ppm 8.22 (d, J=8.3 Hz, 1H), 8.01 (s, 1H), 7.90 (dd, J=7.9, 1.4 Hz, 1H), 7.60-7.49 (m, 3H), 7.24 (s, 1H), 7.12 (t, J=7.6 Hz, 1H), 6.85 (s, 1H), 4.59 (d, J=7.1 Hz, 2H), 3.67 (t, J=8.3 Hz, 2H), 3.52-3.30 (m, 1H), 2.91 (dd, J=18.1, 9.7 Hz, 2H), 2.65-2.19 (m, 3H), 1.91-1.53 (m, 10H), 1.08-0.94 (m, 6H).

Example 83

N-isopropyl-2-(2-(2-methoxy-4-(2-oxopyridin-1(2H)-yl)phenylamino)-6,7-dihydro-5H-pyrrolo[2,3-d]pyrimidin-4-ylamino)benzenesulfonamide

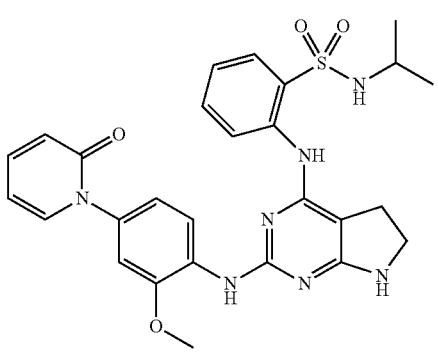 [SMILES: COc1cc(-n2ccccc2=O)ccc1Nc1nc2c(c(Nc3ccccc3S(=O)(=O)NC(C)C)n1)CCN2]

$^1$H NMR (400 MHz, DMSO-d$_6$) δ ppm 8.29 (t, J=8.0 Hz, 2H), 8.21 (s, 1H), 7.81 (d, J=7.7 Hz, 1H), 7.76 (d, J=7.9 Hz, 1H), 7.61 (d, J=4.9 Hz, 1H), 7.55 (t, J=7.8 Hz, 1H), 7.51-7.36 (m, 2H), 7.13-6.95 (m, 2H), 6.90 (s, 1H), 6.82 (dd, J=8.5, 2.2 Hz, 1H), 6.45 (d, J=8.8 Hz, 1H), 6.28 (t, J=6.7 Hz, 1H), 3.85 (s, 3H), 3.55 (t, J=8.8 Hz, 2H), 2.82 (t, J=8.6 Hz, 2H), 0.90 (t, J=19.2 Hz, 6H).

Example 84

2-(2-(4-(3,5-dimethylmorpholino)-2-methoxyphenylamino)-6,7-dihydro-5H-pyrrolo[2,3-d]pyrimidin-4-ylamino)-N-isopropylbenzenesulfonamide

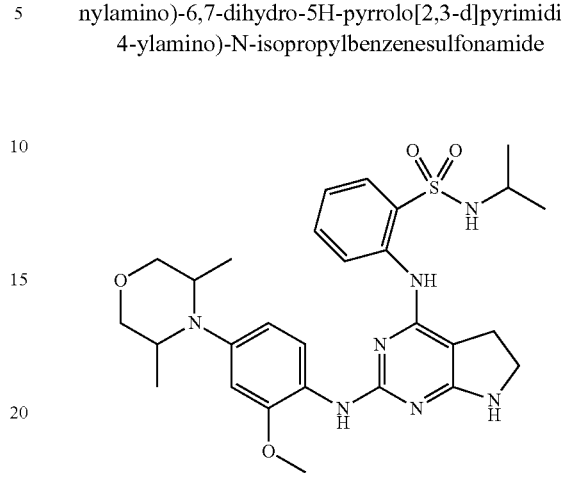

$^1$H NMR (400 MHz, CDCl$_3$) δ ppm 8.26 (d, J=8.2 Hz, 1H), 8.17 (d, J=8.8 Hz, 1H), 7.98-7.87 (m, 2H), 7.51 (dd, J=12.0, 5.0 Hz, 1H), 7.12 (dd, J=15.4, 7.5 Hz, 2H), 6.49 (d, J=2.5 Hz, 1H), 6.36 (dd, J=8.8, 2.5 Hz, 1H), 4.56 (d, J=11.7 Hz, 2H), 3.90-3.78 (m, 5H), 3.65 (t, J=8.4 Hz, 2H), 3.41 (td, J=13.4, 6.7 Hz, 1H), 3.32 (d, J=10.7 Hz, 2H), 2.91 (t, J=8.4 Hz, 2H), 2.44-2.32 (m, 2H), 1.25 (t, J=1.8 Hz, 6H), 1.01 (d, J=6.5 Hz, 6H).

Example 85

N-isopropyl-2-(2-(2-methoxy-4-(2-morpholinoethylamino)phenylamino)-6,7-dihydro-5H-pyrrolo[2,3-d]pyrimidin-4-ylamino)benzenesulfonamide

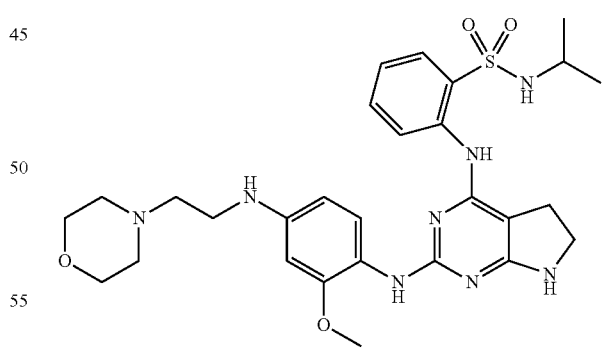

$^1$H NMR (400 MHz, DMSO-d$_6$) δ ppm 8.47 (d, J=8.7 Hz, 1H), 8.27 (s, 1H), 7.82 (d, J=7.8 Hz, 1H), 7.73 (dd, J=8.0, 1.6 Hz, 1H), 7.51 (d, J=8.5 Hz, 1H), 7.41 (t, J=7.7 Hz, 1H), 7.14 (s, 1H), 7.02 (t, J=7.6 Hz, 1H), 6.65 (s, 1H), 6.32 (d, J=2.3 Hz, 1H), 6.12 (dd, J=8.5, 2.3 Hz, 1H), 5.15 (m, 1H), 3.73 (s, 3H), 3.67-3.55 (m, 4H), 3.51 (t, J=8.6 Hz, 2H), 3.39-3.25 (m, 1H), 3.13 (d, J=6.3 Hz, 2H), 2.78 (t, J=8.5 Hz, 2H), 2.43 (s, 4H), 0.95 (d, J=6.5 Hz, 6H).

Example 86

2-(2-(4-(4-hydroxypiperidin-1-yl)-2-methoxyphenylamino)-6,7-dihydro-5H-pyrrolo[2,3-d]pyrimidin-4-ylamino)-N-isopropylbenzenesulfonamide

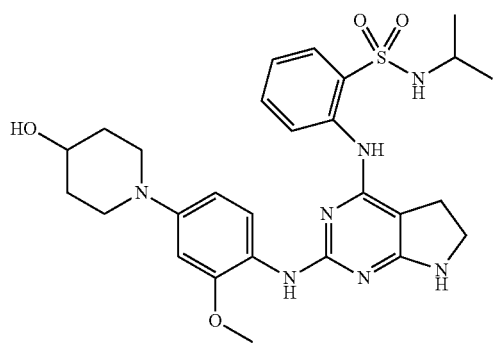 [SMILES: COc1cc(N2CCC(O)CC2)ccc1Nc1nc2c(c(Nc3ccccc3S(=O)(=O)NC(C)C)n1)CCN2]

¹H NMR (400 MHz, DMSO-d₆) δ ppm 8.42 (d, J=8.3 Hz, 2H), 8.26 (s, 1H), 7.77 (t, J=8.4 Hz, 3H), 7.47 (t, J=7.9 Hz, 1H), 7.22 (s, 2H), 7.06 (t, J=7.6 Hz, 1H), 6.74 (s, 2H), 6.61 (d, J=2.5 Hz, 1H), 6.43 (d, J=8.7 Hz, 1H), 4.67 (d, J=4.2 Hz, 1H), 3.81 (s, 3H), 3.54-3.30 (m, 6H), 2.78 (m, 4H), 2.01 (d, J=8.0 Hz, 1H), 1.83 (d, 2H), 1.51 (d, J=9.9 Hz, 2H), 0.95 (d, J=6.5 Hz, 6H).

Example 87

2-(2-(4-(4-(S,S-dioxothio)piperidin-1-yl)-2-methoxyphenylamino)-6,7-dihydro-5H-pyrrolo[2,3-d]pyrimidin-4-ylamino)-N-isopropylbenzenesulfonamide

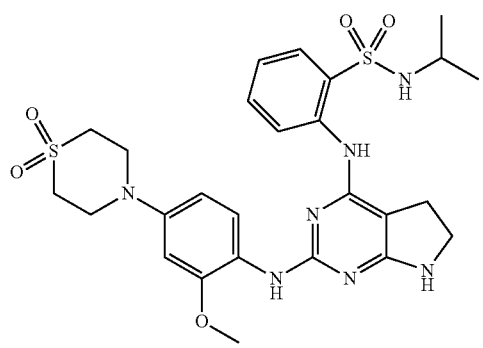 [SMILES: COc1cc(N2CCS(=O)(=O)CC2)ccc1Nc1nc2c(c(Nc3ccccc3S(=O)(=O)NC(C)C)n1)CCN2]

¹H NMR (400 MHz, CDCl₃) δ ppm 8.25 (d, J=8.7 Hz, 2H), 8.04-7.76 (m, 2H), 7.51 (s, 1H), 7.20 (s, 1H), 7.12 (t, 1H), 6.50 (s, 1H), 6.49 (s, 1H), 6.42 (d, J=9.2 Hz, 1H), 4.55 (s, 1H), 4.39 (d, J=7.6 Hz, 1H), 3.86 (s, 3H), 3.69 (t, J=9.3 Hz, 7H), 3.69 (t, J=9.3 Hz, 6H), 3.42 (dd, J=14.0, 6.6 Hz, 1H), 3.18-3.04 (m, 4H), 2.94 (d, J=8.3 Hz, 2H), 1.01 (d, J=6.5 Hz, 6H).

Example 88

N-isopropyl-2-(2-(2-methoxy-4-(2H-tetrazol-2-yl)phenylamino)-6,7-dihydro-5H-pyrrolo[2,3-d]pyrimidin-4-ylamino)benzenesulfonamide

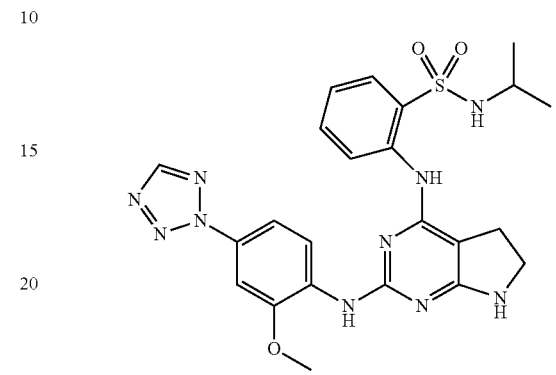

¹H NMR (400 MHz, CDCl₃) δ ppm 8.59 (d, J=9.2 Hz, 2H), 8.18 (d, J=8.4 Hz, 1H), 7.97-7.91 (m, 2H), 7.66-7.49 (m, 4H), 7.18 (t, J=7.6 Hz, 1H), 4.63 (s, 1H), 4.43 (d, J=7.6 Hz, 1H), 3.99 (s, 3H), 3.73 (t, J=8.5 Hz, 2H), 3.47-3.39 (m, 1H), 2.97 (dd, J=20.2, 11.9 Hz, 2H), 1.01 (d, J=6.5 Hz, 6H).

Example 89

2-(2-(4-(3-(dimethylamino)pyrrolidin-1-yl)-2-methoxyphenylamino)-6,7-dihydro-5H-pyrrolo[2,3-d]pyrimidin-4-ylamino)-N-isopropylbenzenesulfonamide

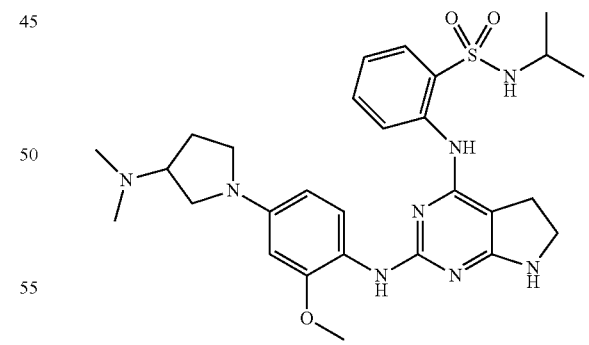

¹H NMR (400 MHz, CDCl₃) δ ppm 8.33 (s, 1H), 8.13-7.94 (m, 2H), 7.89 (d, J=8.0 Hz, 1H), 7.50 (t, J=7.9 Hz, 1H), 7.09 (t, J=7.8 Hz, 1H), 7.00 (s, 1H), 6.13 (d, J=2.2 Hz, 1H), 6.05 (d, J=8.6 Hz, 1H), 4.51 (d, J=30.1 Hz, 2H), 3.85 (s, 3H), 3.65 (t, J=8.4 Hz, 2H), 3.55-3.37 (m, 4H), 3.21 (s, 1H), 2.37 (s, 6H), 2.13 (d, J=67.2 Hz, 2H), 2.11-1.78 (m, 2H), 1.01 (s, 6H).

Example 90

2-(2-(4-(2,4-dimethyl-1H-imidazol-1-yl)-2-methoxyphenylamino)-6,7-dihydro-5H-pyrrolo[2,3-d]pyrimidin-4-ylamino)-N-isopropylbenzenesulfonamide

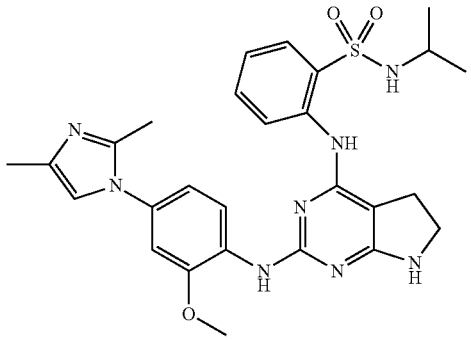 [SMILES: COc1cc(-n2cc(C)nc2C)ccc1Nc1nc2c(c(Nc3ccccc3S(=O)(=O)NC(C)C)n1)CCN2]

$^1$H NMR (400 MHz, CDCl$_3$) δ ppm 8.49 (d, J=8.4 Hz, 1H), 8.21 (d, J=8.3 Hz, 1H), 8.05-7.77 (m, 2H), 7.73-7.48 (m, 1H), 7.43 (s, 1H), 7.15 (dd, J=11.1, 4.1 Hz, 1H), 6.81-6.55 (m, 3H), 4.65 (s, 1H), 4.56 (d, J=7.8 Hz, 1H), 3.90 (s, 3H), 3.73 (t, J=8.4 Hz, 2H), 3.63-3.33 (m, 1H), 3.15-2.79 (m, 2H), 2.34 (s, 3H), 2.29-2.15 (m, 3H), 1.01 (dd, J=17.8, 6.5 Hz, 6H).

Example 91

N-isopropyl-2-(2-(4-methylthiazol-2-ylamino)-6,7-dihydro-5H-pyrrolo[2,3-d]pyrimidin-4-ylamino)benzenesulfonamide

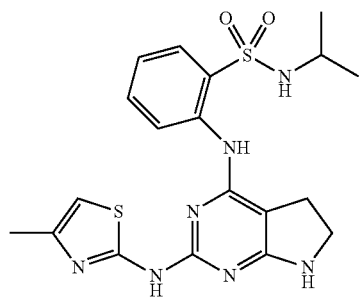 [SMILES: Cc1csc(Nc2nc3c(c(Nc4ccccc4S(=O)(=O)NC(C)C)n2)CCN3)n1]

$^1$H NMR (400 MHz, CDCl$_3$) δ ppm 12.30 (s, 1H), 9.47 (s, 1H), 7.91 (dd, J=13.7, 8.2 Hz, 2H), 7.62 (s, 1H), 7.53 (t, J=7.8 Hz, 1H), 7.15 (t, J=7.7 Hz, 1H), 6.21 (s, 1H), 4.46 (d, J=7.7 Hz, 1H), 3.80 (t, J=8.2 Hz, 2H), 3.40 (dd, J=12.8, 6.6 Hz, 1H), 2.96 (t, J=8.2 Hz, 2H), 2.52-2.10 (m, 3H), 1.01 (dd, J=6.5, 1.4 Hz, 6H).

Example 92

2-(2-(4-(1,4'-bipiperidin-1'-yl)-2-methoxyphenylamino)-6,7-dihydro-5H-pyrrolo[2,3-d]pyrimidin-4-ylamino)-N-isopropylbenzenesulfonamide

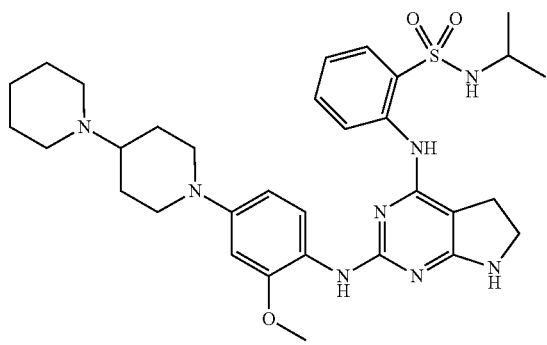 [SMILES: COc1cc(N2CCC(N3CCCCC3)CC2)ccc1Nc1nc2c(c(Nc3ccccc3S(=O)(=O)NC(C)C)n1)CCN2]

$^1$H NMR (400 MHz, CDCl$_3$) δ ppm 8.22 (d, J=8.4 Hz, 1H), 8.17 (d, J=8.8 Hz, 1H), 7.85-7.92 (m, 2H), 7.52 (t, J=7.6 Hz, 1H), 7.17 (s, 1H), 7.12 (t, J=7.6 Hz, 1H), 6.51 (s, 1H), 6.38 (d, J=8.8 Hz, 1H), 4.56 (s, 1H), 4.43-4.49 (brs, 1H), 3.85 (s, 3H), 3.62-3.70 (m, 4H), 3.39-3.44 (m, 1H), 3.28-3.21 (m, 7H), 2.72 (t, J=8.4 Hz, 2H), 2.06-2.09 (m, 2H), 1.81-1.95 (m, 6H), 1.61-1.65 (m, 2H).

Example 93

N-isopropyl-2-(2-(2-methoxy-4-(4-(pyrrolidin-1-yl)piperidin-1-yl)phenylamino)-6,7-dihydro-5H-pyrrolo[2,3-d]pyrimidin-4-ylamino)benzenesulfonamide

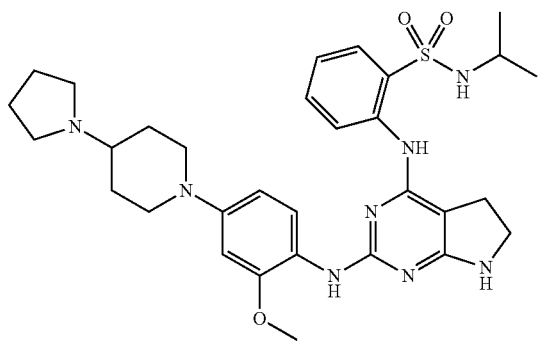 [SMILES: COc1cc(N2CCC(N3CCCC3)CC2)ccc1Nc1nc2c(c(Nc3ccccc3S(=O)(=O)NC(C)C)n1)CCN2]

$^1$H NMR (400 MHz, DMSO-d$_6$) δ ppm 8.38 (d, J=8.4 Hz, 1H), 8.23 (s, 1H), 7.80 (dd, J=8.3, 4.2 Hz, 2H), 7.73 (d, J=8.0 Hz, 1H), 7.45 (t, J=7.8 Hz, 1H), 7.20 (s, 1H), 7.03 (t, J=7.6 Hz, 1H), 6.70 (s, 1H), 6.61 (d, J=2.2 Hz, 1H), 6.50-6.37 (m, 1H), 3.79 (s, 3H), 3.65 (s, 2H), 3.51 (t, J=8.4 Hz, 2H), 2.78 (t, J=8.5 Hz, 2H), 2.64 (t, J=11.5 Hz, 2H), 1.99 (d, J=15.1 Hz, 2H), 1.82 (m, 4H), 1.66 (s, 2H), 0.93 (d, J=6.5 Hz, 6H).

Example 94

N-isopropyl-2-(2-(2-methoxy-4-(1H-pyrazol-1-yl)phenylamino)-6,7-dihydro-5H-pyrrolo[2,3-d]pyrimidin-4-ylamino)benzenesulfonamide

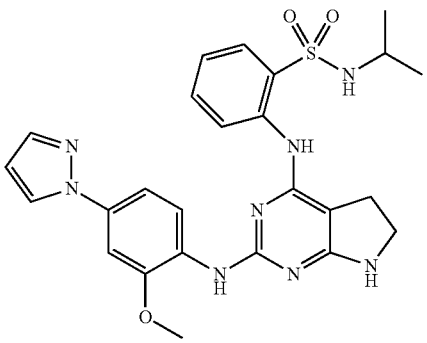 [SMILES: COc1cc(-n2cccn2)ccc1Nc1nc2c(c(Nc3ccccc3S(=O)(=O)NC(C)C)n1)CCN2]

$^1$H NMR (400 MHz, CDCl$_3$) δ ppm 8.45 (d, J=8.8 Hz, 1H), 8.22 (d, J=8.0 Hz, 1H), 8.00-7.90 (m, 2H), 7.87 (d, J=2.4 Hz, 1H), 7.71 (d, J=1.5 Hz, 1H), 7.57 (t, J=7.0 Hz, 1H), 7.40 (s, 1H), 7.30 (d, J=2.3 Hz, 1H), 7.16 (t, J=7.7 Hz, 1H), 7.01 (dd, J=8.8, 2.4 Hz, 1H), 6.52-6.37 (m, 1H), 4.61 (s, 1H), 4.42 (d, J=8.0 Hz, 1H), 3.95 (d, J=18.6 Hz, 3H), 3.73

(t, J=8.5 Hz, 2H), 3.43 (dd, J=13.2, 7.0 Hz, 1H), 2.98 (t, J=8.4 Hz, 2H), 1.00 (dd, J=13.0, 7.0 Hz, 6H).

Example 95

N-isopropyl-2-(2-(2-methoxy-4-(4-morpholinopiperidin-1-yl)phenylamino)-6,7-dihydro-5H-pyrrolo[2,3-d]pyrimidin-4-ylamino)benzenesulfonamide

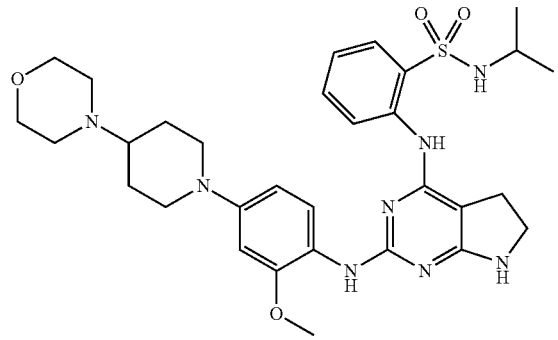 [SMILES: COc1cc(N2CCC(N3CCOCC3)CC2)ccc1Nc1nc2c(c(Nc3ccccc3S(=O)(=O)NC(C)C)n1)CCN2]

$^1$H NMR (400 MHz, CDCl$_3$) δ ppm 8.25 (s, 1H), 8.15 (d, J=8.7 Hz, 1H), 7.93 (d, J=6.8 Hz, 1H), 7.54 (t, J=7.1 Hz, 1H), 7.21 (s, 1H), 7.14 (t, J=7.7 Hz, 1H), 6.56 (t, J=4.0 Hz, 1H), 6.46-6.32 (m, 1H), 4.65 (s, 1H), 4.52 (s, 1H), 3.98 (s, 1H), 3.87-3.72 (m, 7H), 3.71-3.49 (m, 4H), 3.43 (dd, J=13.4, 6.6 Hz, 1H), 2.94 (m, 2H), 2.81-2.56 (m, 6H), 2.38 (s, 2H), 1.98 (d, J=11.7 Hz, 2H), 1.72 (d, J=11.8 Hz, 2H), 1.03 (d, J=6.5 Hz, 6H).

Example 96

N-isopropyl-2-(2-(2-methoxy-4-(4-(4-methylpiperazin-1-yl)piperidin-1-yl)phenylamino)-6,7-dihydro-5H-pyrrolo[2,3-d]pyrimidin-4-ylamino)benzenesulfonamide

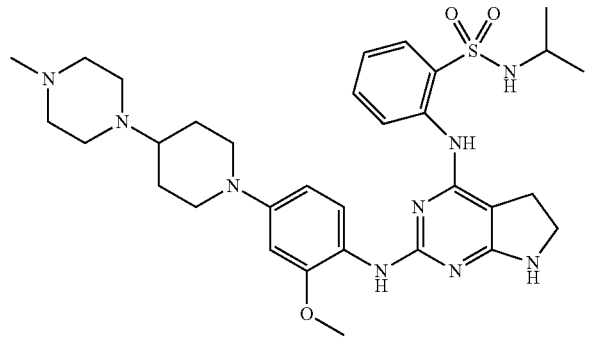 [SMILES: COc1cc(N2CCC(N3CCN(C)CC3)CC2)ccc1Nc1nc2c(c(Nc3ccccc3S(=O)(=O)NC(C)C)n1)CCN2]

$^1$H NMR (400 MHz, DMSO-d$_6$) δ ppm 8.40 (d, J=8.4 Hz, 1H), 8.24 (s, 1H), 7.83 (d, J=8.0 Hz, 1H), 7.78-7.65 (m, 2H), 7.45 (t, J=7.9 Hz, 1H), 7.21 (s, 1H), 7.04 (t, J=7.6 Hz, 1H), 6.72 (s, 1H), 6.59 (d, J=2.2 Hz, 1H), 6.46-6.31 (m, 1H), 3.79 (s, 3H), 3.65 (d, J=12.1 Hz, 2H), 3.52 (t, J=8.3 Hz, 2H), 3.28-3.16 (m, 3H), 2.78 (t, J=8.5 Hz, 2H), 2.69-2.55 (m, 8H), 2.27 (m, 4H), 1.83 (s, 2H), 1.52 (d, J=10.6 Hz, 2H), 0.93 (d, J=6.5 Hz, 6H).

Example 97

N-isopropyl-2-(2-(2-methoxy-4-(4-(piperazin-1-yl)piperidin-1-yl)phenylamino)-6,7-dihydro-5H-pyrrolo[2,3-d]pyrimidin-4-ylamino)benzenesulfonamide

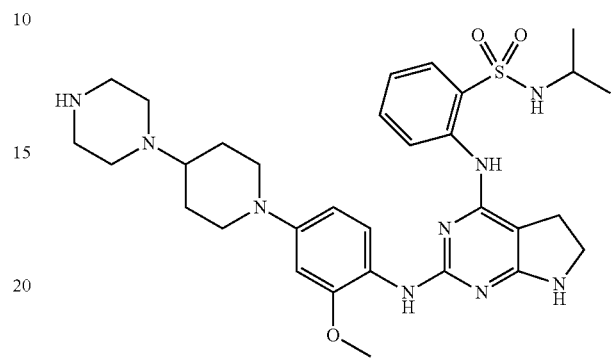

$^1$H NMR (400 MHz, DMSO-d$_6$) δ ppm 8.82-9.03 (m, 2H), 7.79 (t, J=7.6 Hz, 2H), 7.43-7.58 (m, 1H), 7.15-7.22 (m, 1H), 7.11-7.14 (m, 1H), 6.68 (s, 1H), 6.51-6.56 (m, 1H), 3.88-3.92 (m, 2H), 3.80 (s, 3H), 3.21-3.67 (m, 12H), 2.74 (t, J=7.6 Hz, 2H), 2.57-2.65 (m, 2H), 1.61-1.71 (m, 2H), 0.93 (d, J=6.4 Hz, 6H).

Example 98

N-isopropyl-2-(2-(2-methoxy-4-(2-oxopiperidin-1-yl)phenylamino)-6,7-dihydro-5H-pyrrolo[2,3-d]pyrimidin-4-ylamino)benzenesulfonamide

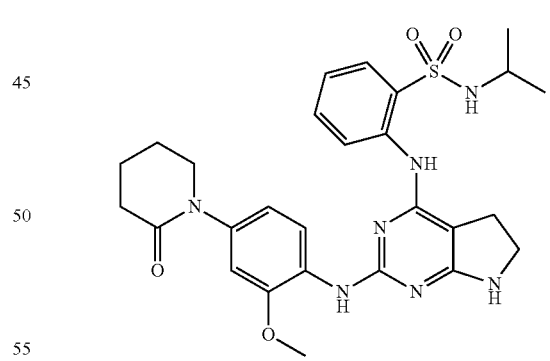

$^1$H NMR (400 MHz, DMSO-d$_6$) δ ppm 8.41 (d, J=8.2 Hz, 1H), 8.25 (s, 1H), 7.78 (m, 3H), 7.47 (t, J=7.1 Hz, 1H), 7.23 (s, 1H), 7.05 (t, J=7.6 Hz, 1H), 6.74 (s, 1H), 6.62 (d, J=2.5 Hz, 1H), 6.44 (dd, J=8.7, 2.5 Hz, 1H), 4.42 (d, J=12.2 Hz, 1H), 3.82 (d, J=9.3 Hz, 3H), 3.76-3.62 (m, 2H), 3.53 (t, J=8.2 Hz, 2H), 3.29-3.19 (m, 1H), 3.18 (t, J=5.6 Hz, 2H), 2.80 (t, J=8.5 Hz, 2H), 2.69 (t, J=11.2 Hz, 2H), 2.25 (t, J=6.4 Hz, 2H), 1.90-1.77 (m, 2H), 1.68 (d, J=4.7 Hz, 2H), 1.57 (d, J=9.8 Hz, 2H), 0.94 (d, J=6.5 Hz, 6H).

Example 99

N-isopropyl-2-(2-(2-methoxy-4-(2-oxo-3,4-dihydro-quinolin-1(2H)-yl)phenylamino)-6,7-dihydro-5H-pyrrolo[2,3-d]pyrimidin-4-ylamino)benzenesulfonamide

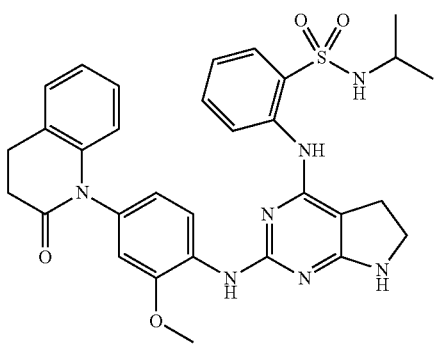 [SMILES: COc1cc(N2C(=O)CCc3ccccc32)ccc1Nc1nc2c(c(Nc3ccccc3S(=O)(=O)NC(C)C)n1)CCN2]

¹H NMR (400 MHz, CDCl₃) δ ppm 8.26 (d, J=8.0 Hz, 1H), 8.16 (d, J=8.8 Hz, 1H), 7.93 (s, 1H), 7.90 (dd, J=8.0 Hz, 1.2 Hz, 1H), 7.52 (t, J=8.8 Hz, 1H), 7.16-7.25 (s, 1H), 7.12 (t, J=7.6 Hz, 1H), 7.02 (t, J=8.0 Hz, 1H), 6.57 (d, J=2.4 Hz, 1H), 6.43 (dd, J=8.8 Hz, 2.0 Hz, 1H), 4.54-4.61 (m, 2H), 4.43-4.50 (m, 1H), 3.86 (s, 3H), 3.65-3.69 (m, 4H), 3.39-3.44 (m, 1H), 2.92 (t, J=8.8 Hz, 2H), 2.79-2.86 (m, 6H), 2.58-2.62 (m, 1H), 1.82-1.84 (m, 2H), 1.01 (d, J=6.4 Hz, 6H).

Example 100

N⁴-(2-(isopropylsulfonyl)phenyl)-N²-(2-methoxy-4-morpholinophenyl)-6,7-dihydro-5H-pyrrolo[2,3-d]pyrimidine-2,4-diamine

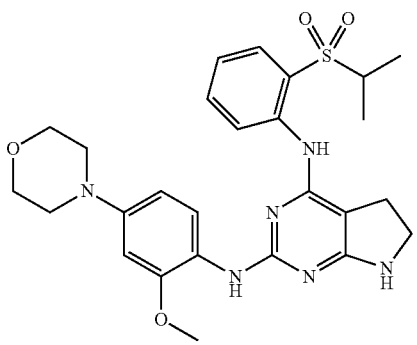 [SMILES: COc1cc(N2CCOCC2)ccc1Nc1nc2c(c(Nc3ccccc3S(=O)(=O)C(C)C)n1)CCN2]

¹H NMR (400 MHz, DMSO-d₆) δ ppm 8.53 (s, 1H), 8.50 (d, J=8.4 Hz, 1H), 7.75 (d, J=8.8 Hz, 1H), 7.71 (dd, J=8.0 Hz, 1.6 Hz, 1H), 7.58 (t, J=8.4 Hz, 1H), 7.27 (s, 1H), 7.14 (t, J=8.0 Hz, 1H), 6.76 (s, 1H), 6.62 (d, J=2.4 Hz, 1H), 6.44 (dd, J=8.8 Hz, 2.8 Hz, 1H), 3.80 (s, 3H), 3.74-3.76 (m, 4H), 3.51 (t, J=8.4 Hz, 2H), 3.38-3.42 (m, 1H), 3.07-3.09 (m, 4H), 2.78 (t, J=8.4 Hz, 2H), 1.17 (d, J=6.8 Hz, 6H).

Example 101

N-isopropyl-2-(2-(2-methoxy-4-morpholinophenylamino)-5-methyl-6,7-dihydro-5H-pyrrolo[2,3-d]pyrimidin-4-ylamino)benzenesulfonamide

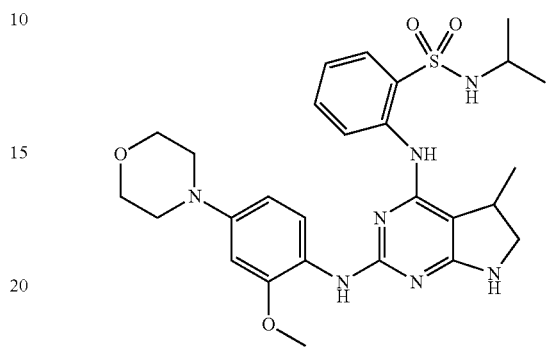

¹H NMR (400 MHz, DMSO-d₆) δ ppm 8.46 (d, J=8.3 Hz, 1H), 8.36 (s, 1H), 7.77 (ddd, J=13.5, 9.5, 4.7 Hz, 3H), 7.44 (t, J=7.9 Hz, 1H), 7.25 (s, 1H), 7.04 (t, J=7.2 Hz, 1H), 6.75 (s, 1H), 6.62 (d, J=2.5 Hz, 1H), 6.40 (dd, J=8.7, 2.5 Hz, 1H), 3.80 (s, 3H), 3.77-3.71 (m, 4H), 3.67 (t, J=9.1 Hz, 1H), 3.27 (d, J=6.9 Hz, 1H), 3.11-3.03 (m, 5H), 1.17 (d, J=6.7 Hz, 3H), 1.01 (d, J=6.5 Hz, 3H), 0.90 (d, J=6.5 Hz, 3H).

Example 102

(R)-2-(2-(2-methoxy-4-morpholinophenylamino)-5-methyl-6,7-dihydro-5H-pyrrolo[2,3-d]pyrimidin-4-ylamino)-N-methylbenzamide

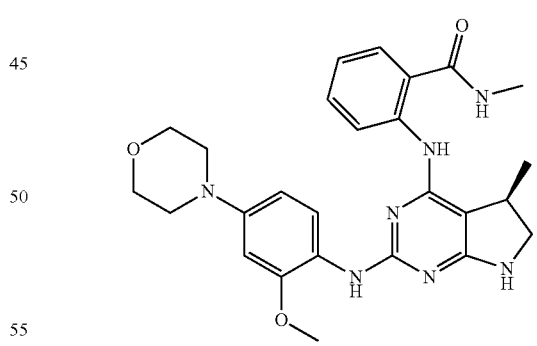

¹H NMR (400 MHz, DMSO-d₆) δ ppm 10.08 (s, 1H), 8.60-8.63 (dd, 1H, J=1.2 Hz, 8.4 Hz), 8.24-8.26 (d, 1H, J=8.8 Hz), 7.39-7.42 (m, 2H), 7.10 (s, 1H), 6.91-6.95 (m, 1H), 6.50-6.51 (d, 1H, J=2.4 Hz), 6.45-6.48 (dd, 1H, J=3.2 Hz, 8.8 Hz), 6.18-6.19 (d, 1H, J=4.4 Hz), 4.13 (s, 1H), 3.85-3.89 (s+m, 7H), 3.76-3.81 (t, 1H, J=9.2 Hz), 3.47-3.49 (m, 1H), 3.20-3.23 (dd, 1H, J=4.4 Hz, 8.8 Hz), 3.00-3.10 (t, 4H, J=4.8 Hz), 2.90-3.00 (d, 3H, J=4.8 Hz), 1.38-1.40 (d, 3H, J=6.4 Hz).

Example 103

2-(2-(2-methoxy-4-morpholinophenylamino)-5,5-dimethyl-6,7-dihydro-5H-pyrrolo[2,3-d]pyrimidin-4-ylamino)-N-methylbenzenesulfonamide

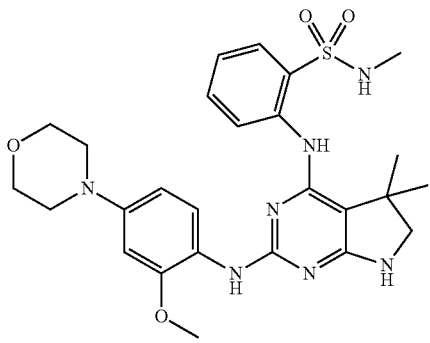

$^1$H NMR (400 MHz, CDCl$_3$) δ ppm 8.32 (d, 1H, J=8.4 Hz), 8.13 (d, 1H, J=8.8 Hz), 8.32 (s, 1H), 7.88 (dd, 1H, J=8.0 Hz, 1.6 Hz), 7.52 (t, 1H, J=8.4 Hz), 7.17 (s, 1H), 7.11 (t, 1H, J=7.2 Hz), 6.50 (d, 1H, J=2.8 Hz), 6.33 (dd, 1H, J=8.8 Hz, 2.4 Hz), 4.71 (s, 1H), 4.49 (q, 1H, J=4.8 Hz), 3.85-3.88 (m, 7H), 3.35 (s, 2H), 3.07-3.10 (m, 4H), 2.59 (d, 3H, J=5.2 Hz), 1.47 (s, 6H).

Example 104

N-cyclobutyl-2-(2-(2-methoxy-4-morpholinophenylamino)-5,5-dimethyl-6,7-dihydro-5H-pyrrolo[2,3-d]pyrimidin-4-ylamino)benzenesulfonamide

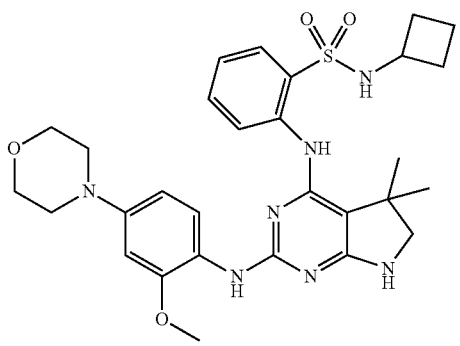 [SMILES: COc1cc(N2CCOCC2)ccc1Nc1nc2c(c(Nc3ccccc3S(=O)(=O)NC3CCC3)n1)C(C)(C)CN2]

$^1$H NMR (400 MHz, CDCl$_3$) δ ppm 8.22 (d, 1H, J=8.4 Hz), 8.13 (d, 1H, J=8.8 Hz), 7.88 (dd, 1H, J=8.8 Hz, 1.2 Hz), 7.87 (s, 1H), 7.50 (t, 1H, J=7.2 Hz), 7.17 (s, 1H), 7.12 (t, 1H, J=7.2 Hz), 6.49 (d, 1H, J=2.4 Hz), 6.26 (dd, 1H, J=8.8 Hz, 2.4 Hz), 4.63 (d, 1H, J=9.6 Hz), 4.57 (s, 1H), 3.85-3.87 (m, 7H), 3.70-3.76 (m, 1H), 3.37 (s, 2H), 3.05-3.08 (m, 4H), 1.93-2.00 (m, 2H), 1.62-1.70 (m, 2H), 1.47 (s, 6H), 1.41-1.49 (m, 2H).

Example 105

N-isopropyl-2-(2-(2-methoxy-4-morpholinophenylamino)-5,5-dimethyl-6,7-dihydro-5H-pyrrolo[2,3-d]pyrimidin-4-ylamino)benzenesulfonamide

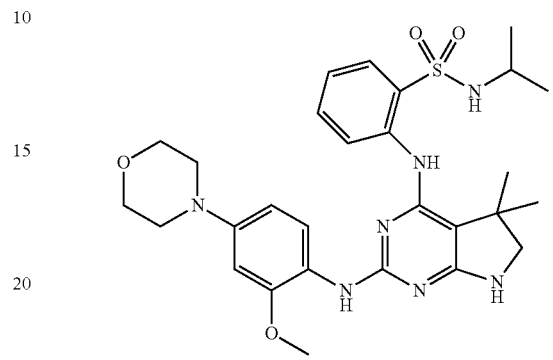

$^1$H NMR (400 MHz, CDCl$_3$) δ ppm 8.21 (d, 1H, J=8.4 Hz), 8.13 (d, 1H, J=8.8 Hz), 7.92 (dd, 1H, J=8.0 Hz, 1.2 Hz), 7.83 (s, 1H), 7.51 (t, 1H, J=7.2 Hz), 7.17 (s, 1H), 7.14 (t, 1H, J=7.2 Hz), 6.49 (d, 1H, J=2.0 Hz), 6.27 (dd, 1H, J=8.8 Hz, 2.4 Hz), 4.58 (s, 1H), 4.29 (d, 1H, J=4.0 Hz), 3.85-3.88 (m, 7H), 3.36-3.40 (m, 1H), 3.36 (s, 2H), 3.06-3.07 (m, 4H), 1.49 (s, 6H), 0.97 (d, 6H), J=6.8 Hz).

Example 106

2-(2-(2-methoxy-4-morpholinophenylamino)-5,5-dimethyl-6,7-dihydro-5H-pyrrolo[2,3-d]pyrimidin-4-ylamino)-N-propylbenzenesulfonamide

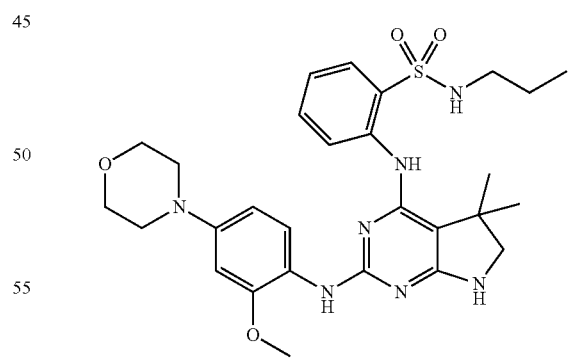

$^1$H NMR (400 MHz, CDCl$_3$) δ ppm 8.26 (d, 1H, J=8.4 Hz), 8.12 (d, 1H, J=8.8 Hz), 7.93 (s, 1H), 7.89 (dd, 1H, J=8.0 Hz, 1.6 Hz), 7.52 (t, 1H, J=8.4 Hz), 7.17 (s, 1H), 7.14 (t, 1H, J=8.0 Hz), 6.49 (d, 1H, J=2.4 Hz), 6.31 (dd, 1H, J=8.8 Hz, 2.8 Hz), 4.61 (s, 1H), 4.46 (t, 1H, J=6.4 Hz), 3.85-3.88 (m, 7H), 3.36 (s, 1H), 3.07-3.09 (m, 4H), 2.86 (q, 2H, J=6.4 Hz), 1.47 (s, 6H), 1.28-1.39 (m, 2H), 0.72 (t, 3H, J=7.6 Hz).

Example 107

N-isobutyl-2-(2-(2-methoxy-4-morpholinophenylamino)-5,5-dimethyl-6,7-dihydro-5H-pyrrolo[2,3-d]pyrimidin-4-ylamino)benzenesulfonamide

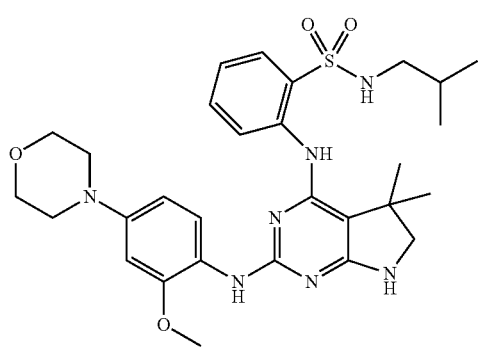 [SMILES: COc1cc(N2CCOCC2)ccc1Nc1nc2c(c(Nc3ccccc3S(=O)(=O)NCC(C)C)n1)C(C)(C)CN2]

$^1$H NMR (400 MHz, CDCl$_3$) δ ppm 8.25 (d, 1H, J=8.0 Hz), 8.11 (d, 1H, J=8.8 Hz), 7.88-7.90 (m, 2H), 7.52 (t, 1H, J=8.8 Hz), 7.16 (s, 1H), 7.14 (t, 1H, J=8.4 Hz), 6.49 (d, 1H, J=2.8 Hz), 6.29 (dd, 1H, J=8.8 Hz, 2.4 Hz), 4.57 (s, 1H), 4.44 (t, 1H, J=6.4 Hz), 3.85-3.88 (m, 7H), 3.36 (s, 2H), 3.07-3.09 (m, 4H), 2.70 (t, 2H, J=6.8 Hz), 1.55-1.63 (m, 1H), 1.48 (s, 6H), 0.72 (d, 6H, J=6.8 Hz).

Example 108

N-cyclopentyl-2-(2-(2-methoxy-4-morpholinophenylamino)-5,5-dimethyl-6,7-dihydro-5H-pyrrolo[2,3-d]pyrimidin-4-ylamino)benzenesulfonamide

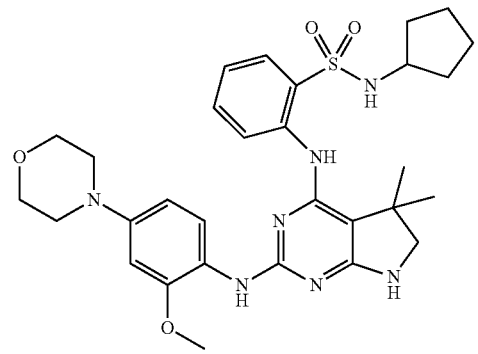 [SMILES: COc1cc(N2CCOCC2)ccc1Nc1nc2c(c(Nc3ccccc3S(=O)(=O)NC3CCCC3)n1)C(C)(C)CN2]

$^1$H NMR (400 MHz, DMSO-d$_6$) δ ppm 8.35 (d, J=8.0 Hz, 1H), 8.32 (s, 1H), 7.83 (d, J=7.6 Hz, 1H), 7.78 (d, J=8.8 Hz, 1H), 7.70 (dd, J=8.0 Hz, 1.6 Hz, 1H), 7.41 (t, J=8.4 Hz, 1H), 7.17 (s, 1H), 7.05 (t, J=8.0 Hz, 1H), 6.76 (s, 1H), 6.59 (d, J=2.8 Hz, 1H), 6.32 (dd, J=8.8 Hz, 2.4 Hz, 1H), 3.79 (s, 3H), 3.71-3.73 (m, 4H), 3.43-3.47 (m, 1H), 3.19 (s, 2H), 3.02-3.05 (m, 4H), 1.55-1.69 (m, 2H), 1.41-1.53 (m, 2H), 1.30-1.35 (m, 10H).

Example 109

N-cyclohexyl-2-(2-(2-methoxy-4-morpholinophenylamino)-5,5-dimethyl-6,7-dihydro-5H-pyrrolo[2,3-d]pyrimidin-4-ylamino)benzenesulfonamide

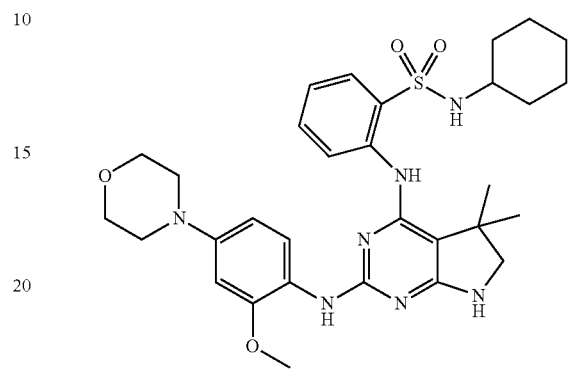

$^1$H NMR (400 MHz, DMSO-d$_6$) δ ppm 8.30 (s, 1H), 8.25 (d, J=8.8 Hz, 1H), 7.79 (d, J=8.8 Hz, 1H), 7.72 (d, J=8.6 Hz, 1H), 7.42 (t, J=8.0 Hz, 1H), 7.14 (s, 1H), 7.07 (t, J=8.0 Hz, 1H), 6.76 (s, 1H), 6.59 (s, 1H), 6.28 (d, J=8.8 Hz, 1H), 3.79 (s, 3H), 3.70-3.72 (m, 4H), 3.20 (s, 2H), 2.95-3.03 (m, 5H), 1.55-1.61 (m, 2H), 1.45-1.52 (m, 2H), 1.35 (s, 6H), 1.19-1.24 (m, 2H), 1.05-1.12 (m, 2H), 0.94-1.09 (m, 2H).

Example 110

N-butyl-2-(2-(2-methoxy-4-morpholinophenylamino)-5,5-dimethyl-6,7-dihydro-5H-pyrrolo[2,3-d]pyrimidin-4-ylamino)benzenesulfonamide

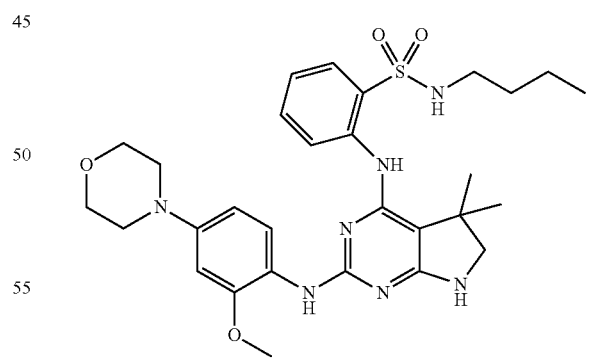

$^1$H NMR (400 MHz, CDCl$_3$) δ ppm 8.28 (d, J=8.2 Hz, 1H), 8.13 (d, J=8.8 Hz, 1H), 7.93-7.86 (m, 2H), 7.52 (s, 1H), 7.14 (d, J=5.5 Hz, 2H), 6.49 (d, J=2.5 Hz, 1H), 6.31 (dd, J=8.8, 2.4 Hz, 1H), 4.53 (s, 1H), 4.36 (s, 1H), 3.86 (dd, J=8.1, 3.2 Hz, 7H), 3.36 (s, 2H), 3.11-3.03 (m, 4H), 2.90 (dd, J=13.6, 6.8 Hz, 2H), 1.47 (s, 6H), 1.31 (dd, J=14.8, 7.3 Hz, 4H), 1.13 (dd, J=15.0, 7.3 Hz, 2H), 0.72 (t, J=7.3 Hz, 3H).

Example 111

2-(2-(2-methoxy-4-morpholinophenylamino)-5,5-dimethyl-6,7-dihydro-5H-pyrrolo[2,3-d]pyrimidin-4-ylamino)-N,N-dimethylbenzenesulfonamide

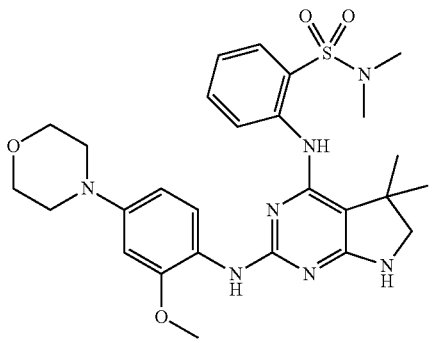 [SMILES: COc1cc(N2CCOCC2)ccc1Nc1nc2c(c(Nc3ccccc3S(=O)(=O)N(C)C)n1)C(C)(C)CN2]

$^1$H NMR (400 MHz, CDCl$_3$) δ ppm 8.42 (s, 1H), 8.35 (d, 1H, J=8.8 Hz), 8.20 (d, 1H, J=8.8 Hz), 7.77 (dd, 1H, J=8.0 Hz, 1.6 Hz), 7.50 (t, 1H, J=8.4 Hz), 7.16 (s, 1H), 7.10 (t, 1H, J=8.0 Hz), 6.50 (d, 1H, J=2.4 Hz), 6.35 (dd, 1H, J=8.8 Hz, 2.4 Hz), 4.54 (s, 1H), 3.86-3.88 (m, 7H), 3.35 (s, 2H), 3.08-3.10 (m, 4H), 2.72 (s, 6H), 1.48 (s, 2H).

Example 112

N-sec-butyl-2-(2-(2-methoxy-4-morpholinophenylamino)-5,5-dimethyl-6,7-dihydro-5H-pyrrolo[2,3-d]pyrimidin-4-ylamino)benzenesulfonamide

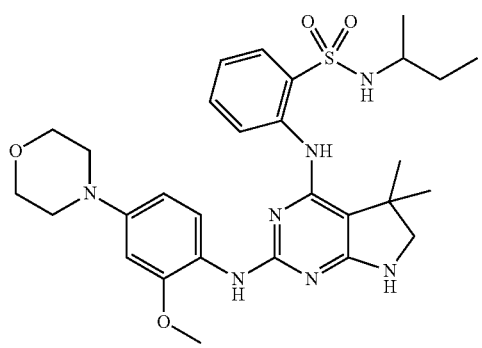 [SMILES: CCC(C)NS(=O)(=O)c1ccccc1Nc1nc(Nc2ccc(N3CCOCC3)cc2OC)nc2c1C(C)(C)CN2]

$^1$H NMR (400 MHz, CDCl$_3$) δ ppm 8.21 (d, J=8.3 Hz, 1H), 8.14 (d, J=8.8 Hz, 1H), 7.92 (dd, J=7.8, 1.6 Hz, 2H), 7.53-7.46 (m, 1H), 7.18 (s, 1H), 7.15-7.09 (m, 1H), 6.49 (d, J=2.5 Hz, 1H), 6.26 (dd, J=8.8, 2.5 Hz, 1H), 4.67 (s, 1H), 4.32 (d, J=8.1 Hz, 1H), 3.91-3.81 (m, 7H), 3.35 (s, 2H), 3.17 (dt, J=14.6, 6.6 Hz, 1H), 3.10-3.03 (m, 4H), 1.45 (d, J=12.4 Hz, 6H), 1.38-1.19 (m, 2H), 0.96 (d, J=6.6 Hz, 3H), 0.67 (t, J=7.4 Hz, 3H).

Example 113

N-ethyl-2-(2-(2-methoxy-4-morpholinophenylamino)-5,5-dimethyl-6,7-dihydro-5H-pyrrolo[2,3-d]pyrimidin-4-ylamino)benzenesulfonamide

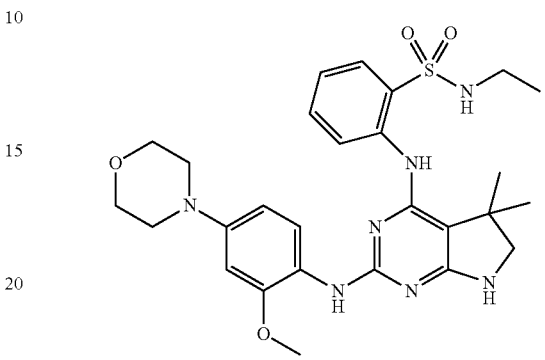

$^1$H NMR (400 MHz, CDCl$_3$) δ ppm 8.29 (d, J=7.9 Hz, 1H), 8.14 (d, J=8.8 Hz, 1H), 7.95 (s, 1H), 7.89 (dd, J=8.0, 1.5 Hz, 1H), 7.54-7.48 (m, 1H), 7.17-7.09 (m, 2H), 6.50 (d, J=2.5 Hz, 1H), 6.32 (dd, J=8.9, 2.6 Hz, 1H), 4.54 (s, 1H), 4.37 (t, J=6.1 Hz, 1H), 3.89-3.83 (m, 7H), 3.36 (d, J=0.9 Hz, 2H), 3.11-3.05 (m, 4H), 3.02-2.91 (m, 2H), 1.47 (s, 6H), 1.00 (t, J=7.2 Hz, 3H).

Example 114

2-(2-(2-methoxy-4-morpholinophenylamino)-5,5-dimethyl-6,7-dihydro-5H-pyrrolo[2,3-d]pyrimidin-4-ylamino)-N-(3-methoxypropyl)benzenesulfonamide

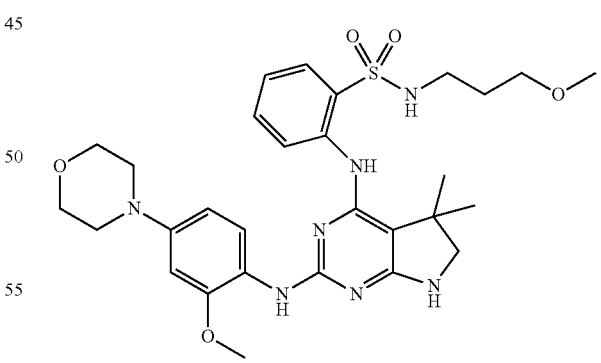

$^1$H NMR (400 MHz, CDCl$_3$) δ ppm 8.32 (d, J=8.3 Hz, 1H), 8.19 (d, J=8.8 Hz, 1H), 7.96 (s, 1H), 7.90 (d, J=8.0 Hz, 1H), 7.52 (t, J=7.8 Hz, 1H), 7.21-7.08 (m, 2H), 6.51 (d, J=2.5 Hz, 1H), 6.33 (dd, J=8.8, 2.4 Hz, 1H), 5.50 (t, J=5.6 Hz, 1H), 4.51 (s, 1H), 3.95-3.78 (m, 7H), 3.36 (s, 2H), 3.24 (t, J=5.5 Hz, 2H), 3.13-3.06 (m, 4H), 3.04-2.97 (m, 5H), 1.48 (s, 6H).

Example 115

2-(2-(2-methoxy-4-morpholinophenylamino)-5,5-dimethyl-6,7-dihydro-5H-pyrrolo[2,3-d]pyrimidin-4-ylamino)-N-(2-methoxyethyl)benzenesulfonamide

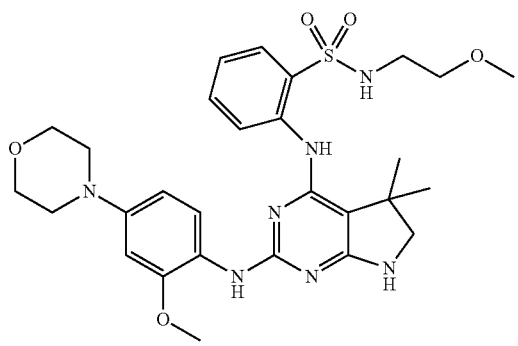 [SMILES: COCCNS(=O)(=O)c1ccccc1Nc1nc(Nc2ccc(N3CCOCC3)cc2OC)nc2c1C(C)(C)CN2]

$^1$H NMR (400 MHz, CDCl$_3$) δ ppm 8.29 (d, J=8.0 Hz, 1H), 8.04 (s, 2H), 7.90 (d, J=8.1 Hz, 1H), 7.51 (t, J=7.2 Hz, 1H), 7.15 (t, J=7.6 Hz, 1H), 6.49 (s, 1H), 6.32 (d, J=6.4 Hz, 1H), 4.93 (s, 1H), 3.87 (d, J=9.9 Hz, 7H), 3.41 (s, 2H), 3.26 (t, J=5.1 Hz, 2H), 3.09 (dd, J=12.5, 7.7 Hz, 9H), 1.48 (s, 6H).

Example 116

2-(2-(2-methoxy-4-morpholinophenylamino)-5,5-dimethyl-6,7-dihydro-5H-pyrrolo[2,3-d]pyrimidin-4-ylamino)-N-phenylbenzenesulfonamide

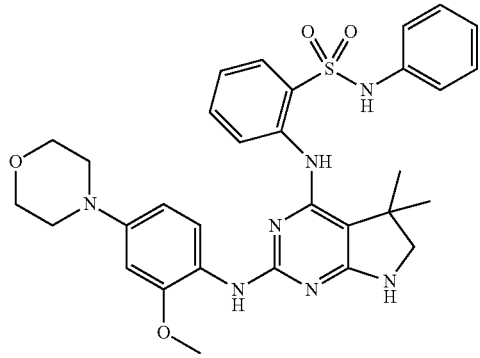 [SMILES: COc1cc(N2CCOCC2)ccc1Nc1nc2c(c(Nc3ccccc3S(=O)(=O)Nc3ccccc3)n1)C(C)(C)CN2]

$^1$H NMR (400 MHz, CDCl$_3$) δ ppm 8.11 (d, J=8.8 Hz, 1H), 8.05 (d, J=8.2 Hz, 1H), 7.73 (s, 1H), 7.63 (d, J=8.0 Hz, 1H), 7.46 (t, J=7.0 Hz, 1H), 7.23 (s, 1H), 7.02 (m, J=7.3 Hz, 6H), 6.51 (d, J=2.5 Hz, 1H), 6.43 (s, 1H), 6.20 (d, J=8.8 Hz, 1H), 4.64 (s, 1H), 3.88 (d, J=6.6 Hz, 7H), 3.38 (s, 2H), 3.11-3.04 (m, 4H), 1.49 (s, 6H).

Example 117

N-tert-butyl-2-(2-(2-methoxy-4-morpholinophenylamino)-5,5-dimethyl-6,7-dihydro-5H-pyrrolo[2,3-d]pyrimidin-4-ylamino)benzenesulfonamide

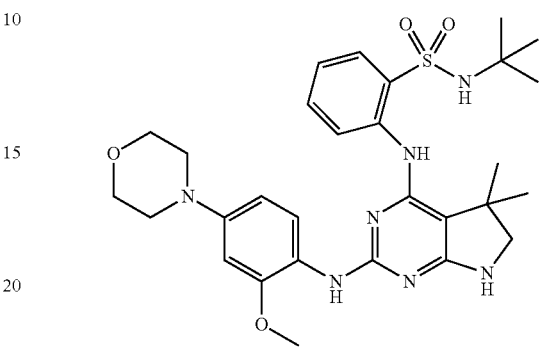

$^1$H NMR (400 MHz, CDCl$_3$) δ ppm 8.44 (s, 1H), 8.19 (s, 1H), 7.96 (d, J=7.6 Hz, 1H), 7.88 (t, J=9.3 Hz, 2H), 7.50 (t, J=7.7 Hz, 1H), 7.31 (d, J=7.6 Hz, 1H), 6.88 (s, 1H), 6.56 (d, J=8.3 Hz, 1H), 4.43 (s, 1H), 4.04 (s, 4H), 3.88 (d, J=19.0 Hz, 3H), 3.60 (s, 2H), 3.37 (s, 4H), 1.52 (s, 6H), 1.16 (d, J=17.1 Hz, 9H).

Example 118

N-(cyclopropylmethyl)-2-(2-(2-methoxy-4-morpholinophenylamino)-5,5-dimethyl-6,7-dihydro-5H-pyrrolo[2,3-d]pyrimidin-4-ylamino)benzenesulfonamide

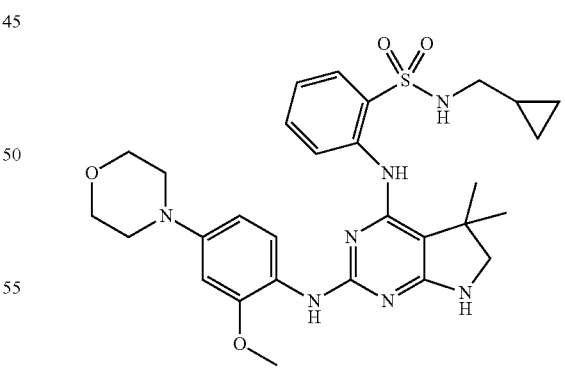

$^1$H NMR (400 MHz, CDCl$_3$) δ ppm 8.28 (d, J=8.3 Hz, 1H), 8.13 (d, J=8.8 Hz, 1H), 7.95 (d, J=6.4 Hz, 1H), 7.89 (s, 1H), 7.57 (t, J=7.1 Hz, 1H), 7.23-7.15 (m, 2H), 6.54 (d, J=2.5 Hz, 1H), 6.32 (d, J=9.0 Hz, 1H), 4.60-4.53 (m, 2H), 3.98-3.85 (m, 7H), 3.41 (s, 2H), 3.14-3.07 (m, 4H), 2.83-2.74 (m, 2H), 1.53 (s, 6H), 0.082-0.072 (m, 1H), 0.35-0.25 (m, 2H), −0.05-0.09 (m, 2H).

Example 119

N-(2-hydroxyethyl)-2-(2-(2-methoxy-4-morpholino-phenylamino)-5,5-dimethyl-6,7-dihydro-5H-pyrrolo[2,3-d]pyrimidin-4-ylamino)benzenesulfonamide

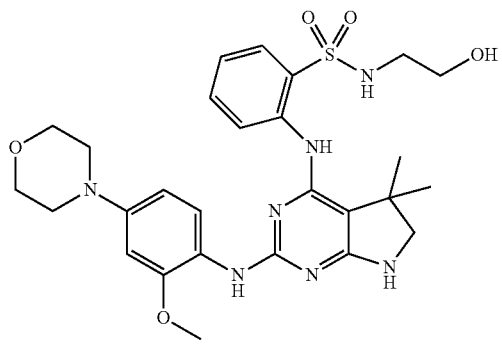 [SMILES: COc1cc(N2CCOCC2)ccc1Nc1nc2c(c(Nc3ccccc3S(=O)(=O)NCCO)n1)C(C)(C)CN2]

¹H NMR (400 MHz, CDCl₃) δ ppm 9.10 (s, 1H), 8.20 (s, 1H), 8.10 (d, J=8.7 Hz, 1H), 7.95 (d, J=8.0 Hz, 1H), 7.58 (d, J=5.5 Hz, 1H), 7.32 (s, 1H), 7.04 (s, 1H), 6.92 (s, 1H), 4.17-4.07 (m, 4H), 3.87 (s, 3H), 3.61 (s, 3H), 3.57-3.49 (m, 6H), 3.11 (s, 2H), 1.53 (s, 6H).

Example 120

N-(2-(dimethylamino)ethyl)-2-(2-(2-methoxy-4-morpholinophenylamino)-5,5-dimethyl-6,7-dihydro-5H-pyrrolo[2,3-d]pyrimidin-4-ylamino)benzenesulfonamide

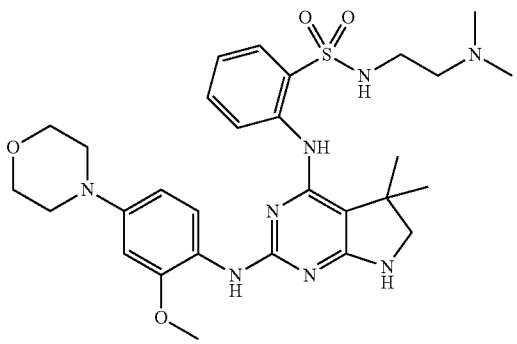 [SMILES: COc1cc(N2CCOCC2)ccc1Nc1nc2c(c(Nc3ccccc3S(=O)(=O)NCCN(C)C)n1)C(C)(C)CN2]

¹H NMR (400 MHz, CDCl₃) δ ppm 8.17 (s, 1H), 8.03 (d, 1H, J=8.8 Hz), 8.01 (s, 1H), 7.82 (dd, 1H, J=8.0 Hz, 1.2 Hz), 7.53 (t, 1H, J=8.4 Hz), 7.16 (t, 1H, J=7.2 Hz), 6.48 (d, 1H, J=2.4 Hz), 6.30 (dd, 1H, J=8.8 Hz, 2.4 Hz), 4.99 (brs, 1H), 3.85-3.88 (m, 7H), 3.37 (s, 2H), 3.20-3.25 (m, 2H), 3.08-3.11 (m, 4H), 2.71-2.75 (m, 2H), 2.37 (s, 6H), 1.48 (s, 6H).

Example 121

(2-(2-(2-methoxy-4-morpholinophenylamino)-5,5-dimethyl-6,7-dihydro-5H-pyrrolo[2,3-d]pyrimidin-4-ylamino)phenyl)(pyrrolidin-1-yl)methanone

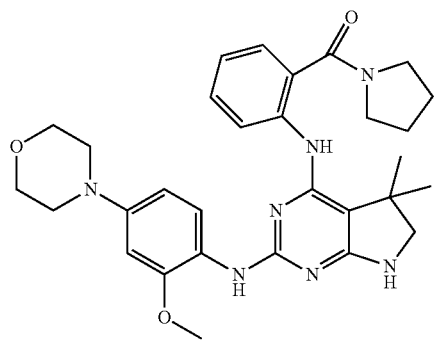 [SMILES: COc1cc(N2CCOCC2)ccc1Nc1nc2c(c(Nc3ccccc3C(=O)N3CCCC3)n1)C(C)(C)CN2]

¹H NMR (400 MHz, CDCl₃) δ ppm 8.71 (s, 1H), 8.42 (d, J=8.3 Hz, 1H), 8.28 (d, J=8.8 Hz, 1H), 7.35 (dd, J=12.2, 8.1 Hz, 2H), 7.13 (s, 1H), 6.97 (t, J=7.5 Hz, 1H), 6.52 (s, 1H), 6.45 (d, J=8.8 Hz, 1H), 4.45 (s, 1H), 3.95-3.78 (m, 7H), 3.64 (t, J=6.7 Hz, 2H), 3.54 (t, J=6.2 Hz, 2H), 3.33 (s, 2H), 3.11 (d, J=4.5 Hz, 4H), 2.04-1.90 (m, 2H), 1.89-1.79 (m, 2H), 1.47 (s, 6H).

Example 122

N-(2-(2-(2-methoxy-4-morpholinophenylamino)-5,5-dimethyl-6,7-dihydro-5H-pyrrolo[2,3-d]pyrimidin-4-ylamino)phenyl)-N-methylmethanesulfonamide

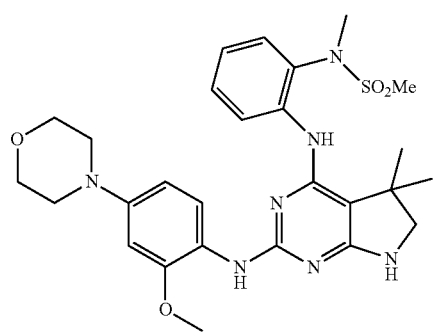 [SMILES: COc1cc(N2CCOCC2)ccc1Nc1nc2c(c(Nc3ccccc3N(C)S(C)(=O)=O)n1)C(C)(C)CN2]

¹H NMR (400 MHz, CDCl₃) δ ppm 8.42 (d, J=8.7 Hz, 1H), 8.16 (d, J=8.5 Hz, 1H), 7.40-7.30 (m, 2H), 7.15-7.04 (m, 2H), 6.51 (s, 1H), 6.42 (d, J=8.6 Hz, 1H), 5.35 (m, 2H), 3.88 (m, 4H), 3.85 (s, 3H), 3.35 (s, 2H), 3.27 (d, J=2.4 Hz, 3H), 3.10 (m, 4H), 2.99 (s, 3H).

Example 123

N²-(2-methoxy-4-morpholinophenyl)-5,5-dimethyl-N⁴-(6-methylpyridin-2-yl)-6,7-dihydro-5H-pyrrolo[2,3-d]pyrimidine-2,4-diamine

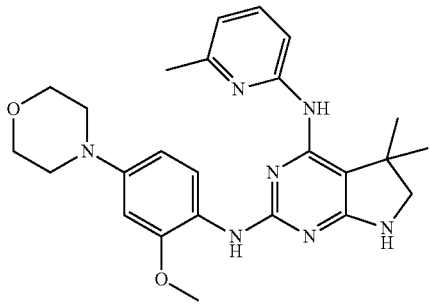 [SMILES: COc1cc(N2CCOCC2)ccc1Nc1nc2c(c(Nc3cccc(C)n3)n1)C(C)(C)CN2]

¹H NMR (400 MHz, CDCl₃) δ ppm 8.09 (t, J=8.2 Hz, 2H), 7.48 (t, J=7.9 Hz, 1H), 7.10 (s, 1H), 6.75 (d, J=7.3 Hz, 1H), 6.52 (d, J=2.5 Hz, 1H), 6.47 (dd, J=8.7, 2.5 Hz, 1H), 4.82 (s, 1H), 3.94-3.80 (m, 7H), 3.35 (s, 2H), 3.15-3.09 (m, 4H), 2.44 (s, 3H), 1.49 (s, 6H).

Example 124

N-(2-(2-(2-methoxy-4-morpholinophenylamino)-5,5-dimethyl-6,7-dihydro-5H-pyrrolo[2,3-d]pyrimidin-4-ylamino)phenyl)acetamide

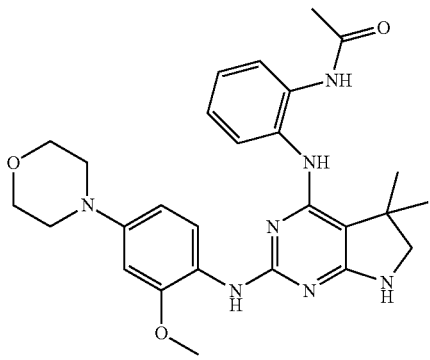 [SMILES: COc1cc(N2CCOCC2)ccc1Nc1nc2c(c(Nc3ccccc3NC(C)=O)n1)C(C)(C)CN2]

¹H NMR (400 MHz, CDCl₃) δ ppm 8.52 (s, 1H), 7.87 (d, J=8.8 Hz, 1H), 7.47 (t, J=9.8 Hz, 2H), 7.24-7.08 (m, 3H), 6.53-6.40 (m, 2H), 6.28 (d, J=8.7 Hz, 1H), 4.74 (s, 1H), 3.91-3.83 (m, 4H), 3.81 (s, 3H), 3.36 (s, 2H), 3.12-3.00 (m, 4H), 1.97 (s, 3H), 1.45 (s, 6H).

Example 125

N⁴-(3,4-difluorophenyl)-N²-(2-methoxy-4-morpholinophenyl)-5,5-dimethyl-6,7-dihydro-5H-pyrrolo[2,3-d]pyrimidine-2,4-diamine

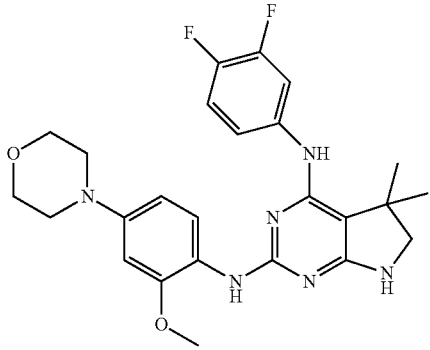 [SMILES: COc1cc(N2CCOCC2)ccc1Nc1nc2c(c(Nc3ccc(F)c(F)c3)n1)C(C)(C)CN2]

¹H NMR (400 MHz, CDCl₃) δ ppm 8.05 (d, J=8.6 Hz, 1H), 7.73 (ddd, J=12.8, 7.3, 2.7 Hz, 1H), 7.11-6.98 (m, 2H), 6.95 (d, J=9.0 Hz, 1H), 6.52-6.41 (m, 2H), 5.94 (s, 1H), 4.59 (s, 1H), 3.91-3.81 (m, 7H), 3.34 (s, 2H), 3.15-3.06 (m, 4H), 1.42 (s, 6H).

Example 126

4-(2-(2-methoxy-4-morpholinophenylamino)-5,5-dimethyl-6,7-dihydro-5H-pyrrolo[2,3-d]pyrimidin-4-ylamino)-N-methylbenzo[d][1,3]dioxole-5-carboxamide

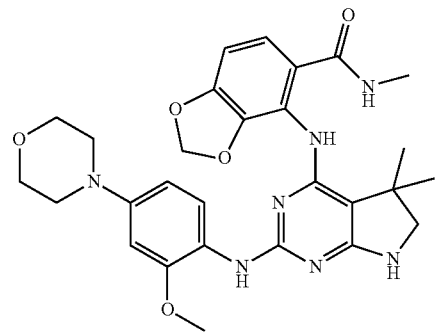 [SMILES: CNC(=O)c1ccc2c(c1Nc1nc(Nc3ccc(N4CCOCC4)cc3OC)nc3c1C(C)(C)CN3)OCO2]

¹H NMR (400 MHz, CDCl₃) δ ppm 8.79 (s, 1H), 8.09 (d, J=8.8 Hz, 1H), 7.22 (s, 1H), 7.08 (d, J=8.2 Hz, 1H), 6.70 (d, J=8.1 Hz, 1H), 6.50 (d, J=2.5 Hz, 1H), 6.32 (dd, J=8.8, 2.5 Hz, 1H), 6.12 (d, J=4.8 Hz, 1H), 5.84 (s, 2H), 4.80-4.60 (s, 1H), 3.94-3.88 (m, 4H), 3.86 (s, 3H), 3.38 (s, 2H), 3.14-3.06 (m, 4H), 2.96 (d, J=4.9 Hz, 3H), 1.54 (s, 6H).

Example 127

N-(2-(2-(2-methoxy-4-morpholinophenylamino)-5,5-dimethyl-6,7-dihydro-5H-pyrrolo[2,3-d]pyrimidin-4-ylamino)cyclohexyl)-N-methylmethanesulfonamide

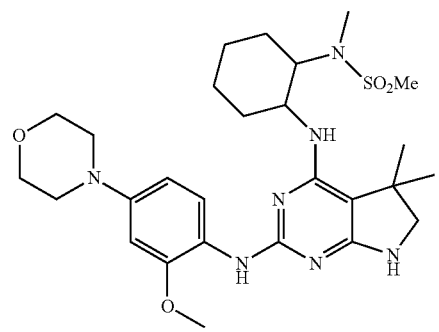 [SMILES: COc1cc(N2CCOCC2)ccc1Nc1nc2c(c(NC3CCCCC3N(C)S(C)(=O)=O)n1)C(C)(C)CN2]

¹H NMR (400 MHz, CDCl₃) δ ppm 8.00 (d, J=8.4 Hz, 1H), 6.48 (s, 1H), 6.43 (d, J=8.4 Hz, 2H), 3.96-3.78 (m, 7H), 3.38 (s, 2H), 3.18-3.05 (m, 4H), 2.85 (s, 3H), 2.75 (m, 3H), 2.52 (m, 1H), 2.38-2.28 (t, 1H), 2.24-2.18 (t, 2H), 2.08-1.96 (m, 4H), 1.60 (s, 6H), 1.40-1.30 (m, 4H).

Example 128

2-(2-(2,3-dihydrobenzo[b][1,4]dioxin-5-ylamino)-5,5-dimethyl-6,7-dihydro-5H-pyrrolo[2,3-d]pyrimidin-4-ylamino)-N-methylbenzamide

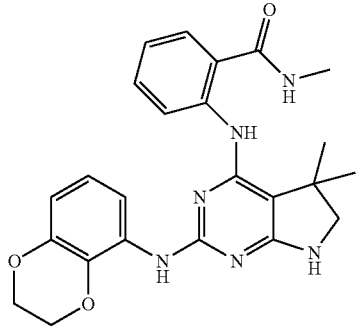 [SMILES: CNC(=O)c1ccccc1Nc1nc(Nc2cccc3c2OCCO3)nc2c1C(C)(C)CN2]

$^1$H NMR (400 MHz, CDCl$_3$) δ ppm 9.87 (s, 1H), 8.50 (d, 1H, J=8.0 Hz), 7.99 (dd, 1H, J=8.4 Hz, 1.2 Hz), 7.39-7.43 (m, 2H), 7.12 (s, 1H), 6.95 (t, 1H, J=8.4 Hz), 6.72 (t, 1H, J=8.0 Hz), 6.48 (dd, 1H, J=8.4 Hz, 1.6 Hz), 6.12-6.14 (brs, 1H), 4.48 (s, 1H), 4.25-4.31 (m, 4H), 3.34 (s, 2H), 2.99 (d, 3H, J=5.2 Hz), 1.53 (s, 6H).

Example 129

2-(5,5-dimethyl-2-(8-morpholino-2,3-dihydrobenzo[b][1,4]dioxin-5-ylamino)-6,7-dihydro-5H-pyrrolo[2,3-d]pyrimidin-4-ylamino)-N-methylbenzamide

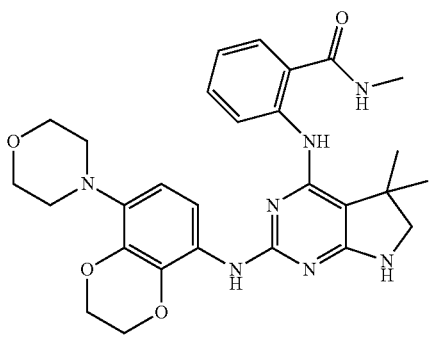 [SMILES: CNC(=O)c1ccccc1Nc1nc(Nc2ccc(N3CCOCC3)c3c2OCCO3)nc2c1C(C)(C)CN2]

$^1$H NMR (400 MHz, DMSO-d$_6$) δ ppm 10.97-10.64 (m, 1H), 8.79 (s, 1H), 8.44 (s, 1H), 7.69 (d, J=7.7 Hz, 1H), 7.35 (s, 2H), 7.08 (s, 1H), 6.47 (d, J=8.8 Hz, 1H), 4.31 (s, 4H), 3.80-3.73 (m, 4H), 3.40 (s, 4H), 2.99 (s, 4H), 2.82 (d, J=4.5 Hz, 3H), 1.47 (s, 6H).

Example 130

2-(5,5-dimethyl-2-(3,4,5-trimethoxyphenylamino)-6,7-dihydro-5H-pyrrolo[2,3-d]pyrimidin-4-ylamino)-N-methylbenzamide

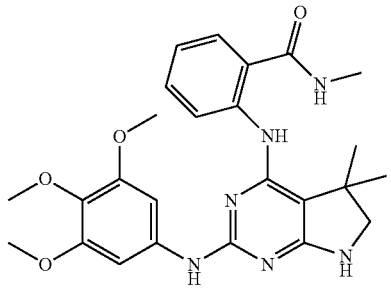

$^1$H NMR (400 MHz, CDCl$_3$) δ ppm 10.14 (s, 1H), 8.50 (d, J=8.5 Hz, 1H), 7.43 (d, J=6.5 Hz, 1H), 7.35 (d, J=7.4 Hz, 1H), 6.96 (t, J=7.5 Hz, 1H), 6.82 (s, 2H), 6.18 (s, 1H), 3.85 (s, 3H), 3.71 (s, 6H), 3.41 (s, 2H), 3.04 (d, J=4.9 Hz, 3H), 1.55 (s, 6H).

Example 131

2-(2-(benzofuran-7-ylamino)-5,5-dimethyl-6,7-dihydro-5H-pyrrolo[2,3-d]pyrimidin-4-ylamino)-N-methylbenzamide

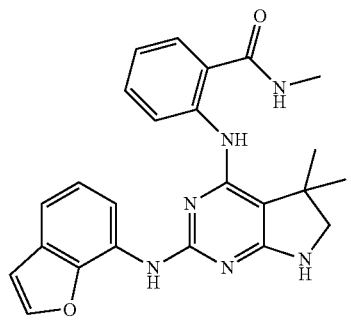 [SMILES: CNC(=O)c1ccccc1Nc1nc(Nc2cccc3ccoc23)nc2c1C(C)(C)CN2]

$^1$H NMR (400 MHz, CDCl$_3$) δ ppm 9.91 (s, 1H), 8.50 (d, 1H, J=8.8 Hz), 8.23 (d, 1H, J=7.6 Hz), 7.59 (d, 1H, J=2.0 Hz), 7.39-7.42 (m, 2H), 7.21 (s, 1H), 7.18 (dd, 1H, J=8.0 Hz, 1.2 Hz), 7.12 (t, 1H, J=8.0 Hz), 6.96 (t, 1H, J=8.0 Hz), 6.76 (d, 1H, J=2.0 Hz), 6.13-6.14 (brs, 1H), 4.54 (s, 1H), 3.37 (s, 1H), 2.99 (d, 3H, J=5.2 Hz), 1.54 (s, 6H).

Example 132

2-(2-(1,3-dimethyl-1H-pyrazol-5-ylamino)-5,5-dimethyl-6,7-dihydro-5H-pyrrolo[2,3-d]pyrimidin-4-ylamino)-N-methylbenzamide

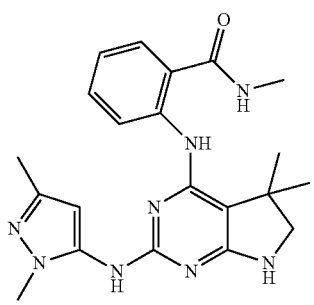 [SMILES: CNC(=O)c1ccccc1Nc1nc(Nc2cc(C)nn2C)nc2c1C(C)(C)CN2]

$^1$H NMR (400 MHz, CDCl$_3$) δ ppm 10.09 (s, 1H), 8.37 (d, 1H, J=8.8 Hz), 7.36 (dd, 1H, J=8.0 Hz, 1.6 Hz), 7.30 (t, 1H, J=8.0 Hz), 6.91 (t, 1H, J=7.2 Hz), 6.53 (brs, 1H), 6.11-6.14 (brs, 1H), 6.01 (s, 1H), 4.63 (s, 1H), 3.66 (s, 3H), 3.56 (s, 2H), 2.99 (d, 3H, J=4.8 Hz), 2.25 (s, 3H), 1.52 (s, 6H).

Example 133

2-(2-(1-ethyl-6-methoxy-2-oxo-2,3,4,5-tetrahydro-1H-benzo[b]azepin-7-ylamino)-5,5-dimethyl-6,7-dihydro-5H-pyrrolo[2,3-d]pyrimidin-4-ylamino)-N-methylbenzamide

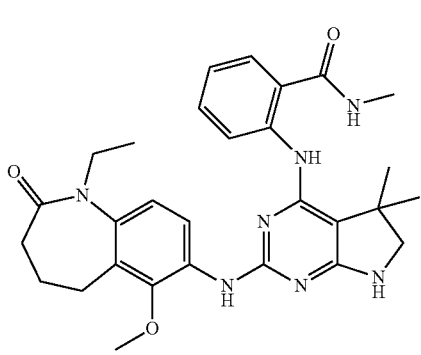 [SMILES: CCN1C(=O)CCCc2c1ccc(Nc1nc3c(c(Nc4ccccc4C(=O)NC)n1)C(C)(C)CN3)c2OC]

$^1$H NMR (400 MHz, DMSO-d$_6$) δ ppm 10.35 (s, 1H), 8.64 (d, J=4.6 Hz, 1H), 8.48 (d, J=8.4 Hz, 1H), 8.07 (d, J=8.8 Hz, 1H), 7.60 (d, J=7.7 Hz, 1H), 7.46 (s, 1H), 7.33 (t, J=7.9 Hz, 1H), 7.01 (d, J=8.8 Hz, 1H), 6.94 (t, J=7.5 Hz, 1H), 6.76 (s, 1H), 3.70 (s, 3H), 3.23 (s, 2H), 2.78 (d, J=4.4 Hz, 3H), 2.12 (s, 3H), 1.98 (s, 1H), 1.44 (s, 6H), 0.99 (t, J=7.1 Hz, 3H).

Example 134

2-(5,5-dimethyl-2-(1-(3-morpholinopropyl)-1H-indol-5-ylamino)-6,7-dihydro-5H-pyrrolo[2,3-d]pyrimidin-4-ylamino)-N-methylbenzamide

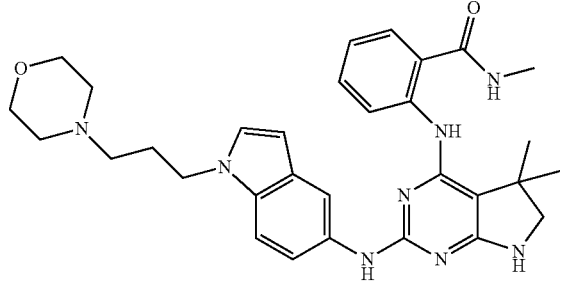 [SMILES: CNC(=O)c1ccccc1Nc1nc(Nc2ccc3c(ccn3CCCN3CCOCC3)c2)nc2c1C(C)(C)CN2]

$^1$H NMR (400 MHz, CDCl$_3$) δ ppm 10.04 (s, 1H), 8.53 (d, J=8.9 Hz, 1H), 7.88 (s, 1H), 7.43-7.30 (m, 2H), 7.09-7.12 (m, 3H), 6.97 (d, J=7.4 Hz, 1H), 6.57 (s, 1H), 6.12 (s, 1H), 4.20 (t, J=6.6 Hz, 2H), 3.73 (s, 4H), 3.40 (s, 2H), 2.99 (s, J=4.6 Hz, 3H), 2.41 (m, 4H), 2.28 (s, 2H), 2.01 (m, J=6.3 Hz, 2H), 1.55 (s, 6H).

Example 135

2-(2'-(2-methoxy-4-morpholinophenylamino)-6',7'-dihydrospiro[cyclopropane-1,5'-pyrrolo[2,3-d]pyrimidine]-4'-ylamino)-N-methylbenzenesulfonamide

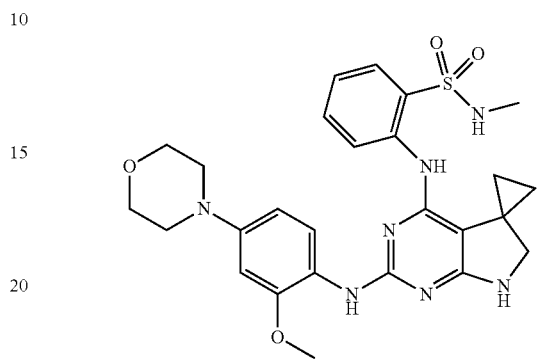

$^1$H NMR (400 MHz, CDCl$_3$) δ ppm 8.11 (dd, J=8.5, 5.3 Hz, 2H), 7.87 (dd, J=8.0, 1.4 Hz, 1H), 7.52 (t, J=7.8 Hz, 1H), 7.42 (s, 1H), 7.20-7.08 (m, 2H), 6.55-6.44 (m, 1H), 6.29 (dd, J=8.8, 2.4 Hz, 1H), 4.76 (brs, 2H), 3.96-3.77 (m, 7H), 3.56 (s, 2H), 3.17-3.00 (m, 4H), 2.59 (d, J=5.0 Hz, 3H), 1.52 (t, J=6.1 Hz, 2H), 0.84 (t, J=6.1 Hz, 2H).

Example 136

N-tert-butyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

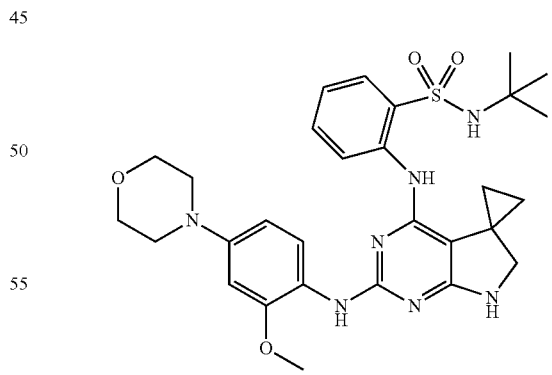

$^1$H NMR (400 MHz, CDCl$_3$) δ ppm 8.03 (d, J=8.9 Hz, 1H), 7.88 (dd, J=19.7, 8.1 Hz, 2H), 7.43 (t, J=7.8 Hz, 1H), 7.09 (dd, J=15.0, 7.0 Hz, 3H), 6.41 (d, J=2.4 Hz, 1H), 6.14 (dd, J=8.9, 2.4 Hz, 1H), 4.60 (s, 1H), 4.34 (s, 1H), 3.87-3.71 (m, 7H), 3.52 (s, 2H), 3.13-2.86 (m, 5H), 1.60-1.30 (m, 3H), 1.04 (s, 9H), 0.79 (t, J=6.1 Hz, 2H).

Example 137

N-isobutyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

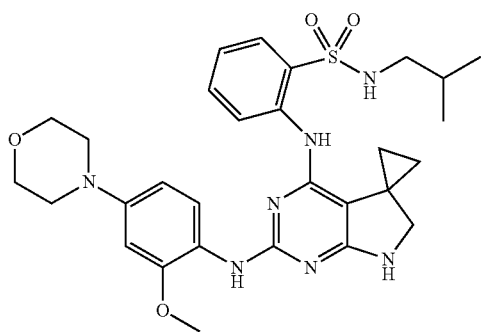 [SMILES: COc1cc(N2CCOCC2)ccc1Nc1nc2c(c(Nc3ccccc3S(=O)(=O)NCC(C)C)n1)C1(CC1)CN2]

¹H NMR (400 MHz, CDCl₃) δ ppm 8.07 (t, J=9.1 Hz, 2H), 7.86 (d, J=8.2 Hz, 1H), 7.53-7.46 (m, 1H), 7.33 (s, 1H), 7.17-7.09 (m, 2H), 6.48 (d, J=2.4 Hz, 1H), 6.25 (d, J=11.5 Hz, 1H), 4.64 (s, 1H), 4.44 (s, 1H), 3.90-3.80 (m, 7H), 3.58 (s, 2H), 3.11-3.00 (m, 4H), 2.67 (t, J=6.6 Hz, 2H), 1.52 (d, J=6.2 Hz, 2H), 0.86 (d, J=6.2 Hz, 2H), 0.71 (d, J=6.7 Hz, 6H).

Example 138

N-isopropyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

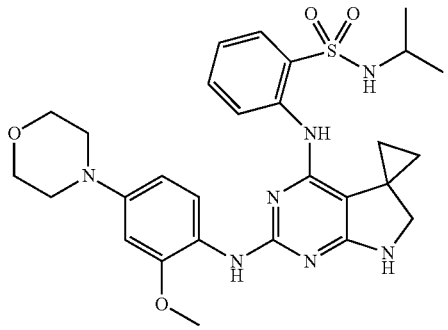 [SMILES: COc1cc(N2CCOCC2)ccc1Nc1nc2c(c(Nc3ccccc3S(=O)(=O)NC(C)C)n1)C1(CC1)CN2]

¹H NMR (400 MHz, CDCl₃) δ ppm 8.12 (d, J=8.8 Hz, 1H), 8.04 (d, J=8.3 Hz, 1H), 7.92 (d, J=6.9 Hz, 1H), 7.52 (t, J=7.9 Hz, 1H), 7.16 (dd, J=16.4, 9.0 Hz, 2H), 6.50 (d, J=2.3 Hz, 1H), 6.24 (d, J=8.9 Hz, 1H), 4.68 (s, 1H), 4.33 (d, J=7.9 Hz, 1H), 3.88 (d, J=8.6 Hz, 7H), 3.60 (s, 2H), 3.37 (dd, J=13.8, 6.7 Hz, 1H), 3.14-3.01 (m, 4H), 1.53 (t, J=6.2 Hz, 2H), 0.93 (d, 6H), 0.84-0.87 (m, 2H).

Example 139

N-ethyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

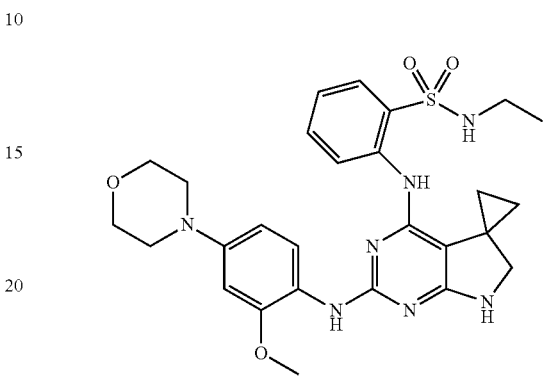

¹H NMR (400 MHz, CDCl₃) δ ppm 8.09 (dd, J=8.5, 4.1 Hz, 1H), 7.87 (d, J=6.9 Hz, 1H), 7.50 (t, J=7.4 Hz, 1H), 7.35 (s, 1H), 7.20-7.08 (m, 2H), 6.48 (d, J=2.3 Hz, 1H), 6.26 (d, J=8.8 Hz, 1H), 4.69 (s, 1H), 4.51 (t, J=5.8 Hz, 1H), 3.94-3.76 (m, 7H), 3.57 (s, 2H), 3.18-2.98 (m, 4H), 2.98-2.87 (m, 2H), 1.51 (d, J=6.0 Hz, 2H), 0.97 (t, J=7.2 Hz, 3H), 0.90-0.77 (m, 2H).

Example 140

N-(cyclopropylmethyl)-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

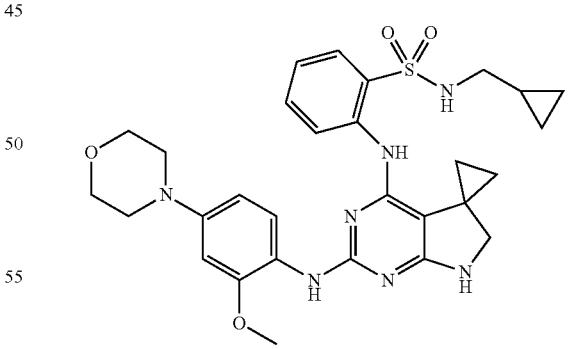

¹H NMR (400 MHz, CDCl₃) δ ppm 8.05 (d, J=9.1 Hz, 2H), 7.90 (d, J=8.0 Hz, 1H), 7.53 (t, J=7.7 Hz, 1H), 7.21-7.02 (m, 2H), 6.50 (d, J=2.3 Hz, 1H), 6.24 (d, J=8.9 Hz, 1H), 4.66 (s, 1H), 4.56 (s, 1H), 3.99-3.79 (m, 7H), 3.61 (s, 2H), 3.19-2.95 (m, 4H), 2.84-2.59 (m, 2H), 1.55 (dd, J=12.9, 6.6 Hz, 2H), 0.88 (t, J=6.1 Hz, 1H), 0.74 (m, 2H), 0.34-0.13 (m, 2H).

Example 141

2-(2'-(2-methoxy-4-morpholinophenylamino)-6',7'-dihydrospiro[cyclopropane-1,5'-pyrrolo[2,3-d]pyrimidine]-4'-ylamino)-N-(2-methoxyethyl)benzenesulfonamide

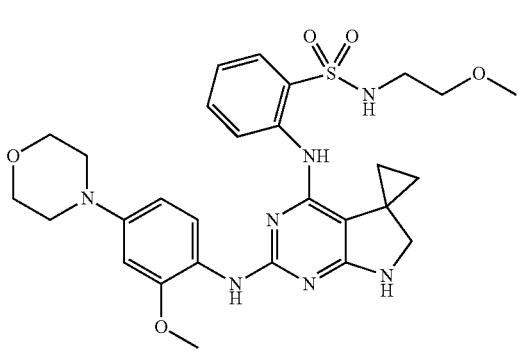 [SMILES: COCCNS(=O)(=O)c1ccccc1Nc1nc(Nc2ccc(N3CCOCC3)cc2OC)nc2c1C1(CC1)CN2]

$^1$H NMR (400 MHz, CDCl$_3$) δ ppm 8.25-8.02 (m, 2H), 7.86 (dd, J=8.0, 1.4 Hz, 1H), 7.56-7.46 (m, 1H), 7.41 (s, 1H), 7.16 (s, 1H), 7.10 (dd, J=11.2, 4.0 Hz, 1H), 6.49 (d, J=2.5 Hz, 1H), 6.29 (dd, J=8.8, 2.5 Hz, 1H), 5.12 (s, 1H), 4.69 (s, 1H), 3.94-3.77 (m, 7H), 3.55 (s, 2H), 3.25 (t, J=5.1 Hz, 2H), 3.16-3.01 (m, 9H), 1.51 (t, J=6.1 Hz, 2H), 0.82 (t, J=6.2 Hz, 2H).

Example 142

N-(2-hydroxyethyl)-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

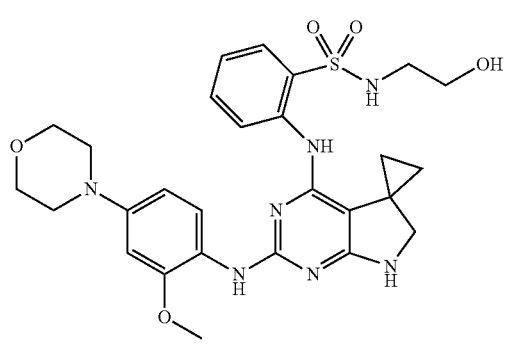 [SMILES: COc1cc(N2CCOCC2)ccc1Nc1nc2c(c(Nc3ccccc3S(=O)(=O)NCCO)n1)C1(CC1)CN2]

$^1$H NMR (400 MHz, CDCl$_3$) δ ppm 8.08 (d, J=8.2 Hz, 1H), 7.69 (d, J=7.6 Hz, 1H), 7.26 (s, 9H), 6.77 (s, 1H), 6.70 (d, J=8.3 Hz, 1H), 6.52 (m, 2H), 5.65 (brs, 1H), 4.79 (s, 2H), 4.58 (s, 1H), 4.25 (s, 2H), 3.87 (s, 7H), 3.52 (d, J=18.3 Hz, 4H), 3.21 (s, 2H), 3.11 (s, 4H), 1.21 (s, 2H), 0.67 (s, 2H).

Example 143

2-(2'-(2-methoxy-4-morpholinophenylamino)-6',7'-dihydrospiro[cyclopropane-1,5'-pyrrolo[2,3-d]pyrimidine]-4'-ylamino)-N-phenylbenzenesulfonamide

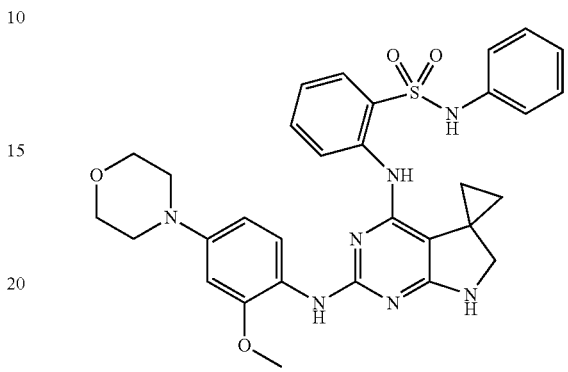

$^1$H NMR (400 MHz, CDCl$_3$) δ ppm 8.12 (t, J=25.8 Hz, 1H), 7.89 (d, J=8.3 Hz, 1H), 7.59 (t, J=22.1 Hz, 1H), 7.44 (t, J=7.8 Hz, 1H), 7.18 (m, 2H), 6.99 (t, J=5.8 Hz, 6H), 6.50 (d, J=2.4 Hz, 1H), 6.26-6.08 (m, 1H), 4.66 (s, 1H), 3.87 (d, J=7.1 Hz, 7H), 3.58 (s, 2H), 3.24-2.96 (m, 4H), 1.51 (t, J=6.2 Hz, 2H), 0.86 (t, J=6.1 Hz, 2H).

Example 144

N-allyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

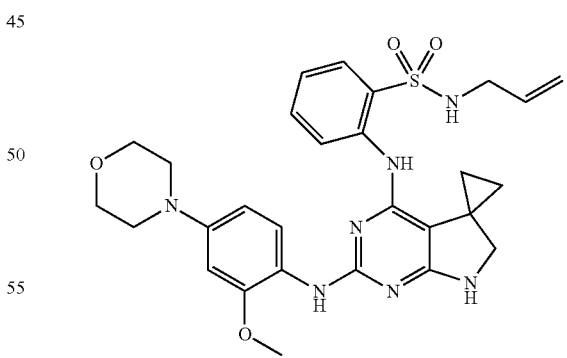

$^1$H NMR (400 MHz, CDCl$_3$) δ ppm 8.10 (dd, J=14.2, 8.6 Hz, 2H), 7.88 (d, J=7.9 Hz, 1H), 7.52 (t, J=7.2 Hz, 1H), 7.33 (s, 1H), 7.15 (dd, J=15.0, 7.3 Hz, 2H), 6.50 (d, J=2.4 Hz, 1H), 6.28 (dd, J=8.9, 2.4 Hz, 1H), 5.74-5.39 (m, 1H), 4.99 (dd, J=34.0, 13.6 Hz, 2H), 4.68-4.52 (m, 2H), 4.02-3.77 (m, 7H), 3.55 (dd, J=16.6, 10.6 Hz, 4H), 3.25-2.93 (m, 4H), 1.52 (t, J=6.1 Hz, 2H), 0.86 (t, J=6.1 Hz, 2H).

Example 145

N-cyclopentyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

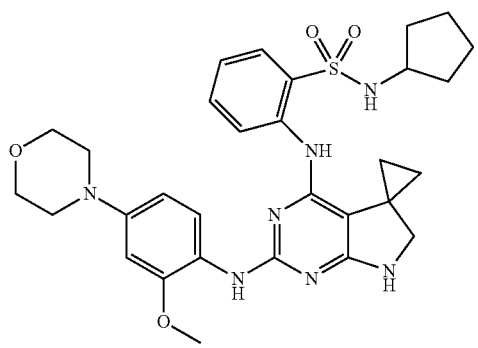 [SMILES: COc1cc(N2CCOCC2)ccc1Nc1nc2c(c(Nc3ccccc3S(=O)(=O)NC3CCCC3)n1)C1(CC1)CN2]

$^1$H NMR (400 MHz, CDCl$_3$) δ ppm 8.19 (d, J=8.8 Hz, 1H), 8.10 (d, J=8.2 Hz, 1H), 8.00 (d, J=8.0 Hz, 1H), 7.61 (t, J=7.3 Hz, 1H), 7.36 (d, J=7.9 Hz, 8H), 7.16 (dd, J=14.6, 6.8 Hz, 2H), 6.59 (d, J=2.2 Hz, 1H), 6.32 (d, J=8.8 Hz, 1H), 4.80 (s, 1H), 4.51 (d, J=7.8 Hz, 1H), 3.97 (d, J=8.6 Hz, 7H), 3.70 (s, 2H), 3.83-3.53 (m, 1H), 3.26-3.07 (m, 4H), 1.62 (m, 10H)), 0.87 (t, J=6.2 Hz, 2H).

Example 146

N-cyclopropyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

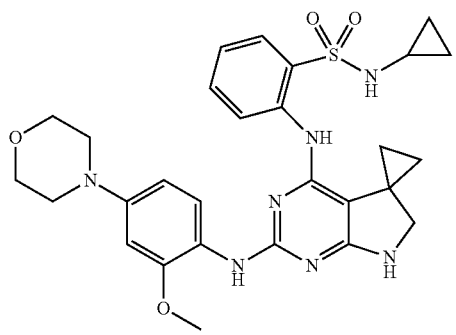 [SMILES: COc1cc(N2CCOCC2)ccc1Nc1nc2c(c(Nc3ccccc3S(=O)(=O)NC3CC3)n1)C1(CC1)CN2]

$^1$H NMR (400 MHz, CDCl$_3$) δ ppm 8.11 (s, 1H), 7.85 (s, 1H), 7.60 (d, J=7.5 Hz, 1H), 7.16 (s, 1H), 6.77 (d, J=7.5 Hz, 1H), 6.54-6.36 (m, 2H), 6.18 (s, 1H), 4.96-4.80 (m, 2H), 3.87 (d, J=10.6 Hz, 7H), 3.56 (d, J=13.8 Hz, 2H), 3.05 (s, 4H), 2.48 (d, J=22.6 Hz, 2H), 2.20 (d, J=20.0 Hz, 2H), 1.29 (d, J=26.4 Hz, 5H), 0.89 (s, 4H).

Example 147

N-sec-butyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

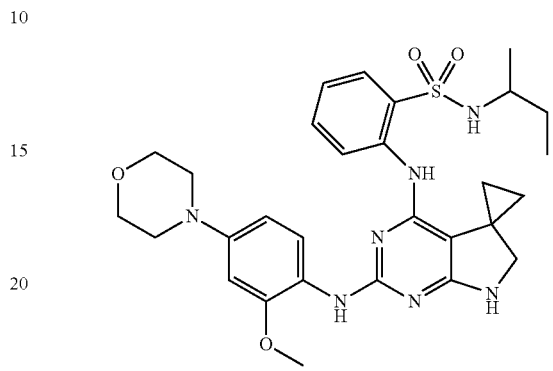

$^1$H NMR (400 MHz, CDCl$_3$) δ ppm 8.11 (d, J=8.8 Hz, 1H), 8.02 (d, J=8.3 Hz, 1H), 7.88 (dd, J=8.0, 1.4 Hz, 1H), 7.47 (t, J=7.8 Hz, 1H), 7.34 (s, 1H), 7.17 (s, 1H), 7.11 (t, J=7.6 Hz, 1H), 6.47 (d, J=2.5 Hz, 1H), 6.20 (dd, J=8.9, 2.5 Hz, 1H), 4.64 (s, 1H), 4.31 (d, J=8.2 Hz, 1H), 3.91-3.79 (m, 7H), 3.57 (s, 2H), 3.18-2.95 (m, 5H), 1.62 (s, 1H), 1.50 (t, J=6.1 Hz, 2H), 0.93 (d, J=6.6 Hz, 3H), 0.83 (d, J=6.1 Hz, 2H), 0.65 (t, J=7.4 Hz, 3H).

Example 148

2-(2'-(2-methoxy-4-morpholinophenylamino)-6',7'-dihydrospiro[cyclopropane-1,5'-pyrrolo[2,3-d]pyrimidine]-4'-ylamino)-N-propylbenzenesulfonamide

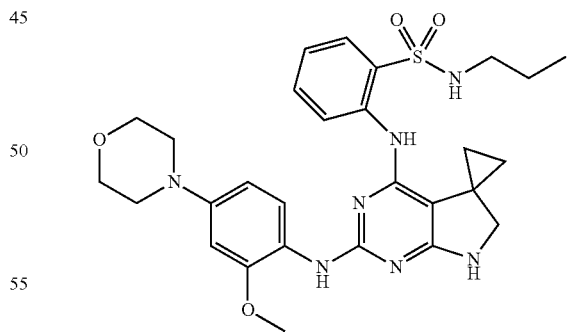

$^1$H NMR (400 MHz, CDCl$_3$) δ ppm 8.08 (t, J=9.0 Hz, 2H), 7.87 (d, J=7.9 Hz, 1H), 7.51 (t, J=7.2 Hz, 1H), 7.33 (s, 1H), 7.20-7.10 (m, 2H), 6.48 (d, J=2.4 Hz, 1H), 6.26 (d, J=8.9 Hz, 1H), 4.64 (s, 1H), 4.44 (t, J=6.0 Hz, 1H), 3.93-3.79 (m, 7H), 3.58 (s, 2H), 3.13-3.01 (m, 4H), 2.84 (dd, J=13.6, 6.8 Hz, 2H), 1.52 (t, J=6.1 Hz, 2H), 1.33 (dd, J=14.5, 7.2 Hz, 3H), 0.86 (dd, J=11.9, 6.0 Hz, 2H), 0.70 (t, J=7.4 Hz, 3H).

Example 149

N-cyclohexyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

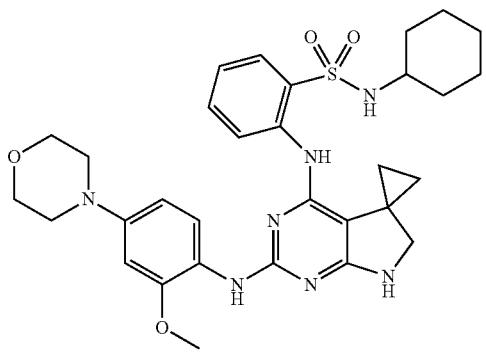 [SMILES: COc1cc(N2CCOCC2)ccc1Nc1nc2c(c(Nc3ccccc3S(=O)(=O)NC3CCCCC3)n1)C1(CC1)CN2]

¹H NMR (400 MHz, CDCl₃) δ ppm 8.09 (d, J=8.8 Hz, 1H), 7.99 (d, J=8.3 Hz, 1H), 7.91 (dd, J=7.9, 1.4 Hz, 1H), 7.51 (1, J=7.8 Hz, 1H), 7.17 (dd, J=13.8, 5.8 Hz, 2H), 6.49 (d, J=2.4 Hz, 1H), 6.21 (dd, J=8.9, 2.4 Hz, 1H), 4.69 (s, 1H), 4.44 (d, J=7.9 Hz, 1H), 3.94-3.77 (m, 7H), 3.60 (s, 2H), 3.13-2.98 (m, 5H), 1.64 (d, J=8.6 Hz, 3H), 1.53 (t, J=6.1 Hz, 2H), 1.45 (s, 2H), 1.36-1.22 (m, 7H), 1.12-0.94 (m, 5H), 0.88 (dd, J=11.2, 5.1 Hz, 3H).

Example 150

N-cyclobutyl-2-(2'-(2-methoxy-4-morpholinophenylamino)-6',7'-dihydrospiro[cyclopropane-1,5'-pyrrolo[2,3-d]pyrimidine]-4'-ylamino)benzenesulfonamide

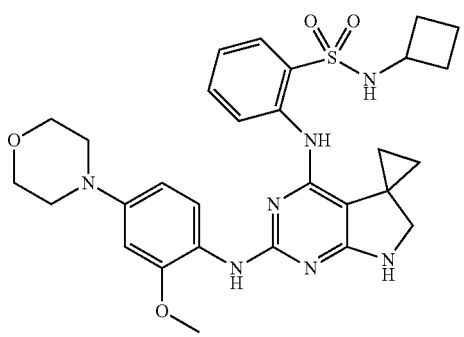 [SMILES: COc1cc(N2CCOCC2)ccc1Nc1nc2c(c(Nc3ccccc3S(=O)(=O)NC3CCC3)n1)C1(CC1)CN2]

¹H NMR (400 MHz, CDCl₃) δ ppm 8.11 (d, J=8.8 Hz, 1H), 8.03 (d, J=8.3 Hz, 1H), 7.86 (d, J=7.8 Hz, 1H), 7.49 (t, J=7.7 Hz, 1H), 7.31 (s, 1H), 7.18 (s, 1H), 7.11 (t, J=7.6 Hz, 1H), 6.48 (d, J=2.2 Hz, 1H), 6.28-6.15 (m, 1H), 4.80 (d, J=9.4 Hz, 1H), 4.74 (s, 1H), 3.93-3.78 (m, 7H), 3.78-3.64 (m, 1H), 3.58 (s, 2H), 3.10-2.96 (m, 4H), 2.12-1.86 (m, 4H), 1.74-1.59 (m, 3H), 1.51 (t, J=6.1 Hz, 2H), 1.48-1.36 (m, 2H), 1.26 (t, J=7.0 Hz, 6H), 0.92-0.78 (m, 3H).

Example 151

2-(2'-(2-methoxy-4-morpholinophenylamino)-6',7'-dihydrospiro[cyclopropane-1,5'-pyrrolo[2,3-d]pyrimidine]-4'-ylamino)-N,N-dimethylbenzenesulfonamide

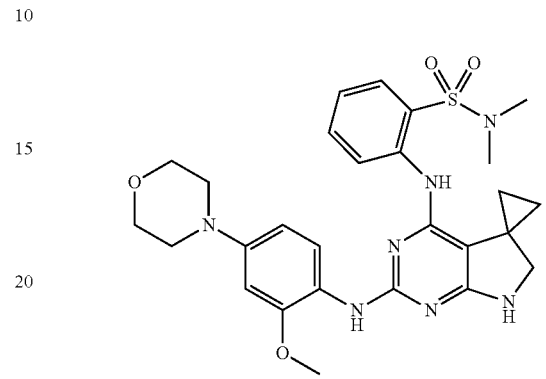

¹H NMR (400 MHz, CDCl₃) δ ppm 8.16 (dd, J=11.7, 8.8 Hz, 2H), 7.83 (s, 1H), 7.75 (d, J=7.4 Hz, 1H), 7.51 (dd, J=18.2, 9.9 Hz, 2H), 7.19 (s, 1H), 7.11 (t, J=7.6 Hz, 1H), 6.51 (d, J=2.3 Hz, 1H), 6.32 (d, J=8.9 Hz, 1H), 4.67 (s, 1H), 3.87 (d, J=8.9 Hz, 7H), 3.58 (s, 2H), 3.14-3.02 (m, 4H), 2.70 (s, 6H), 1.58 (t, J=6.0 Hz, 2H), 0.84 (s, 2H).

Example 152

2-(2'-(2-methoxy-4-morpholinophenylamino)-6',7'-dihydrospiro[cyclopropane-1,5'-pyrrolo[2,3-d]pyrimidine]-4'-ylamino)-N-methylbenzamide

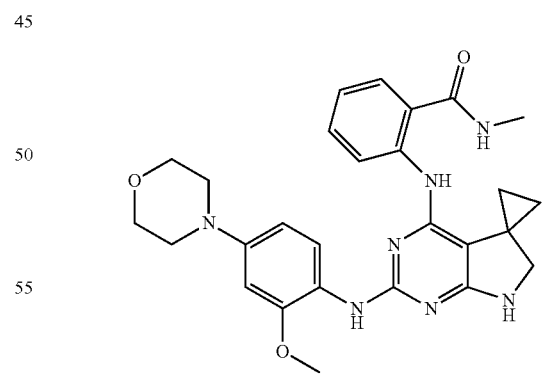

¹H NMR (400 MHz, CDCl₃) δ ppm 9.39 (s, 1H), 8.34 (s, 1H), 8.25 (d, J=8.8 Hz, 1H), 7.38 (d, J=7.8 Hz, 2H), 7.12 (s, 1H), 6.94 (t, J=7.5 Hz, 1H), 6.51 (d, J=2.5 Hz, 1H), 6.40 (dd, J=8.8, 2.5 Hz, 1H), 6.11 (s, 1H), 3.90-3.83 (m, 7H), 3.57 (s, 2H), 3.11-3.07 (m, 4H), 2.99 (d, J=4.9 Hz, 3H), 1.75 (t, J=6.0 Hz, 2H), 0.83 (t, J=6.1 Hz, 2H).

Example 153

N4'-(3,4-difluorophenyl)-N2'-(2-methoxy-4-morpholinophenyl)-6',7'-dihydrospiro[cyclopropane-1,5'-pyrrolo[2,3-d]pyrimidine]-2',4'-diamine

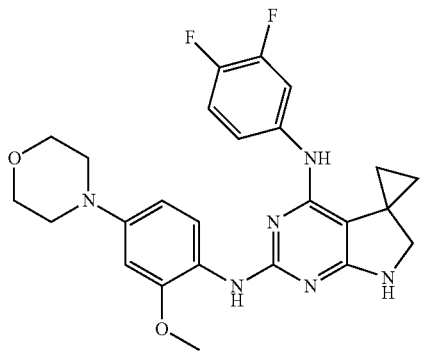 [SMILES: COc1cc(N2CCOCC2)ccc1Nc1nc2c(c(Nc3ccc(F)c(F)c3)n1)C1(CC1)CN2]

$^1$H NMR (400 MHz, CDCl$^3$) δ ppm 8.07 (d, J=8.8 Hz, 1H), 7.69-7.45 (m, 1H), 7.14-6.93 (m, 2H), 6.87 (s, 1H), 6.54-6.31 (m, 2H), 5.35 (s, 1H), 4.55 (s, 1H), 3.87 (dd, J=10.3, 5.7 Hz, 7H), 3.56 (s, 2H), 3.21-2.91 (m, 4H), 1.31 (m, 2H), 0.89 (m, 2H).

Example 154

N2'-(2-methoxy-4-morpholinophenyl)-N4'-(6-methylpyridin-2-yl)-6',7'-dihydrospiro[cyclopropane-1,5'-pyrrolo[2,3-d]pyrimidine]-2',4'-diamine

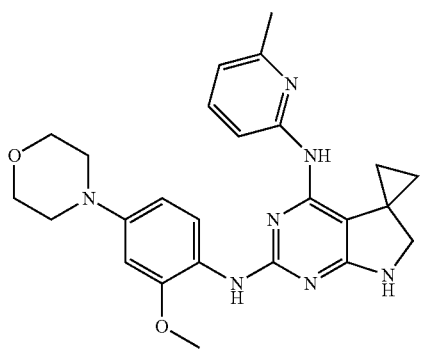 [SMILES: COc1cc(N2CCOCC2)ccc1Nc1nc2c(c(Nc3cccc(C)n3)n1)C1(CC1)CN2]

$^1$H NMR (400 MHz, CDCl$_3$) δ ppm 8.17 (d, J=8.7 Hz, 1H), 7.98 (d, J=8.3 Hz, 1H), 7.46 (dd, J=21.9, 14.2 Hz, 1H), 7.02 (d, J=20.3 Hz, 1H), 6.72 (d, J=7.3 Hz, 1H), 6.58-6.35 (m, 2H), 6.17 (s, 1H), 4.60 (s, 1H), 3.87 (dd, J=8.6, 3.6 Hz, 7H), 3.67 (s, 2H), 3.34-2.98 (m, 4H), 2.40 (s, 3H), 1.57-1.41 (m, 2H), 0.87 (t, J=6.2 Hz, 2H).

Example 155

N-(2-(2'-(2-methoxy-4-morpholinophenylamino)-6',7'-dihydrospiro[cyclopropane-1,5'-pyrrolo[2,3-d]pyrimidine]-4'-ylamino)phenyl)acetamide

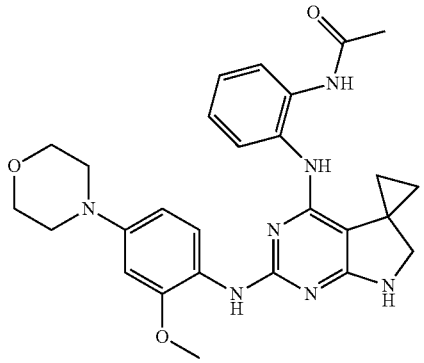 [SMILES: COc1cc(N2CCOCC2)ccc1Nc1nc2c(c(Nc3ccccc3NC(C)=O)n1)C1(CC1)CN2]

$^1$H NMR (400 MHz, CDCl$_3$) δ ppm 8.41 (s, 1H), 7.86 (d, J=8.8 Hz, 1H), 7.48 (s, 1H), 7.36 (d, J=4.9 Hz, 1H), 7.23-7.14 (m, 2H), 7.05 (s, 1H), 6.44 (d, J=15.2 Hz, 1H), 6.26 (d, J=9.0 Hz, 1H), 5.84 (s, 1H), 4.60 (s, 1H), 3.90-3.83 (m, 4H), 3.81 (s, 3H), 3.57 (s, 2H), 3.13-3.01 (m, 4H), 1.98 (s, 3H), 1.42 (s, 2H), 0.87 (d, J=7.0 Hz, 2H).

Example 156

N-(2-(2'-(2-methoxy-4-morpholinophenylamino)-6',7'-dihydrospiro[cyclopropane-1,5'-pyrrolo[2,3-d]pyrimidine]-4'-ylamino)phenyl)-N-methylmethanesulfonamide

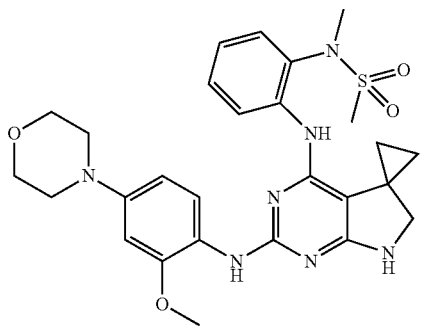 [SMILES: COc1cc(N2CCOCC2)ccc1Nc1nc2c(c(Nc3ccccc3N(C)S(C)(=O)=O)n1)C1(CC1)CN2]

$^1$H NMR (400 MHz, CDCl$_3$) δ ppm 8.11 (d, J=8.8 Hz, 1H), 8.03 (d, J=8.3 Hz, 1H), 7.86 (d, J=7.8 Hz, 1H), 7.49 (t, J=7.7 Hz, 1H), 7.31 (s, 1H), 7.18 (s, 1H), 7.11 (t, J=7.6 Hz, 1H), 6.70) s, 1H), 6.48 (d, J=2.2 Hz, 1H), 6.28-6.15 (m, 1H), 4.74 (s, 1H), 3.93-3.78 (m, 7H), 3.58 (s, 2H), 3.25 (s, 2H), 3.10-2.96 (m, 4H), 1.74-1.59 (m, 3H), 1.51 (t, J=6.1 Hz, 2H), 1.26 (t, J=7.0 Hz, 2H), 0.92-0.78 (m, 2H).

Example 157

N-methyl-2-(2'-(3,4,5-trimethoxyphenylamino)-6',7'-dihydrospiro[cyclopropane-1,5'-pyrrolo[2,3-d]pyrimidine]-4'-ylamino)benzenesulfonamide

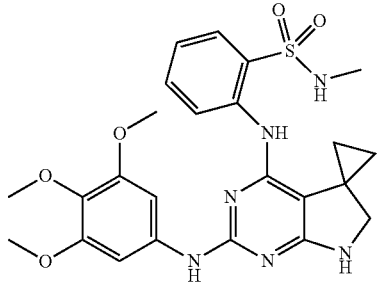 [SMILES: CNS(=O)(=O)c1ccccc1Nc1nc(Nc2cc(OC)c(OC)c(OC)c2)nc2c1C1(CC1)CN2]

$^1$H NMR (400 MHz, CDCl$_3$) δ ppm 8.05 (d, J=8.4 Hz, 1H), 7.83 (dd, J=8.0, 1.4 Hz, 1H), 7.54-7.36 (m, 2H), 7.04 (dd, J=19.5, 12.2 Hz, 1H), 6.79 (s, 2H), 6.74 (s, 1H), 4.80-4.44 (m, 2H), 3.85-3.74 (s, 3H), 3.62 (m, 7H), 2.58 (d, J=4.9 Hz, 3H), 1.54-1.41 (m, 2H), 0.84 (t, J=6.1 Hz, 2H).

Example 158

N-methyl-2-(2-(4-morpholinophenylamino)-6,7-dihydro-5H-pyrrolo[2,3-d]pyrimidin-4-ylamino)benzamide

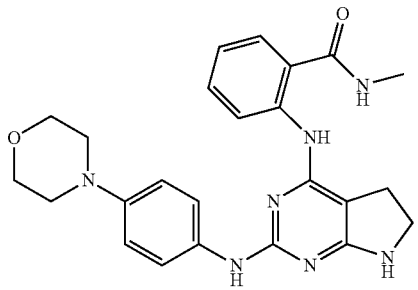 [SMILES: CNC(=O)c1ccccc1Nc1nc(Nc2ccc(N3CCOCC3)cc2)nc2c1CCN2]

$^1$H NMR (400 MHz, DMSO-d$_6$) δ ppm 10.66 (s, 1H), 8.62 (dd, J=22.0, 17.5 Hz, 3H), 7.82-7.18 (m, 4H), 6.94-6.68 (m, 3H), 6.59 (s, 1H), 3.72 (s, 4H), 3.49 (dd, J=23.3, 14.7 Hz, 2H), 3.00 (s, 4H), 2.82-2.56 (m, 5H).

Example 159

2-(2-(2-methoxyphenylamino)-6,7-dihydro-5H-pyrrolo[2,3-d]pyrimidin-4-ylamino)-N-methylbenzamide

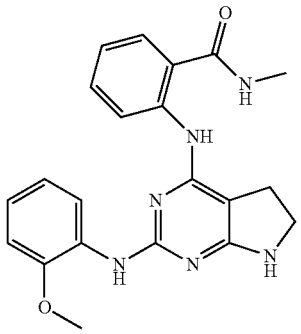 [SMILES: CNC(=O)c1ccccc1Nc1nc(Nc2ccccc2OC)nc2c1CCN2]

$^1$H NMR (400 MHz, DMSO-d$_6$) δ ppm 10.67 (d, J=34.1 Hz, 1H), 8.63 (d, J=4.5 Hz, 1H), 8.52 (d, J=8.4 Hz, 1H), 8.22 (dd, J=7.8, 1.6 Hz, 1H), 7.65 (d, J=6.8 Hz, 1H), 7.35 (dd, J=18.9, 11.7 Hz, 2H), 7.05-6.77 (m, 4H), 6.71 (s, 1H), 4.01-3.72 (m, 3H), 3.68-3.40 (m, 2H), 2.89-2.59 (m, 5H).

Example 160

2-(2-(2-methoxy-4-morpholinophenylamino)-6,7-dihydro-5H-pyrrolo[2,3-d]pyrimidin-4-ylamino)benzoic acid

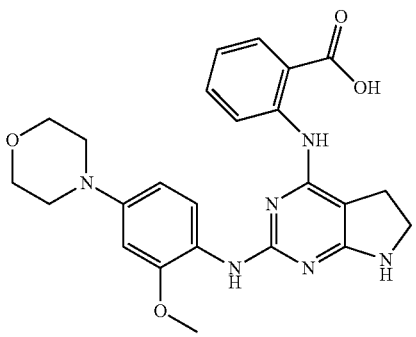 [SMILES: COc1cc(N2CCOCC2)ccc1Nc1nc2c(c(Nc3ccccc3C(=O)O)n1)CCN2]

$^1$H NMR (400 MHz, DMSO-d$_6$) δ ppm 11.54-10.76 (m, 1H), 8.69 (d, J=8.2 Hz, 1H), 7.91 (d, J=8.0 Hz, 1H), 7.80 (d, J=8.7 Hz, 1H), 7.32 (d, J=7.4 Hz, 1H), 7.19 (s, 1H), 6.85 (s, 2H), 6.61 (d, 2H), 6.46 (d, J=8.8 Hz, 1H), 3.79 (s, 3H), 3.76-3.62 (m, 6H), 3.58-3.45 (m, 2H), 3.13-2.97 (m, 4H), 2.81 (t, 2H).

Example 161

2-(2-(2-methoxy-4-morpholinophenylamino)-6,7-dihydro-5H-pyrrolo[2,3-d]pyrimidin-4-ylamino)benzaldehyde

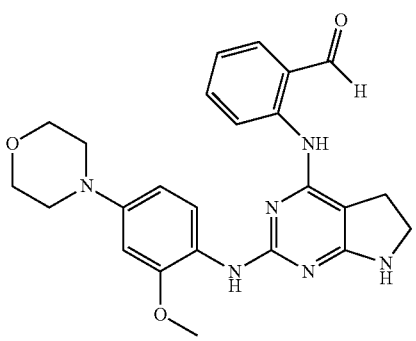 [SMILES: COc1cc(N2CCOCC2)ccc1Nc1nc2c(c(Nc3ccccc3C=O)n1)CCN2]

$^1$H NMR (400 MHz, DMSO-d$_6$) δ ppm 10.31 (s, 1H), 9.93 (s, 1H), 8.70 (d, J=8.6 Hz, 1H), 7.78 (d, J=7.7 Hz, 1H), 7.68 (d, J=8.7 Hz, 1H), 7.46 (d, J=8.5 Hz, 1H), 7.32 (s, 1H), 7.05 (t, J=7.1 Hz, 1H), 6.76 (s, 1H), 6.62 (d, J=2.5 Hz, 1H), 6.46 (dd, J=8.7, 2.5 Hz, 1H), 3.85-3.66 (m, 7H), 3.53 (dd, J=18.5, 10.1 Hz, 2H), 3.15-3.02 (m, 4H), 2.86 (t, J=8.4 Hz, 2H).

Example 162

2-(2-(2-(2-methoxy-4-morpholinophenylamino)-6,7-dihydro-5H-pyrrolo[2,3-d]pyrimidin-4-ylamino)phenyl)ethanol

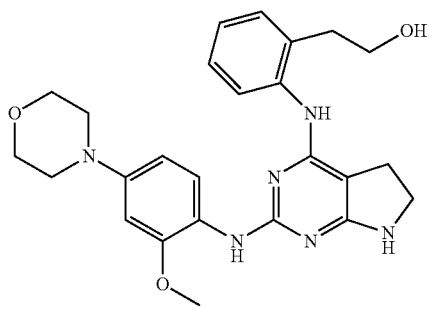 [SMILES: COc1cc(N2CCOCC2)ccc1Nc1nc2c(c(Nc3ccccc3CCO)n1)CCN2]

$^1$H NMR (400 MHz, CDCl$_3$) δ ppm 8.26 (d, J=8.8 Hz, 1H), 7.94 (d, J=8.2 Hz, 1H), 7.36 (d, J=8.3 Hz, 2H), 7.31-7.25 (m, 1H), 7.21 (s, 1H), 7.10 (s, 1H), 6.54 (d, J=2.6 Hz, 1H), 6.47 (d, J=8.8 Hz, 1H), 4.79 (s, 2H), 4.55 (s, 1H), 3.90 (dd, J=9.7, 4.8 Hz, 7H), 3.66 (t, J=8.5 Hz, 2H), 3.19-3.06 (m, 1H), 2.83 (t, J=8.4 Hz, 2H).

Example 163

N$^4$-(2-(dimethylphosphoryl)phenyl)-N$^2$-(2-methoxy-4-(4-(piperazin-1-yl)piperidin-1-yl)phenyl)-6,7-dihydro-5H-pyrrolo[2,3-d]pyrimidine-2,4-diamine

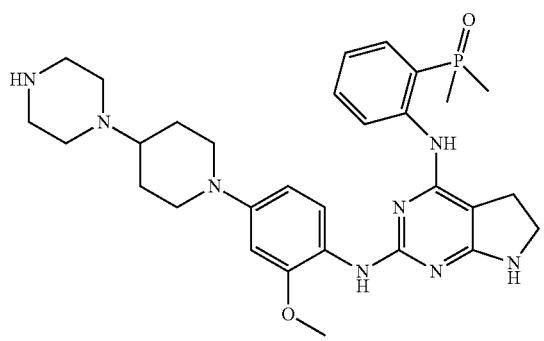 [SMILES: COc1cc(N2CCC(N3CCNCC3)CC2)ccc1Nc1nc2c(c(Nc3ccccc3P(C)(C)=O)n1)CCN2]

$^1$H NMR (400 MHz, CDCl$_3$) δ ppm 10.08 (s, 1H), 8.26 (dd, J=8.0 Hz, 4.4 Hz, 1H), 8.22 (d, J=8.8 Hz, 1H), 7.43 (t, J=8.4 Hz, 1H), 8.26 (ddd, J=14.4 Hz, 8.0 Hz, 1.6 Hz, 1H), 7.06 (s, 1H), 6.97 (t, J=8.8 Hz, 1H), 6.54 (d, J=2.8 Hz, 1H), 6.50 (dd, J=8.8 Hz, 2.4 Hz, 1H), 4.43 (s, 1H), 3.85 (s, 3H), 3.61-3.65 (m, 4H), 3.01 (t, J=8.0 Hz, 2H), 2.64-2.71 (m, 6H), 2.41-2.58 (m, 4H), 2.34-2.40 (m, 1H), 2.31 (s, 3H), 1.94 (d, J=13.2 Hz, 2H), 1.81 (d, J=13.2 Hz, 6H), 1.70-1.74 (m, 2H).

Biochemical Assay for FAK/Pyk2 Activity

GST-tagged FAK was purchased from Invitrogen (PV3832). GST-tagged PYK2 was purchased from Invitrogen (PV4567). The activity of FAK/PYK2 was measured by monitoring the phosphorylation of a fluorophore labeled ULight-poly Glu, Ala, Tyr (1:1:1) peptide substrate from Perkin Elmer (TRF0101) in the presence of ATP. The phosphorylated tyrosine residue was recognized by a LANCE Europium chelate labeled anti-phosphotyrosine (PY20) antibody from Perkin Elmer (AD0066). This brought the fluorophore and europium chelate in close proximity (>10 nm) that upon excitation at 320 nm by an Envision (PerkinElmer), energy can be transferred from the donor Europium chelate to the acceptor fluorophore. This results in the emission of light at 665 nm and can be captured by Envision. The strength of the signal was, therefore, directly proportional to the FAK/PYK2 activity.

To measure inhibitory activity of FAK/PYK2 inhibitors, compounds were first prepare as a 1 mM stock in 100% DMSO and 3-fold serial dilution was performed in a 96-well plate (Corning, 3897) to generate 12 different concentration of 100× stock. A 5 μl of 100× stock of each concentration was added to wells containing 95 μl of 1× reaction buffer (40 mM Tris, pH7.5, mM MgCl$_2$, 1 mM DTT and 1 mM CHAPS) to generate 5× stock. Then 2 μl of 5× stock of each concentration was added to a 384 wells-OptiPlate (PerkinElmer, 6007299).

For FAK, 4 μl of 2.5 nM FAK, 1 ul of 8 μg/μl BSA and 1.5 μl of 666 nM ULight-poly Glu, Ala, Tyr (1:1:1) peptide substrate, prepared in above reaction buffer, were added to each well. The reaction was initiated by adding 1.5 μl of 33.3 μM ATP. The reaction was allowed to proceed for 120 min before being quenched with 5 μl of 40 mM EDTA stop buffer prepared in 1×LANCE detection buffer (PerkinElmer, CR97-100).

For PYK2, 5 μl of 2 nM PYK2 and 1.5 μl of 666 nM ULight-poly Glu, Ala, Tyr (1:1:1) peptide substrate, prepared in above reaction buffer, were added to each well. The reaction was initiated by adding 1.5 μl of 46.6 μM ATP. The reaction was allowed to proceed for 40 min before being quenched with 5 μl of 40 mM EDTA stop buffer prepared in 1×LANCE detection buffer (PerkinElmer, CR97-100).

Upon quenching of the reaction, 5 μl of 8 nM anti-phosphotyrosine antibody was added to each well and incubated for 60 minutes. The plate was measured using an Envision (PerkinElmer) based on the theory mentioned above.

TABLE 1

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 1 | 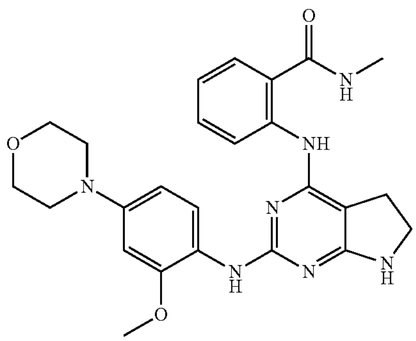 [SMILES: CNC(=O)c1ccccc1Nc1nc(Nc2ccc(N3CCOCC3)cc2OC)nc2c1CCN2] | 2-(2-(2-methoxy-4-morpholinophenyl-amino)-6,7-dihydro-5H-pyrrolo[2,3-d]pyrimidin-4-ylamino)-N-methylbenzamide | 476 | <100 | <100 |
| 2 | 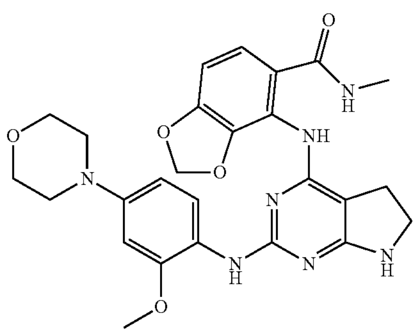 [SMILES: CNC(=O)c1ccc2c(c1Nc1nc(Nc3ccc(N4CCOCC4)cc3OC)nc3c1CCN3)OCO2] | 4-(2-(2-methoxy-4-morpholinophenyl-amino)-6,7-dihydro-5H-pyrrolo[2,3-d]pyrimidin-4-ylamino)-N-methylbenzo[d][1,3]-dioxole-5-carboxamide | 520 | >1000 | >1000 |
| 3 | 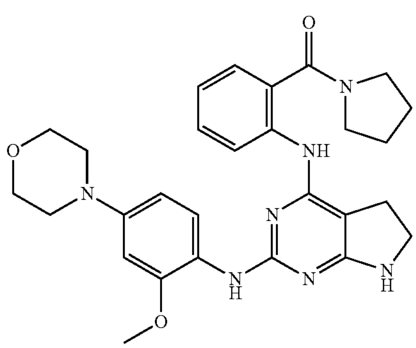 [SMILES: COc1cc(N2CCOCC2)ccc1Nc1nc2c(c(Nc3ccccc3C(=O)N3CCCC3)n1)CCN2] | (2-(2-(2-methoxy-4-morpholinophenyl-amino)-6,7-dihydro-5H-pyrrolo[2,3-d]pyrimidin-4-ylamino)-phenyl)(pyrrolidin-1-yl)-methanone | 516 | >1000 | >1000 |
| 4 | 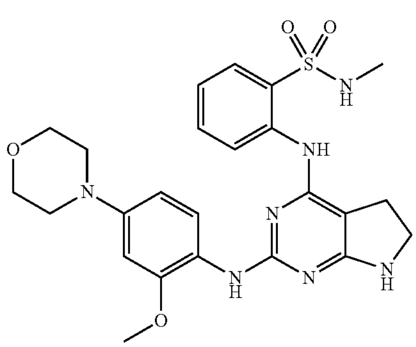 [SMILES: CNS(=O)(=O)c1ccccc1Nc1nc(Nc2ccc(N3CCOCC3)cc2OC)nc2c1CCN2] | 2-(2-(2-methoxy-4-morpholinophenyl-amino)-6,7-dihydro-5H-pyrrolo[2,3-d]-pyrimidin-4-ylamino)-N-methylbenzene-sulfonamide | 512 | <20 | <50 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 5 | 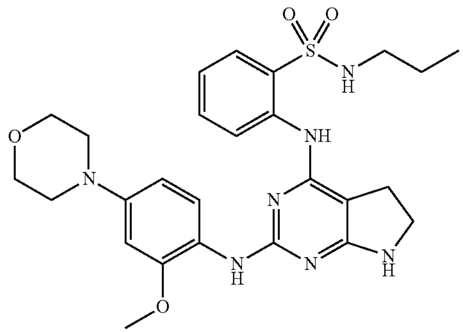 [SMILES: CCCNS(=O)(=O)c1ccccc1Nc1nc(Nc2ccc(N3CCOCC3)cc2OC)nc2c1CCN2] | 2-(2-(2-methoxy-4-morpholinophenylamino)-6,7-dihydro-5H-pyrrolo-[2,3-d]pyrimidin-4-ylamino)-N-propylbenzenesulfonamide | 540 | <20 | <20 |
| 6 | 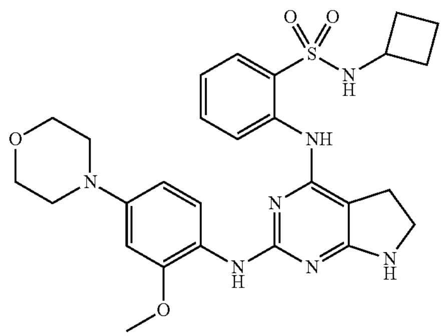 [SMILES: COc1cc(N2CCOCC2)ccc1Nc1nc2c(c(Nc3ccccc3S(=O)(=O)NC3CCC3)n1)CCN2] | N-cyclobutyl-2-(2-(2-methoxy-4-morpholinophenylamino)-6,7-dihydro-5H-pyrrolo-[2,3-d]pyrimidin-4-ylamino)benzenesulfonamide | 552 | <20 | <20 |
| 7 | 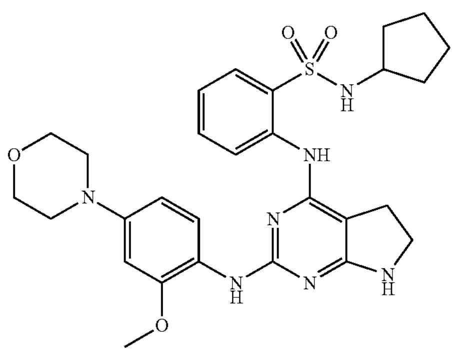 [SMILES: COc1cc(N2CCOCC2)ccc1Nc1nc2c(c(Nc3ccccc3S(=O)(=O)NC3CCCC3)n1)CCN2] | N-cyclopentyl-2-(2-(2-methoxy-4-morpholinophenylamino)-6,7-dihydro-5H-pyrrolo[2,3-d]pyrimidin-4-ylamino)benzene-sulfonamide | 566 | <50 | <100 |
| 8 | 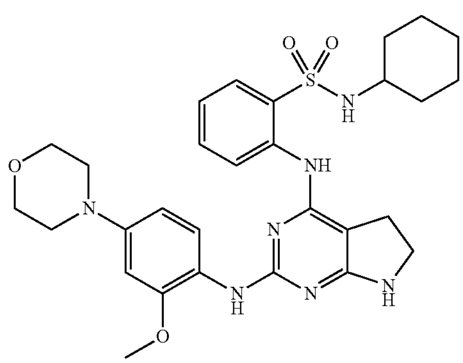 [SMILES: COc1cc(N2CCOCC2)ccc1Nc1nc2c(c(Nc3ccccc3S(=O)(=O)NC3CCCCC3)n1)CCN2] | N-cyclohexyl-2-(2-(2-methoxy-4-morpholinophenylamino)-6,7-dihydro-5H-pyrrolo[2,3-d]pyrimidin-4-ylamino)benzene-sulfonamide | 580 | <200 | <500 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 9 | 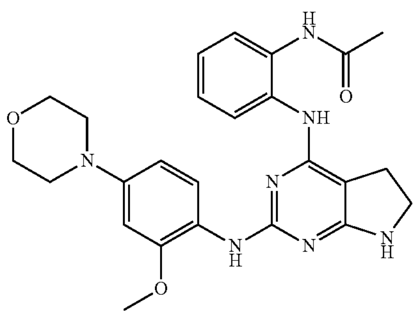 [SMILES: COc1cc(N2CCOCC2)ccc1Nc1nc2c(c(Nc3ccccc3NC(C)=O)n1)CCN2] | N-(2-(2-(2-methoxy-4-morpholinophenylamino)-6,7-dihydro-5H-pyrrolo-[2,3-d]pyrimidin-4-ylamino)phenyl)acetamide | 476 | <1000 | <1000 |
| 10 | 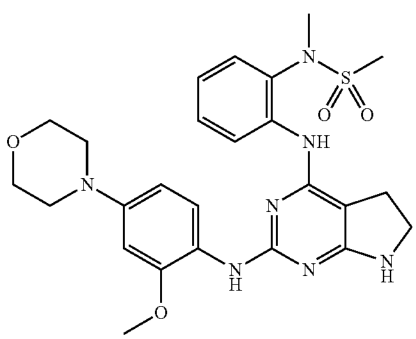 [SMILES: COc1cc(N2CCOCC2)ccc1Nc1nc2c(c(Nc3ccccc3N(C)S(C)(=O)=O)n1)CCN2] | N-(2-(2-(2-methoxy-4-morpholinophenylamino)-6,7-dihydro-5H-pyrrolo-[2,3-d]pyrimidin-4-ylamino)phenyl)-N-methylmethanesulfonamide | 526 | <100 | <50 |
| 11 | 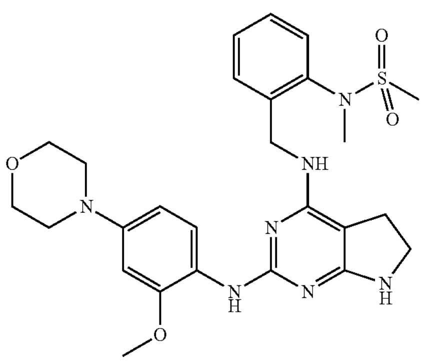 [SMILES: COc1cc(N2CCOCC2)ccc1Nc1nc2c(c(NCc3ccccc3N(C)S(C)(=O)=O)n1)CCN2] | N-(2-((2-(2-methoxy-4-morpholinophenylamino)-6,7-dihydro-5H-pyrrolo-[2,3-d]pyrimidin-4-ylamino)methyl)phenyl)-N-methylmethanesulfonamide | 540 | <100 | >2000 |
| 12 | 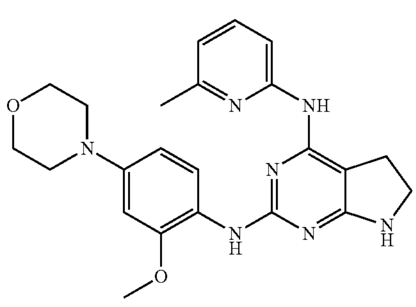 [SMILES: COc1cc(N2CCOCC2)ccc1Nc1nc2c(c(Nc3cccc(C)n3)n1)CCN2] | N$^2$-(2-methoxy-4-morpholinophenyl)-N$^4$-(6-methylpyridin-2-yl)-6,7-dihydro-5H-pyrrolo-[2,3-d]pyrimidine-2,4-diamine | 434 | <100 | <100 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 13 | 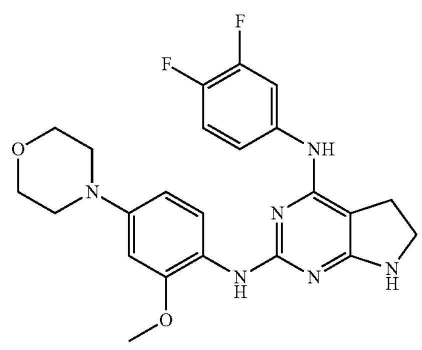 [SMILES: COc1cc(N2CCOCC2)ccc1Nc1nc2c(c(Nc3ccc(F)c(F)c3)n1)CCN2] | N$^4$-(3,4-difluorophenyl)-N$^2$-(2-methoxy-4-morpholinophenyl)-6,7-dihydro-5H-pyrrolo[2,3-d]-pyrimidine-2,4-diamine | 454 | >1000 | <1000 |
| 14 | 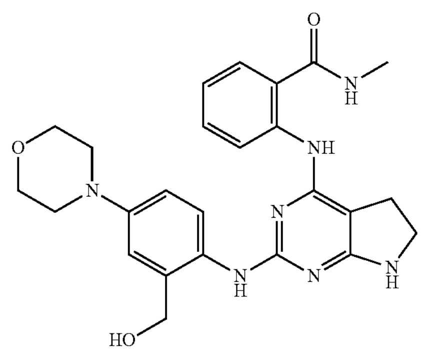 [SMILES: CNC(=O)c1ccccc1Nc1nc(Nc2ccc(N3CCOCC3)cc2CO)nc2c1CCN2] | 2-(2-(2-(hydroxymethyl)-4-morpholinophenylamino)-6,7-dihydro-5H-pyrrolo[2,3-d]pyrimidin-4-ylamino)-N-methylbenzamide | 476 | >1000 | >1000 |
| 15 | 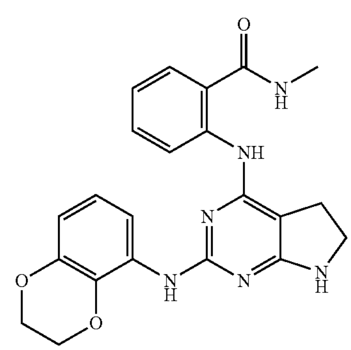 [SMILES: CNC(=O)c1ccccc1Nc1nc(Nc2cccc3c2OCCO3)nc2c1CCN2] | 2-(2-(2,3-dihydrobenzo-[b][1,4]dioxin-5-ylamino)-6,7-dihydro-5-pyrrolo[2,3-d]pyrimidin-4-ylamino)-N-methylbenzamide | 419 | <500 | <500 |
| 16 | 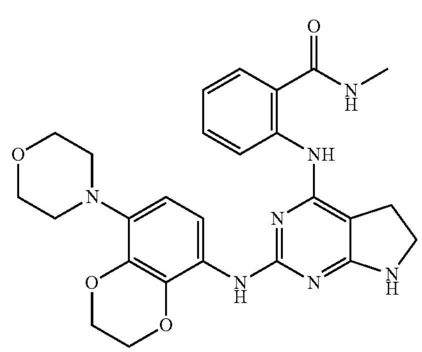 [SMILES: CNC(=O)c1ccccc1Nc1nc(Nc2ccc(N3CCOCC3)c3c2OCCO3)nc2c1CCN2] | N-methyl-2-(2-(8-morpholino-2,3-dihydrobenzo[b][1,4]dioxin-5-ylamino)-6,7-dihydro-5H-pyrrolo[2,3-d]pyrimidin-4-ylamino)benzamide | 504 | <500 | <200 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 17 | 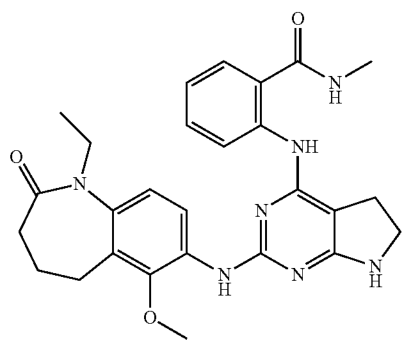 [SMILES: CCN1C(=O)CCCc2c1ccc(Nc1nc3c(c(Nc4ccccc4C(=O)NC)n1)CCN3)c2OC] | 2-(2-(1-ethyl-6-methoxy-2-oxo-2,3,4,5-tetrahydro-1H-benzo[b]azepin-7-ylamino)-6,7-dihydro-5H-pyrrolo[2,3-d]pyrimidin-4-ylamino)-N-methylbenzamide | 502 | <1000 | <200 |
| 19 | 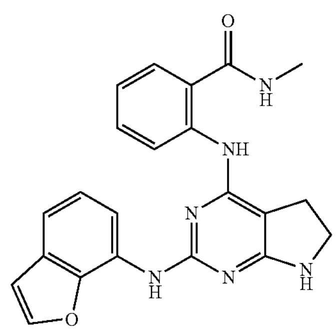 [SMILES: CNC(=O)c1ccccc1Nc1nc(Nc2cccc3ccoc23)nc2c1CCN2] | 2-(2-(benzofuran-7-ylamino)-6,7-dihydro-5H-pyrrolo[2,3-d]pyrimidin-4-ylamino)-N-methylbenzamide | 401 | <200 | <100 |
| 20 | 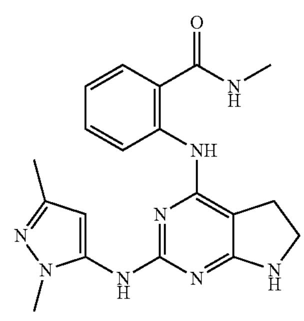 [SMILES: CNC(=O)c1ccccc1Nc1nc(Nc2cc(C)nn2C)nc2c1CCN2] | 2-(2-(1,3-dimethyl-1H-pyrazol-5-ylamino)-6,7-dihydro-5H-pyrrolo[2,3-d]-pyrimidin-4-ylamino)-N-methylbenzamide | 379 | <1000 | <500 |
| 21 | 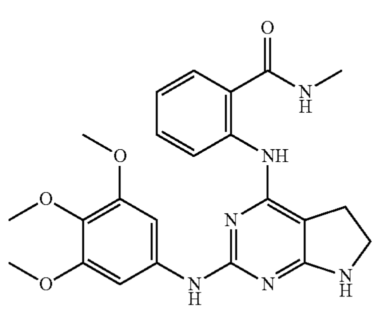 [SMILES: CNC(=O)c1ccccc1Nc1nc(Nc2cc(OC)c(OC)c(OC)c2)nc2c1CCN2] | N-methyl-2-(2-(3,4,5-trimethoxyphenylamino)-6,7-dihydro-5H-pyrrolo-[2,3-d]pyrimidin-4-ylamino)benzamide | 451 | <1000 | <300 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 22 | 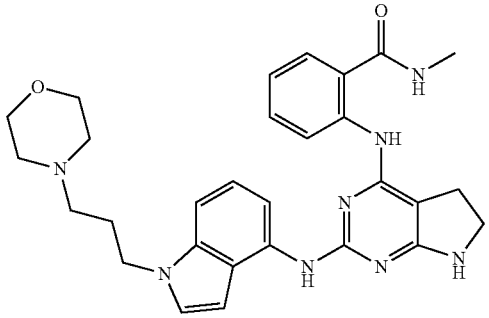 [SMILES: CNC(=O)c1ccccc1Nc1nc(Nc2cccc3c2ccn3CCCN2CCOCC2)nc2c1CCN2] | N-methyl-2-(2-(1-(3-morpholinopropyl)-1H-indol-4-ylamino)-6,7-dihydro-5H-pyrrolo[2,3-d]-pyrimidin-4-ylamino)-benzamide | 527 | <100 | <200 |
| 23 | 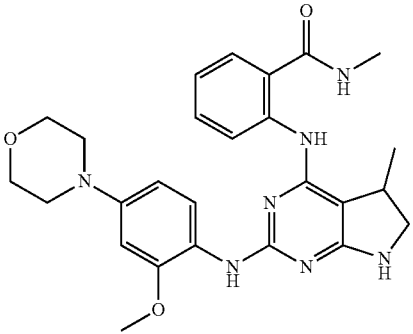 [SMILES: CNC(=O)c1ccccc1Nc1nc(Nc2ccc(N3CCOCC3)cc2OC)nc2c1C(C)CN2] | (±)-2-(2-(2-methoxy-4-morpholinophenylamino)-5-methyl-6,7-dihydro-5H-pyrrolo[2,3-d]-pyrimidin-4-ylamino)-N-methylbenzamide | 490 | <50 | <50 |
| 24 | 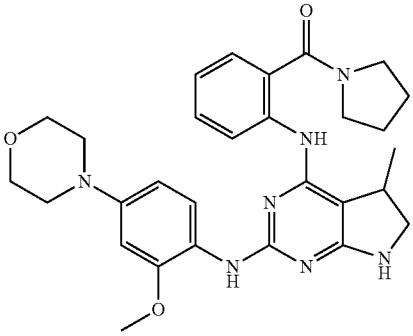 [SMILES: COc1cc(N2CCOCC2)ccc1Nc1nc2c(c(Nc3ccccc3C(=O)N3CCCC3)n1)C(C)CN2] | (±)-(2-(2-(2-methoxy-4-morpholinophenylamino)-5-methyl-6,7-dihydro-5H-pyrrolo[2,3-d]pyrimidin-4-ylamino)phenyl)-(pyrrolidin-1-yl)methanone | 530 | <200 | <500 |
| 25 | 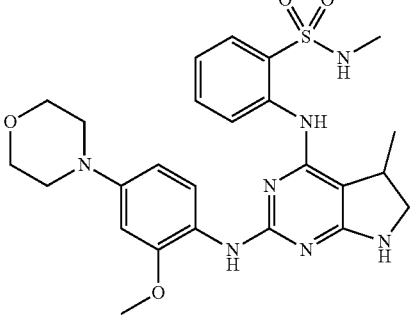 | (±)-2-(2-(2-methoxy-4-morpholinophenylamino)-5-methyl-6,7-dihydro-5H-pyrrolo[2,3-d]-pyrimidin-4-ylamino)-N-methylbenzenesulfonamide | 526 | <50 | <20 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 26 | 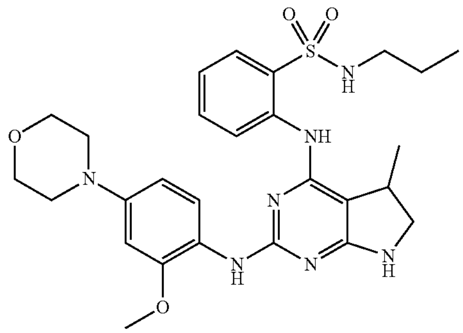 [SMILES: CCCNS(=O)(=O)c1ccccc1Nc1nc(Nc2ccc(N3CCOCC3)cc2OC)nc2c1C(C)CN2] | (±)-2-(2-(2-methoxy-4-morpholinophenylamino)-5-methyl-6,7-dihydro-5H-pyrrolo[2,3-d]pyrimidin-4-ylamino)-N-propyl-benzenesulfonamide | 554 | <20 | <20 |
| 27 | 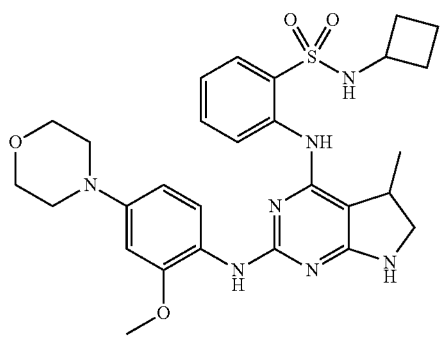 [SMILES: COc1cc(N2CCOCC2)ccc1Nc1nc2c(c(Nc3ccccc3S(=O)(=O)NC3CCC3)n1)C(C)CN2] | (±)-N-cyclobutyl-2-(2-(2-methoxy-4-morpholino-phenylamino)-5-methyl-6,7-dihydro-5H-pyrrolo-[2,3-d]pyrimidin-4-ylamino)-benzenesulfonamide | 566 | <20 | <20 |
| 28 | 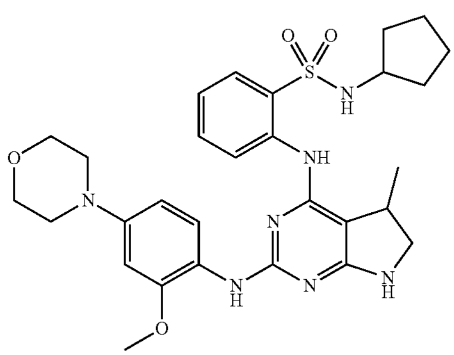 [SMILES: COc1cc(N2CCOCC2)ccc1Nc1nc2c(c(Nc3ccccc3S(=O)(=O)NC3CCCC3)n1)C(C)CN2] | (±)-N-cyclopentyl-2-(2-(2-methoxy-4-morpholino-phenylamino)-5-methyl-6,7-dihydro-5H-pyrrolo-[2,3-d]pyrimidin-4-ylamino)benzenesulfonamide | 580 | <300 | <50 |
| 29 | 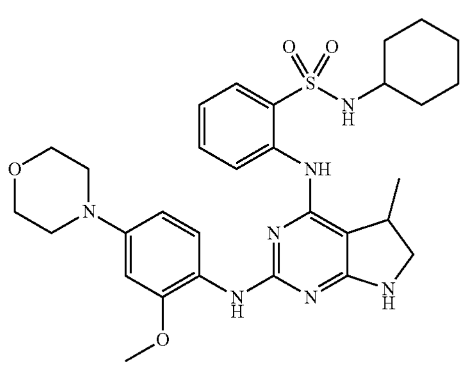 [SMILES: COc1cc(N2CCOCC2)ccc1Nc1nc2c(c(Nc3ccccc3S(=O)(=O)NC3CCCCC3)n1)C(C)CN2] | (±)-N-cyclohexyl-2-(2-(2-methoxy-4-morpholino-phenylamino)-5-methyl-6,7-dihydro-5H-pyrrolo-[2,3-d]pyrimidin-4-ylamino)benzenesulfonamide | 594 | <50 | <500 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 30 | 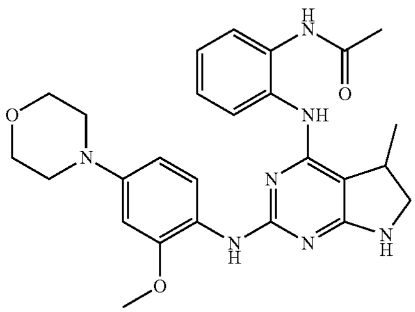 [SMILES: COc1cc(N2CCOCC2)ccc1Nc1nc2c(c(Nc3ccccc3NC(C)=O)n1)C(C)CN2] | (±)-N-(2-(2-(2-methoxy-4-morpholinophenylamino)-5-methyl-6,7-dihydro-5H-pyrrolo[2,3-d]pyrimidin-4-ylamino)phenyl)acetamide | 490 | <200 | <200 |
| 31 | 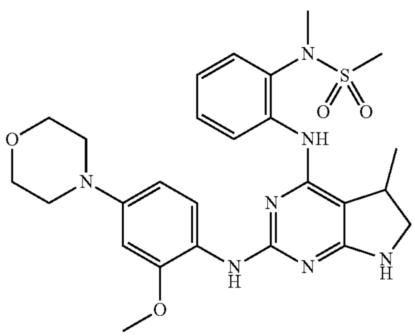 [SMILES: COc1cc(N2CCOCC2)ccc1Nc1nc2c(c(Nc3ccccc3N(C)S(C)(=O)=O)n1)C(C)CN2] | (±)-N-(2-(2-(2-methoxy-4-morpholinophenylamino)-5-methyl-6,7-dihydro-5H-pyrrolo[2,3-d]pyrimidin-4-ylamino)phenyl)-N-methylmethanesulfonamide | 540 | <30 | <20 |
| 32 | 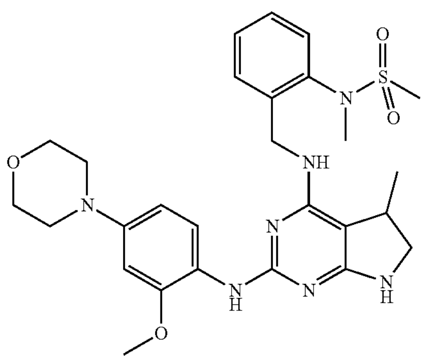 [SMILES: COc1cc(N2CCOCC2)ccc1Nc1nc(NCc2ccccc2N(C)S(C)(=O)=O)c2c(n1)NCC2C] | N-(2-((2-(2-methoxy-4-morpholinophenylamino)-5-methyl-6,7-dihydro-5H-pyrrolo[2,3-d]pyrimidin-4-ylamino)methyl)phenyl)-N-methylmethanesulfonamide | 554 | <20 | >1000 |
| 33 | 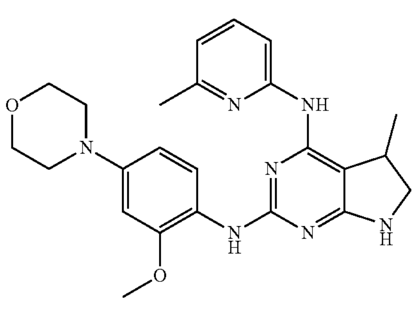 [SMILES: COc1cc(N2CCOCC2)ccc1Nc1nc2c(c(Nc3cccc(C)n3)n1)C(C)CN2] | (±)-N$^2$-(2-methoxy-4-morpholinophenyl)-5-methyl-N$^4$-(6-methylpyridin-2-yl)-6,7-dihydro-5H-pyrrolo[2,3-d]pyrimidine-2,4-diamine | 448 | <500 | <1000 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 34 | 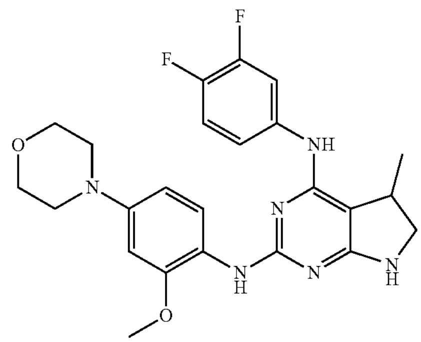 [SMILES: COc1cc(N2CCOCC2)ccc1Nc1nc2c(c(Nc3ccc(F)c(F)c3)n1)C(C)CN2] | N$^4$-(3,4-difluorophenyl)-N2-(2-methoxy-4-morpholinophenyl)-5-methyl-6,7-dihydro-5H-pyrrolo[2,3-d]pyrimidine-2,4-diamine | 469 | >1000 | <1000 |
| 35 | 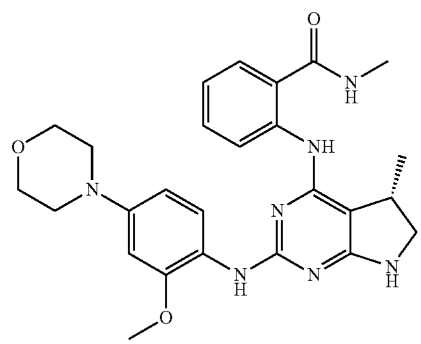 [SMILES: CNC(=O)c1ccccc1Nc1nc(Nc2ccc(N3CCOCC3)cc2OC)nc2c1[C@H](C)CN2] | (S)-2-(2-(2-methoxy-4-morpholinophenylamino)-5-methyl-6,7-dihydro-5H-pyrrolo[2,3-d]pyrimidin-4-ylamino)-N-methylbenzamide | 490 | <20 | <20 |
| 36 | 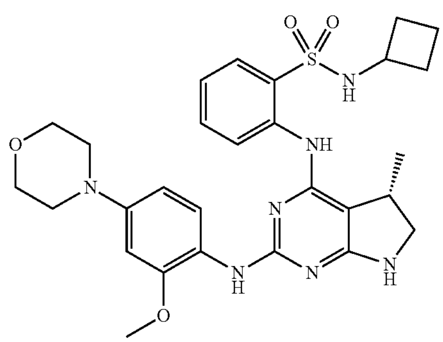 [SMILES: COc1cc(N2CCOCC2)ccc1Nc1nc2c(c(Nc3ccccc3S(=O)(=O)NC3CCC3)n1)[C@H](C)CN2] | (S)-N-cyclobutyl-2-(2-(2-methoxy-4-morpholinophenylamino)-5-methyl-6,7-dihydro-5H-pyrrolo[2,3-d]pyrimidin-4-ylamino)benzenesulfonamide | 566 | <20 | <20 |
| 37 | 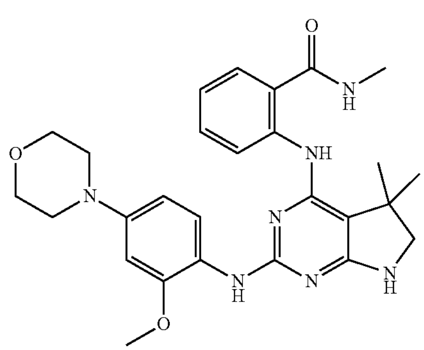 [SMILES: CNC(=O)c1ccccc1Nc1nc(Nc2ccc(N3CCOCC3)cc2OC)nc2c1C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N-methylbenzamide | 504 | <20 | <20 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 38 | 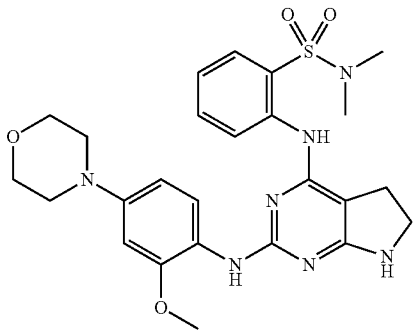 [SMILES: COc1cc(N2CCOCC2)ccc1Nc1nc2c(c(Nc3ccccc3S(=O)(=O)N(C)C)n1)CCN2] | 2-(2-(2-methoxy-4-morpholinophenylamino)-6,7-dihydro-5H-pyrrolo[2,3-d]pyrimidin-4-ylamino)-N,N-dimethylbenzenesulfonamide | 526 | <50 | <200 |
| 39 | 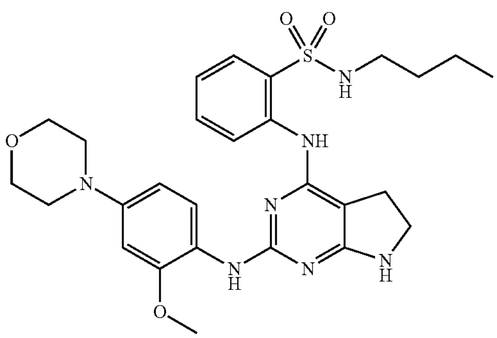 [SMILES: CCCCNS(=O)(=O)c1ccccc1Nc1nc(Nc2ccc(N3CCOCC3)cc2OC)nc2c1CCN2] | N-butyl-2-(2-(2-methoxy-4-morpholinophenylamino)-6,7-dihydro-5H-pyrrolo-[2,3-d]pyrimidin-4-ylamino)-benzenesulfonamide | 554 | <50 | <100 |
| 40 | 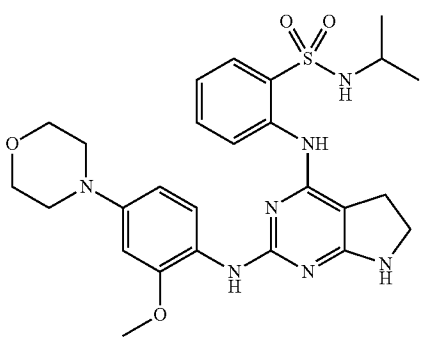 [SMILES: COc1cc(N2CCOCC2)ccc1Nc1nc2c(c(Nc3ccccc3S(=O)(=O)NC(C)C)n1)CCN2] | N-isopropyl-2-(2-(2-methoxy-4-morpholino-phenylamino)-6,7-dihydro-5H-pyrrolo[2,3-d]pyrimidin-4-ylamino)-benzenesulfonamide | 540 | <20 | <20 |
| 41 | 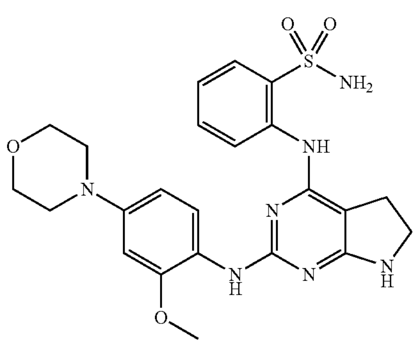 [SMILES: COc1cc(N2CCOCC2)ccc1Nc1nc2c(c(Nc3ccccc3S(N)(=O)=O)n1)CCN2] | 2-(2-(2-methoxy-4-morpholinophenylamino)-6,7-dihydro-5H-pyrrolo-[2,3-d]pyrimidin-4-ylamino)-benzenesulfonamide | 498 | <50 | <200 |

TABLE 1-continued

Biological Activities of Selected Pyrrolo[2,3-d]pyrimidines of Formula (I)

| Ex # | Structure | Name | MS $[M + H]^+$ | FAK IC$_{50}$ (nM) | PYK2 IC$_{50}$ (nM) |
|---|---|---|---|---|---|
| 42 | 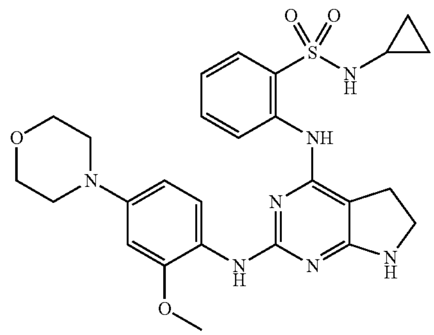 [SMILES: COc1cc(N2CCOCC2)ccc1Nc1nc2c(c(Nc3ccccc3S(=O)(=O)NC3CC3)n1)CCN2] | N-cyclopropyl-2-(2-(2-methoxy-4-morpholino-phenylamino)-6,7-dihydro-5H-pyrrolo[2,3-d]-pyrimidin-4-ylamino)-benzenesulfonamide | 538 | <20 | <50 |
| 43 | 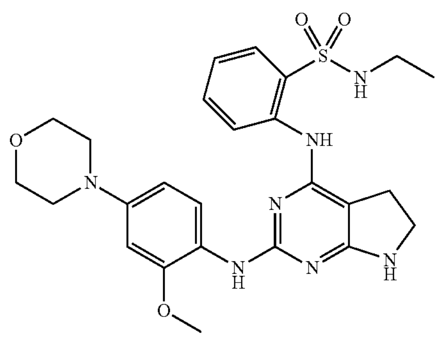 [SMILES: CCNS(=O)(=O)c1ccccc1Nc1nc(Nc2ccc(N3CCOCC3)cc2OC)nc2c1CCN2] | N-ethyl-2-(2-(2-methoxy-4-morpholinophenyl-amino)-6,7-dihydro-5H-pyrrolo[2,3-d]pyrimidin-4-ylamino)-benzenesulfonamide | 526 | <100 | <20 |
| 44 | 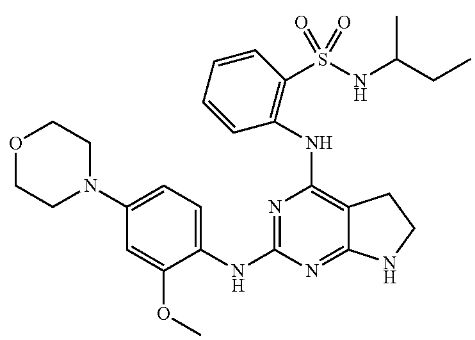 [SMILES: CCC(C)NS(=O)(=O)c1ccccc1Nc1nc(Nc2ccc(N3CCOCC3)cc2OC)nc2c1CCN2] | N-sec-butyl-2-(2-(2-methoxy-4-morpholinophenylamino)-6,7-dihydro-5H-pyrrolo-[2,3-d]pyrimidin-4-ylamino)benzenesulfonamide | 554 | <20 | <20 |
| 45 | 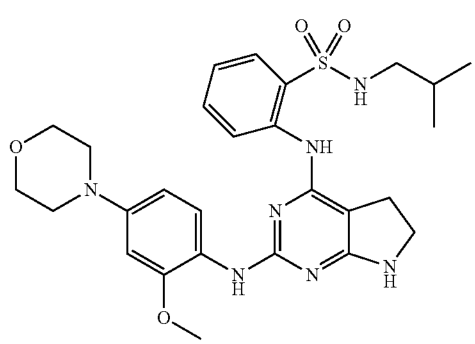 [SMILES: COc1cc(N2CCOCC2)ccc1Nc1nc2c(c(Nc3ccccc3S(=O)(=O)NCC(C)C)n1)CCN2] | N-isobutyl-2-(2-(2-methoxy-4-morpholinophenylamino)-6,7-dihydro-5H-pyrrolo[2,3-d]pyrimidin-4-ylamino)-benzenesulfonamide | 554 | <100 | <100 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 46 | 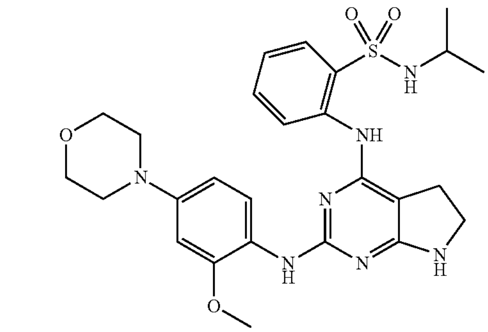 [SMILES: COc1cc(N2CCOCC2)ccc1Nc1nc2c(c(Nc3ccccc3S(=O)(=O)NC(C)C)n1)CCN2] | N-isopropyl-2-(2-(2-methoxy-4-morpholinophenylamino)-6,7-dihydro-5H-pyrrolo-[2,3-d]pyrimidin-4-ylamino)-benzenesulfonamide | 554 | <20 | <20 |
| 47 | 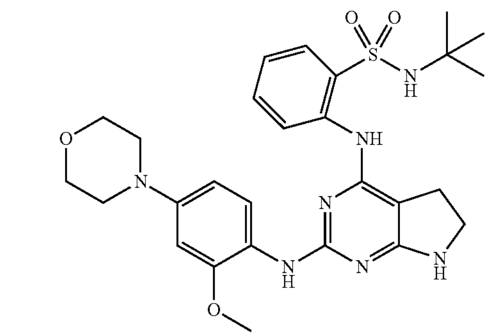 [SMILES: COc1cc(N2CCOCC2)ccc1Nc1nc2c(c(Nc3ccccc3S(=O)(=O)NC(C)(C)C)n1)CCN2] | N-tert-butyl-2-(2-(2-methoxy-4-morpholino-phenylamino)-6,7-dihydro-5H-pyrrolo[2,3-d]pyrimidin-4-ylamino)benzenesulfonamide | 554 | <200 | <100 |
| 48 | 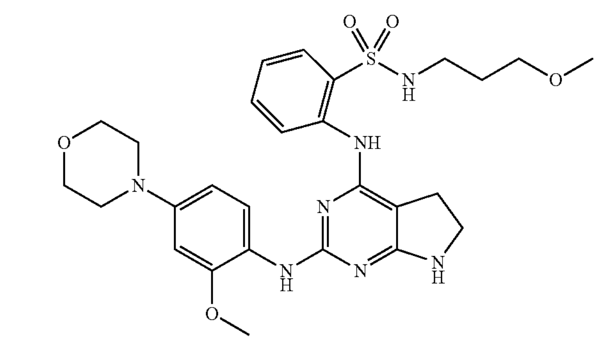 [SMILES: COCCCNS(=O)(=O)c1ccccc1Nc1nc(Nc2ccc(N3CCOCC3)cc2OC)nc2c1CCN2] | 2-(2-(2-methoxy-4-morpholinophenylamino)-6,7-dihydro-5H-pyrrolo[2,3-d]pyrimidin-4-ylamino)-N-(3-methoxypropyl)-benzenesulfonamide | 570 | <100 | <100 |
| 49 | 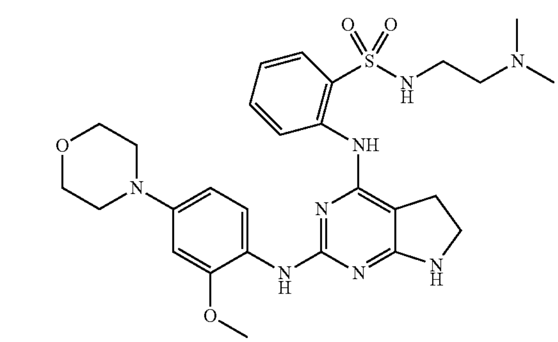 [SMILES: COc1cc(N2CCOCC2)ccc1Nc1nc2c(c(Nc3ccccc3S(=O)(=O)NCCN(C)C)n1)CCN2] | N-(2-(dimethylamino)ethyl)-2-(2-(2-methoxy-4-morpholinophenylamino)-6,7-dihydro-5H-pyrrolo-[2,3-d]pyrimidin-4-ylamino)-benzenesulfonamide | 569 | <500 | <500 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 50 | 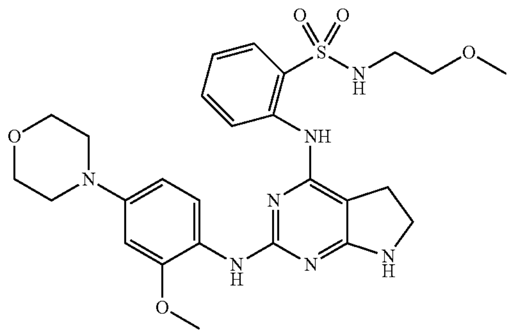 [SMILES: COCCNS(=O)(=O)c1ccccc1Nc1nc(Nc2ccc(N3CCOCC3)cc2OC)nc2c1CCN2] | 2-(2-(2-methoxy-4-morpholinophenylamino)-6,7-dihydro-5H-pyrrolo[2,3-d]pyrimidin-4-ylamino)-N-(2-methoxyethyl)-benzenesulfonamide | 556 | <50 | <50 |
| 51 | 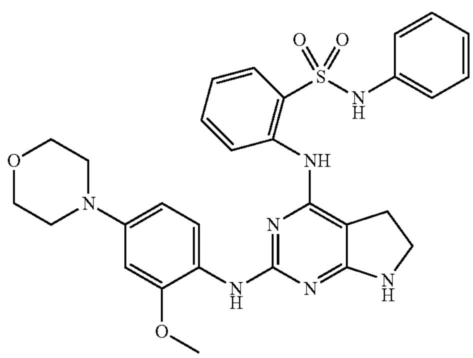 [SMILES: COc1cc(N2CCOCC2)ccc1Nc1nc2c(c(Nc3ccccc3S(=O)(=O)Nc3ccccc3)n1)CCN2] | 2-(2-(2-methoxy-4-morpholinophenylamino)-6,7-dihydro-5H-pyrrolo[2,3-d]pyrimidin-4-ylamino)-N-phenylbenzenesulfonamide | 574 | <200 | <500 |
| 52 | 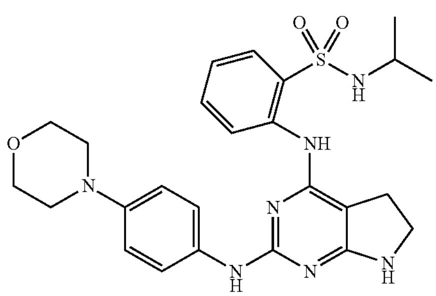 [SMILES: CC(C)NS(=O)(=O)c1ccccc1Nc1nc(Nc2ccc(N3CCOCC3)cc2)nc2c1CCN2] | N-isopropyl-2-(2-(4-morpholinophenylamino)-6,7-dihydro-5H-pyrrolo[2,3-d]pyrimidin-4-ylamino)-benzenesulfonamide | 510 | <20 | <20 |
| 53 | 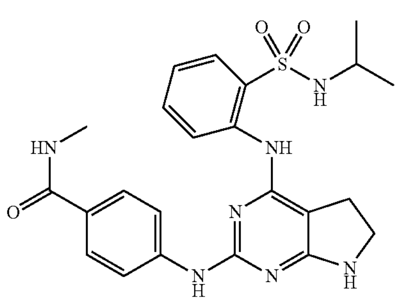 [SMILES: CNC(=O)c1ccc(Nc2nc3c(c(Nc4ccccc4S(=O)(=O)NC(C)C)n2)CCN3)cc1] | 4-(4-(2-(N-isopropylsulfamoyl)-phenylamino)-6,7-dihydro-5H-pyrrolo[2,3-d]pyrimidin-2-ylamino)-N-methylbenzamide | 482 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 54 | 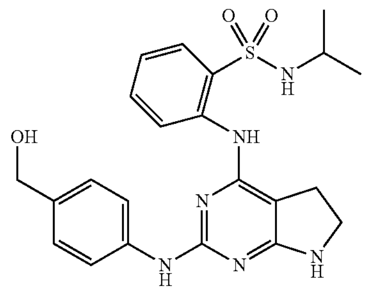 [SMILES: CC(C)NS(=O)(=O)c1ccccc1Nc1nc(Nc2ccc(CO)cc2)nc2c1CCN2] | 2-(2-(4-(hydroxymethyl)-phenylamino)-6,7-dihydro-5H-pyrrolo[2,3-d]pyrimidin-4-ylamino)-N-isopropylbenzene-sulfonamide | 455 | <20 | <20 |
| 55 | 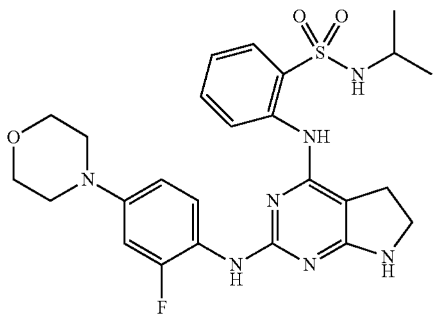 [SMILES: CC(C)NS(=O)(=O)c1ccccc1Nc1nc(Nc2ccc(N3CCOCC3)cc2F)nc2c1CCN2] | 2-(2-(2-fluoro-4-morpholinophenylamino)-6,7-dihydro-5H-pyrrolo[2,3-d]pyrimidin-4-ylamino)-N-isopropylbenzenesulfonamide | 528 | <20 | <20 |
| 56 | 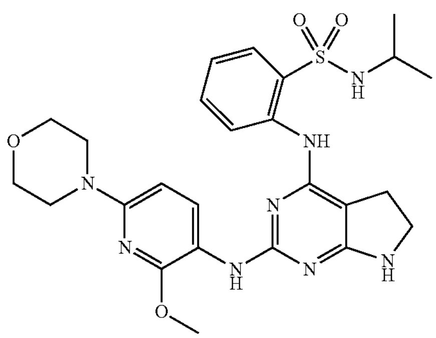 [SMILES: COc1nc(N2CCOCC2)ccc1Nc1nc2c(c(Nc3ccccc3S(=O)(=O)NC(C)C)n1)CCN2] | N-isopropyl-2-(2-(2-methoxy-6-morpholinopyridin-3-ylamino)-6,7-dihydro-5H-pyrrolo[2,3-d]pyrimidin-4-ylamino)-benzenesulfonamide | 541 | <20 | <50 |
| 57 | 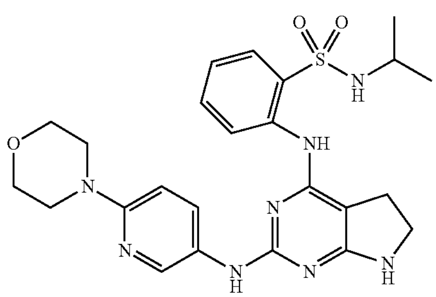 [SMILES: CC(C)NS(=O)(=O)c1ccccc1Nc1nc(Nc2ccc(N3CCOCC3)nc2)nc2c1CCN2] | N-isopropyl-2-(2-(6-morpholinopyridin-3-ylamino)-6,7-dihydro-5H-pyrrolo[2,3-d]-pyrimidin-4-ylamino)-benzenesulfonamide | 511 | <20 | <20 |
| 58 | 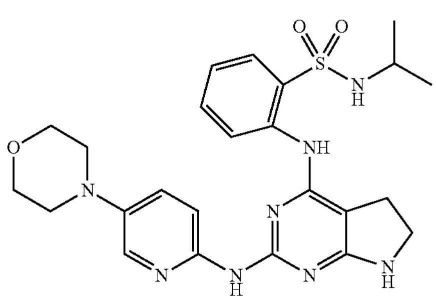 [SMILES: CC(C)NS(=O)(=O)c1ccccc1Nc1nc(Nc2ccc(N3CCOCC3)cn2)nc2c1CCN2] | N-isopropyl-2-(2-(5-morpholinopyridin-2-ylamino)-6,7-dihydro-5H-pyrrolo[2,3-d]-pyrimidin-4-ylamino)-benzenesulfonamide | 511 | <20 | <50 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 59 | 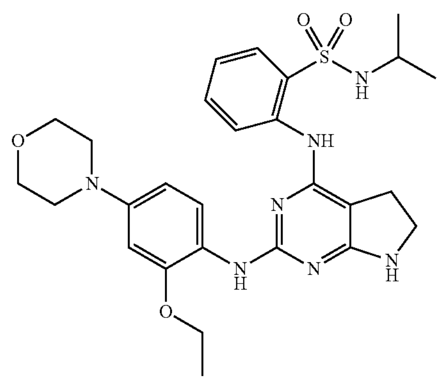 [SMILES: CCOc1cc(N2CCOCC2)ccc1Nc1nc2c(c(Nc3ccccc3S(=O)(=O)NC(C)C)n1)CCN2] | 2-(2-(2-ethoxy-4-morpholinophenylamino)-6,7-dihydro-5H-pyrrolo[2,3-d]pyrimidin-4-ylamino)-N-isopropylbenzenesulfonamide | 553 | <50 | <100 |
| 60 | 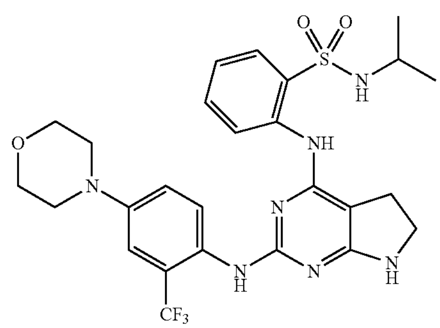 [SMILES: CC(C)NS(=O)(=O)c1ccccc1Nc1nc(Nc2ccc(N3CCOCC3)cc2C(F)(F)F)nc2c1CCN2] | N-isopropyl-2-(2-(4-morpholino-2-(trifluoromethyl)-phenylamino)-6,7-dihydro-5H-pyrrolo[2,3-d]pyrimidin-4-ylamino)benzenesulfonamide | 578 | <500 | >1000 |
| 61 | 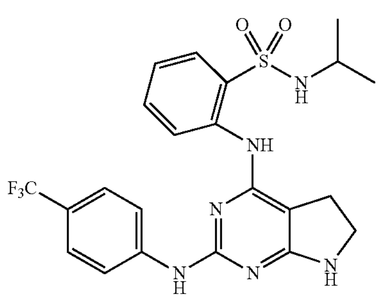 [SMILES: CC(C)NS(=O)(=O)c1ccccc1Nc1nc(Nc2ccc(C(F)(F)F)cc2)nc2c1CCN2] | N-isopropyl-2-(2-(4-(trifluoromethyl)phenylamino)-6,7-dihydro-5H-pyrrolo[2,3-d]pyrimidin-4-ylamino)-benzenesulfonamide | 493 | <1000 | <500 |
| 62 | 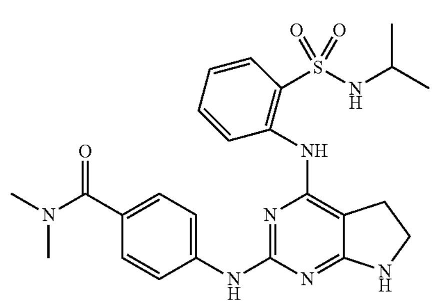 [SMILES: CC(C)NS(=O)(=O)c1ccccc1Nc1nc(Nc2ccc(C(=O)N(C)C)cc2)nc2c1CCN2] | 4-(4-(2-(N-isopropyl-sulfamoyl)phenylamino)-6,7-dihydro-5H-pyrrolo[2,3-d]pyrimidin-2-ylamino)-N,N-dimethylbenzamide | 496 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 63 | 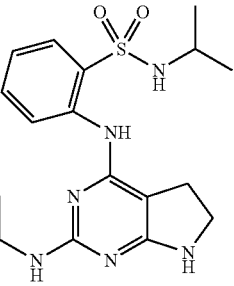 | N-(4-(4-(2-(N-isopropylsulfamoyl)-phenylamino)-6,7-dihydro-5H-pyrrolo[2,3-d]pyrimidin-2-ylamino)phenyl)acetamide | 482 | <20 | <20 |
| 64 | 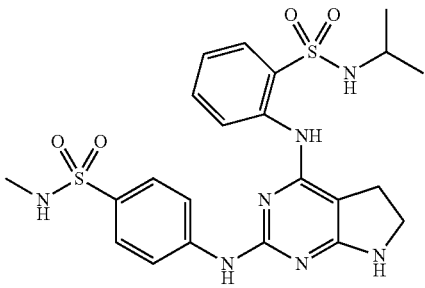 [SMILES: CNS(=O)(=O)c1ccc(Nc2nc3c(c(Nc4ccccc4S(=O)(=O)NC(C)C)n2)CCN3)cc1] | N-isopropyl-2-(2-(4-(N-methylsulfamoyl)phenyl-amino)-6,7-dihydro-5H-pyrrolo[2,3-d]pyrimidin-4-ylamino)-benzenesulfonamide | 518 | <20 | <20 |
| 65 | 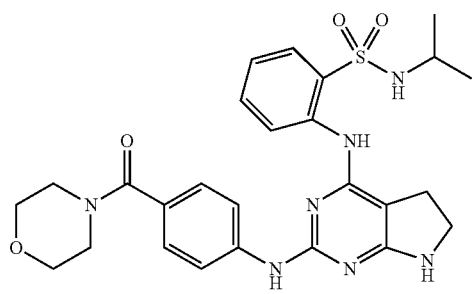 [SMILES: CC(C)NS(=O)(=O)c1ccccc1Nc1nc(Nc2ccc(C(=O)N3CCOCC3)cc2)nc2c1CCN2] | N-isopropyl-2-(2-(4-(morpholine-4-carbonyl)-phenylamino)-6,7-dihydro-5H-pyrrolo[2,3-d]pyrimidin-4-ylamino)-benzenesulfonamide | 538 | <20 | <20 |
| 66 | 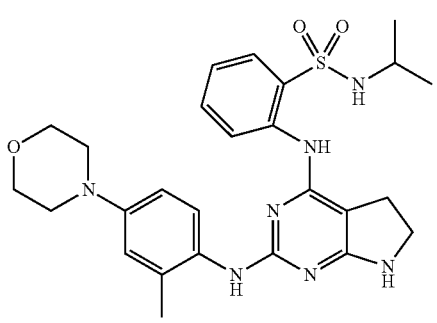 [SMILES: Cc1cc(N2CCOCC2)ccc1Nc1nc2c(c(Nc3ccccc3S(=O)(=O)NC(C)C)n1)CCN2] | N-isopropyl-2-(2-(2-methyl-4-morpholinophenyl-amino)-6,7-dihydro-5H-pyrrolo[2,3-d]pyrimidin-4-ylamino)-benzenesulfonamide | 524 | <20 | <50 |
| 67 | 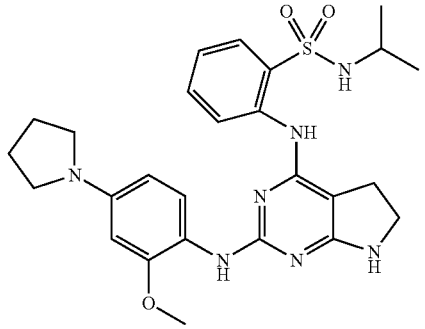 [SMILES: COc1cc(N2CCCC2)ccc1Nc1nc2c(c(Nc3ccccc3S(=O)(=O)NC(C)C)n1)CCN2] | N-isopropyl-2-(2-(2-methoxy-4-(pyrrolidin-1-yl)-phenylamino)-6,7-dihydro-5H-pyrrolo[2,3-d]pyrimidin-4-ylamino)benzenesulfonamide | 524 | <50 | <100 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 68 | 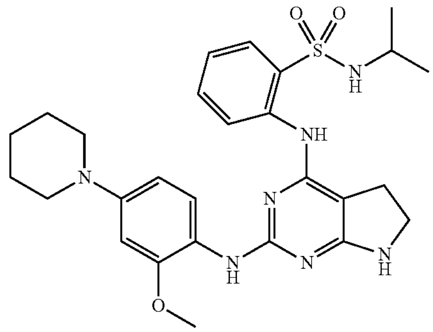 [SMILES: COc1cc(N2CCCCC2)ccc1Nc1nc2c(c(Nc3ccccc3S(=O)(=O)NC(C)C)n1)CCN2] | N-isopropyl-2-(2-(2-methoxy-4-(piperidin-1-yl)phenylamino)-6,7-dihydro-5H-pyrrolo[2,3-d]-pyrimidin-4-ylamino)-benzenesulfonamide | 538 | <50 | <200 |
| 69 | 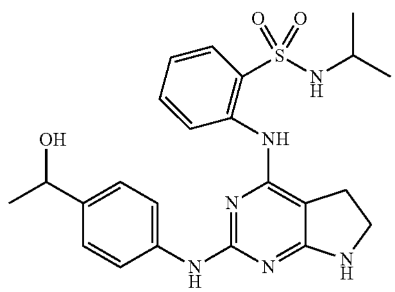 [SMILES: CC(C)NS(=O)(=O)c1ccccc1Nc1nc(Nc2ccc(C(C)O)cc2)nc2c1CCN2] | 2-(2-(4-(1-hydroxyethyl)-phenylamino)-6,7-dihydro-5H-pyrrolo[2,3-d]pyrimidin-4-ylamino)-N-isopropylbenzenesulfonamide | 469 | <20 | <20 |
| 70 | 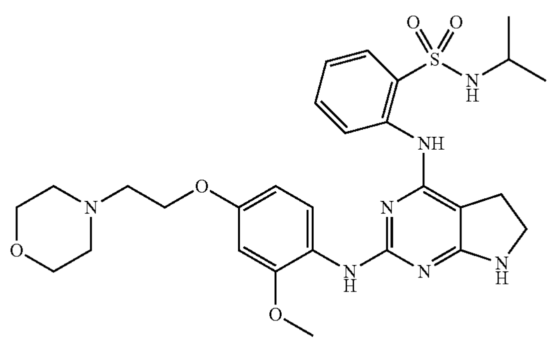 [SMILES: COc1cc(OCCN2CCOCC2)ccc1Nc1nc2c(c(Nc3ccccc3S(=O)(=O)NC(C)C)n1)CCN2] | N-isopropyl-2-(2-(2-methoxy-4-(2-morpholinoethoxy)-phenylamino)-6,7-dihydro-5H-pyrrolo[2,3-d]pyrimidin-4-ylamino)-benzenesulfonamide | 584 | <20 | <20 |
| 71 | 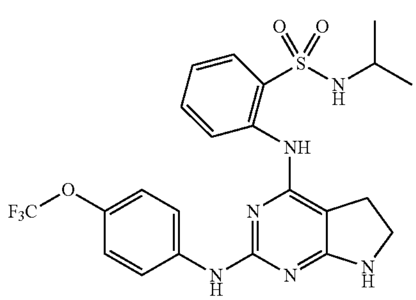 [SMILES: CC(C)NS(=O)(=O)c1ccccc1Nc1nc(Nc2ccc(OC(F)(F)F)cc2)nc2c1CCN2] | N-isopropyl-2-(2-(4-(trifluoromethoxy)-phenylamino)-6,7-dihydro-5H-pyrrolo[2,3-d]pyrimidin-4-ylamino)benzenesulfonamide | 509 | <200 | <100 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 72 | 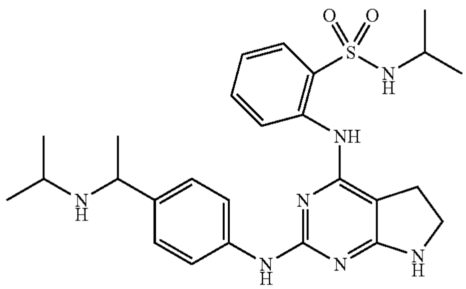 [SMILES: CC(C)NC(C)c1ccc(Nc2nc3c(c(Nc4ccccc4S(=O)(=O)NC(C)C)n2)CCN3)cc1] | N-isopropyl-2-(2-(4-(1-(isopropylamino)ethyl)-phenylamino)-6,7-dihydro-5H-pyrrolo[2,3-d]pyrimidin-4-ylamino)benzenesulfonamide | 510 | <20 | <20 |
| 73 | 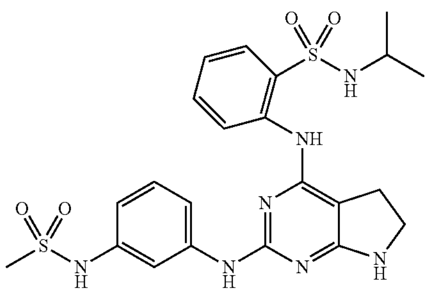 [SMILES: CC(C)NS(=O)(=O)c1ccccc1Nc1nc(Nc2cccc(NS(C)(=O)=O)c2)nc2c1CCN2] | N-isopropyl-2-(2-(3-(methylsulfonamido)-phenylamino)-6,7-dihydro-5H-pyrrolo[2,3-d]pyrimidin-4-ylamino)benzenesulfonamide | 518 | <20 | <20 |
| 74 | 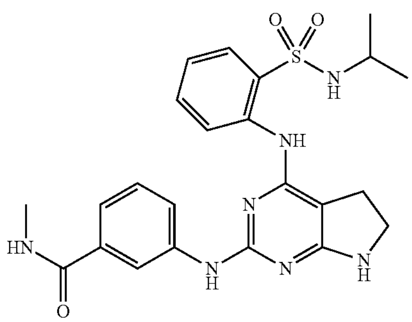 [SMILES: CNC(=O)c1cccc(Nc2nc3c(c(Nc4ccccc4S(=O)(=O)NC(C)C)n2)CCN3)c1] | 3-(4-(2-(N-isopropyl-sulfamoyl)phenylamino)-6,7-dihydro-5H-pyrrolo[2,3-d]pyrimidin-2-ylamino)-N-methylbenzamide | 482 | <20 | <50 |
| 75 | 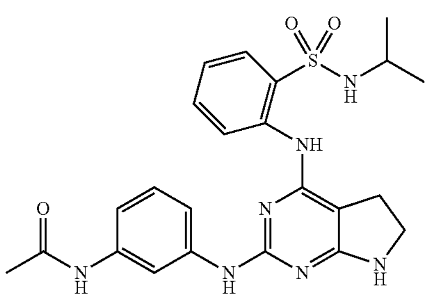 [SMILES: CC(=O)Nc1cccc(Nc2nc3c(c(Nc4ccccc4S(=O)(=O)NC(C)C)n2)CCN3)c1] | N-(3-(4-(2-(N-isopropylsulfamoyl)-phenylamino)-6,7-dihydro-5H-pyrrolo[2,3-d]pyrimidin-2-ylamino)phenyl)acetamide | 482 | <20 | <20 |
| 76 | 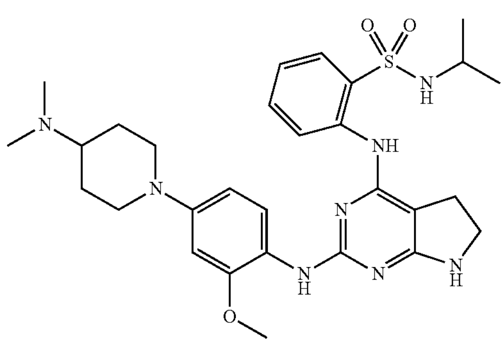 [SMILES: COc1cc(N2CCC(N(C)C)CC2)ccc1Nc1nc2c(c(Nc3ccccc3S(=O)(=O)NC(C)C)n1)CCN2] | 2-(2-(4-(4-(dimethylamino)-piperidin-1-yl)-2-methoxyphenylamino)-6,7-dihydro-5H-pyrrolo[2,3-d]pyrimidin-4-ylamino)-N-isopropylbenzenesulfonamide | 581 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 77 | 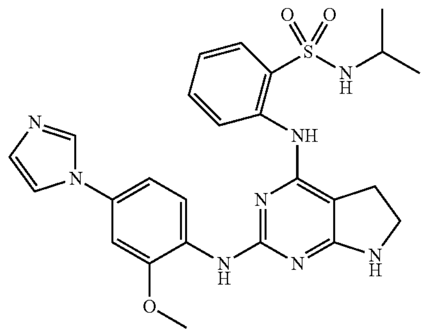 [SMILES: COc1cc(-n2ccnc2)ccc1Nc1nc2c(c(Nc3ccccc3S(=O)(=O)NC(C)C)n1)CCN2] | 2-(2-(4-(1H-imidazol-1-yl)-2-methoxyphenylamino)-6,7-dihydro-5H-pyrrolo[2,3-d]pyrimidin-4-ylamino)-N-isopropylbenzenesulfonamide | 521 | <500 | <500 |
| 78 | 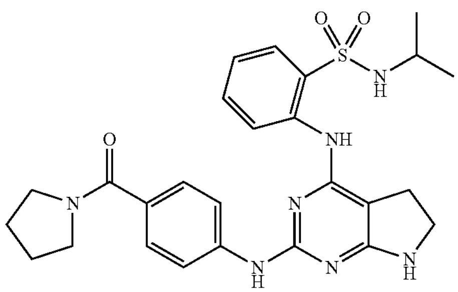 [SMILES: CC(C)NS(=O)(=O)c1ccccc1Nc1nc(Nc2ccc(C(=O)N3CCCC3)cc2)nc2c1CCN2] | N-isopropyl-2-(2-(4-(pyrrolidine-1-carbonyl)phenylamino)-6,7-dihydro-5H-pyrrolo[2,3-d]pyrimidin-4-ylamino)benzenesulfonamide | 522 | <20 | <20 |
| 79 | 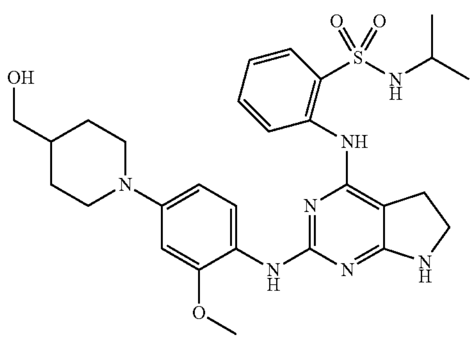 [SMILES: COc1cc(N2CCC(CO)CC2)ccc1Nc1nc2c(c(Nc3ccccc3S(=O)(=O)NC(C)C)n1)CCN2] | 2-(2-(4-(4-(hydroxymethyl)-piperidin-1-yl)-2-methoxyphenylamino)-6,7-dihydro-5H-pyrrolo[2,3-d]-pyrimidin-4-ylamino)-N-isopropylbenzenesulfonamide | 568 | <20 | <20 |
| 80 | 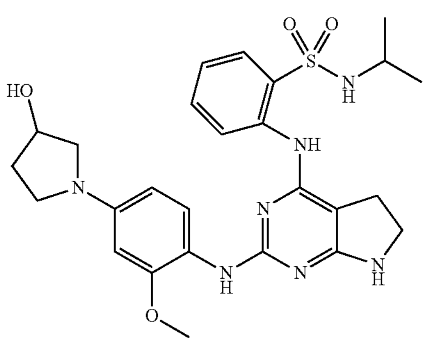 [SMILES: COc1cc(N2CCC(O)C2)ccc1Nc1nc2c(c(Nc3ccccc3S(=O)(=O)NC(C)C)n1)CCN2] | 2-(2-(4-(3-hydroxypyrrolidin-1-yl)-2-methoxyphenylamino)-6,7-dihydro-5H-pyrrolo[2,3-d]pyrimidin-4-ylamino)-N-isopropylbenzenesulfonamide | 540 | <20 | <100 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 81 | 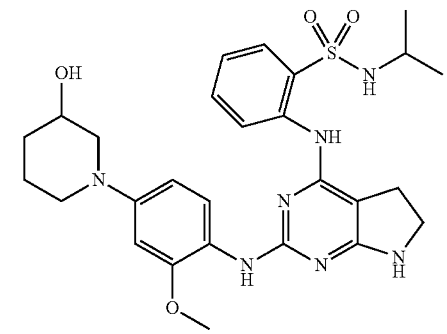 [SMILES: COc1cc(N2CCCC(O)C2)ccc1Nc1nc2c(c(Nc3ccccc3S(=O)(=O)NC(C)C)n1)CCN2] | 2-(2-(4-(3-hydroxypiperidin-1-yl)-2-methoxyphenylamino)-6,7-dihydro-5H-pyrrolo[2,3-d]pyrimidin-4-ylamino)-N-isopropylbenzenesulfonamide | 554 | <20 | <50 |
| 82 | 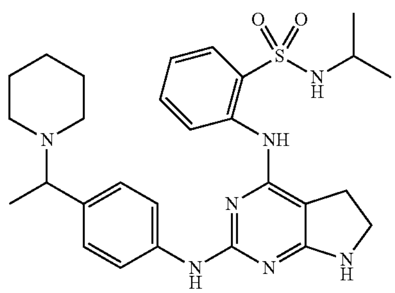 [SMILES: CC(C)NS(=O)(=O)c1ccccc1Nc1nc(Nc2ccc(C(C)N3CCCCC3)cc2)nc2c1CCN2] | N-isopropyl-2-(2-(4-(1-(piperidin-1-yl)ethyl)-phenylamino)-6,7-dihydro-5H-pyrrolo[2,3-d]pyrimidin-4-ylamino)benzenesulfonamide | 566 | <20 | <20 |
| 83 | 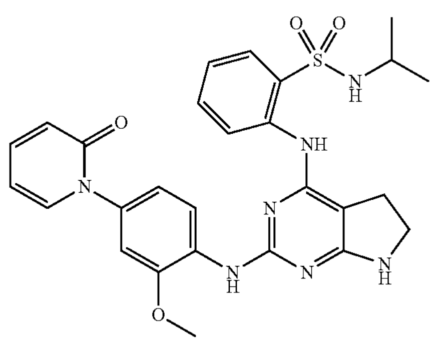 [SMILES: COc1cc(-n2ccccc2=O)ccc1Nc1nc2c(c(Nc3ccccc3S(=O)(=O)NC(C)C)n1)CCN2] | N-isopropyl-2-(2-(2-methoxy-4-(2-oxopyridin-1(2H)-yl)phenylamino)-6,7-dihydro-5H-pyrrolo[2,3-d]pyrimidin-4-ylamino)benzenesulfonamide | 548 | <20 | <20 |
| 84 | 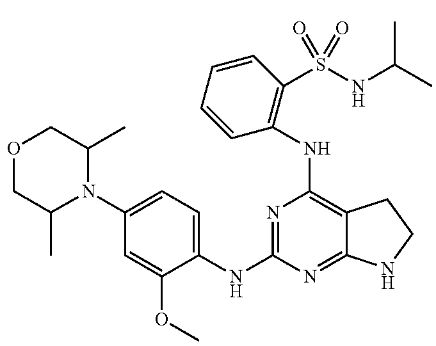 [SMILES: COc1cc(N2C(C)COCC2C)ccc1Nc1nc2c(c(Nc3ccccc3S(=O)(=O)NC(C)C)n1)CCN2] | 2-(2-(4-(3,5-dimethylmorpholino)-2-methoxyphenylamino)-6,7-dihydro-5H-pyrrolo[2,3-d]pyrimidin-4-ylamino)-N-isopropylbenzenesulfonamide | 568 | <50 | <100 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 85 | 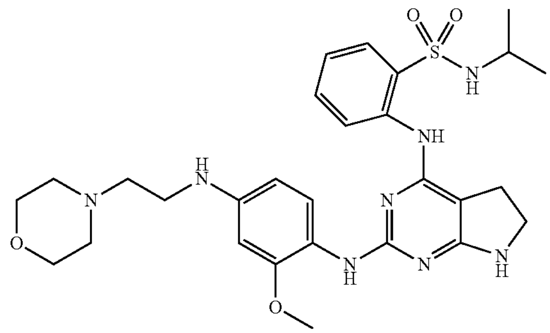 [SMILES: COc1cc(NCCN2CCOCC2)ccc1Nc1nc2c(c(Nc3ccccc3S(=O)(=O)NC(C)C)n1)CCN2] | N-isopropyl-2-(2-(2-methoxy-4-(2-morpholinoethylamino)phenylamino)-6,7-dihydro-5H-pyrrolo[2,3-d]pyrimidin-4-ylamino)-benzenesulfonamide | 583 | <20 | <20 |
| 86 | 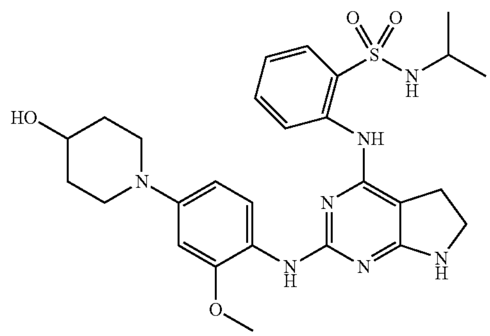 [SMILES: COc1cc(N2CCC(O)CC2)ccc1Nc1nc2c(c(Nc3ccccc3S(=O)(=O)NC(C)C)n1)CCN2] | 2-(2-(4-(4-hydroxypiperidin-1-yl)-2-methoxyphenylamino)-6,7-dihydro-5H-pyrrolo[2,3-d]pyrimidin-4-ylamino)-N-isopropylbenzenesulfonamide | 554 | <20 | <20 |
| 87 | 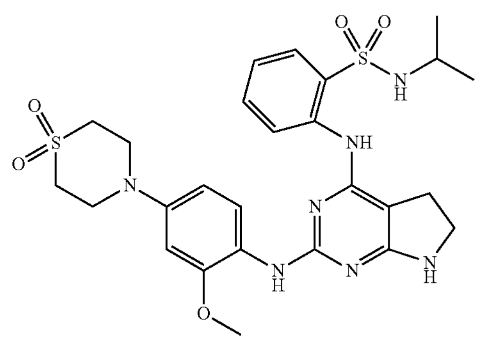 [SMILES: COc1cc(N2CCS(=O)(=O)CC2)ccc1Nc1nc2c(c(Nc3ccccc3S(=O)(=O)NC(C)C)n1)CCN2] | 2-(2-(4-(4-(S,S-dioxothio)piperidin-1-yl)-2-methoxyphenylamino)-6,7-dihydro-5H-pyrrolo[2,3-d]-pyrimidin-4-ylamino)-N-isopropylbenzenesulfonamide | 588 | <20 | <20 |
| 88 | 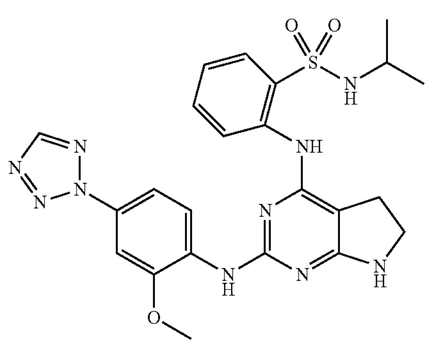 [SMILES: COc1cc(-n2ncnn2)ccc1Nc1nc2c(c(Nc3ccccc3S(=O)(=O)NC(C)C)n1)CCN2] | N-isopropyl-2-(2-(2-methoxy-4-(2H-tetrazol-2-yl)phenylamino)-6,7-dihydro-5H-pyrrolo[2,3-d]pyrimidin-4-ylamino)benzenesulfonamide | 523 | <50 | <200 |

TABLE 1-continued

Biological Activities of Selected Pyrrolo[2,3-d]pyrimidines of Formula (I)

| Ex # | Structure | Name | MS [M + H]+ | FAK IC50 (nM) | PYK2 IC50 (nM) |
|---|---|---|---|---|---|
| 89 | 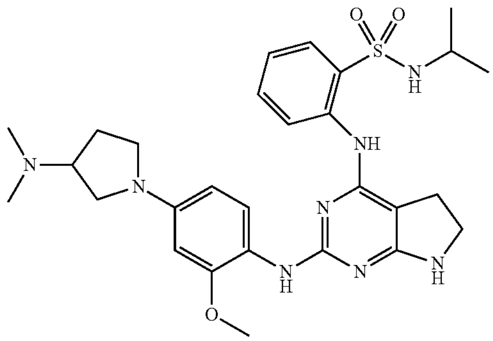 [SMILES: COc1cc(N2CCC(N(C)C)C2)ccc1Nc1nc2c(c(Nc3ccccc3S(=O)(=O)NC(C)C)n1)CCN2] | 2-(2-(4-(3-(dimethylamino)-pyrrolidin-1-yl)-2-methoxyphenylamino)-6,7-dihydro-5H-pyrrolo[2,3-d]pyrimidin-4-ylamino)-N-isopropylbenzenesulfonamide | 567 | <20 | <20 |
| 90 | 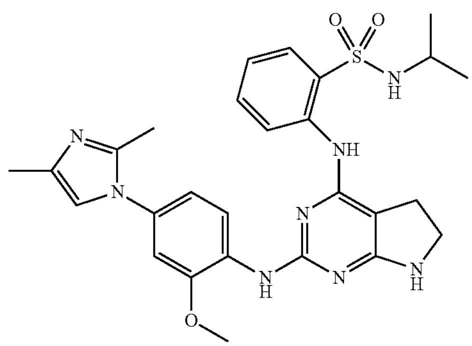 [SMILES: COc1cc(-n2cc(C)nc2C)ccc1Nc1nc2c(c(Nc3ccccc3S(=O)(=O)NC(C)C)n1)CCN2] | 2-(2-(4-(2,4-dimethyl-1H-imidazol-1-yl)-2-methoxyphenylamino)-6,7-dihydro-5H-pyrrolo[2,3-d]-pyrimidin-4-ylamino)-N-isopropylbenzenesulfonamide | 549 | <20 | <20 |
| 91 | 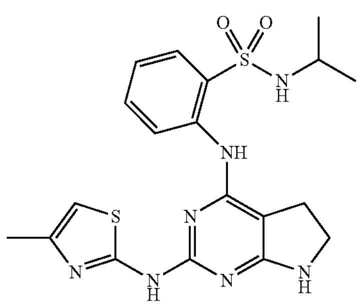 [SMILES: Cc1csc(Nc2nc3c(c(Nc4ccccc4S(=O)(=O)NC(C)C)n2)CCN3)n1] | N-isopropyl-2-(2-(4-methylthiazol-2-ylamino)-6,7-dihydro-5H-pyrrolo[2,3-d]-pyrimidin-4-ylamino)-benzenesulfonamide | 446 | >1000 | <1000 |
| 92 | 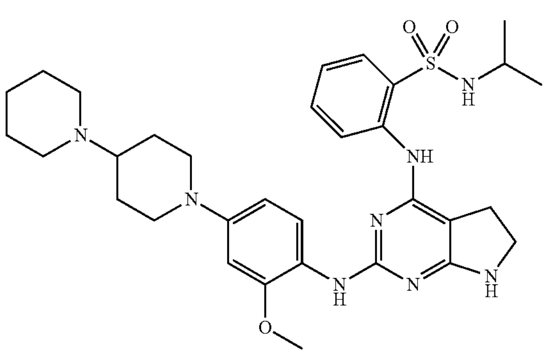 [SMILES: COc1cc(N2CCC(N3CCCCC3)CC2)ccc1Nc1nc2c(c(Nc3ccccc3S(=O)(=O)NC(C)C)n1)CCN2] | 2-(2-(4-(1,4'-bipiperidin-1'-yl)-2-methoxyphenyl-amino)-6,7-dihydro-5H-pyrrolo[2,3-d]pyrimidin-4-ylamino)-N-isopropyl-benzenesulfonamide | 621 | <20 | <20 |

TABLE 1-continued

Biological Activities of Selected Pyrrolo[2,3-d]pyrimidines of Formula (I)

| Ex # | Structure | Name | MS [M + H]⁺ | FAK IC$_{50}$ (nM) | PYK2 IC$_{50}$ (nM) |
|---|---|---|---|---|---|
| 93 | 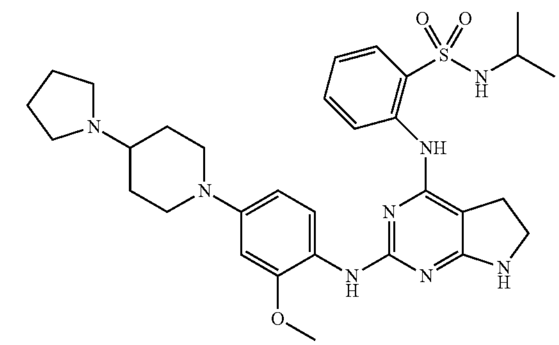 [SMILES: COc1cc(N2CCC(N3CCCC3)CC2)ccc1Nc1nc2c(c(Nc3ccccc3S(=O)(=O)NC(C)C)n1)CCN2] | N-isopropyl-2-(2-(2-methoxy-4-(4-(pyrrolidin-1-yl)-piperidin-1-yl)phenylamino)-6,7-dihydro-5H-pyrrolo-[2,3-d]pyrimidin-4-ylamino)benzenesulfonamide | 607 | <20 | <20 |
| 94 | 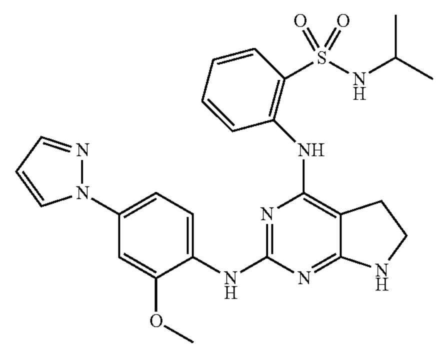 [SMILES: COc1cc(-n2cccn2)ccc1Nc1nc2c(c(Nc3ccccc3S(=O)(=O)NC(C)C)n1)CCN2] | N-isopropyl-2-(2-(2-methoxy-4-(1H-pyrazol-1-yl)-phenylamino)-6,7-dihydro-5H-pyrrolo[2,3-d]-pyrimidin-4-ylamino)-benzenesulfonamide | 521 | <50 | <200 |
| 95 | 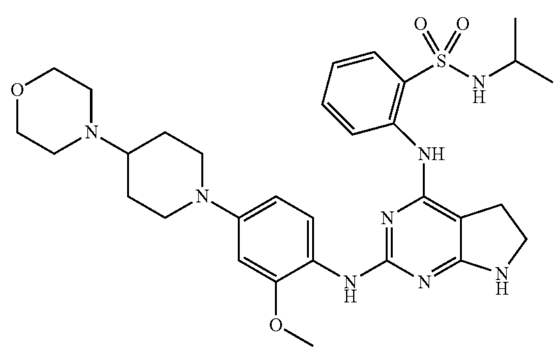 [SMILES: COc1cc(N2CCC(N3CCOCC3)CC2)ccc1Nc1nc2c(c(Nc3ccccc3S(=O)(=O)NC(C)C)n1)CCN2] | N-isopropyl-2-(2-(2-methoxy-4-(4-morpholinopiperidin-1-yl)phenylamino)-6,7-dihydro-5H-pyrrolo[2,3-d]-pyrimidin-4-ylamino)-benzenesulfonamide | 621 | <20 | <20 |
| 96 | 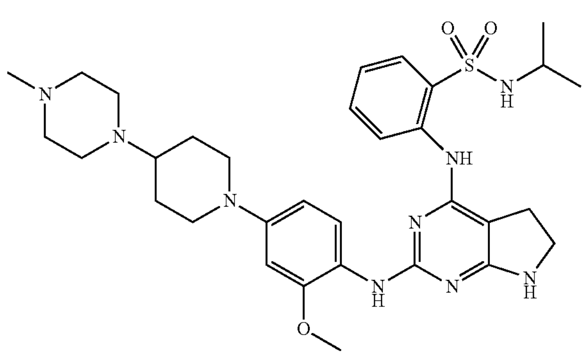 [SMILES: COc1cc(N2CCC(N3CCN(C)CC3)CC2)ccc1Nc1nc2c(c(Nc3ccccc3S(=O)(=O)NC(C)C)n1)CCN2] | N-isopropyl-2-(2-(2-methoxy-4-(4-(4-methylpiperazin-1-yl)-piperidin-1-yl)phenylamino)-6,7-dihydro-5H-pyrrolo[2,3-d]pyrimidin-4-ylamino)-benzenesulfonamide | 636 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 97 | 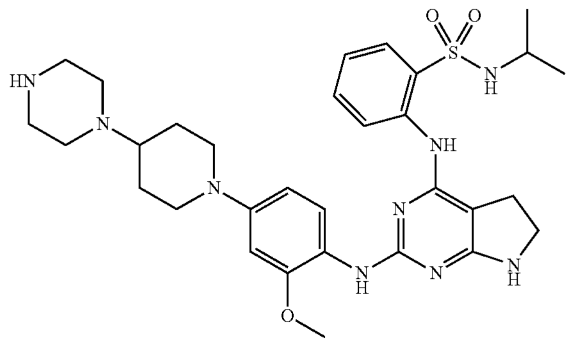 [SMILES: COc1cc(N2CCC(N3CCNCC3)CC2)ccc1Nc1nc2c(c(Nc3ccccc3S(=O)(=O)NC(C)C)n1)CCN2] | N-isopropyl-2-(2-(2-methoxy-4-(4-(piperazin-1-yl)piperidin-1-yl)phenylamino)-6,7-dihydro-5H-pyrrolo[2,3-d]pyrimidin-4-ylamino)benzenesulfonamide | 622 | <100 | <500 |
| 98 | 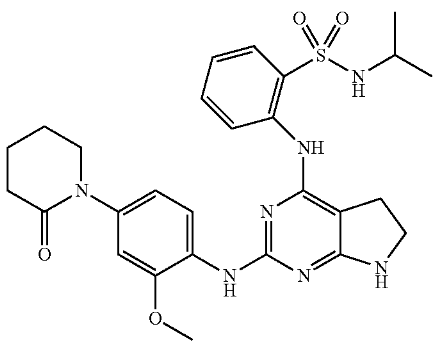 [SMILES: COc1cc(N2CCCCC2=O)ccc1Nc1nc2c(c(Nc3ccccc3S(=O)(=O)NC(C)C)n1)CCN2] | N-isopropyl-2-(2-(2-methoxy-4-(2-oxopiperidin-1-yl)phenylamino)-6,7-dihydro-5H-pyrrolo[2,3-d]-pyrimidin-4-ylamino)benzenesulfonamide | 635 | <20 | <20 |
| 99 | 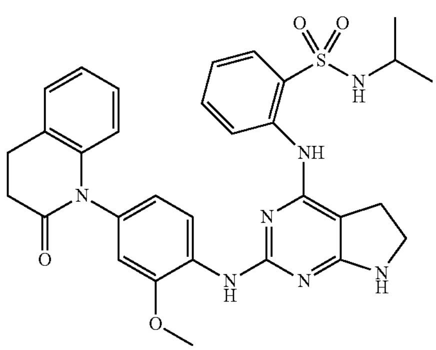 [SMILES: COc1cc(N2C(=O)CCc3ccccc32)ccc1Nc1nc2c(c(Nc3ccccc3S(=O)(=O)NC(C)C)n1)CCN2] | N-isopropyl-2-(2-(2-methoxy-4-(2-oxo-3,4-dihydroquinolin-1(2H)-yl)phenylamino)-6,7-dihydro-5H-pyrrolo[2,3-d]pyrimidin-4-ylamino)benzenesulfonamide | 683 | <500 | <500 |
| 100 | 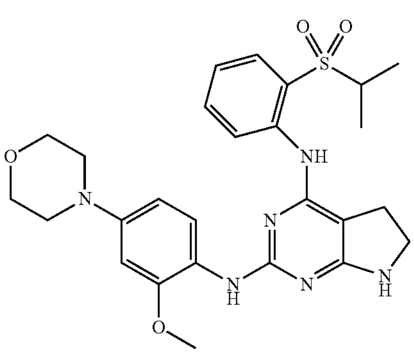 [SMILES: COc1cc(N2CCOCC2)ccc1Nc1nc2c(c(Nc3ccccc3S(=O)(=O)C(C)C)n1)CCN2] | N$^4$-(2-(isopropylsulfonyl)-phenyl)-N$^2$-(2-methoxy-4-morpholinophenyl)-6,7-dihydro-5H-pyrrolo[2,3-d]pyrimidine-2,4-diamine | 525 | <20 | <50 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 101 | 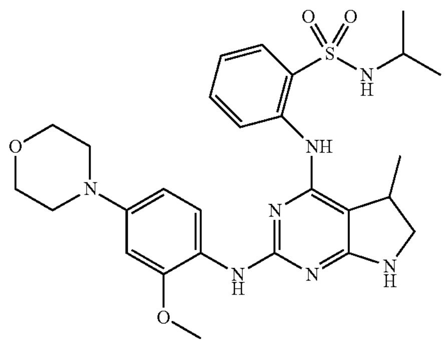 [SMILES: COc1cc(N2CCOCC2)ccc1Nc1nc2c(c(Nc3ccccc3S(=O)(=O)NC(C)C)n1)C(C)CN2] | N-isopropyl-2-(2-(2-methoxy-4-morpholinophenylamino)-5-methyl-6,7-dihydro-5H-pyrrolo[2,3-d]-pyrimidin-4-ylamino)-benzenesulfonamide | 554 | <20 | <20 |
| 102 | 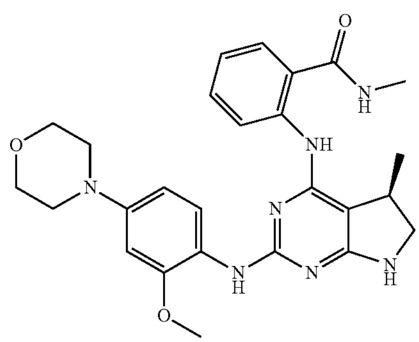 [SMILES: CNC(=O)c1ccccc1Nc1nc(Nc2ccc(N3CCOCC3)cc2OC)nc2c1[C@@H](C)CN2] | (R)-2-(2-(2-methoxy-4-morpholinophenylamino)-5-methyl-6,7-dihydro-5H-pyrrolo[2,3-d]pyrimidin-4-ylamino)-N-methylbenzamide | 490 | <20 | <50 |
| 103 | 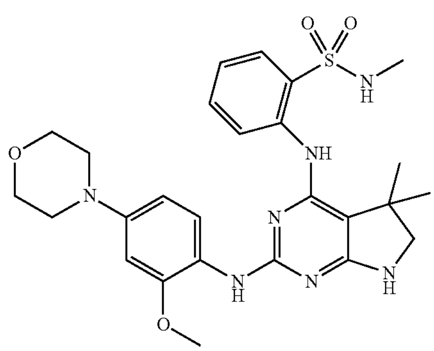 [SMILES: CNS(=O)(=O)c1ccccc1Nc1nc(Nc2ccc(N3CCOCC3)cc2OC)nc2c1C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N-methylbenzenesulfonamide | 540 | <20 | <20 |
| 104 | 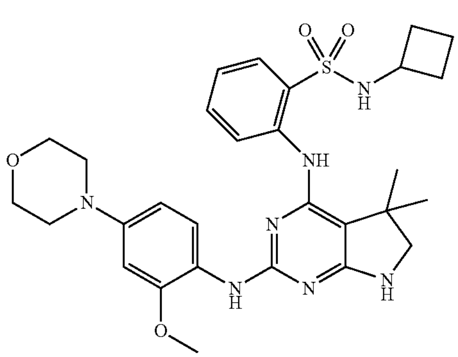 [SMILES: COc1cc(N2CCOCC2)ccc1Nc1nc2c(c(Nc3ccccc3S(=O)(=O)NC3CCC3)n1)C(C)(C)CN2] | N-cyclobutyl-2-(2-(2-methoxy-4-morpholinophenylamino)-5,5-dimethyl-6,7-dihydro-5H-pyrrolo[2,3-d]-pyrimidin-4-ylamino)-benzenesulfonamide | 580 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
| --- | --- | --- | --- | --- | --- |
| 105 | 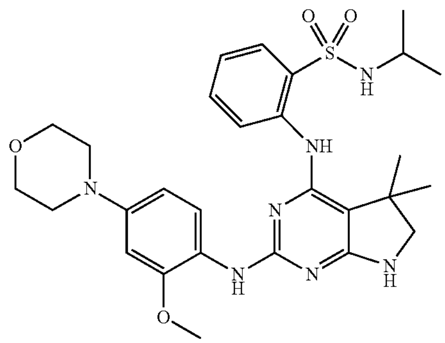 [SMILES: COc1cc(N2CCOCC2)ccc1Nc1nc2c(c(Nc3ccccc3S(=O)(=O)NC(C)C)n1)C(C)(C)CN2] | N-isopropyl-2-(2-(2-methoxy-4-morpholino-phenylamino)-5,5-dimethyl-6,7-dihydro-5H-pyrrolo-[2,3-d]pyrimidin-4-ylamino)-benzenesulfonamide | 568 | <20 | <20 |
| 106 | 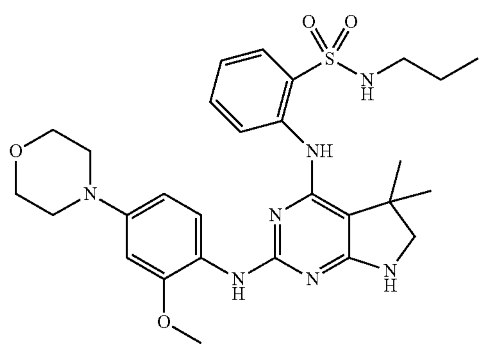 [SMILES: CCCNS(=O)(=O)c1ccccc1Nc1nc(Nc2ccc(N3CCOCC3)cc2OC)nc2c1C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N-propylbenzenesulfonamide | 568 | <20 | <20 |
| 107 | 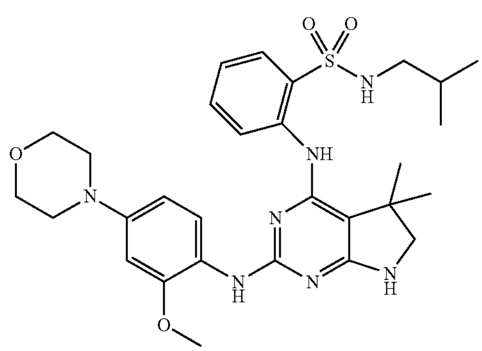 [SMILES: COc1cc(N2CCOCC2)ccc1Nc1nc2c(c(Nc3ccccc3S(=O)(=O)NCC(C)C)n1)C(C)(C)CN2] | N-isobutyl-2-(2-(2-methoxy-4-morpholinophenylamino)-5,5-dimethyl-6,7-dihydro-5H-pyrrolo[2,3-d]pyrimidin-4-ylamino)benzenesulfonamide | 582 | <20 | <20 |
| 108 | 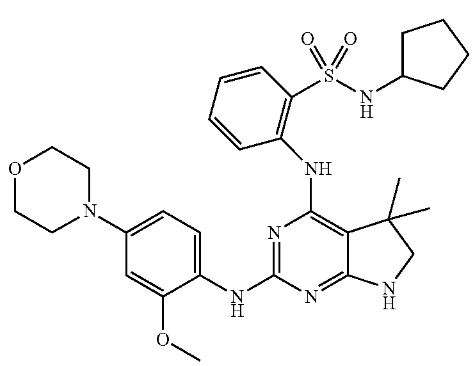 [SMILES: COc1cc(N2CCOCC2)ccc1Nc1nc2c(c(Nc3ccccc3S(=O)(=O)NC3CCCC3)n1)C(C)(C)CN2] | N-cyclopentyl-2-(2-(2-methoxy-4-morpholino-phenylamino)-5,5-dimethyl-6,7-dihydro-5H-pyrrolo[2,3-d]pyrimidin-4-ylamino)-benzenesulfonamide | 594 | <200 | <500 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 109 | 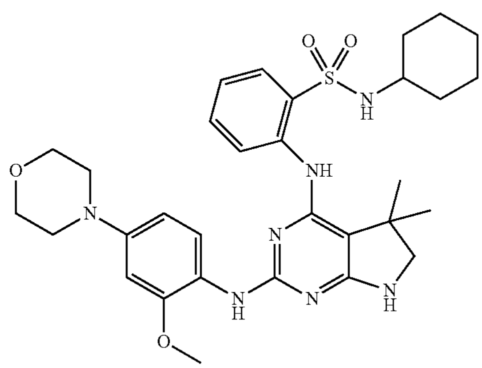 [SMILES: COc1cc(N2CCOCC2)ccc1Nc1nc2c(c(Nc3ccccc3S(=O)(=O)NC3CCCCC3)n1)C(C)(C)CN2] | N-cyclohexyl-2-(2-(2-methoxy-4-morpholino-phenylamino)-5,5-dimethyl-6,7-dihydro-5H-pyrrolo-[2,3-d]pyrimidin-4-ylamino)-benzenesulfonamide | 608 | <200 | <200 |
| 110 | 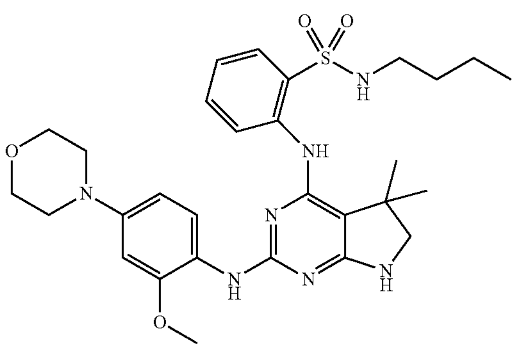 | N-butyl-2-(2-(2-methoxy-4-morpholinophenylamino)-5,5-dimethyl-6,7-dihydro-5H-pyrrolo[2,3-d]-pyrimidin-4-ylamino)-benzenesulfonamide | 582 | <20 | <20 |
| 111 | 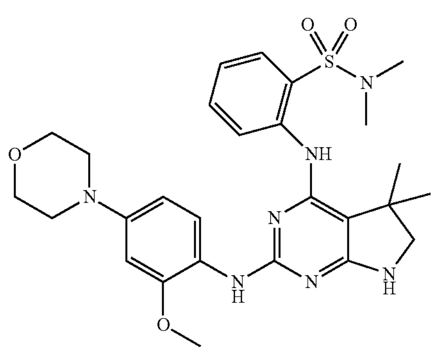 [SMILES: COc1cc(N2CCOCC2)ccc1Nc1nc2c(c(Nc3ccccc3S(=O)(=O)N(C)C)n1)C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N,N-dimethyl-benzenesulfonamide | 554 | <20 | <20 |
| 112 | 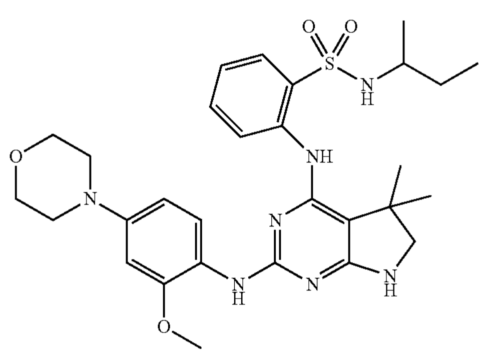 [SMILES: CCC(C)NS(=O)(=O)c1ccccc1Nc1nc(Nc2ccc(N3CCOCC3)cc2OC)nc2c1C(C)(C)CN2] | N-sec-butyl-2-(2-(2-methoxy-4-morpholino-phenylamino)-5,5-dimethyl-6,7-dihydro-5H-pyrrolo[2,3-d]pyrimidin-4-ylamino)-benzenesulfonamide | 582 | <20 | <20 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 113 | 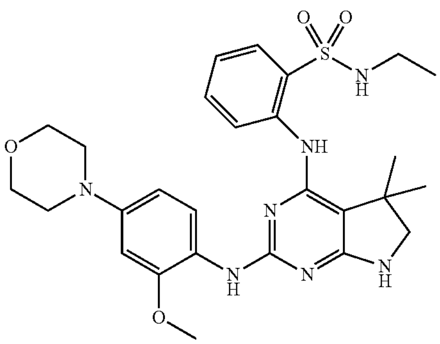 [SMILES: CCNS(=O)(=O)c1ccccc1Nc1nc(Nc2ccc(N3CCOCC3)cc2OC)nc2c1C(C)(C)CN2] | N-ethyl-2-(2-(2-methoxy-4-morpholinophenylamino)-5,5-dimethyl-6,7-dihydro-5H-pyrrolo[2,3-d]-pyrimidin-4-ylamino)-benzenesulfonamide | 554 | <20 | <20 |
| 114 | 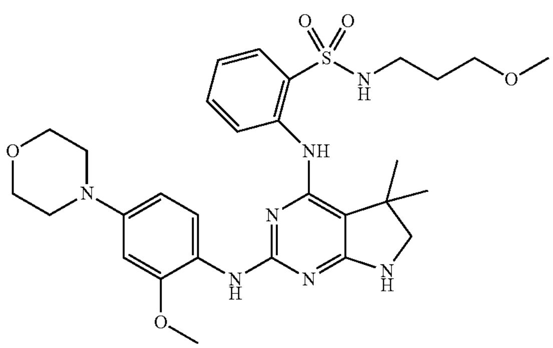 [SMILES: COCCCNS(=O)(=O)c1ccccc1Nc1nc(Nc2ccc(N3CCOCC3)cc2OC)nc2c1C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N-(3-methoxypropyl)-benzenesulfonamide | 598 | <20 | <20 |
| 115 | 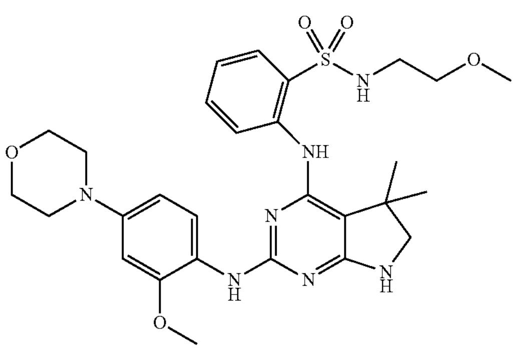 [SMILES: COCCNS(=O)(=O)c1ccccc1Nc1nc(Nc2ccc(N3CCOCC3)cc2OC)nc2c1C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N-(2-methoxyethyl)-benzenesulfonamide | 584 | <20 | <20 |
| 116 | 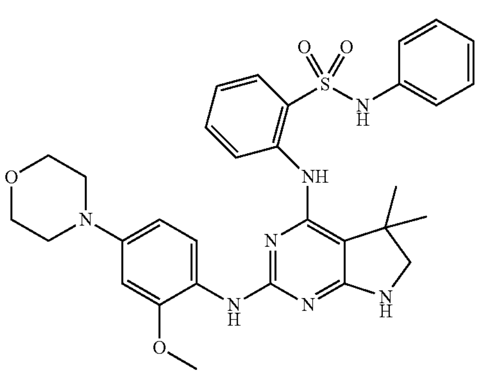 [SMILES: COc1cc(N2CCOCC2)ccc1Nc1nc2c(c(Nc3ccccc3S(=O)(=O)Nc3ccccc3)n1)C(C)(C)CN2] | 2-(2-(2-methoxy-4-morpholinophenylamino)-5,5-dimethyl-6,7-dihydro-5H-pyrrolo[2,3-d]pyrimidin-4-ylamino)-N-phenylbenzenesulfonamide | 602 | <200 | <500 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 117 | 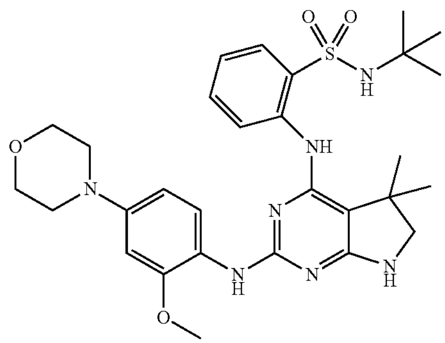 [SMILES: COc1cc(N2CCOCC2)ccc1Nc1nc2c(c(Nc3ccccc3S(=O)(=O)NC(C)(C)C)n1)C(C)(C)CN2] | N-tert-butyl-2-(2-(2-methoxy-4-morpholino-phenylamino)-5,5-dimethyl-6,7-dihydro-5H-pyrrolo[2,3-d]pyrimidin-4-ylamino)-benzenesulfonamide | 582 | <20 | <20 |
| 118 | 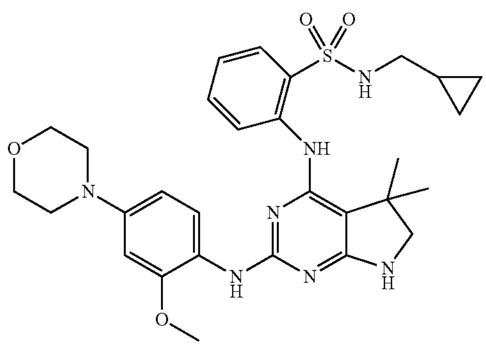 [SMILES: COc1cc(N2CCOCC2)ccc1Nc1nc2c(c(Nc3ccccc3S(=O)(=O)NCC3CC3)n1)C(C)(C)CN2] | N-(cyclopropylmethyl)-2-(2-(2-methoxy-4-morpholinophenylamino)-5,5-dimethyl-6,7-dihydro-5H-pyrrolo[2,3-d]pyrimidin-4-ylamino)-benzenesulfonamide | 580 | <50 | <50 |
| 119 | 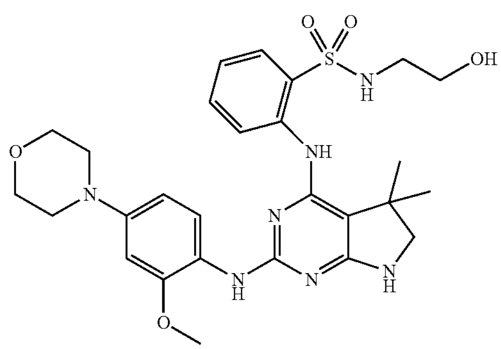 [SMILES: COc1cc(N2CCOCC2)ccc1Nc1nc2c(c(Nc3ccccc3S(=O)(=O)NCCO)n1)C(C)(C)CN2] | N-(2-hydroxyethyl)-2-(2-(2-methoxy-4-morpholino-phenylamino)-5,5-dimethyl-6,7-dihydro-5H-pyrrolo[2,3-d]pyrimidin-4-ylamino)-benzenesulfonamide | 570 | <500 | <200 |
| 120 | 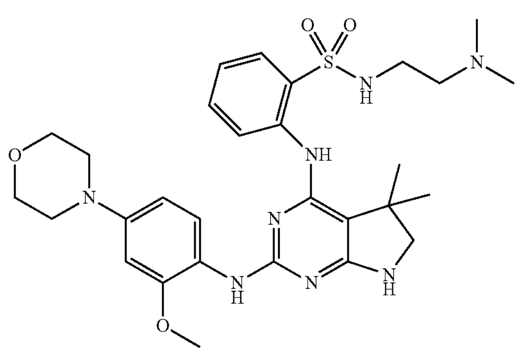 | N-(2-(dimethylamino)-ethyl)-2-(2-(2-methoxy-4-morpholinophenylamino)-5,5-dimethyl-6,7-dihydro-5H-pyrrolo[2,3-d]-pyrimidin-4-ylamino)-benzenesulfonamide | 597 | <20 | <50 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 121 | 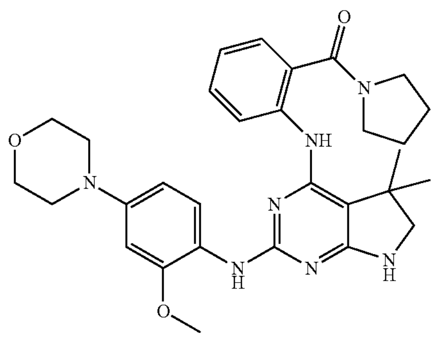 [SMILES: COc1cc(N2CCOCC2)ccc1Nc1nc2c(c(Nc3ccccc3C(=O)N3CCCC3)n1)C(C)(C)CN2] | (2-(2-(2-methoxy-4-morpholinophenylamino)-5,5-dimethyl-6,7-dihydro-5H-pyrrolo[2,3-d]pyrimidin-4-ylamino)phenyl)-(pyrrolidin-1-yl)methanone | 544 | <200 | <200 |
| 122 | 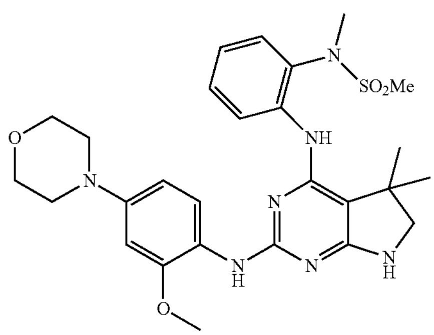 [SMILES: COc1cc(N2CCOCC2)ccc1Nc1nc2c(c(Nc3ccccc3N(C)S(C)(=O)=O)n1)C(C)(C)CN2] | N-(2-(2-(2-methoxy-4-morpholinophenylamino)-5,5-dimethyl-6,7-dihydro-5H-pyrrolo[2,3-d]-pyrimidin-4-ylamino)-phenyl)-N-methyl-methanesulfonamide | 554 | <50 | <100 |
| 123 | 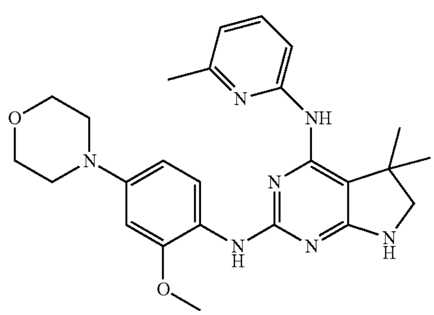 [SMILES: COc1cc(N2CCOCC2)ccc1Nc1nc2c(c(Nc3cccc(C)n3)n1)C(C)(C)CN2] | N$^2$-(2-methoxy-4-morpholinophenyl)-5,5-dimethyl-N$^4$-(6-methylpyridin-2-yl)-6,7-dihydro-5H-pyrrolo-[2,3-d]pyrimidine-2,4-diamine | 462 | <200 | <500 |
| 124 | 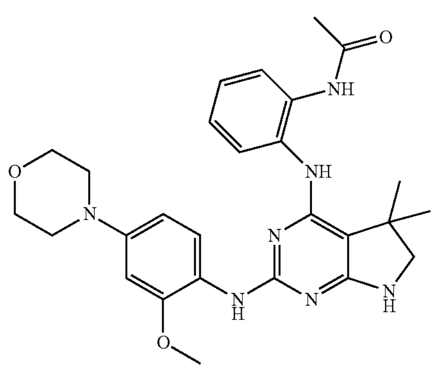 [SMILES: COc1cc(N2CCOCC2)ccc1Nc1nc2c(c(Nc3ccccc3NC(C)=O)n1)C(C)(C)CN2] | N-(2-(2-(2-methoxy-4-morpholinophenylamino)-5,5-dimethyl-6,7-dihydro-5H-pyrrolo[2,3-d]-pyrimidin-4-ylamino)-phenyl)acetamide | 504 | <200 | <200 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 125 | 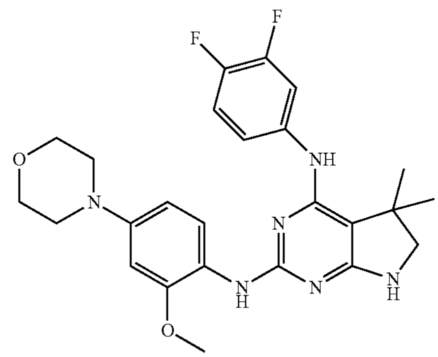 [SMILES: COc1cc(N2CCOCC2)ccc1Nc1nc2c(c(Nc3ccc(F)c(F)c3)n1)C(C)(C)CN2] | N$^4$-(3,4-difluorophenyl)-N2-(2-methoxy-4-morpholinophenyl)-5,5-dimethyl-6,7-dihydro-5H-pyrrolo[2,3-d]pyrimidine-2,4-diamine | 483 | <1000 | >1000 |
| 126 | 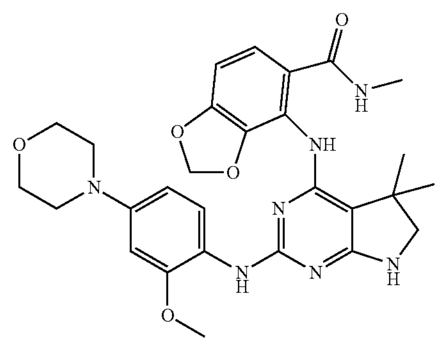 [SMILES: CNC(=O)c1ccc2c(c1Nc1nc(Nc3ccc(N4CCOCC4)cc3OC)nc3c1C(C)(C)CN3)OCO2] | 4-(2-(2-methoxy-4-morpholinophenylamino)-5,5-dimethyl-6,7-dihydro-5H-pyrrolo[2,3-d]pyrimidin-4-ylamino)-N-methylbenzo-[d][1,3]dioxole-5-carboxamide | 548 | <1000 | >1000 |
| 127 | 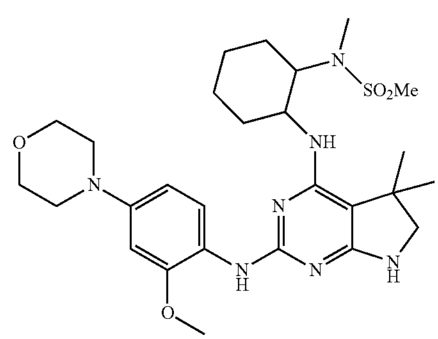 [SMILES: COc1cc(N2CCOCC2)ccc1Nc1nc2c(c(NC3CCCCC3N(C)S(C)(=O)=O)n1)C(C)(C)CN2] | N-(2-(2-(2-methoxy-4-morpholinophenylamino)-5,5-dimethyl-6,7-dihydro-5H-pyrrolo[2,3-d]-pyrimidin-4-ylamino)-cyclohexyl)-N-methylmethanesulfonamide | 560 | <100 | <100 |
| 128 | 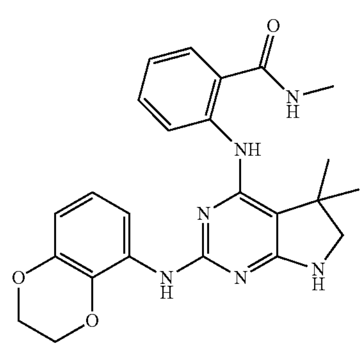 [SMILES: CNC(=O)c1ccccc1Nc1nc(Nc2cccc3c2OCCO3)nc2c1C(C)(C)CN2] | 2-(2-(2,3-dihydrobenzo[b][1,4]dioxin-5-ylamino)-5,5-dimethyl-6,7-dihydro-5H-pyrrolo[2,3-d]pyrimidin-4-ylamino)-N-methylbenzamide | 447 | <20 | <20 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 129 | 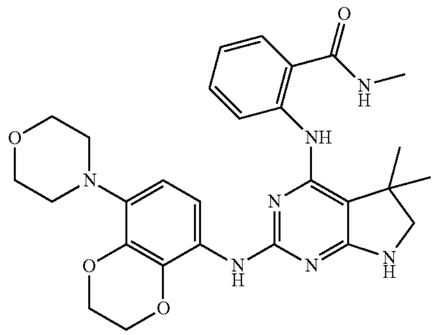 [SMILES: CNC(=O)c1ccccc1Nc1nc(Nc2ccc(N3CCOCC3)c3c2OCCO3)nc2c1C(C)(C)CN2] | 2-(5,5-dimethyl-2-(8-morpholino-2,3-dihydrobenzo-[b][1,4]dioxin-5-ylamino)-6,7-dihydro-5H-pyrrolo[2,3-d]pyrimidin-4-ylamino)-N-methylbenzamide | 532 | <50 | <100 |
| 130 | 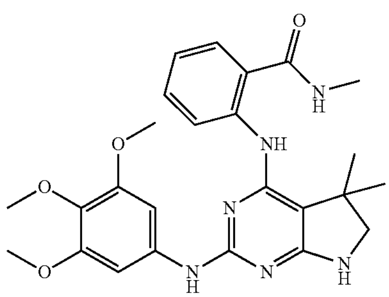 | 2-(5,5-dimethyl-2-(3,4,5-trimethoxyphenylamino)-6,7-dihydro-5H-pyrrolo-[2,3-d]pyrimidin-4-ylamino)-N-methylbenzamide | 479 | <200 | <200 |
| 131 | 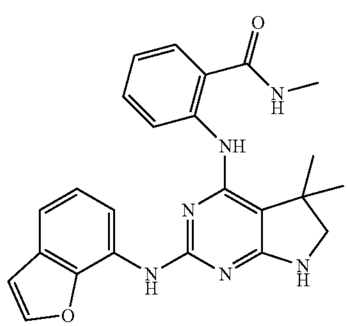 [SMILES: CNC(=O)c1ccccc1Nc1nc(Nc2cccc3ccoc23)nc2c1C(C)(C)CN2] | 2-(2-(benzofuran-7-ylamino)-5,5-dimethyl-6,7-dihydro-5H-pyrrolo[2,3-d]pyrimidin-4-ylamino)-N-methylbenzamide | 429 | <20 | <20 |
| 132 | 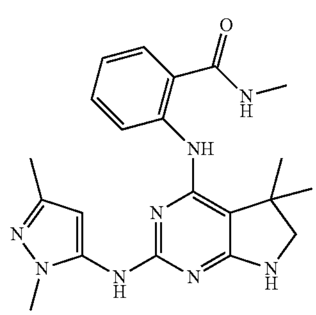 [SMILES: CNC(=O)c1ccccc1Nc1nc(Nc2cc(C)nn2C)nc2c1C(C)(C)CN2] | 2-(2-(1,3-dimethyl-1H-pyrazol-5-ylamino)-5,5-dimethyl-6,7-dihydro-5H-pyrrolo[2,3-d]pyrimidin-4-ylamino)-N-methylbenzamide | 407 | <20 | <50 |

TABLE 1-continued

Biological Activities of Selected Pyrrolo[2,3-d]pyrimidines of Formula (I)

| Ex # | Structure | Name | MS [M + H]$^+$ | FAK IC$_{50}$ (nM) | PYK2 IC$_{50}$ (nM) |
|---|---|---|---|---|---|
| 133 | 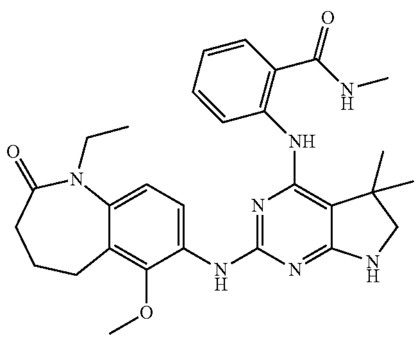 [SMILES: CCN1C(=O)CCCc2c1ccc(Nc1nc3c(c(Nc4ccccc4C(=O)NC)n1)C(C)(C)CN3)c2OC] | 2-(2-(1-ethyl-6-methoxy-2-oxo-2,3,4,5-tetrahydro-1H-benzo[b]azepin-7-ylamino)-5,5-dimethyl-6,7-dihydro-5H-pyrrolo-[2,3-d]pyrimidin-4-ylamino)-N-methylbenzamide | 530 | <20 | <50 |
| 134 | 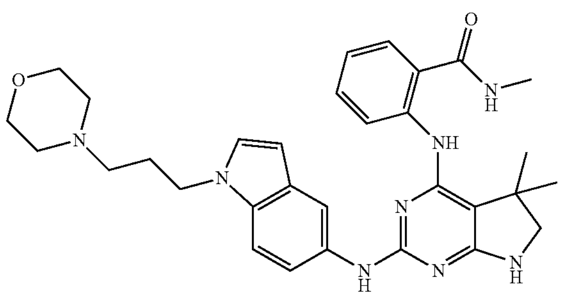 [SMILES: CNC(=O)c1ccccc1Nc1nc(Nc2ccc3c(ccn3CCCN3CCOCC3)c2)nc2c1C(C)(C)CN2] | 2-(5,5-dimethyl-2-(1-(3-morpholinopropyl)-1H-indol-5-ylamino)-6,7-dihydro-5H-pyrrolo[2,3-d]pyrimidin-4-ylamino)-N-methylbenzamide | 555 | <200 | <200 |
| 135 | 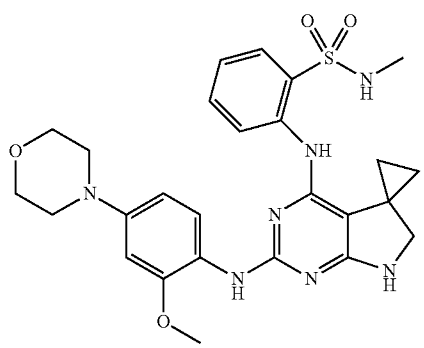 [SMILES: CNS(=O)(=O)c1ccccc1Nc1nc(Nc2ccc(N3CCOCC3)cc2OC)nc2c1C1(CC1)CN2] | 2-(2'-(2-methoxy-4-morpholinophenylamino)-6',7'-dihydrospiro-[cyclopropane-1,5'-pyrrolo[2,3-d]-pyrimidine]-4'-ylamino)-N-methylbenzenesulfonamide | 538 | <50 | <20 |
| 136 | 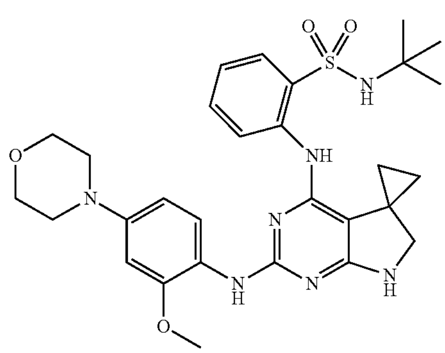 [SMILES: COc1cc(N2CCOCC2)ccc1Nc1nc2c(c(Nc3ccccc3S(=O)(=O)NC(C)(C)C)n1)C1(CC1)CN2] | N-tert-butyl-2-(2'-(2-methoxy-4-morpholino-phenylamino)-6',7'-dihydrospiro[cyclopropane-1,5'-pyrrolo[2,3-d]-pyrimidine]-4'-ylamino)-benzenesulfonamide | 580 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 137 | 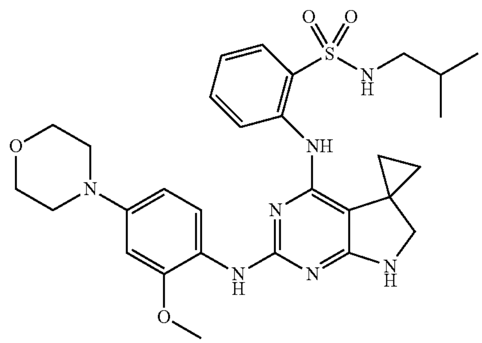 [SMILES: COc1cc(N2CCOCC2)ccc1Nc1nc2c(c(Nc3ccccc3S(=O)(=O)NCC(C)C)n1)C1(CC1)CN2] | N-isobutyl-2-(2'-(2-methoxy-4-morpholino-phenylamino)-6',7'-dihydrospiro-[cyclopropane-1,5'-pyrrolo[2,3-d]pyrimidine]-4'-ylamino)benzenesulfonamide | 580 | <20 | <20 |
| 138 | 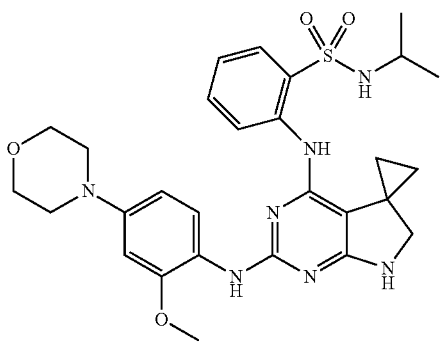 [SMILES: COc1cc(N2CCOCC2)ccc1Nc1nc2c(c(Nc3ccccc3S(=O)(=O)NC(C)C)n1)C1(CC1)CN2] | N-isopropyl-2-(2'-(2-methoxy-4-morpholino-phenylamino)-6',7'-dihydrospiro-[cyclopropane-1,5'-pyrrolo[2,3-d]pyrimidine]-4'-ylamino)-benzenesulfonamide | 566 | <20 | <20 |
| 139 | 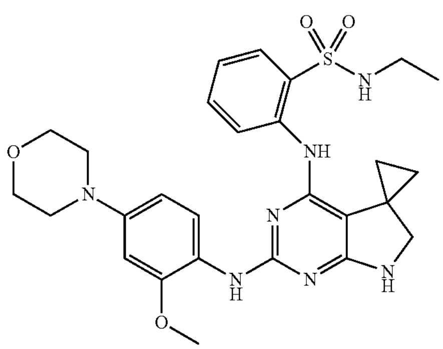 [SMILES: CCNS(=O)(=O)c1ccccc1Nc1nc(Nc2ccc(N3CCOCC3)cc2OC)nc2c1C1(CC1)CN2] | N-ethyl-2-(2'-(2-methoxy-4-morpholinophenyl-amino)-6',7'-dihydrospiro-[cyclopropane-1,5'-pyrrolo[2,3-d]pyrimidine]-4'-ylamino)-benzenesulfonamide | 552 | <20 | <20 |
| 140 | 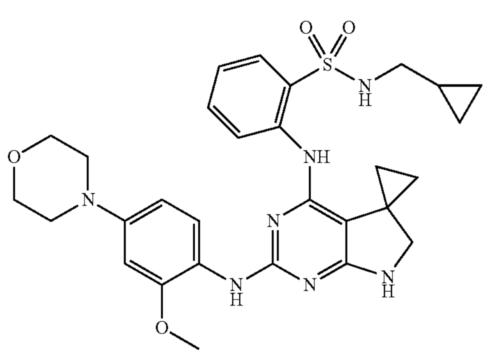 [SMILES: COc1cc(N2CCOCC2)ccc1Nc1nc2c(c(Nc3ccccc3S(=O)(=O)NCC3CC3)n1)C1(CC1)CN2] | N-(cyclopropylmethyl)-2-(2'-(2-methoxy-4-morpholinophenylamino)-6',7-dihydrospiro-[cyclopropane-1,5'-pyrrolo-[2,3-d]pyrimidine]-4'-ylamino)benzenesulfonamide | 578 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 141 | 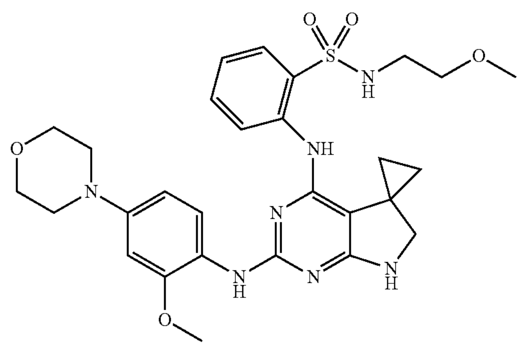 [SMILES: COCCNS(=O)(=O)c1ccccc1Nc1nc(Nc2ccc(N3CCOCC3)cc2OC)nc2c1C1(CC1)CN2] | 2-(2'-(2-methoxy-4-morpholinophenylamino)-6',7'-dihydrospiro-[cyclopropane-1,5'-pyrrolo-[2,3-d]pyrimidine]-4'-ylamino)-N-(2-methoxyethyl)-benzenesulfonamide | 582 | <20 | <20 |
| 142 | 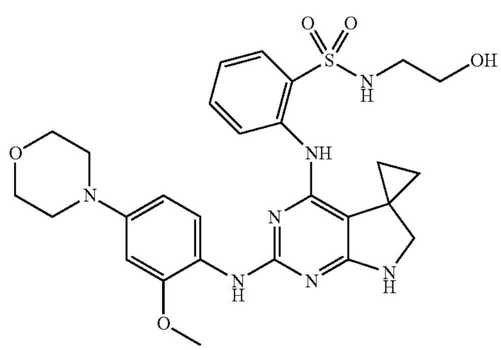 [SMILES: COc1cc(N2CCOCC2)ccc1Nc1nc2c(c(Nc3ccccc3S(=O)(=O)NCCO)n1)C1(CC1)CN2] | N-(2-hydroxyethyl)-2-(2'-(2-methoxy-4-morpholinophenylamino)-6',7'-dihydrospiro-[cyclopropane-1,5'-pyrrolo-[2,3-d]pyrimidine]-4'-ylamino)benzenesulfonamide | 568 | >1000 | >1000 |
| 143 | 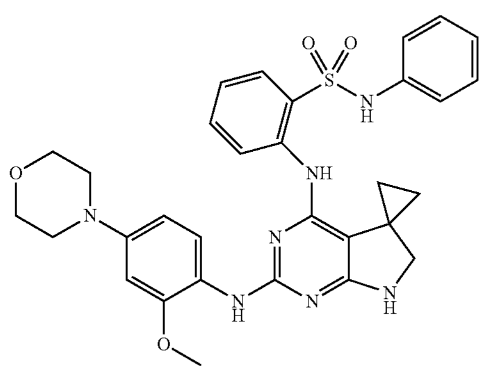 [SMILES: COc1cc(N2CCOCC2)ccc1Nc1nc2c(c(Nc3ccccc3S(=O)(=O)Nc3ccccc3)n1)C1(CC1)CN2] | 2-(2-(2-methoxy-4-morpholinophenylamino)-6',7'-dihydrospiro-[cyclopropane-1,5'-pyrrolo-[2,3-d]pyrimidine]-4'-ylamino)-N-phenylbenzenesulfonamide | 600 | <100 | <200 |
| 144 | 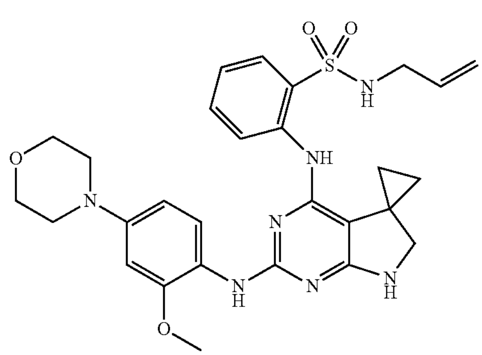 [SMILES: C=CCNS(=O)(=O)c1ccccc1Nc1nc(Nc2ccc(N3CCOCC3)cc2OC)nc2c1C1(CC1)CN2] | N-allyl-2-(2'-(2-methoxy-4-morpholinophenyl-amino)-6',7'-dihydrospiro-[cyclopropane-1,5'-pyrrolo-[2,3-d]pyrimidine]-4'-ylamino)benzenesulfonamide | 564 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 145 | 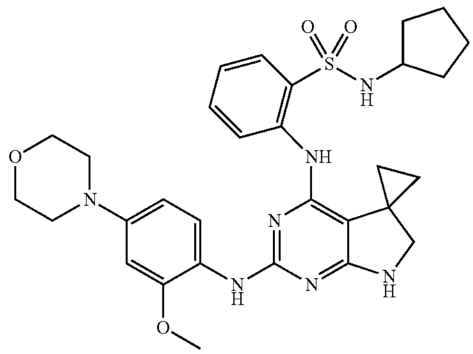 [SMILES: COc1cc(N2CCOCC2)ccc1Nc1nc2c(c(Nc3ccccc3S(=O)(=O)NC3CCCC3)n1)C1(CC1)CN2] | N-cyclopentyl-2-(2'-(2-methoxy-4-morpholino-phenylamino)-6',7'-dihydrospiro[cyclopropane-1,5'-pyrrolo[2,3-d]-pyrimidine]-4'-ylamino)-benzenesulfonamide | 592 | <100 | <100 |
| 146 | 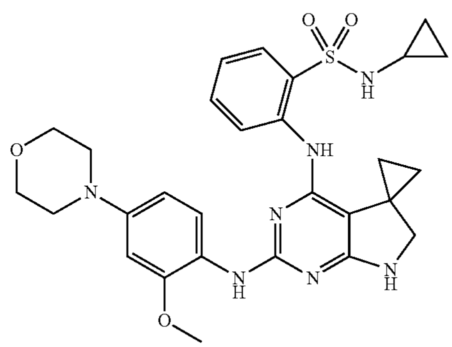 [SMILES: COc1cc(N2CCOCC2)ccc1Nc1nc2c(c(Nc3ccccc3S(=O)(=O)NC3CC3)n1)C1(CC1)CN2] | N-cyclopropyl-2-(2'-(2-methoxy-4-morpholino-phenylamino)-6',7'-dihydrospiro[cyclopropane-1,5'-pyrrolo[2,3-d]pyrimidine]-4'-ylamino)benzenesulfonamide | 564 | >1000 | >1000 |
| 147 | 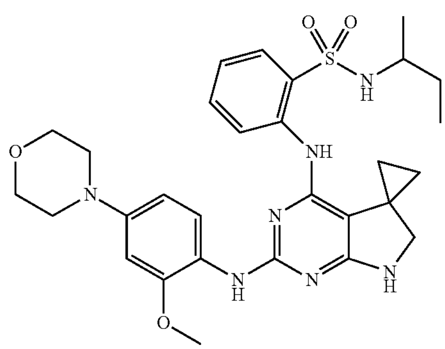 [SMILES: CCC(C)NS(=O)(=O)c1ccccc1Nc1nc(Nc2ccc(N3CCOCC3)cc2OC)nc2c1C1(CC1)CN2] | N-sec-butyl-2-(2'-(2-methoxy-4-morpholino-phenylamino)-6',7'-dihydrospiro[cyclopropane-1,5'-pyrrolo[2,3-d]-pyrimidine]-4'-ylamino)-benzenesulfonamide | 508 | <20 | <20 |
| 148 | 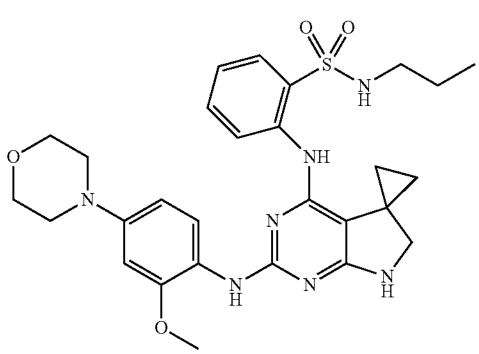 [SMILES: CCCNS(=O)(=O)c1ccccc1Nc1nc(Nc2ccc(N3CCOCC3)cc2OC)nc2c1C1(CC1)CN2] | 2-(2'-(2-methoxy-4-morpholinophenylamino)-6',7'-dihydrospiro-[cyclopropane-1,5'-pyrrolo-[2,3-d]pyrimidine]-4'-ylamino)-N-propylbenzenesulfonamide | 566 | <20 | <20 |

TABLE 1-continued

Biological Activities of Selected Pyrrolo[2,3-d]pyrimidines of Formula (I)

| Ex # | Structure | Name | MS [M + H]+ | FAK IC50 (nM) | PYK2 IC50 (nM) |
|---|---|---|---|---|---|
| 149 | 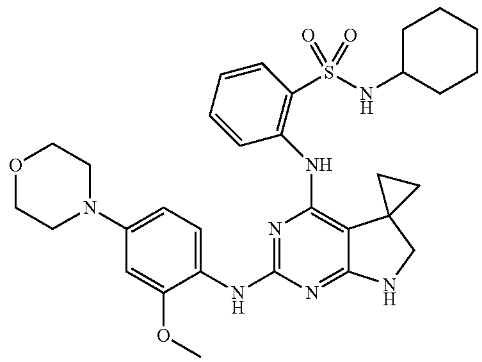 [SMILES: COc1cc(N2CCOCC2)ccc1Nc1nc2c(c(Nc3ccccc3S(=O)(=O)NC3CCCCC3)n1)C1(CC1)CN2] | N-cyclohexyl-2-(2'-(2-methoxy-4-morpholino-phenylamino)-6',7'-dihydrospiro[cyclopropane-1,5'-pyrrolo[2,3-d]-pyrimidine]-4'-ylamino)-benzenesulfonamide | 606 | <500 | <500 |
| 150 | 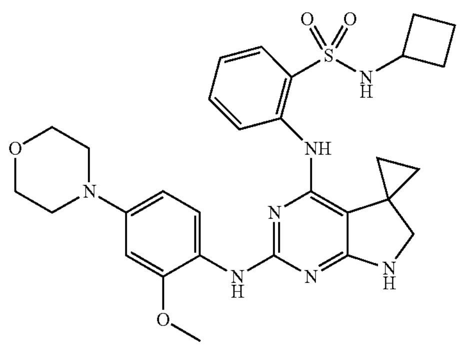 [SMILES: COc1cc(N2CCOCC2)ccc1Nc1nc2c(c(Nc3ccccc3S(=O)(=O)NC3CCC3)n1)C1(CC1)CN2] | N-cyclobutyl-2-(2'-(2-methoxy-4-morpholino-phenylamino)-6',7'-dihydrospiro[cyclopropane-1,5'-pyrrolo[2,3-d]-pyrimidine]-4'-ylamino)-benzenesulfonamide | 578 | <20 | <20 |
| 151 | 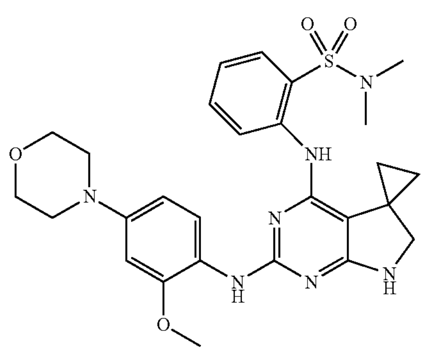 [SMILES: COc1cc(N2CCOCC2)ccc1Nc1nc2c(c(Nc3ccccc3S(=O)(=O)N(C)C)n1)C1(CC1)CN2] | 2-(2'-(2-methoxy-4-morpholinophenylamino)-6',7'-dihydrospiro-[cyclopropane-1,5'-pyrrolo[2,3-d]-pyrimidine]-4'-ylamino)-N,N-dimethyl-benzenesulfonamide | 552 | <20 | <20 |
| 152 | 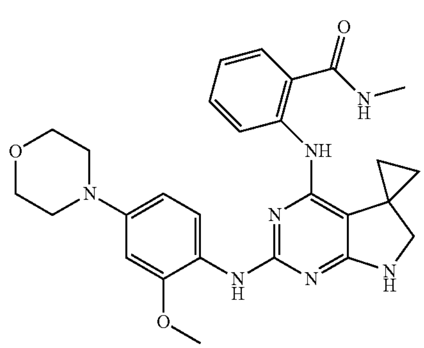 [SMILES: CNC(=O)c1ccccc1Nc1nc(Nc2ccc(N3CCOCC3)cc2OC)nc2c1C1(CC1)CN2] | 2-(2'-(2-methoxy-4-morpholinophenylamino)-6',7'-dihydrospiro-[cyclopropane-1,5'-pyrrolo[2,3-d]pyrimidine]-4'-ylamino)-N-methylbenzamide | 502 | <50 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 153 | 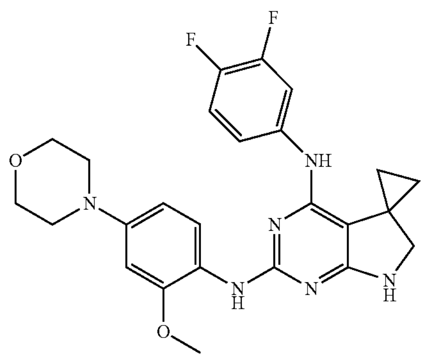 [SMILES: COc1cc(N2CCOCC2)ccc1Nc1nc2c(c(Nc3ccc(F)c(F)c3)n1)C1(CC1)CN2] | N$^{4'}$-(3,4-difluorophenyl)-N$^{2'}$-(2-methoxy-4-morpholinophenyl)-6',7'-dihydrospiro[cyclopropane-1,5'-pyrrolo[2,3-d]-pyrimidine]-2',4'-diamine | 481 | <200 | <500 |
| 154 | 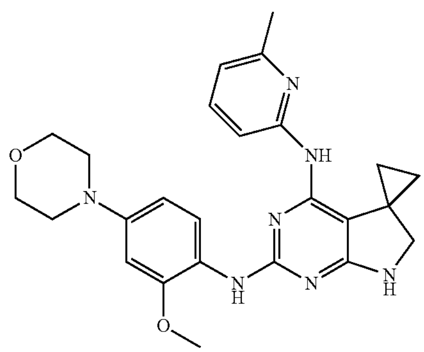 [SMILES: COc1cc(N2CCOCC2)ccc1Nc1nc2c(c(Nc3cccc(C)n3)n1)C1(CC1)CN2] | N$^{2'}$-(2-methoxy-4-morpholinophenyl)-N$^{4'}$-(6-methylpyridin-2-yl)-6',7'-dihydrospiro[cyclopropane-1,5'-pyrrolo[2,3-d]-pyrimidine]-2',4'-diamine | 460 | <50 | <100 |
| 155 | 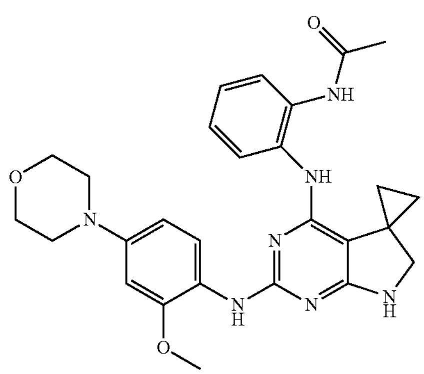 [SMILES: COc1cc(N2CCOCC2)ccc1Nc1nc2c(c(Nc3ccccc3NC(C)=O)n1)C1(CC1)CN2] | N-(2-(2'-(2-methoxy-4-morpholinophenylamino)-6',7'-dihydrospiro-[cyclopropane-1,5'-pyrrolo-[2,3-d]pyrimidine]-4'-ylamino)phenyl)acetamide | 502 | <50 | <50 |
| 156 | 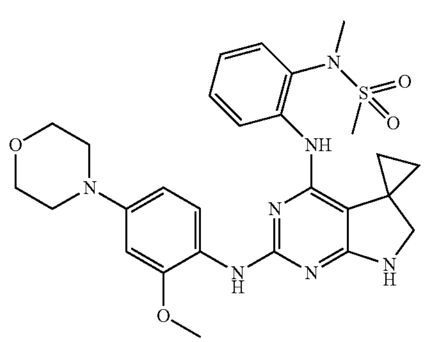 [SMILES: COc1cc(N2CCOCC2)ccc1Nc1nc2c(c(Nc3ccccc3N(C)S(C)(=O)=O)n1)C1(CC1)CN2] | N-(2-(2'-(2-methoxy-4-morpholinophenylamino)-6',7'-dihydrospiro-[cyclopropane-1,5'-pyrrolo-[2,3-d]pyrimidine]-4'-ylamino)phenyl)-N-methylmethanesulfonamide | 552 | <20 | <20 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 157 | 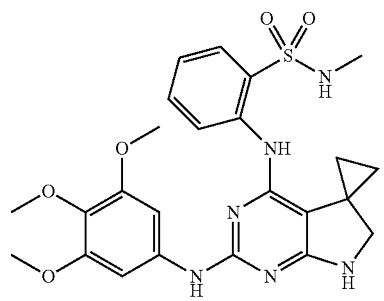 [SMILES: CNS(=O)(=O)c1ccccc1Nc1nc(Nc2cc(OC)c(OC)c(OC)c2)nc2c1C1(CC1)CN2] | N-methyl-2-(2'-(3,4,5-trimethoxyphenylamino)-6',7'-dihydrospiro-[cyclopropane-1,5'-pyrrolo-[2,3-d]pyrimidine]-4'-ylamino)benzenesulfonamide | 513 | <20 | <20 |
| 158 | 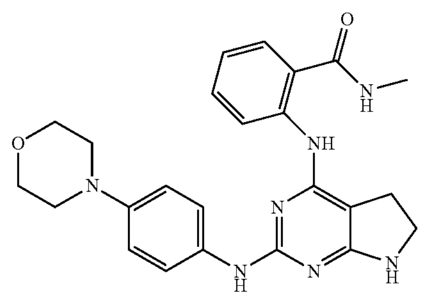 [SMILES: CNC(=O)c1ccccc1Nc1nc(Nc2ccc(N3CCOCC3)cc2)nc2c1CCN2] | N-methyl-2-(2-(4-morpholinophenylamino)-6,7-dihydro-5H-pyrrolo[2,3-d]pyrimidin-4-ylamino)-benzamide | 446 | <100 | <100 |
| 159 | 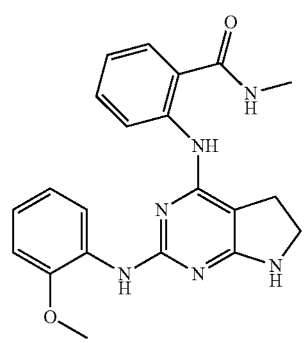 [SMILES: CNC(=O)c1ccccc1Nc1nc(Nc2ccccc2OC)nc2c1CCN2] | 2-(2-(2-methoxy-phenylamino)-6,7-dihydro-5H-pyrrolo[2,3-d]pyrimidin-4-ylamino)-N-methylbenzamide | 391 | <200 | <200 |
| 160 | 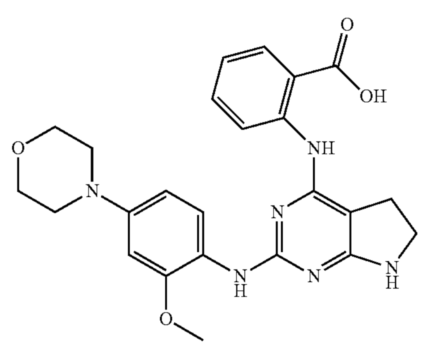 [SMILES: COc1cc(N2CCOCC2)ccc1Nc1nc2c(c(Nc3ccccc3C(=O)O)n1)CCN2] | 2-(2-(2-methoxy-4-morpholinophenylamino)-6,7-dihydro-5H-pyrrolo[2,3-d]pyrimidin-4-ylamino)-benzoic acid | 463 | <500 | <1000 |

TABLE 1-continued

Biological Activities of Selected Pyrrolo[2,3-d]pyrimidines of Formula (I)

| Ex # | Structure | Name | MS [M + H]+ | FAK IC$_{50}$ (nM) | PYK2 IC$_{50}$ (nM) |
|---|---|---|---|---|---|
| 161 | 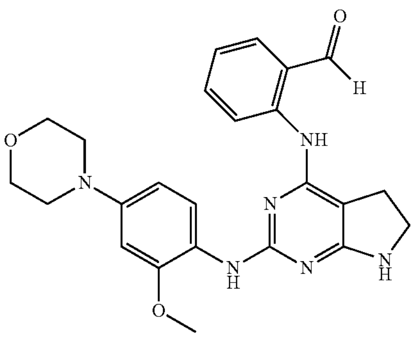 [SMILES: COc1cc(N2CCOCC2)ccc1Nc1nc2c(c(Nc3ccccc3C=O)n1)CCN2] | 2-(2-(2-mothoxy-4-morpholinophenylamino)-6,7-dihydro-5H-pyrrolo[2,3-d]pyrimidin-4-ylamino)-benzaldehyde | 447 | <1000 | <1000 |
| 162 | 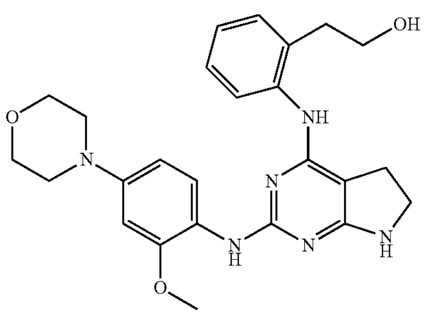 [SMILES: COc1cc(N2CCOCC2)ccc1Nc1nc2c(c(Nc3ccccc3CCO)n1)CCN2] | 2-(2-(2-(2-methoxy-4-morpholinophenylamino)-6,7-dihydro-5H-pyrrolo[2,3-d]pyrimidin-4-ylamino)-phenyl)ethanol | 449 | <1000 | <1000 |
| 163 | 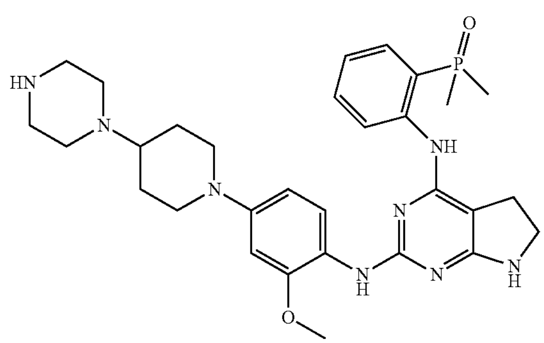 [SMILES: COc1cc(N2CCC(N3CCNCC3)CC2)ccc1Nc1nc2c(c(Nc3ccccc3P(C)(C)=O)n1)CCN2] | N$^4$-(2-(dimethylphosphoryl)-phenyl)-N$^2$-(2-methoxy-4-(4-(piperazin-1-yl)-piperidin-1-yl)phenyl)-6,7-dihydro-5H-pyrrolo[2,3-d]pyrimidine-2,4-diamine | 577 | <100 | <50 |

The invention claimed is:

1. A compound selected from:

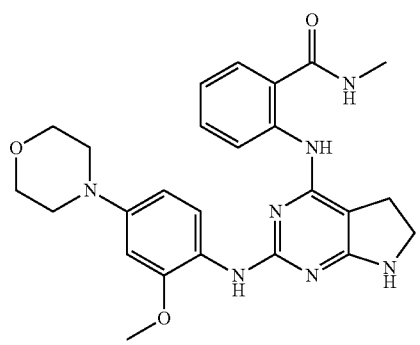

-continued

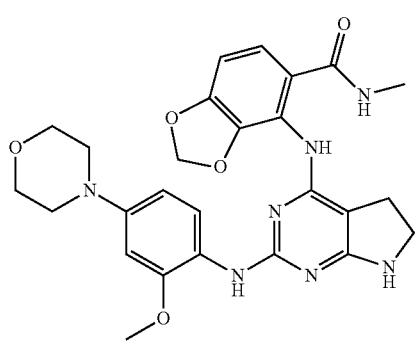

271
-continued
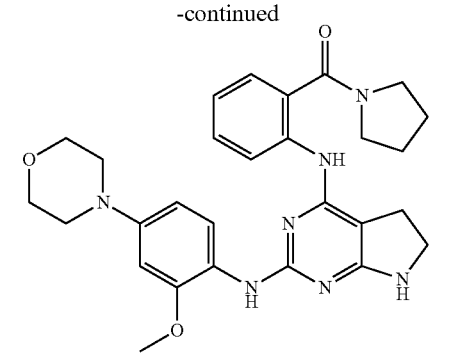
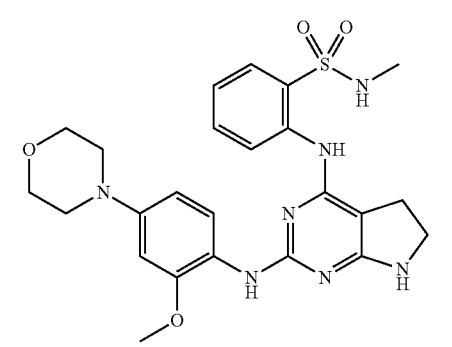
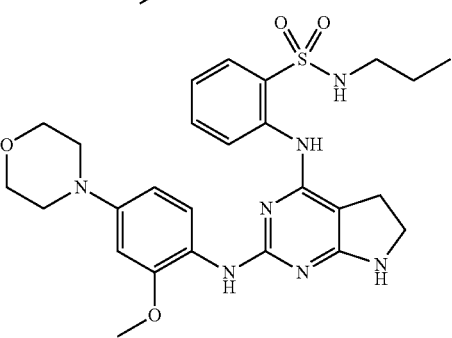
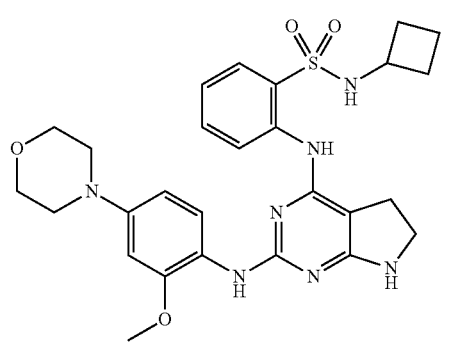
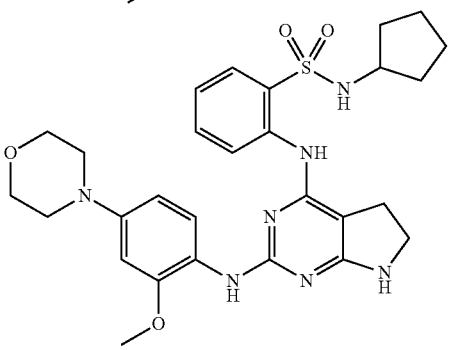
272
-continued
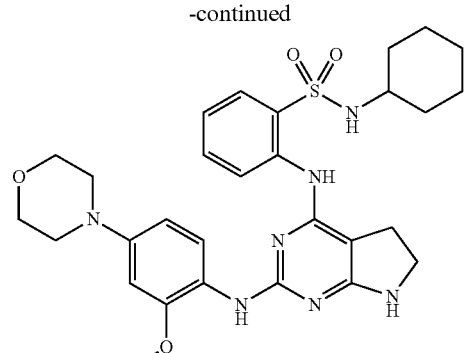
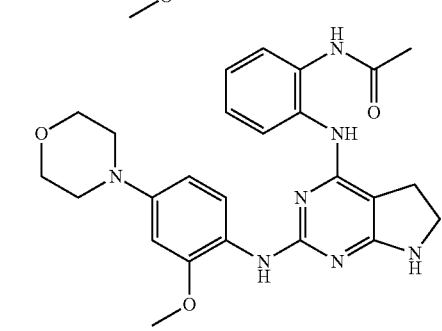
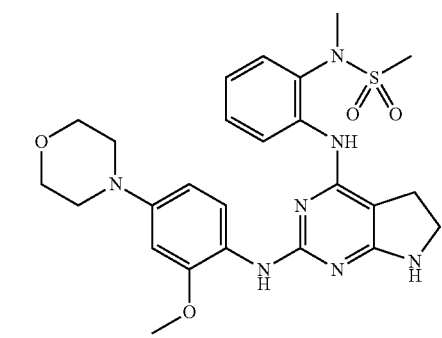
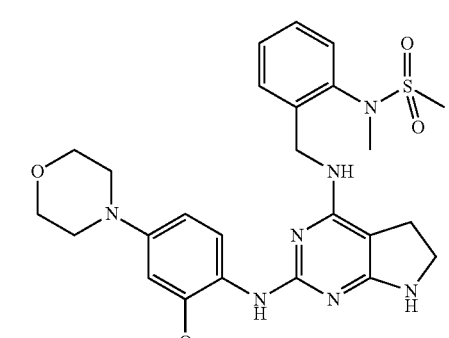
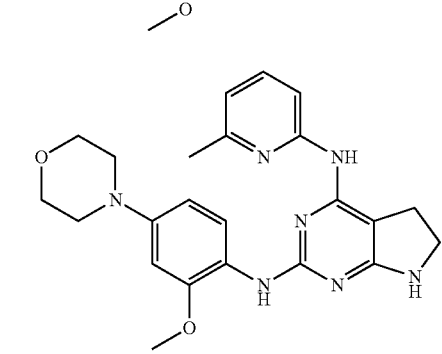

273
-continued
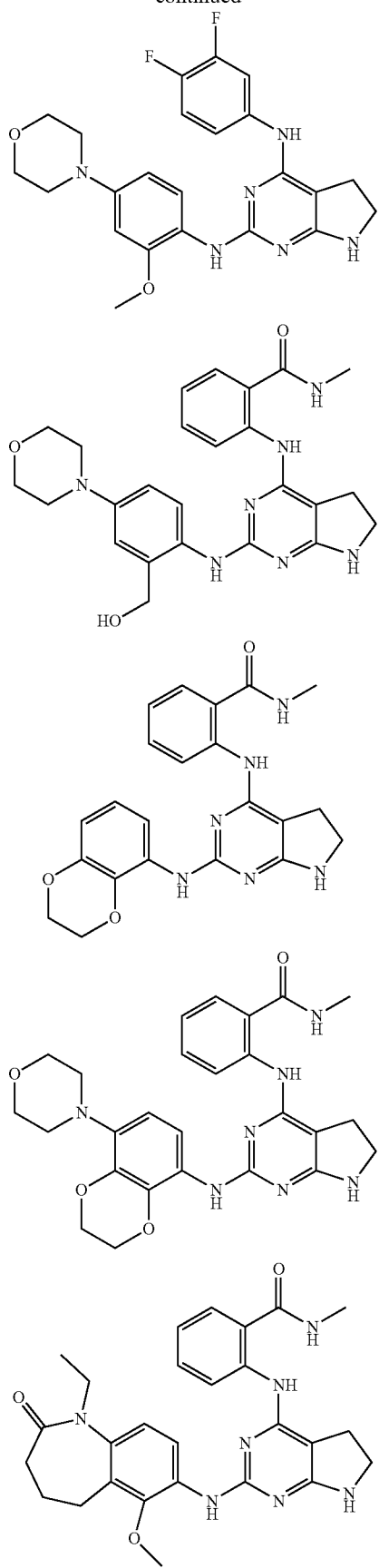
274
-continued
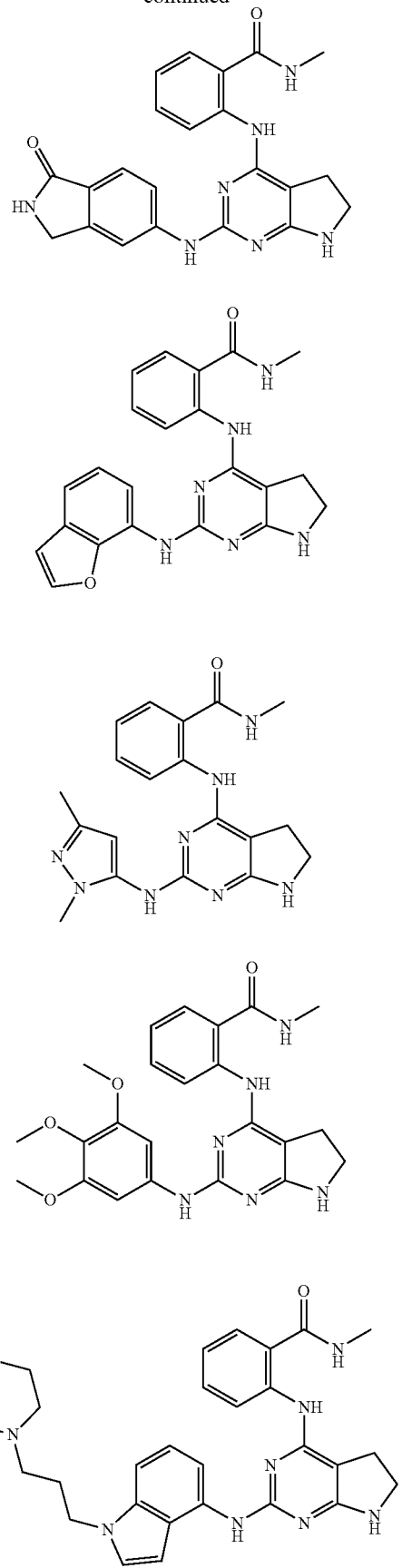

275
-continued
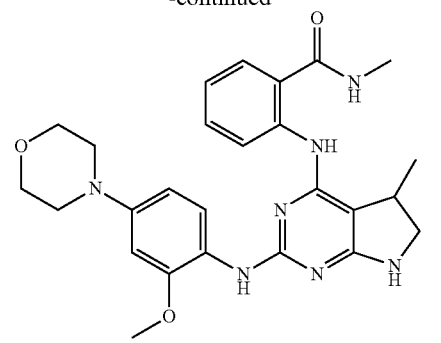
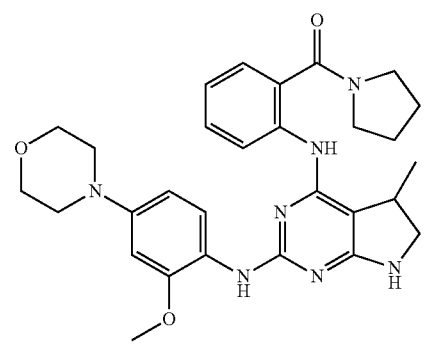
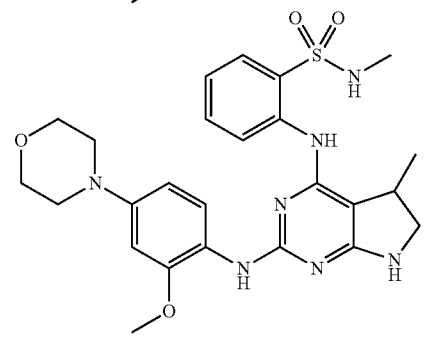
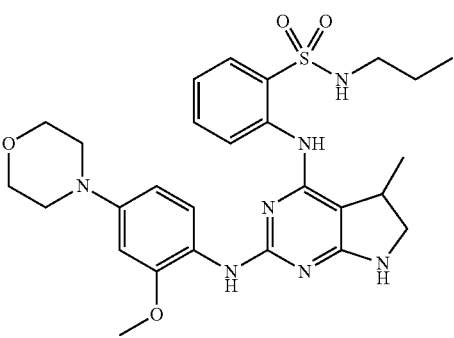
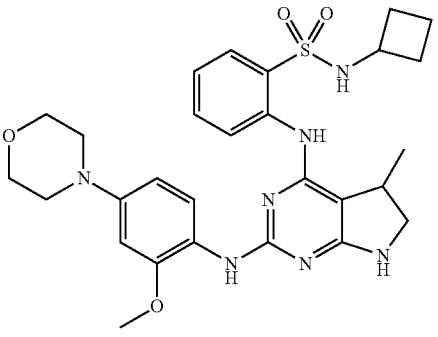
276
-continued
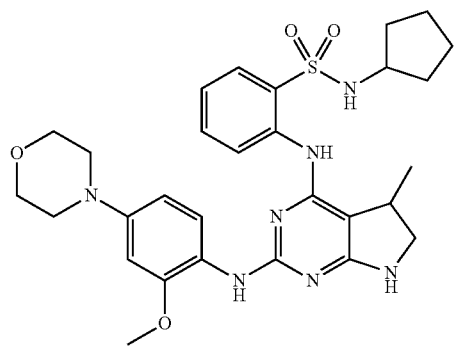
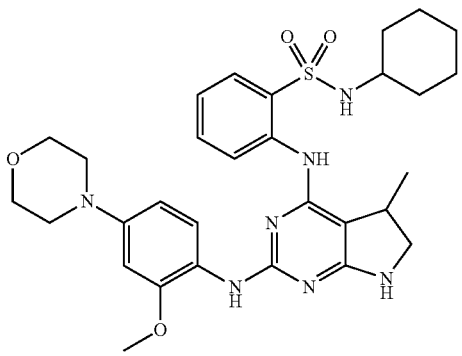
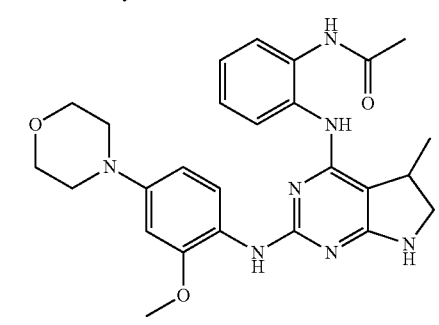
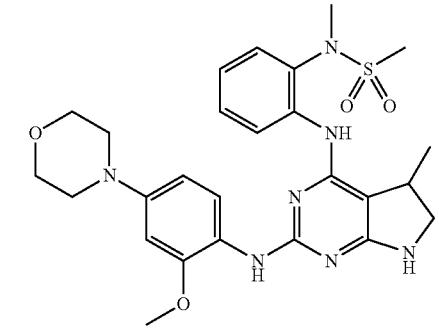
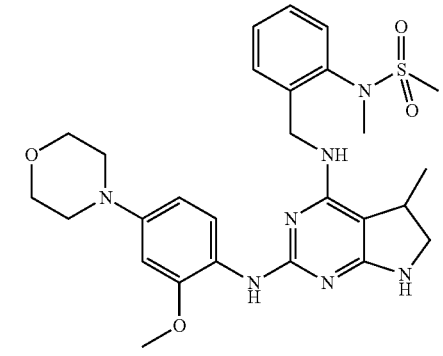

277
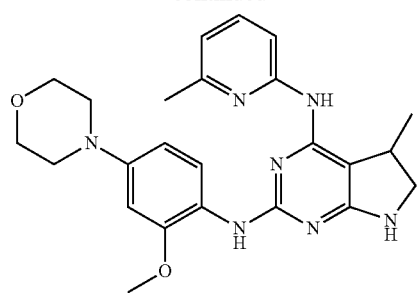
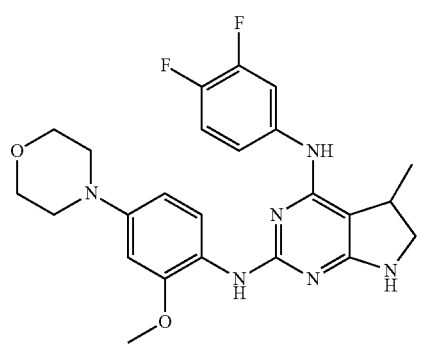
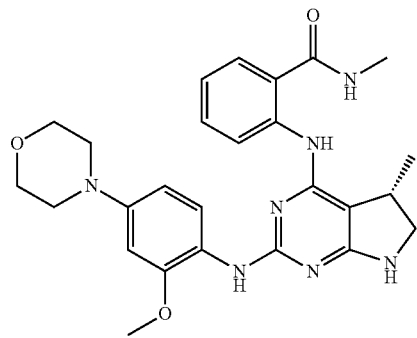
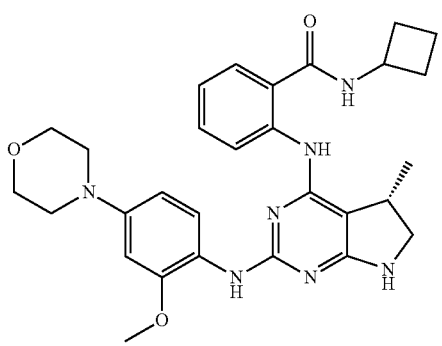
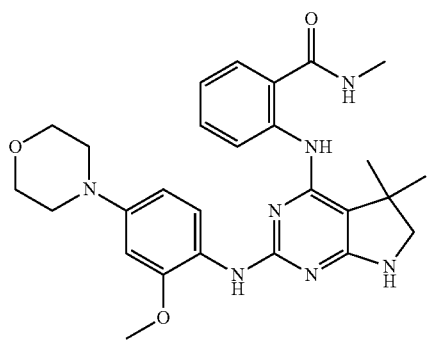
278
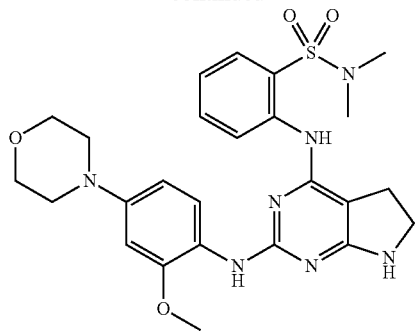
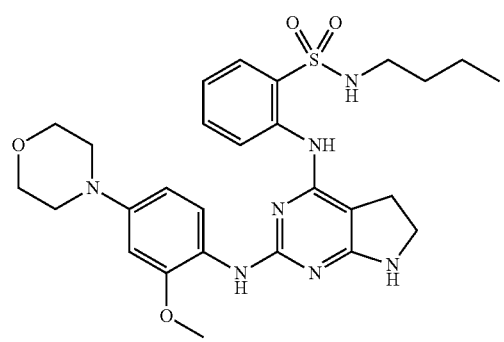
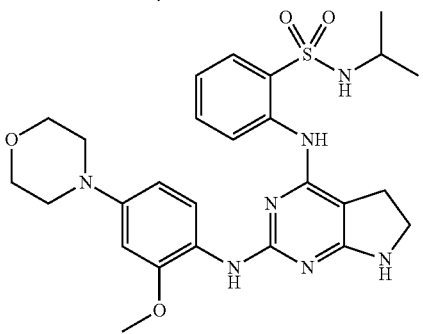
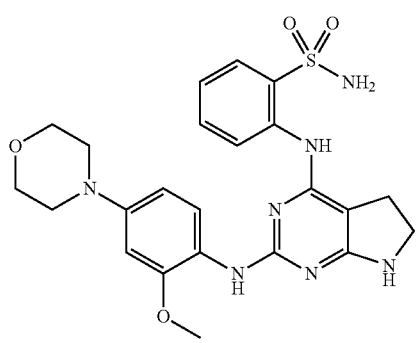
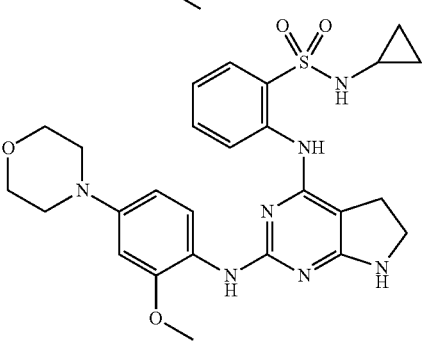

279
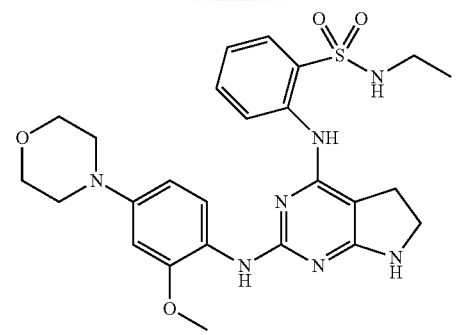
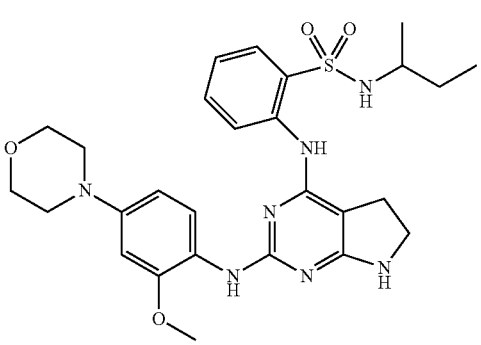
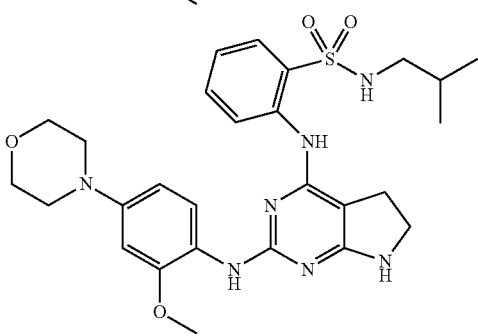
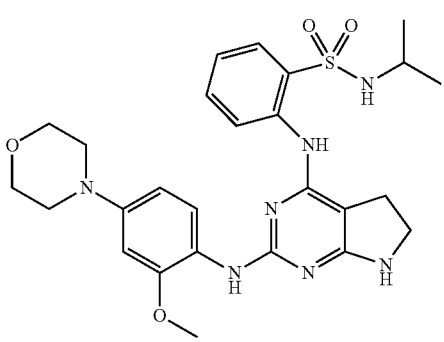
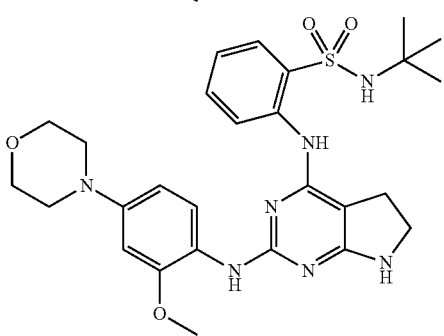
280
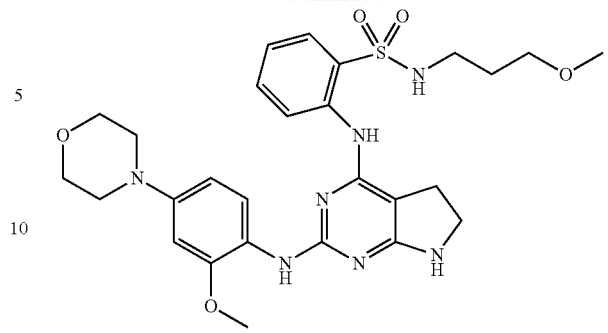
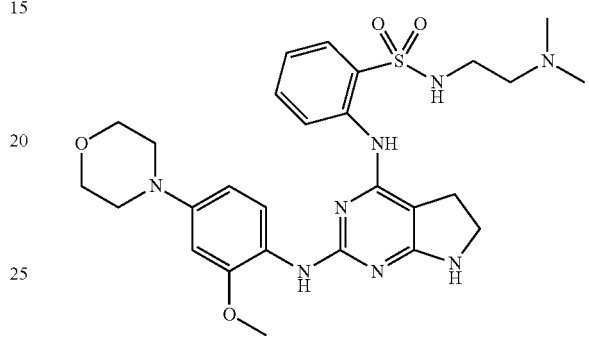
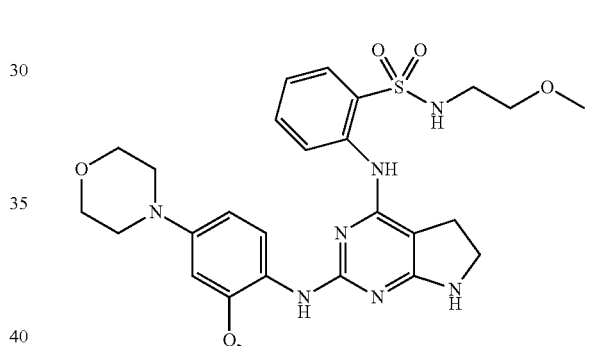
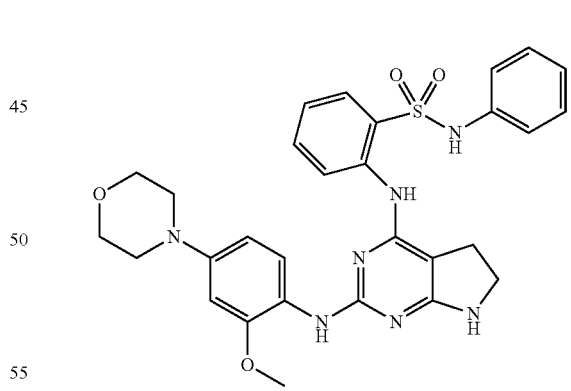
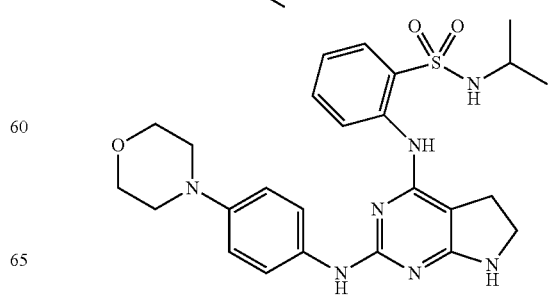

-continued
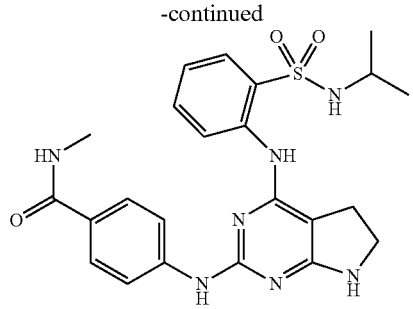
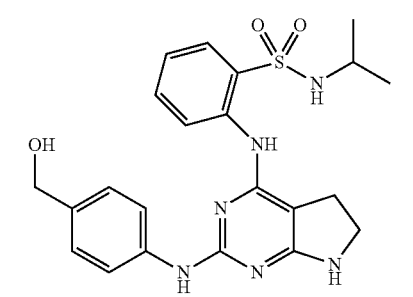
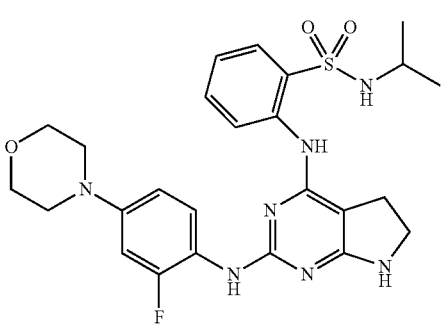
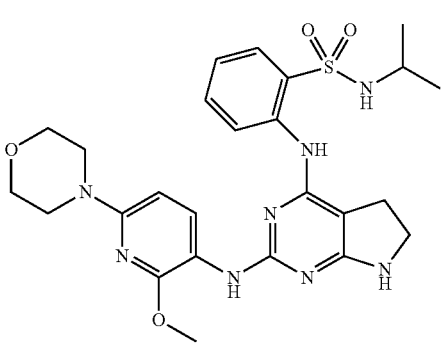
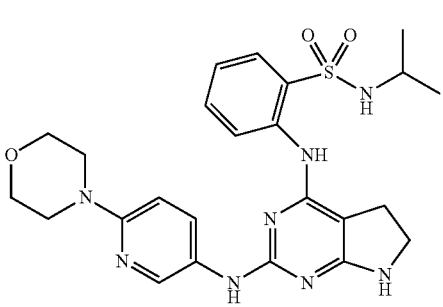
-continued
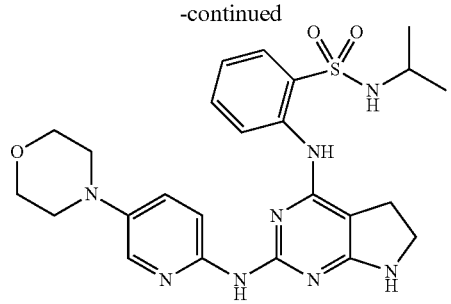
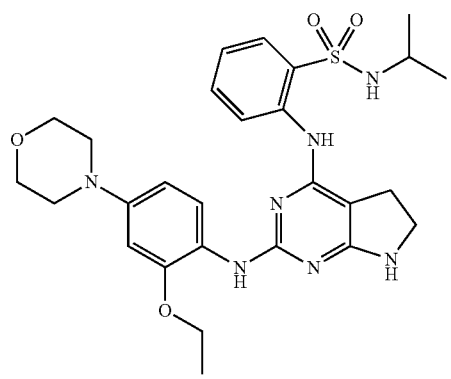
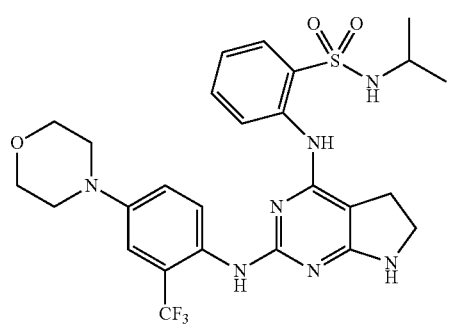
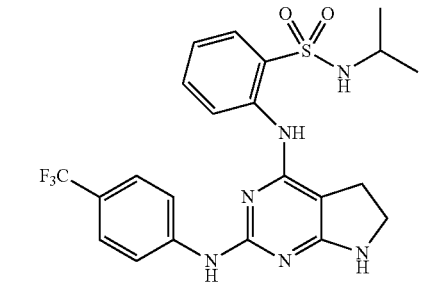
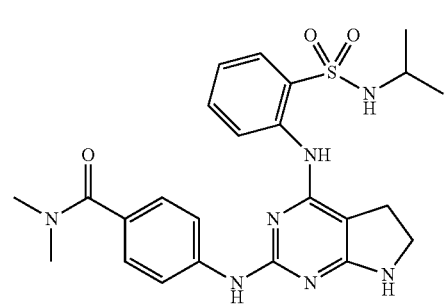

283
-continued
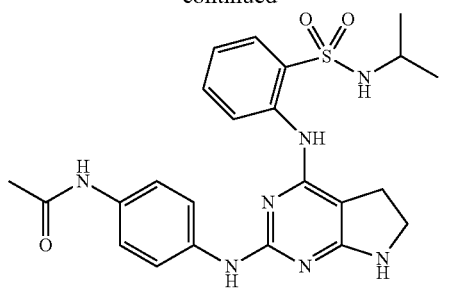
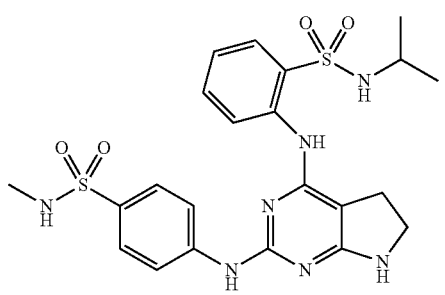
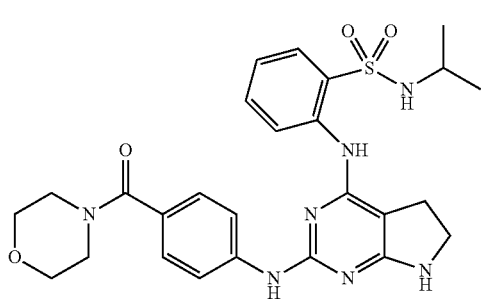
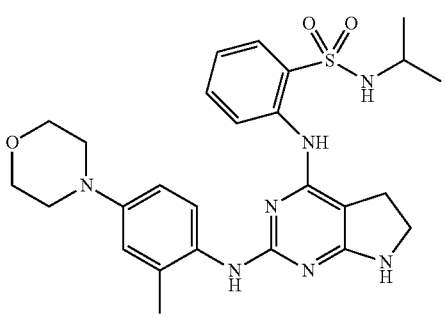
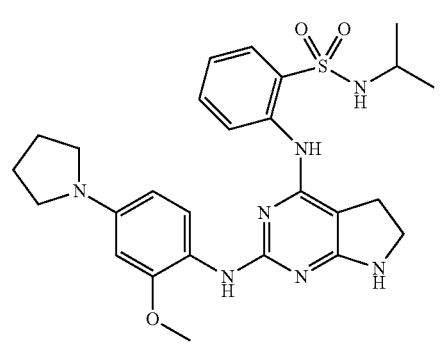
284
-continued
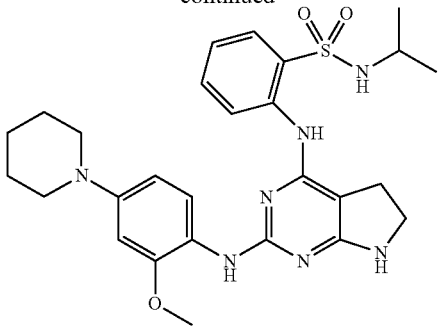
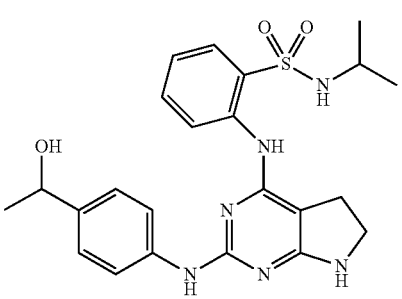
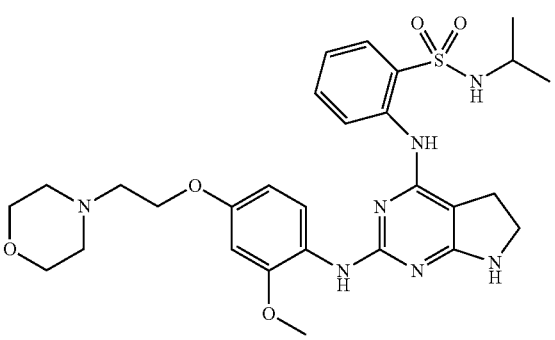
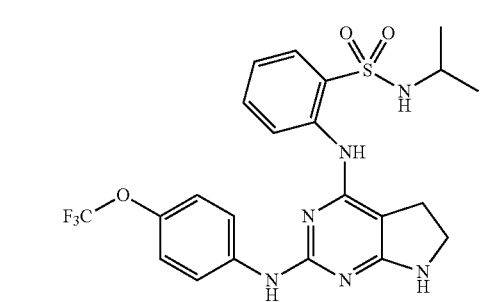
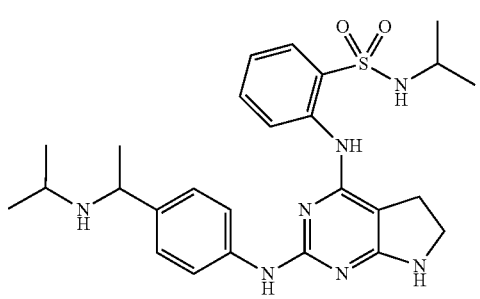

285
-continued
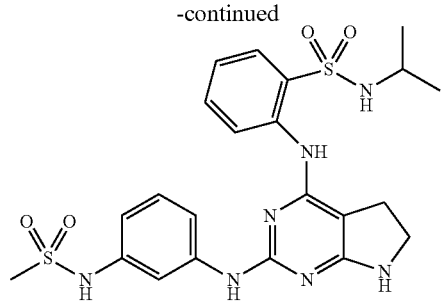
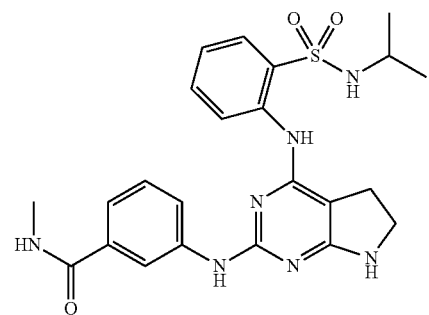
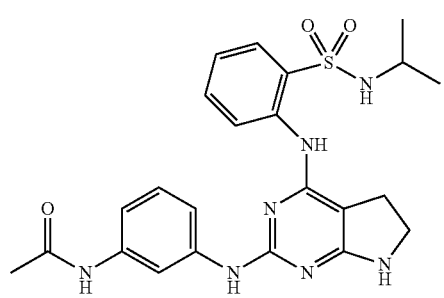
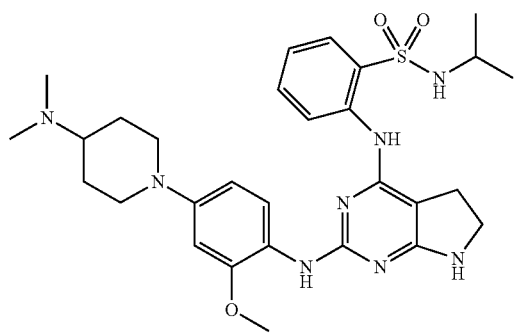
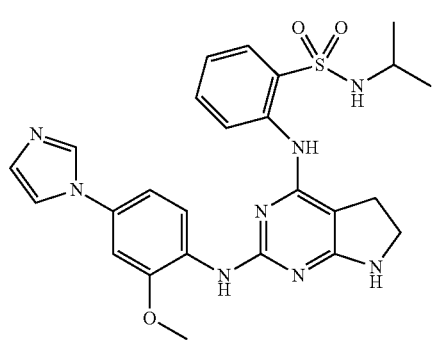
286
-continued
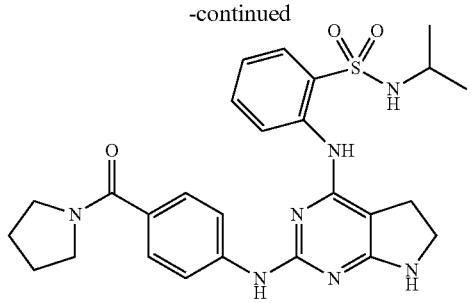
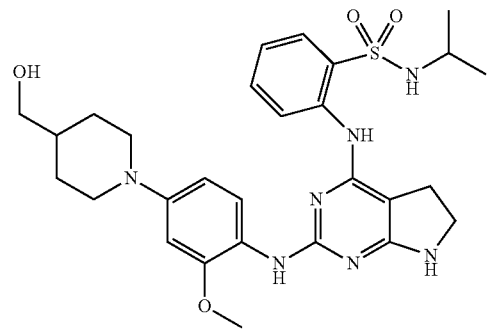
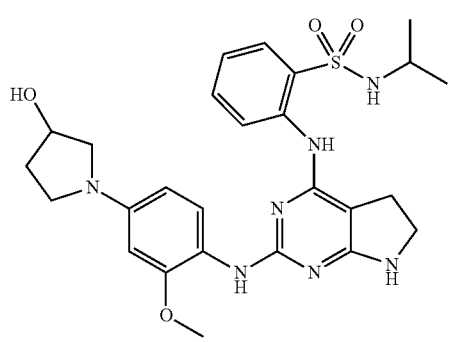
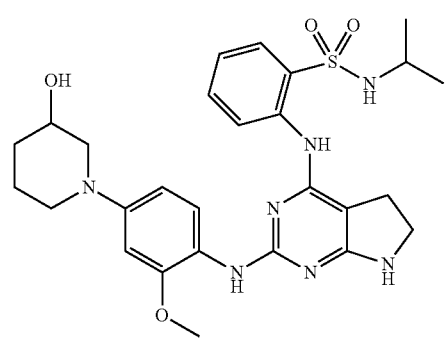
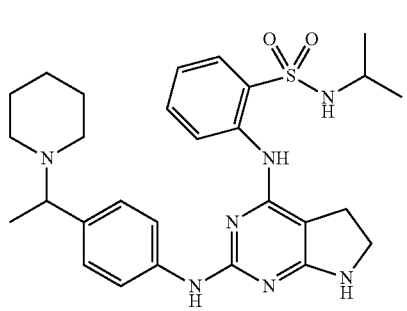

287
-continued
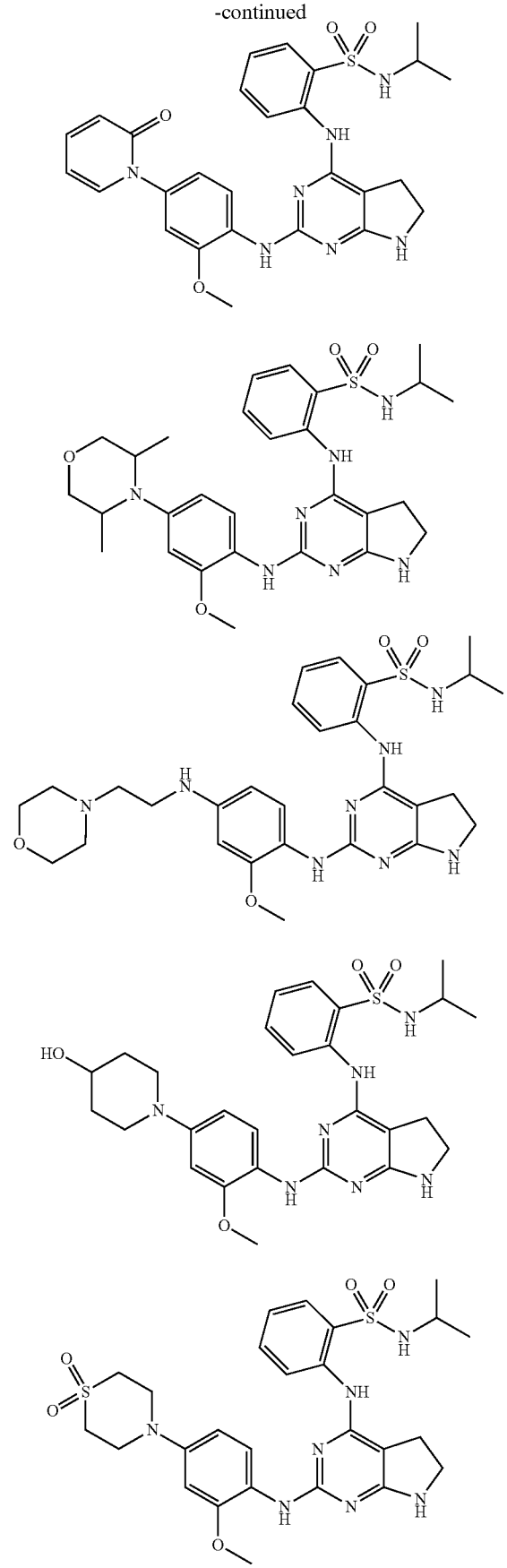
288
-continued
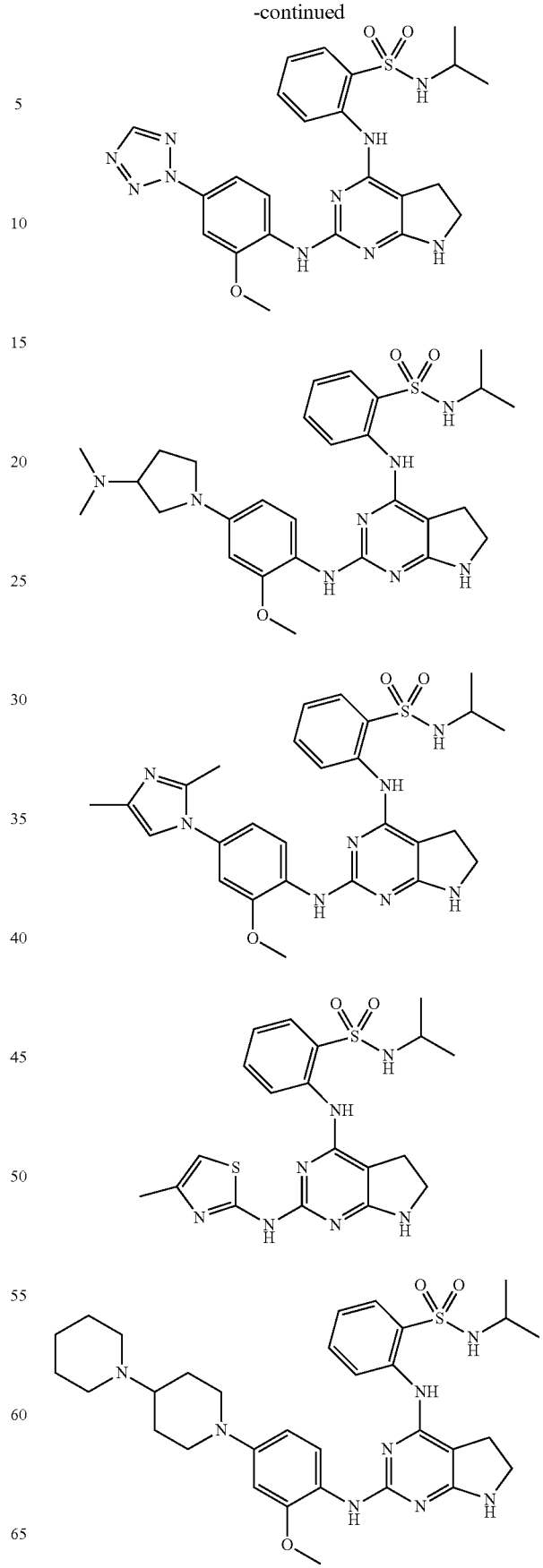

289
-continued
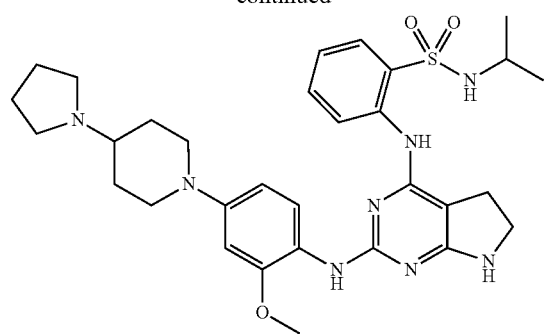
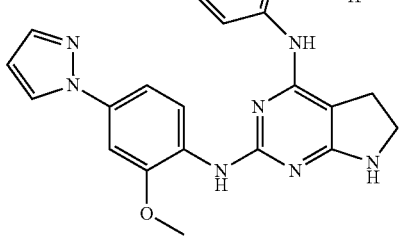
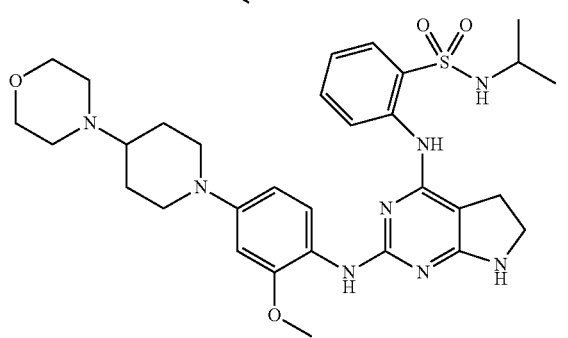
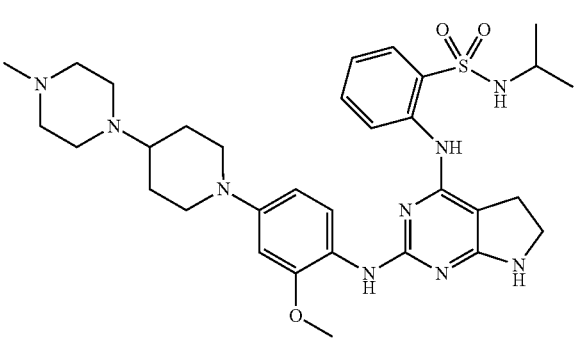
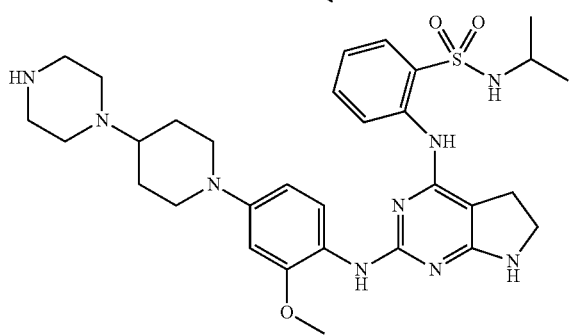
290
-continued
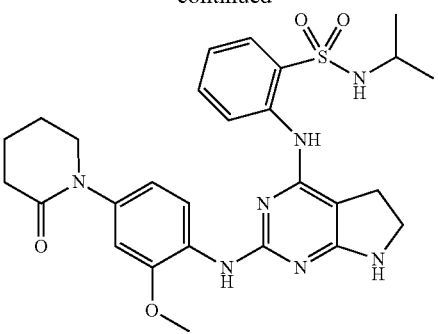
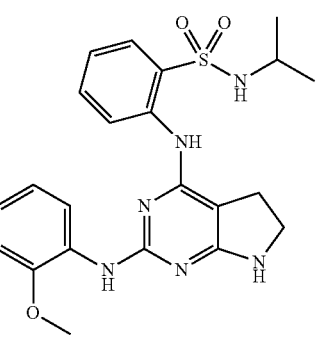
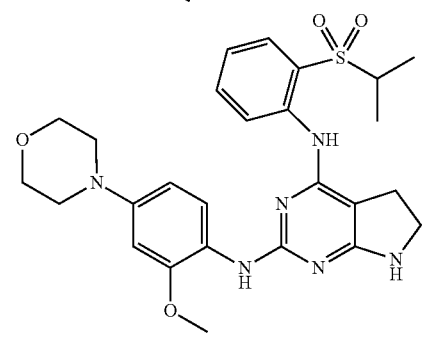
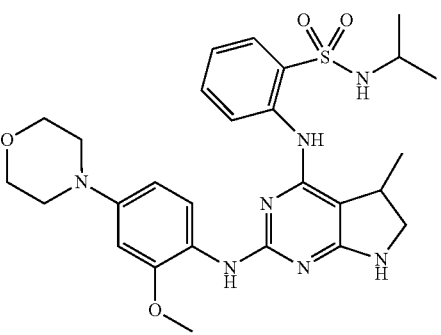
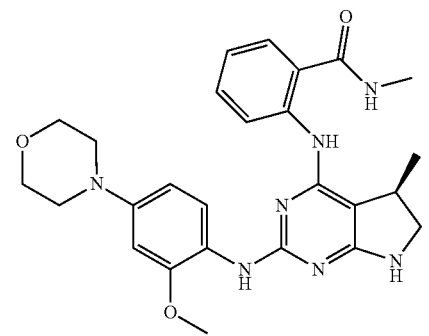

291
-continued
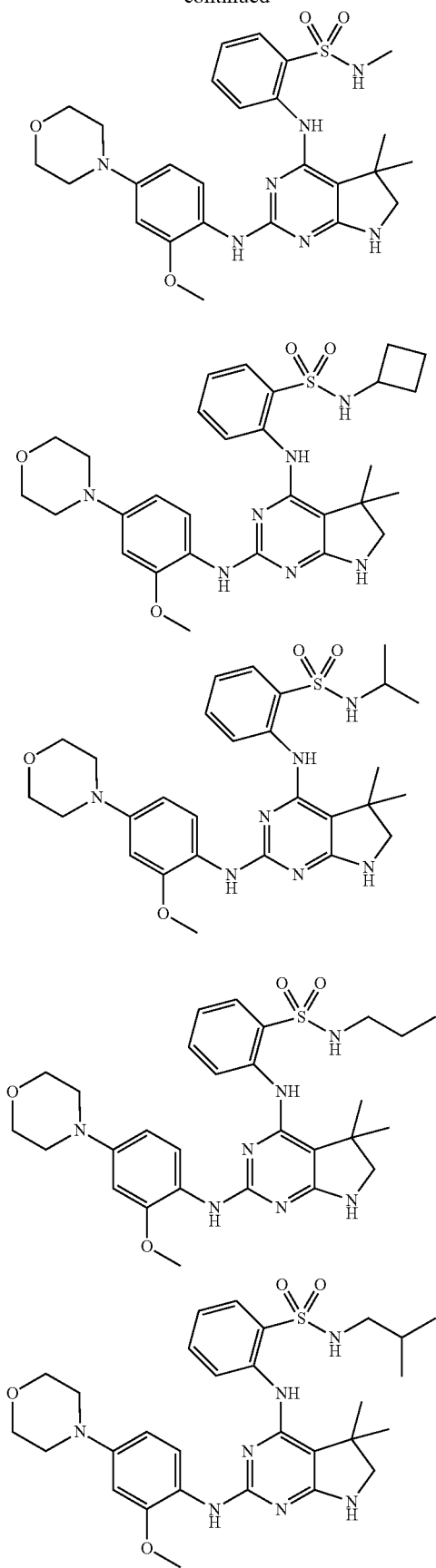
292
-continued
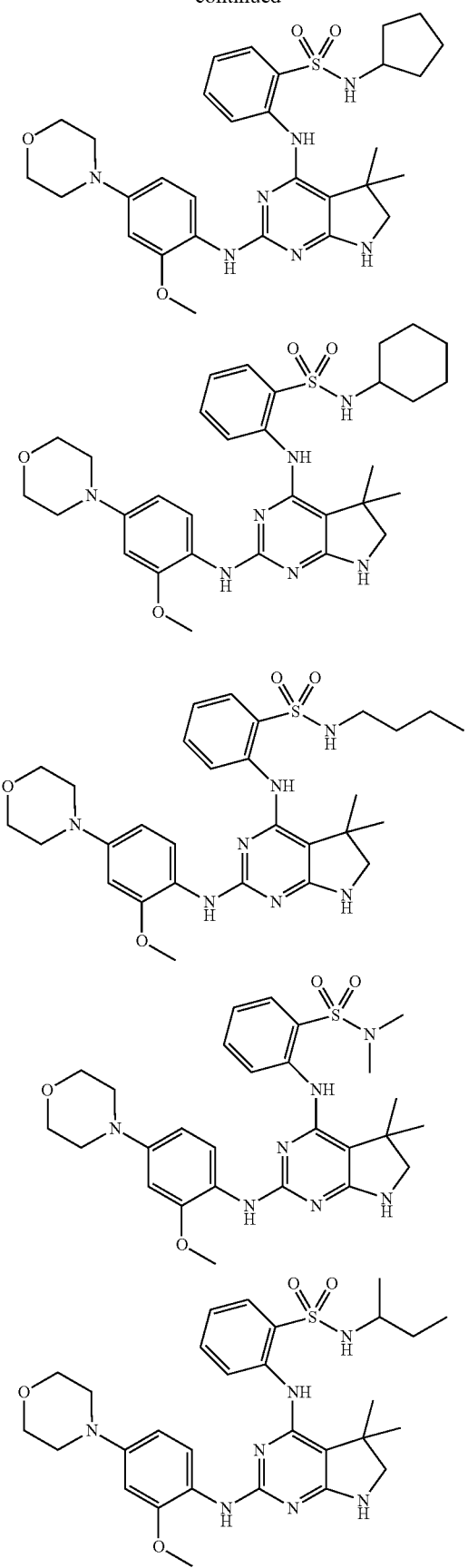

293
-continued
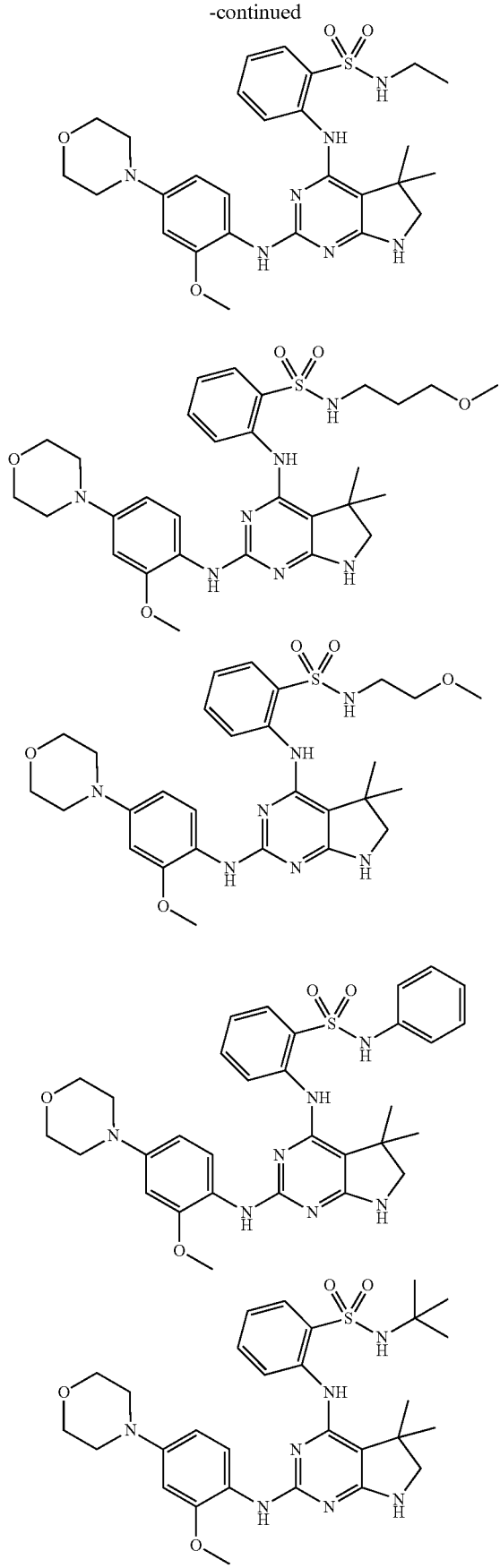
294
-continued
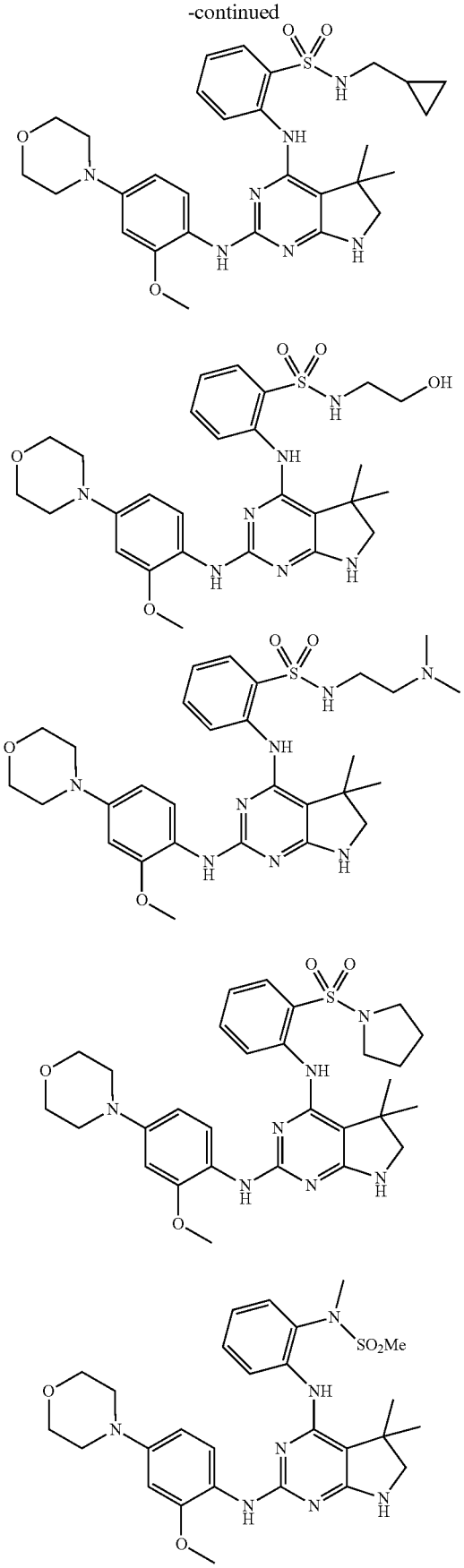

-continued
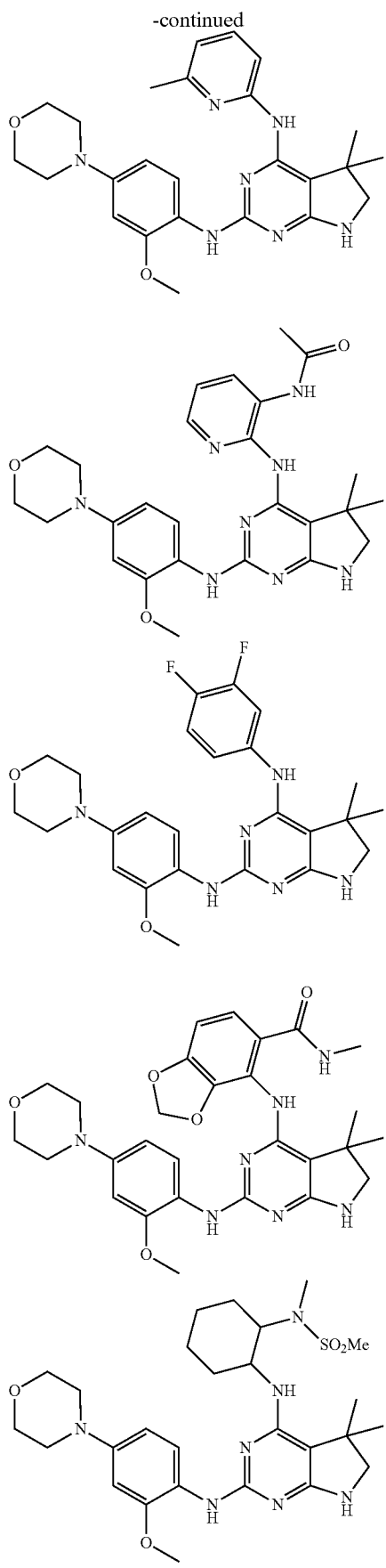
-continued
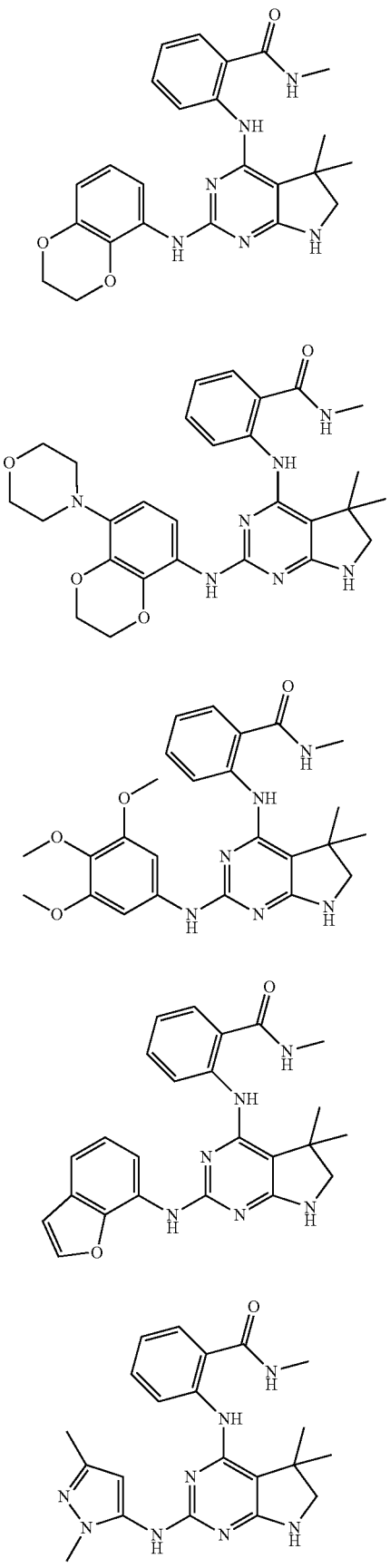

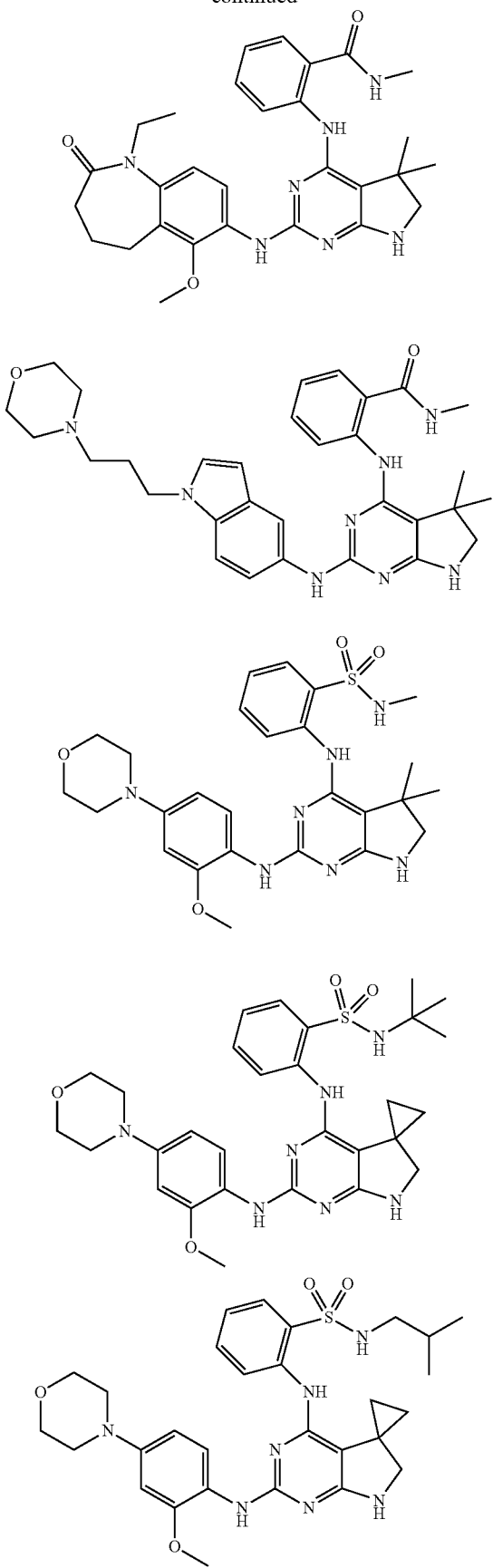
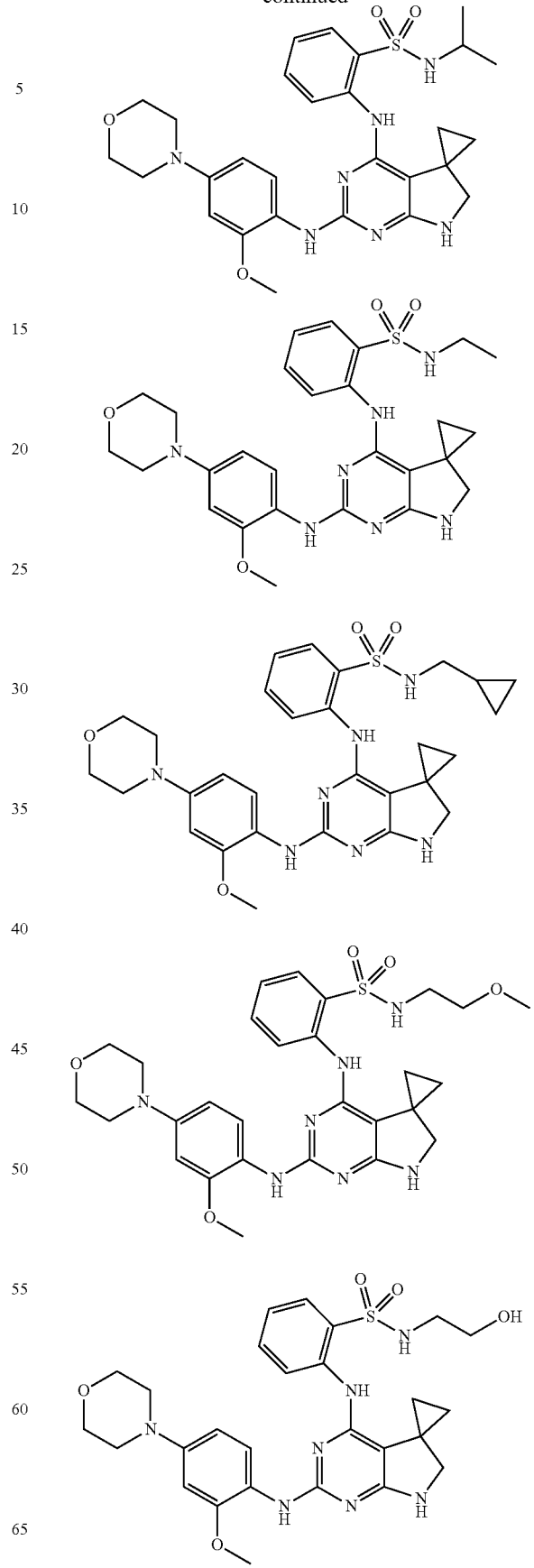

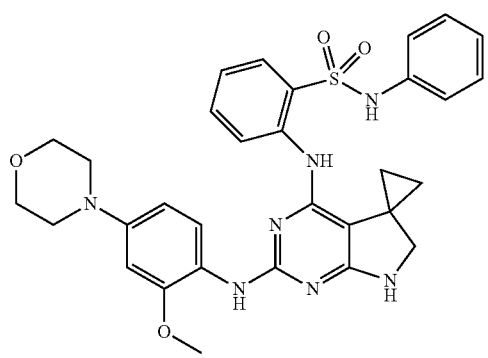
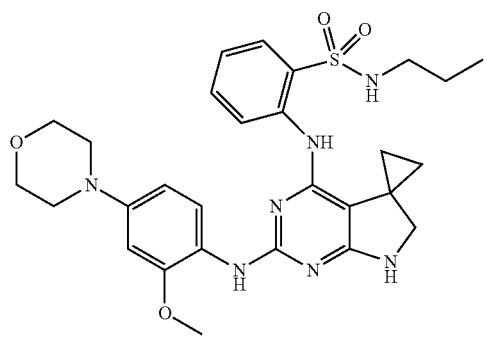
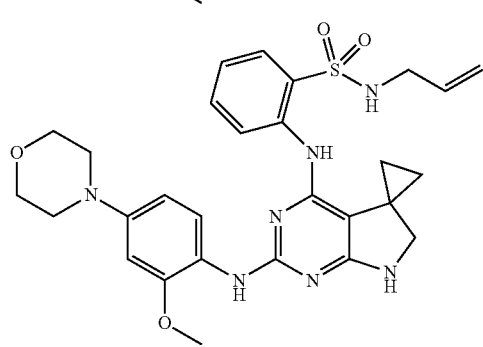
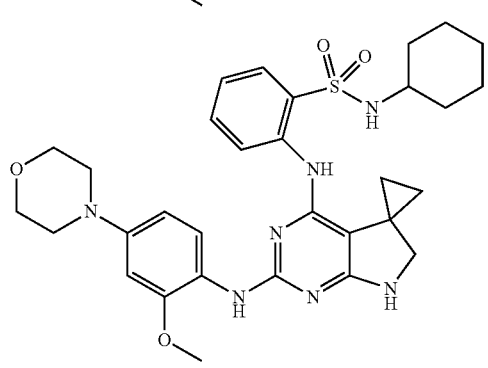
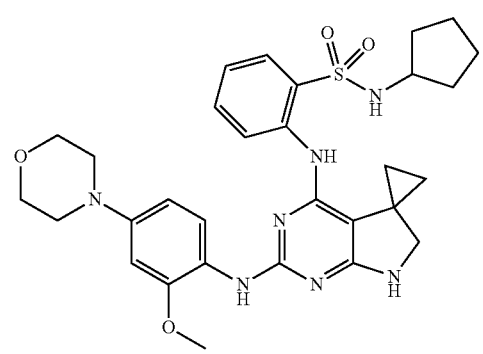
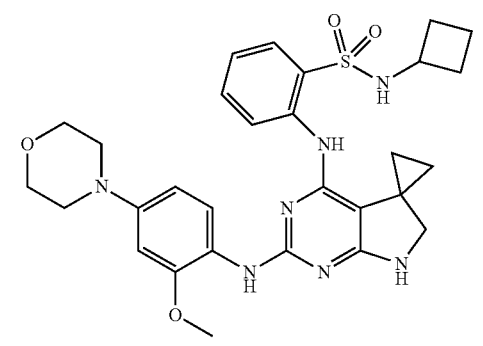
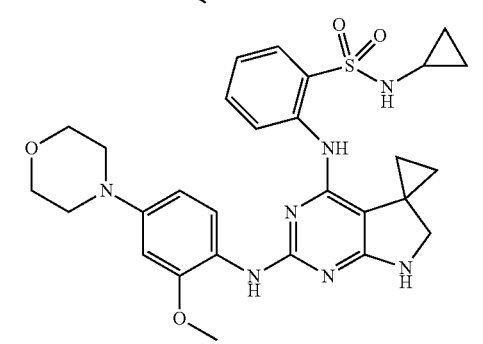
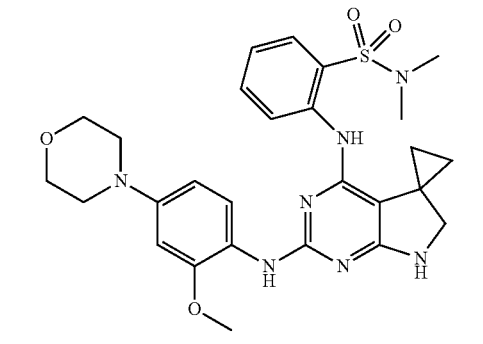
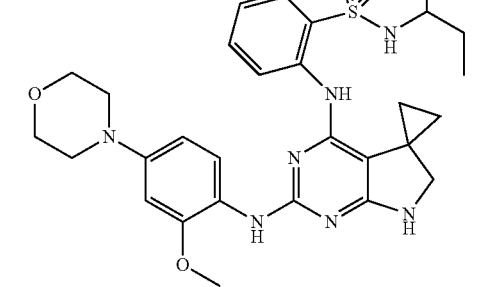
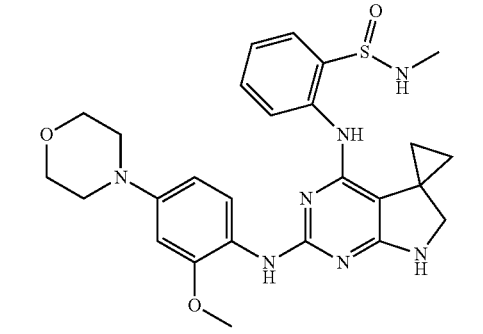

301
-continued
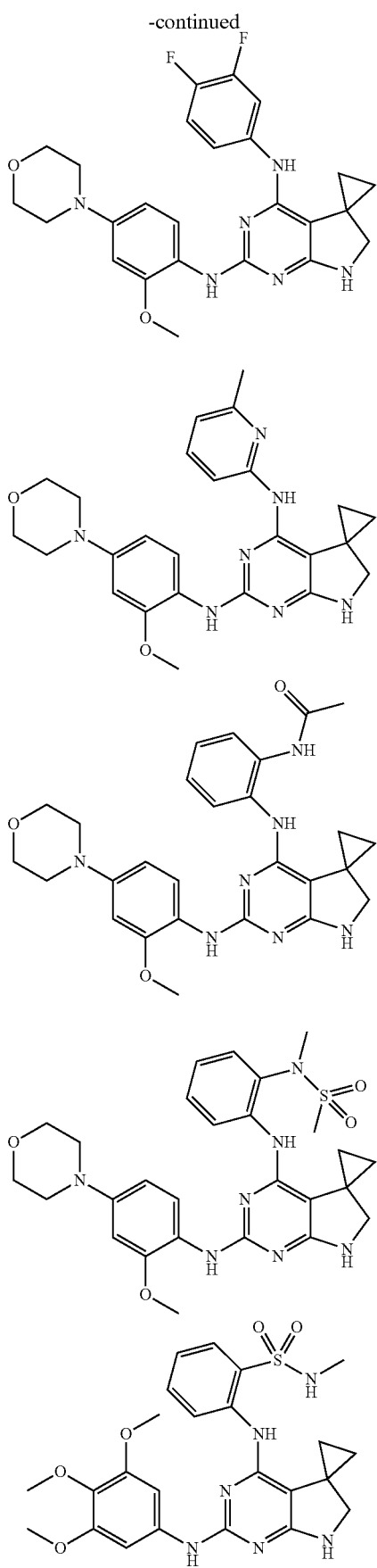
302
-continued
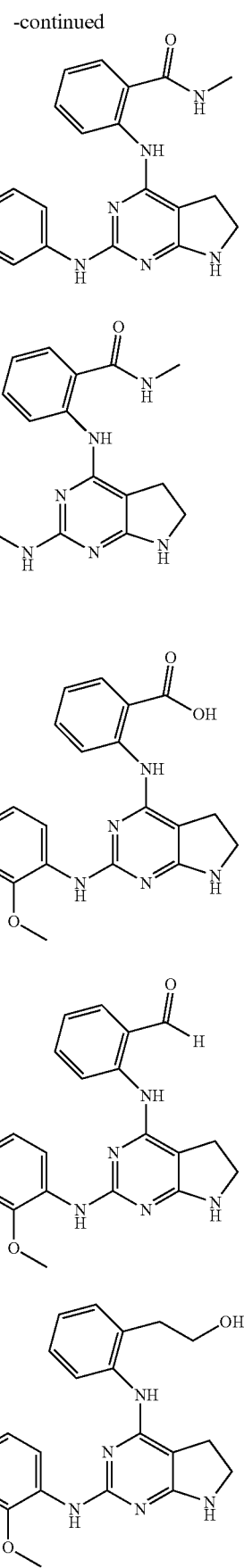

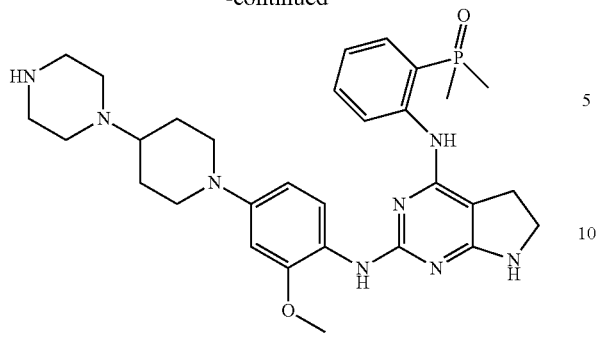

or a pharmaceutically acceptable salt, solvate, or tautomer thereof.

2. A pharmaceutical composition comprising a) the compound of claim 1 or a pharmaceutically acceptable salt, solvate, or tautomer thereof, and b) a pharmaceutically acceptable carrier, diluent, excipient and/or adjuvant.

3. A method of treatment of a FAK and/or Pyk2 mediated disorder or disease comprising administering to a patient in need thereof a therapeutically effective amount of a compound of claim 1,
wherein the disorder or disease is ovarian carcinoma or breast cancer.

* * * * *